United States Patent
Davison et al.

(10) Patent No.: US 11,254,986 B2
(45) Date of Patent: Feb. 22, 2022

(54) GENE SIGNATURE FOR IMMUNE THERAPIES IN CANCER

(71) Applicant: ALMAC DIAGNOSTICS LIMITED, Craigvon (GB)

(72) Inventors: Timothy Davison, Hillsborough (GB); Jude O'Donnell, Galbally (GB); Max Bylesjo, Belfast (GB); Fionnuala Patterson, Belfast (GB); Steve Deharo, Lisburn (GB); Laura A. Hill, Lisburn (GB); Katherine E. Keating, Magherafelt (GB); Vitali Proutski, Hillsborough (GB); Denis Paul Harkin, Dromore (GB); Richard Kennedy, Belfast (GB); Nicolas Goffard, Craigavon (GB); Steven Walker, Craigavon (GB); Laura Taggart, Craigavon (GB); Eileen Parkes, Craigavon (GB)

(73) Assignee: Almac Diagnostics Services Limited, Craigvon (GB)

( * ) Notice: Subject to any disclaimer, the term of this patent is extended or adjusted under 35 U.S.C. 154(b) by 49 days.

(21) Appl. No.: 15/746,097

(22) PCT Filed: Jul. 21, 2016

(86) PCT No.: PCT/GB2016/052213
§ 371 (c)(1),
(2) Date: Jan. 19, 2018

(87) PCT Pub. No.: WO2017/013436
PCT Pub. Date: Jan. 26, 2017

(65) Prior Publication Data
US 2019/0316203 A1    Oct. 17, 2019

Related U.S. Application Data

(60) Provisional application No. 62/237,497, filed on Oct. 5, 2015.

(30) Foreign Application Priority Data

Jul. 21, 2015 (GB) ...................... 1512869

(51) Int. Cl.
*C12Q 1/6886* (2018.01)
*G16H 50/30* (2018.01)

(52) U.S. Cl.
CPC .......... *C12Q 1/6886* (2013.01); *G16H 50/30* (2018.01); *C12Q 2600/106* (2013.01); *C12Q 2600/158* (2013.01)

(58) Field of Classification Search
None
See application file for complete search history.

(56) References Cited

U.S. PATENT DOCUMENTS

| 2014/0031260 A1* | 1/2014 | O'Donnell | ........... | C12Q 1/6886 506/9 |
| 2014/0079706 A1* | 3/2014 | Cannarile | .............. | C07K 16/30 424/139.1 |

OTHER PUBLICATIONS

Enard et al. (Science 2002 vol. 296 p. 340) (Year: 2002).*
Cobb et al. (Crit Care Med 2002 vol. 30 p. 2711) (Year: 2002).*

* cited by examiner

*Primary Examiner* — Katherine D Salmon
(74) *Attorney, Agent, or Firm* — Finnegan, Henderson, Farabow, Garrett & Dunner, LLP

(57) ABSTRACT

An immune response subtype of cancer is associated with DNA damage which allows subjects to be stratified for particular therapies including immune therapies which may be combined with DNA damage therapeutics. A method for predicting responsiveness to an antagonist of an inhibitory immune checkpoint and/or an agonist of a stimulatory immune checkpoint comprises determining the expression level of at least one gene selected from Table 2B, 2A or 1 in a sample from the subject. The determined expression level is used to predict responsiveness to an antagonist of an inhibitory immune checkpoint and/or an agonist of a stimulatory immune checkpoint.

17 Claims, 46 Drawing Sheets
(21 of 46 Drawing Sheet(s) Filed in Color)
Specification includes a Sequence Listing.

FIG. 2 Con't.
C.
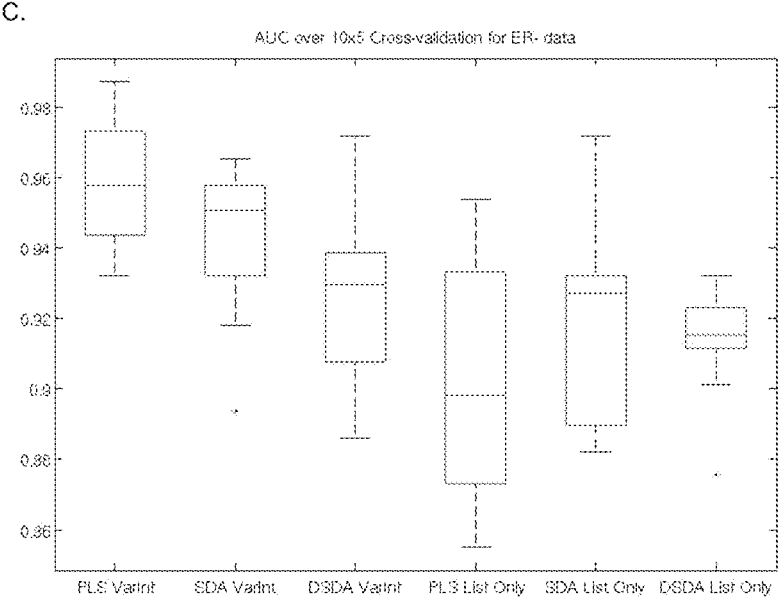
D.
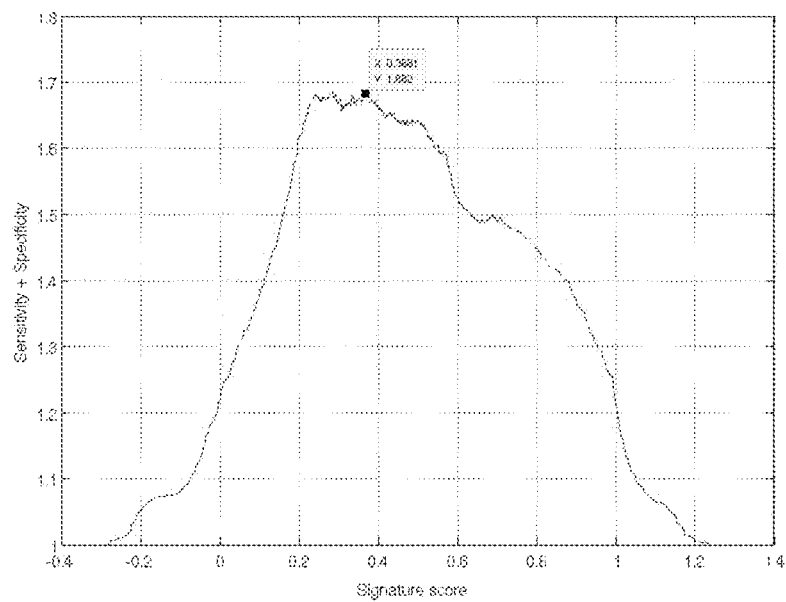

FIG. 9A

Intratumoral Lymphocytic Infiltrate

| CD8+ score | DDRD pos (n=66) | DDRD neg (n=119) | Fisher's exact test |
|---|---|---|---|
| 3 | | | P<0.0001 |
| 2 | | | |
| 1 | | | |
| 0 | | | |

| CD4+ score | DDRD pos (n=66) | DDRD neg (n=121) | Fisher's exact test |
|---|---|---|---|
| 3 | 3 (4.5%) | 1 (0.82%) | P<0.0001 |
| 2 | 14 (21.2%) | 9 (7.4%) | |
| 1 | 43 (65.1%) | 77 (63.6%) | |
| 0 | 6 (9.0%) | 40 (33.0%) | |

Stromal Lymphocytic Infiltrate

| CD8+ score | DDRD pos (n=66) | DDRD neg (n=119) | Fisher's exact test |
|---|---|---|---|
| 3 | 20 (30.3%) | 8 (6.72%) | P<0.0001 |
| 2 | 35 (53.0%) | 58 (48.7%) | |
| 1 | 7 (10.6%) | 46 (38.6%) | |
| 0 | 4 (6%) | 7 (5.88%) | |

| CD4+ score | DDRD pos (n=66) | DDRD neg (n=121) | Fisher's exact test |
|---|---|---|---|
| 3 | 21 (31.82%) | 7 (5.79%) | P<0.0001 |
| 2 | 32 (48.48%) | 32 (26.45%) | |
| 1 | 13 (19.70%) | 68 (56.20%) | |
| 0 | 0 (0%) | 14 (11.57%) | |

A

Correction of
MDA-436 cell lines

B

C

MDA436-EV           MDA436 +BRCA1
DDRD +ve            DDRD -ve

D

48hr conditioned media

>5% cut off

| TUMOUR | DDRD pos | DDRD neg |
|---|---|---|
| PDL1 pos | 21.5% (14) | 3.6% (4) |
| PDL1 neg | 78.5% (51) | 96.5% (109) |
| P=0.0004 | | |

| LYMPHOCYTES | DDRD pos | DDRD neg |
|---|---|---|
| PDL1 pos | 40.0% (26) | 2.7% (3) |
| PDL1 neg | 60.0% (39) | 97.3% (110) |
| p<0.0001 | | |

>1% cut off

| TUMOUR | DDRD pos | DDRD neg |
|---|---|---|
| PDL1 pos | 46.2% (30) | 4.4% (5) |
| PDL1 neg | 53.8% (35) | 95.6% (108) |
| p<0.0001 | | |

| LYMPHOCYTES | DDRD pos | DDRD neg |
|---|---|---|
| PDL1 pos | 75.4% (49) | 8.85% (10) |
| PDL1 neg | 24.6% (16) | 91.2% (103) |
| p<0.0001 | | |

A

B

FIG. 27 Con't.

A

DDRD molecular subgroup highly
enriched for MSI colorectal cancers

B

MSI    MSS
80% of MSI tumours are
DDRD positive

|  | dMMR | pMMR |
|---|---|---|
| DDRD Positive | 60 | 101 |
| DDRD Negative | 15 | 343 |

FIG. 29 Con't.
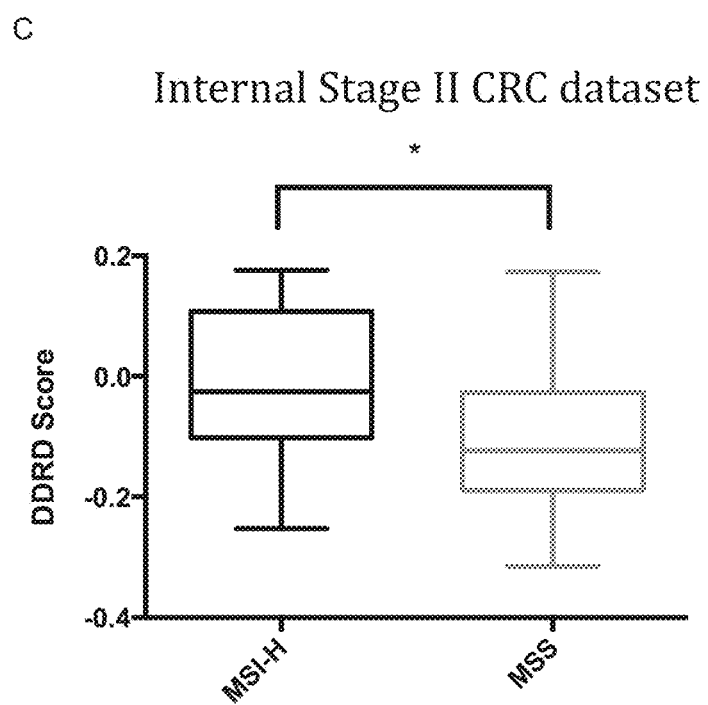
C
Internal Stage II CRC dataset

GENE SIGNATURE FOR IMMUNE THERAPIES IN CANCER

CROSS-REFERENCE TO RELATED APPLICATIONS

This application is the U.S. national phase entry under 35 U.S. C. § 371 from PCT International Application No. PCT/GB2016/052213, filed Jul. 21, 2016, which claims the benefit of priority of Great Britain Application No. 1512869.7, filed Jul. 21, 2015, which claims the benefit of priority of U.S. Provisional Application No. 62/237,497, filed Oct. 5, 2015. The contents of these applications are each incorporated herein by reference.

SEQUENCE LISTING

The instant application contains a Sequence Listing which has been submitted electronically in ASCII format and is hereby incorporated by reference in its entirety. Said ASCII copy, created on Jan. 19, 2018, is named SequenceListing.txt and is 143 kilobytes in size.

FIELD OF THE INVENTION

The present invention relates to a molecular diagnostic test useful for diagnosing cancers from different anatomical sites that includes the use of an immune response subtype associated with DNA damage. The invention includes the use of a 44-gene classification model to identify this immune response associated with DNA damage repair deficiency molecular subtype. One application is the stratification of response to, and selection of patients for therapeutic drug classes, including antagonists of an inhibitory immune checkpoint and/or agonists of a stimulatory immune checkpoint. Another application is the stratification of cancer patients into those that respond and those that do not respond to antagonists of an inhibitory immune checkpoint and/or agonists of a stimulatory immune checkpoint. The present invention provides a test that can guide conventional therapy selection as well as selecting patient groups for enrichment strategies during clinical trial evaluation of novel therapeutics. Cancer subtypes with activation of the innate immune pathway STING/TBK1/IRF3 can be identified from fresh/frozen (FF) or formalin fixed paraffin embedded (FFPE) patient samples.

BACKGROUND

The biopharmaceutical industry continuously pursues new drug treatment options that are more effective, more specific or have fewer adverse side effects than currently administered drugs. Novel or alternate drug therapies are constantly being developed because genetic variability within the human population results in substantial differences in the effectiveness of many drugs. Therefore, although a wide variety of drug therapeutic options are currently available, more drug therapies are always needed in the event that a patient fails to benefit.

Traditionally, the treatment paradigm used by physicians has been to prescribe a first-line drug therapy that results in the highest success rate possible for treating a disease. Alternative drug therapies are then prescribed if the first is ineffective. This treatment paradigm is clearly not the optimal method for certain diseases. For example, in diseases such as cancer, the first treatment is often the most important and offers the best opportunity for successful therapy, so there exists a heightened need to choose an initial drug that will be the most effective against that particular patient's disease.

It is anticipated that there will be 207,090 new female breast cancer diagnoses in the US this year and 39,840 female breast cancer related deaths (American Cancer Society: Cancer Facts and Figures 2010). Standard chemotherapy typically includes direct DNA damaging agents such as anthracyclines and alkylating agents as well as antimetabolites and anti-microtubule agents.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these histologies arise from different etiologies. The current standard treatment for ovarian cancer is debulking surgery and standard platinum taxane—based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genomic information, thereby providing a genomic fingerprint of an individual. There is much enthusiasm that this is one of the molecular technologies that will provide the necessary tools for custom-made drug treatment regimens.

Currently, healthcare professionals have limited options to help them identify cancer patients who will benefit from chemotherapeutic agents. Identification of the optimal first-line drug has been difficult because methods are not available for accurately predicting which drug treatment would be the most effective for a particular patient's cancer. This results in relatively poor single agent response rates and increased cancer morbidity and death. Furthermore, patients often needlessly undergo ineffective, and often times toxic drug therapy.

Molecular markers have been used to select appropriate treatments in many cancer types. For example, breast tumors that do not express the estrogen and progesterone hormone receptors as well as the HER2 growth factor receptor, called "triple negative", appear to be responsive to PARP-1 inhibitor therapy (Linn, S. C., and Van't Veer, L., J. Eur J Cancer 45 Suppl 1, 11-26 (2009); O'Shaughnessy, J., et al. N Engl J Med 364, 205-214 (2011). Recent studies indicate that the triple negative status of a breast tumor may indicate responsiveness to combination therapy including PARP-1 inhibitors, but may not be sufficient to indicate responsiveness to individual PARP-1 inhibitors. (O'Shaughnessy et al., 2011).

Furthermore, there have been other studies that have attempted to identify gene classifiers associated with molecular subtypes to indicate responsiveness of chemotherapeutic agents (Farmer et al. Nat Med 15, 68-74 (2009); Konstantinopoulos, P. A., et al., J Clin Oncol 28, 3555-3561

(2010)). WO2012/037378 describes a molecular diagnostic test for cancer and is incorporated herein by reference.

SUMMARY OF THE INVENTION

The invention is defined in the claims. Medical uses of the relevant therapeutic agents are contemplated in addition to therapeutic methods. In some embodiments, according to all aspects of the invention, the immune checkpoint is not the PD1/PDL1 (referred to interchangeably as PD-1 and PD-L1 respectively throughout the disclosure) checkpoint. In some embodiments, according to all aspects of the invention, the antagonist of an inhibitory immune checkpoint is not pembrolizumab.

The invention is based on the elucidation of the mechanism of immune response associated with DNA damage repair deficient (DDRD) tumours. DNA damage repair deficient (DDRD) tumours activate the immune pathway STING/TBK1/IRF3 resulting in the production of chemokines. Thus, the invention is in part directed to methods of using a collection of gene expression markers in cancer such that when some or all of the transcripts are over or underexpressed, they identify a subtype of cancer that displays an innate immune response which is associated with a deficiency in DNA damage repair. Designation of this subtype can be considered as a diagnostic test as it is not related to any specific drug but rather describes the biology of the cancer in a manner that has utility in screening and selecting appropriate cancer therapies. The immune response associated with DNA damage does not, however, result in an active T cell anti-tumour response, due to the expression of immune inhibitory molecules associated with T cell exhaustion and anergy, such as IDO1 or PDL1 (CD274). Accordingly, the invention also provides methods for indicating responsiveness or resistance to therapies including antagonists of an inhibitory immune checkpoint and/or agonists of a stimulatory immune checkpoint, optionally in combination with DNA-damage therapeutic agents. In different aspects, this gene or gene product list may form the basis of a single parameter or a multiparametric predictive test that could be delivered using methods known in the art such as microarray, nucleic acid amplification (e.g. Q-PCR), sequencing (including next generation sequencing and RNAseq), immunohistochemistry, ELISA or other technologies that can quantify mRNA or protein expression.

In addition, the biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment of the invention, these genes or gene products are useful for evaluating both breast and ovarian cancer tumors.

The invention described herein is not limited to any one drug; it can be used to identify responders and non-responders to any of a range of drugs that represent antagonists of an inhibitory immune checkpoint and/or agonists of a stimulatory immune checkpoint. Examples are provided herein. Such drugs may be administered in combination with drugs that directly or indirectly affect DNA damage and/or DNA damage repair e.g. neoadjuvant 5-fluorouracil, anthracycline and cyclophosphamide based regimens such as FEC (5-fluorouracil/epirubicin/cyclophosphamide) and FAC (5-fluorouracil/Adriamycin/cyclophosphamide).

The present invention relates to prediction of response to drugs using different classifications of response, such as overall survival, progression free survival, radiological response, as defined by RECIST, complete response, partial response, stable disease and serological markers such as, but not limited to, PSA, CEA, CA125, CA15-3 and CA19-9. In another aspect, the present invention relates to the identification of an innate immune response associated with a DNA damage response deficiency (DDRD) molecular subtype in cancer. This molecular subtype can, inter alia, be detected by the use of two different gene classifiers—one comprising of 40 genes and the other comprising of 44 genes. The DDRD classifier was first defined by a classifier consisting of 53 probesets on the Almac Breast Disease Specific Array (DSA™). So as to validate the functional relevance of this classifier in the context of its ability to predict response to DNA-damaging containing chemotherapy regimens, the classifier needed to be re-defined at a gene level. This would facilitate evaluation of the DDRD classifier using microarray data from independent datasets that were profiled on microarray platforms other than the Almac Breast DSA™. In order to facilitate defining the classifier at a gene level, the genes to which the Almac Breast DSA™ probesets map to needed to be defined. This involved the utilization of publicly available genome browser databases such as Ensembl and NCBI Reference Sequence. Results are provided only for the 44-gene DDRD classifier model, as this model supersedes that of the 40-gene DDRD classifier model. These results demonstrate that the classifier model is an effective and significant predictor of response to chemotherapy regimens that contain DNA damaging therapeutics.

The identification of the subtype by both the 40-gene classifier model and the 44-gene classifier model can be used to predict response to, and select patients for, cancer therapeutic drug classes, in particular antagonists of an inhibitory immune checkpoint and/or agonists of a stimulatory immune checkpoint optionally in combination with DNA damage causing agents and DNA repair targeted therapies.

In another aspect, the present invention relates to kits for conventional diagnostic uses listed above such as qPCR, microarray, sequencing (e.g. RNAseq) and immunoassays such as immunohistochemistry, ELISA, Western blot and the like. Such kits include appropriate reagents and directions to assay the expression of the genes or gene products and quantify mRNA or protein expression.

The invention also provides methods for identifying DNA damage response-deficient (DDRD) human tumors having an increased immune response. It is likely that this invention can be used to identify patients that are sensitive to and respond to, or are resistant to and do not respond to, drugs that influence immune checkpoints, such as antagonists of an inhibitory immune checkpoint and/or agonists of a stimulatory immune checkpoint. These drugs may be combined with drugs that damage DNA directly, damage DNA indirectly or inhibit normal DNA damage signaling and/or repair processes.

The invention also relates to guiding conventional treatment of patients. The invention also relates to selecting patients for clinical trials where novel drugs of the classes that agonise or antagonize specific immune checkpoints.

The present invention and methods accommodate the use of archived formalin fixed paraffin-embedded (FFPE) biopsy material, as well as fresh/frozen (FF) tissue, for assay of all transcripts in the invention, and are therefore compatible with the most widely available type of biopsy material. The expression level may be determined using RNA obtained from FFPE tissue, fresh frozen tissue or fresh tissue that has been stored in solutions such as RNAlater®.

BRIEF DESCRIPTION OF DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1A:
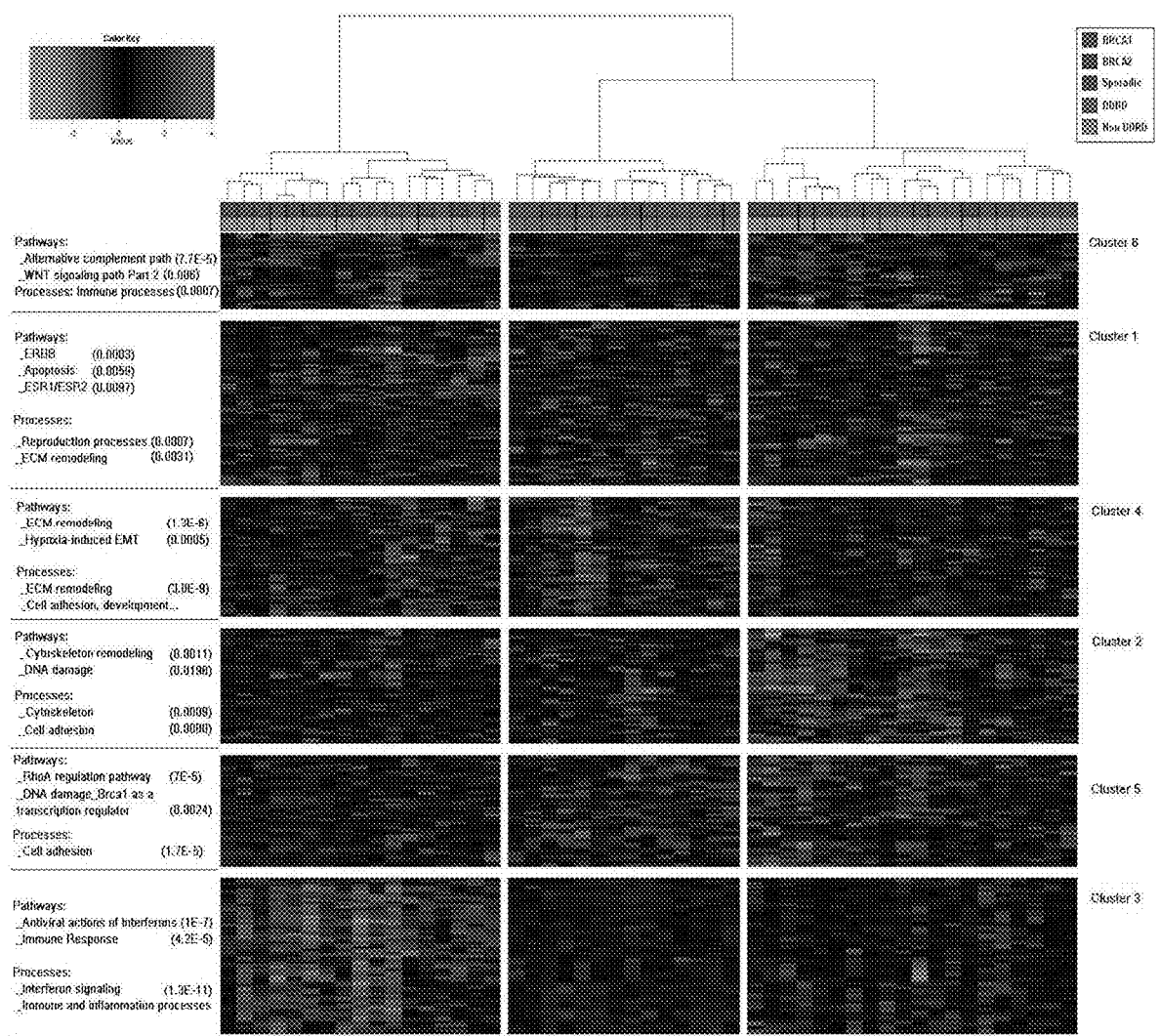
FIG. 1 provides a diagram representing the hierarchical analysis of ER-negative (A) and ER-positive (B) BRCA1/2 mutant and sporadic wildtype control breast samples. Probe-set cluster groups are annotated on the right-hand side and pathway analysis of each probeset cluster group is annotated on the left-hand side of each image. The legend for each image indicates a sample's mutational status as well as the signature group each sample was assigned to for classifier generation.

The invention provides a method for predicting responsiveness to a modulator of an immune checkpoint, such as an antagonist of an inhibitory immune checkpoint and/or an agonist of a stimulatory immune checkpoint, comprising: determining the expression level of at least one gene selected from Table 2B, 2A or 1 in a sample from the subject wherein the determined expression level is used to predict responsiveness to an antagonist of an inhibitory immune checkpoint and/or an agonist of a stimulatory immune checkpoint. In any of the methods of the invention, the expression level of one or more additional genes (i.e. genes other than those provided in Table 2B, 2A or 1) may also be determined and used to predict responsiveness to an antagonist of an inhibitory immune checkpoint and/or an agonist of a stimulatory immune checkpoint.

In the methods an increased expression level of the at least one gene may predict responsiveness to a modulator of an immune checkpoint, such as an antagonist of an inhibitory immune checkpoint and/or an agonist of a stimulatory immune checkpoint.

The methods may comprise determining the expression level of at least 2 of the genes and the determined expression levels may be used to generate a combined test score, wherein a positive combined test score (generally above threshold, but may be equal to or above threshold) predicts responsiveness to an antagonist of an inhibitory immune checkpoint and/or an agonist of a stimulatory immune checkpoint.

The methods may comprise: deriving a combined test score that captures the expression levels; providing a threshold score comprising information correlating the combined test score and responsiveness; and comparing the combined test score to the threshold score; wherein responsiveness is predicted when the combined test score exceeds the threshold score.

The methods may comprise determining the expression level of at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, at least 28 genes, at least 29 genes, at least 30 genes, at least 31 genes, at least 32 genes, at least 33 genes, at least 34 genes, at least 35 genes, at least 36 genes, at least 37 genes, at least 38 genes, at least 39 genes, at least 40 genes, at least 41 genes, at least 42 genes, or at least 43 genes, selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

The methods may comprise determining the expression level of at least 1 gene selected from CD2, ITGAL, PTPRC, CXCL10 and IDO1, together with at least 1 further gene, at least 2 further genes, at least 3 further genes, at least 4 further genes, at least 5 further genes, at least 6 further genes, at least 7 further genes, at least 8 further genes, at least 9 further genes, at least 10 further genes, at least 11 further genes, at least 12 further genes, at least 13 further genes, at least 14 further genes, at least 15 further genes, at least 16 further genes, at least 17 further genes, at least 18 further genes, at least 19 further genes, at least 20 further genes, at least 21 further genes, at least 22 further genes, at least 23 further genes, at least 24 further genes, at least 25 further genes, at least 26 further genes, at least 27 further genes, at least 28 further genes, at least 29 further genes, at least 30 further genes, at least 31 further genes, at least 32 further genes, at least 33 further genes, at least 34 further genes, at least 35 further genes, at least 36 further genes, at least 37 further genes, or at least 38 further genes, selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1. Preferably, the methods comprise determining the expression level of at least 1 gene selected from CD2, ITGAL, PTPRC, CXCL10 and IDO1, together with each of MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

The methods may comprise determining the expression level of at least 2 genes selected from CD2, ITGAL, PTPRC, CXCL10 and IDO1, together with at least 1 further gene, at least 2 further genes, at least 3 further genes, at least 4 further genes, at least 5 further genes, at least 6 further genes, at least 7 further genes, at least 8 further genes, at least 9 further genes, at least 10 further genes, at least 11 further genes, at least 12 further genes, at least 13 further genes, at least 14 further genes, at least 15 further genes, at least 16 further genes, at least 17 further genes, at least 18 further genes, at least 19 further genes, at least 20 further genes, at least 21 further genes, at least 22 further genes, at least 23 further genes, at least 24 further genes, at least 25 further genes, at least 26 further genes, at least 27 further genes, at least 28 further genes, at least 29 further genes, at least 30 further genes, at least 31 further genes, at least 32 further genes, at least 33 further genes, at least 34 further genes, at least 35 further genes, at least 36 further genes, at least 37 further genes, or at least 38 further genes, selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1. Preferably, the methods comprise determining the expression level of at least 2 genes selected from CD2, ITGAL, PTPRC, CXCL10 and IDO1, together with each of MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

The methods may comprise determining the expression level of at least 3 genes selected from CD2, ITGAL, PTPRC, CXCL10 and IDO1, together with at least 1 further gene, at least 2 further genes, at least 3 further genes, at least 4 further genes, at least 5 further genes, at least 6 further genes, at least 7 further genes, at least 8 further genes, at least 9 further genes, at least 10 further genes, at least 11 further genes, at least 12 further genes, at least 13 further genes, at least 14 further genes, at least 15 further genes, at least 16 further genes, at least 17 further genes, at least 18 further genes, at least 19 further genes, at least 20 further genes, at least 21 further genes, at least 22 further genes, at least 23 further genes, at least 24 further genes, at least 25 further genes, at least 26 further genes, at least 27 further genes, at least 28 further genes, at least 29 further genes, at least 30 further genes, at least 31 further genes, at least 32 further genes, at least 33 further genes, at least 34 further genes, at least 35 further genes, at least 36 further genes, at least 37 further genes, or at least 38 further genes, selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1. Preferably, the methods comprise determining the expression level of at least 3 genes selected from CD2, ITGAL, PTPRC, CXCL10 and IDO1, together with each of MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

The methods may comprise determining the expression level of at least 4 genes selected from CD2, ITGAL, PTPRC, CXCL10 and IDO1, together with at least 1 further gene, at least 2 further genes, at least 3 further genes, at least 4 further genes, at least 5 further genes, at least 6 further genes, at least 7 further genes, at least 8 further genes, at least 9 further genes, at least 10 further genes, at least 11 further genes, at least 12 further genes, at least 13 further genes, at least 14 further genes, at least 15 further genes, at least 16 further genes, at least 17 further genes, at least 18 further genes, at least 19 further genes, at least 20 further genes, at least 21 further genes, at least 22 further genes, at least 23 further genes, at least 24 further genes, at least 25 further genes, at least 26 further genes, at least 27 further genes, at least 28 further genes, at least 29 further genes, at least 30 further genes, at least 31 further genes, at least 32 further genes, at least 33 further genes, at least 34 further genes, at least 35 further genes, at least 36 further genes, at least 37 further genes, or at least 38 further genes, selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1. Preferably, the methods comprise determining the expression level of at least 4 genes selected from CD2, ITGAL, PTPRC, CXCL10 and IDO1, together with each of MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

The methods may comprise determining the expression level of each of CD2, ITGAL, PTPRC, CXCL10 and IDO1, together with at least 1 further gene, at least 2 further genes, at least 3 further genes, at least 4 further genes, at least 5 further genes, at least 6 further genes, at least 7 further genes, at least 8 further genes, at least 9 further genes, at least 10 further genes, at least 11 further genes, at least 12 further genes, at least 13 further genes, at least 14 further genes, at least 15 further genes, at least 16 further genes, at least 17 further genes, at least 18 further genes, at least 19 further genes, at least 20 further genes, at least 21 further genes, at least 22 further genes, at least 23 further genes, at least 24 further genes, at least 25 further genes, at least 26 further genes, at least 27 further genes, at least 28 further genes, at least 29 further genes, at least 30 further genes, at least 31 further genes, at least 32 further genes, at least 33 further genes, at least 34 further genes, at least 35 further genes, at least 36 further genes, at least 37 further genes, or at least 38 further genes, selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

The methods may comprise determining the expression level of at least 12 genes selected from Table 1.

The methods may comprise determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

The methods may comprise determining the expression level of each of:
  CXCL10;
  CXCL10 and MX1;
  CXCL10, IDO1 and MX1;
  CXCL10, IDO1, IF144L and MX1;
  CD2, CXCL10, IDO1, IF144L and MX1;
  CD2, CXCL10, GBP5, IDO1, IF144L and MX1;
  CD2, CXCL10, GBP5, IDO1, IF144L, MX1 and PRAME;
  CD2, CXCL10, GBP5, IDO1, IF144L, ITGAL, MX1 and PRAME;
  CD2, CXCL10, GBP5, IDO1, IF144L, ITGAL, LRP4, MX1 and PRAME;
  APOL3, CD2, CXCL10, GBP5, IDO1, IF144L, ITGAL, LRP4, MX1 and PRAME;
  APOL3, CD2, CDR1, CXCL10, GBP5, IDO1, IF144L, ITGAL, LRP4, MX1 and PRAME;
  APOL3, CD2, CDR1, CXCL10, FYB, GBP5, IDO1, IF144L, ITGAL, LRP4, MX1 and PRAME;
  APOL3, CD2, CDR1, CXCL10, FYB, GBP5, IDO1, IF144L, ITGAL, LRP4, MX1, PRAME and TSPAN7;

APOL3, CD2, CDR1, CXCL10, FYB, GBP5, IDO1, IF144L, ITGAL, LRP4, MX1, PRAME, RAC2 and TSPAN7;

APOL3, CD2, CDR1, CXCL10, FYB, GBP5, IDO1, IF144L, ITGAL, KLHDC7B, LRP4, MX1, PRAME, RAC2 and TSPAN7;

APOL3, CD2, CDR1, CXCL10, FYB, GBP5, GRB14, IDO1, IF144L, ITGAL, KLHDC7B, LRP4, MX1, PRAME, RAC2 and TSPAN7;

AC138128.1, APOL3, CD2, CDR1, CXCL10, FYB, GBP5, GRB14, IDO1, IF144L, ITGAL, KLHDC7B, LRP4, MX1, PRAME, RAC2 and TSPAN7;

AC138128.1, APOL3, CD2, CDR1, CXCL10, FYB, GBP5, GRB14, IDO1, IF144L, ITGAL, KIF26A, KLHDC7B, LRP4, MX1, PRAME, RAC2 and TSPAN7;

AC138128.1, APOL3, CD2, CD274, CDR1, CXCL10, FYB, GBP5, GRB14, IDO1, IF144L, ITGAL, KIF26A, KLHDC7B, LRP4, MX1, PRAME, RAC2 and TSPAN7;

AC138128.1, APOL3, CD109, CD2, CD274, CDR1, CXCL10, FYB, GBP5, GRB14, IDO1, IF144L, ITGAL, KIF26A, KLHDC7B, LRP4, MX1, PRAME, RAC2 and TSPAN7;

AC138128.1, APOL3, CD109, CD2, CD274, CDR1, CXCL10, ETV7, FYB, GBP5, GRB14, IDO1, IF144L, ITGAL, KIF26A, KLHDC7B, LRP4, MX1, PRAME, RAC2 and TSPAN7;

AC138128.1, APOL3, CD109, CD2, CD274, CDR1, CXCL10, ETV7, FYB, GBP5, GRB14, IDO1, IF144L, ITGAL, KIF26A, KLHDC7B, LRP4, MFAP5, MX1, PRAME, RAC2 and TSPAN7;

AC138128.1, APOL3, CD109, CD2, CD274, CDR1, CXCL10, ETV7, FYB, GBP5, GRB14, IDO1, IF144L, ITGAL, KIF26A, KLHDC7B, LRP4, MFAP5, MX1, OLFM4, PRAME, RAC2 and TSPAN7;

AC138128.1, APOL3, CD109, CD2, CD274, CDR1, CXCL10, ETV7, FYB, GBP5, GRB14, IDO1, IF144L, ITGAL, KIF26A, KLHDC7B, LRP4, MFAP5, MX1, OLFM4, PI15, PRAME, RAC2 and TSPAN7;

AC138128.1, APOL3, CD109, CD2, CD274, CDR1, CXCL10, ETV7, FOSB, FYB, GBP5, GRB14, IDO1, IF144L, ITGAL, KIF26A, KLHDC7B, LRP4, MFAP5, MX1, OLFM4, PI15, PRAME, RAC2 and TSPAN7;

AC138128.1, APOL3, CD109, CD2, CD274, CDR1, CXCL10, ETV7, FAM19A5, FOSB, FYB, GBP5, GRB14, IDO1, IF144L, ITGAL, KIF26A, KLHDC7B, LRP4, MFAP5, MX1, OLFM4, PI15, PRAME, RAC2 and TSPAN7;

AC138128.1, APOL3, CD109, CD2, CD274, CDR1, CXCL10, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, RAC2 and TSPAN7;

AC138128.1, APOL3, CD109, CD2, CD274, CDR1, CXCL10, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2 and TSPAN7;

AC138128.1, APOL3, CD109, CD2, CD274, CDR1, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2 and TSPAN7;

AC138128.1, APOL3, CD109, CD2, CD274, CDR1, CLDN10, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2 and TSPAN7;

AC138128.1, ADAMTS4, APOL3, CD109, CD2, CD274, CDR1, CLDN10, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2 and TSPAN7;

AC138128.1, ADAMTS4, APOL3, CD109, CD2, CD274, CDR1, CLDN10, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2, SP140L and TSPAN7;

AC138128.1, ADAMTS4, ANXA1, APOL3, CD109, CD2, CD274, CDR1, CLDN10, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2, SP140L and TSPAN7;

AC138128.1, ADAMTS4, ANXA1, APOL3, CD109, CD2, CD274, CDR1, CLDN10, CXCL10, EGR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGR1, ESR1, ETV7, FAM19A5, FOSB, FYB, GBP5, GRB14, IDO1, IF144L, ITGAL, KIF26A, KLHDC7B, LRP4, MFAP5, MX1, NLRC5, OLFM4, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGR1, ESR1, ETV7, FAM19A5, FOSB, FYB, GBP5, GRB14, IDO1, IF144L, IKZF3, ITGAL, KIF26A, KLHDC7B, LRP4, MFAP5, MX1, NLRC5, OLFM4, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGR1, ESR1, ETV7, FAM19A5, FOSB, FYB, GBP5, GRB14, IDO1, IF144L, IKZF3, ITGAL, KIF26A, KLHDC7B, LRP4, MFAP5, MX1, NLRC5, OLFM4, OR2I1P, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGFR, EGR1, ESR1, ETV7, FAM19A5, FOSB, FYB, GBP5, GRB14, IDO1, IF144L, IKZF3, ITGAL, KIF26A, KLHDC7B, LRP4, MFAP5, MX1, NLRC5, OLFM4, OR2I1P, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGFR, EGR1, ESR1, ETV7, FAM19A5, FOSB, FYB, GBP5, GRB14, IDO1, IF144L, IKZF3, ITGAL, KIF26A, KLHDC7B, LRP4, MFAP5, MX1, NAT1, NLRC5, OLFM4, OR2I1P, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, EGFR, EGR1, ESR1, ETV7, FAM19A5, FOSB, FYB, GBP5, GRB14, IDO1, IF144L, IKZF3, ITGAL, KIF26A, KLHDC7B, LATS2, LRP4, MFAP5, MX1, NAT1, NLRC5, OLFM4, OR2I1P, PI15, PRAME, PRICKLE1, RAC2, RSAD2, SP140 and TSPAN7;

AC138128.1, ADAMTS4, ANXA1, APOL3, CD109, CD2, CD274, CDR1, CLDN10, CXCL10, CYP2B6, EGFR, EGR1, ESR1, ETV7, FAM19A5, FOSB, FYB, GBP5, GRB14, IDO1, IF144L, IKZF3, ITGAL, KIF26A, KLHDC7B, LATS2, LRP4, MFAP5, MX1, NAT1, NLRC5, OLFM4, OR2I1P, PI15, PRAME, PRICKLE1, RAC2, RSAD2, SP140L and TSPAN7;

AC138128.1, ADAMTS4, ANXA1, APOL3, CD109, CD2, CD274, CDR1, CLDN10, CXCL10, CYP2B6, EGFR, EGR1, ESR1, ETV7, FAM19A5, FOSB, FYB, GBP5, GRB14, IDO1, IF144L, IKZF3, ITGAL, KIF26A, KLHDC7B, LATS2, LRP4, MFAP5, MX1, NAT1, NLRC5, OLFM4, OR2I1P, PI15, PRAME, PRICKLE1, PTPRC, RAC2, RSAD2, SP140L and TSPAN7;

AC138128.1, ADAMTS4, ANXA1, APOL3, CD109, CD2, CD274, CDR1, CLDN10, CXCL10, CYP2B6, EGFR, EGR1, ESR1, ETV7, FAM19A5, FOSB, FYB, GBP5, GRB14, IDO1, IF144L, IKZF3, ITGAL, KIF26A, KLHDC7B, LATS2, LRP4, MFAP5, MX1, NAT1, NLRC5, OLFM4, OR2I1P, PI15, PPP1R1A, PRAME, PRICKLE1, PTPRC, RAC2, RSAD2, SP140L and TSPAN7; or CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

In the methods the weight values for each gene may be as set out in Table 2B or the weight and/or bias values for each gene may be as set out in any one of Tables 3-45.

The methods may comprise determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

The invention provides a method for predicting responsiveness to a modulator of an immune checkpoint, such as an antagonist of an inhibitory immune checkpoint and/or an agonist of a stimulatory immune checkpoint in combination with a DNA damage therapeutic agent comprising: determining the expression level of at least one gene selected from Table 2B, 2A or 1 in a sample from the subject wherein the determined expression level is used to predict responsiveness to a modulator of an immune checkpoint, such as an antagonist of an inhibitory immune checkpoint and/or an agonist of a stimulatory immune checkpoint in combination with a DNA damage therapeutic agent. The determined expression level can be used to predict responsiveness to the simultaneous, separate or sequential administration (or use) of a modulator of an immune checkpoint, such as an antagonist of an inhibitory immune checkpoint and/or an agonist of a stimulatory immune checkpoint in combination with a DNA damage therapeutic agent In the methods an increased expression level of the at least one gene may predict responsiveness to a modulator of an immune checkpoint, such as an antagonist of an inhibitory immune checkpoint and/or an agonist of a stimulatory immune checkpoint in combination with a DNA damage therapeutic agent.

The methods may comprise determining the expression level of at least 2 of the genes and the determined expression levels may be used to generate a combined test score, wherein a positive combined test score (generally above threshold, but may be equal to or above threshold) predicts responsiveness to a modulator of an immune checkpoint, such as an antagonist of an inhibitory immune checkpoint and/or an agonist of a stimulatory immune checkpoint in combination with a DNA damage therapeutic agent.

The methods for predicting responsiveness to a modulator of an immune checkpoint, such as an antagonist of an inhibitory immune checkpoint and/or an agonist of a stimulatory immune checkpoint in combination with a DNA damage therapeutic agent may comprise determining the expression level of any of the genes or sets of genes described herein.

The invention provides a method for identifying a cancer that can be effectively treated with a modulator of an immune checkpoint, such as an antagonist of an inhibitory immune checkpoint and/or an agonist of a stimulatory immune checkpoint comprising:

determining the expression level of at least one gene selected from Table 2B, 2A or 1 in a sample from the subject wherein the determined expression level is used to identify a cancer that can be effectively treated with a modulator of an immune checkpoint, such as an antagonist of an inhibitory immune checkpoint and/or an agonist of a stimulatory immune checkpoint.

In the methods an increased expression level of the at least one gene may identify a cancer that can be effectively treated with a modulator of an immune checkpoint, such as an antagonist of an inhibitory immune checkpoint and/or an agonist of a stimulatory immune checkpoint.

The methods may comprise determining the expression level of at least 2 genes and the determined expression levels may be used to generate a combined test score, wherein a positive combined test score (generally above threshold, but may be equal to or above threshold) identifies a cancer that can be effectively treated with a modulator of an immune checkpoint, such as an antagonist of an inhibitory immune checkpoint and/or an agonist of a stimulatory immune checkpoint.

The methods may comprise: deriving a combined test score that captures the expression levels; providing a threshold score comprising information correlating the combined test score and responsiveness; and comparing the combined test score to the threshold score; wherein a cancer that can be effectively treated is identified when the combined test score exceeds the threshold score.

The methods for identifying a cancer that can be effectively treated with a modulator of an immune checkpoint, such as an antagonist of an inhibitory immune checkpoint and/or an agonist of a stimulatory immune checkpoint may comprise determining the expression level of any of the genes or sets of genes described herein.

The invention provides a method for identifying a cancer that can be effectively treated with a modulator of an immune checkpoint, such as an antagonist of an inhibitory immune checkpoint and/or an agonist of a stimulatory immune checkpoint in combination with a DNA damage therapeutic agent comprising: determining the expression level of at least one gene selected from Table 2B, 2A or 1 in a sample from the subject wherein the determined expression level is used to identify a cancer that can be effectively treated with a modulator of an immune checkpoint, such as an antagonist of an inhibitory immune checkpoint and/or an agonist of a stimulatory immune checkpoint in combination with a DNA damage therapeutic agent. The determined expression level can be used to identify a cancer that can be effectively treated with the simultaneous, separate or sequential administration (or use) of a modulator of an immune checkpoint, such as an antagonist of an inhibitory immune checkpoint and/or an agonist of a stimulatory immune checkpoint in combination with a DNA damage therapeutic agent.

In the methods an increased expression level of the at least one gene may identify a cancer that can be effectively treated with a modulator of an immune checkpoint, such as an antagonist of an inhibitory immune checkpoint and/or an agonist of a stimulatory immune checkpoint in combination with a DNA damage therapeutic agent.

The methods may comprise determining the expression level of at least 2 of the genes and the determined expression levels may be used to generate a combined test score, wherein a positive combined test score (generally above threshold, but may be equal to or above threshold) identifies a cancer that can be effectively treated with a modulator of an immune checkpoint, such as an antagonist of an inhibitory immune checkpoint and/or an agonist of a stimulatory immune checkpoint in combination with a DNA damage therapeutic agent.

The methods for identifying a cancer that can be effectively treated with a modulator of an immune checkpoint, such as an antagonist of an inhibitory immune checkpoint and/or an agonist of a stimulatory immune checkpoint in combination with a DNA damage therapeutic agent may comprise determining the expression level of any of the genes or sets of genes described herein.

The invention provides a method for selecting treatment for a cancer comprising: determining the expression level of at least one gene selected from Table 2B, 2A or 1 in a sample from the subject wherein the determined expression level is used to select a modulator of an immune checkpoint, such as an antagonist of an inhibitory immune checkpoint and/or an agonist of a stimulatory immune checkpoint for use in treatment of the cancer.

In the methods an increased expression level of the at least one gene is used to select a modulator of an immune checkpoint, such as an antagonist of an inhibitory immune checkpoint and/or an agonist of a stimulatory immune checkpoint for use in treatment of the cancer.

The methods may comprise determining the expression level of at least 2 of the genes and the determined expression levels may be used to generate a combined test score, wherein a positive combined test score (generally above threshold, but may be equal to or above threshold) is used to select a modulator of an immune checkpoint, such as an antagonist of an inhibitory immune checkpoint and/or an agonist of a stimulatory immune checkpoint for use in treatment of the cancer.

The methods may further comprise treating the cancer using the selected antagonist and/or agonist.

The methods may comprise: deriving a combined test score that captures the expression levels; providing a threshold score comprising information correlating the combined test score and responsiveness; and comparing the combined test score to the threshold score; wherein a modulator of an immune checkpoint, such as an antagonist of an inhibitory immune checkpoint and/or an agonist of a stimulatory immune checkpoint is selected for use when the combined test score exceeds the threshold score.

The methods for selecting treatment for a cancer may comprise determining the expression level of any of the genes or sets of genes described herein.

The invention provides a method for selecting treatment for a cancer comprising: determining the expression level of at least one gene selected from 2B, 2A or 1 in a sample from the subject wherein the determined expression level is used to select a modulator of an immune checkpoint, such as an antagonist of an inhibitory immune checkpoint and/or an agonist of a stimulatory immune checkpoint, in combination with a DNA damage therapeutic agent, for use in treatment of the cancer. The determined expression level can be used to select a modulator of an immune checkpoint, such as an antagonist of an inhibitory immune checkpoint and/or an agonist of a stimulatory immune checkpoint, in combination with a DNA damage therapeutic agent, for simultaneous, separate or sequential use in treatment of the cancer.

In the methods an increased expression level of the at least one gene may be used to select a modulator of an immune checkpoint, such as an antagonist of an inhibitory immune checkpoint and/or an agonist of a stimulatory immune checkpoint, in combination with a DNA damage therapeutic agent, for use in treatment of the cancer.

The methods may comprise determining the expression level of at least 2 of the genes and the determined expression levels may be used to generate a combined test score, wherein a positive combined test score (generally above threshold, but may be equal to or above threshold) is used to select a modulator of an immune checkpoint, such as an antagonist of an inhibitory immune checkpoint and/or an agonist of a stimulatory immune checkpoint, in combination with a DNA damage therapeutic agent, for use in treatment of the cancer.

The methods may comprise treating the cancer using the selected modulator, such as antagonist and/or agonist, in combination with a DNA damage therapeutic agent.

The methods may comprise: deriving a combined test score that captures the expression levels; providing a threshold score comprising information correlating the combined test score and responsiveness; and comparing the combined test score to the threshold score; wherein a modulator of an immune checkpoint, such as an antagonist of an inhibitory immune checkpoint and/or an agonist of a stimulatory immune checkpoint in combination with a DNA damage therapeutic agent is selected for use when the combined test score exceeds the threshold score.

In the methods the combined test score (or "signature score") may be derived according to the formula:

$$SignatureScore = \sum_i w_i \times (ge_i - b_i) + k$$

Where $w_i$ is a weight for each gene, $b_i$ is a gene-specific bias, $ge_i$ is the gene expression after pre-processing, and $k$ is a constant offset.

The combined test score may be derived using the expression level(s) of any of the genes or groups of genes described herein. The combined test score may be derived using the expression level of one or more additional genes.

The invention provides a method of treating cancer comprising administration of a modulator of an immune checkpoint, such as an antagonist of an inhibitory immune checkpoint and/or an agonist of a stimulatory immune checkpoint to a subject, characterised in that a sample from the subject, prior to administration, displays a positive combined test score derived from the determined expression levels of at least 2 genes from Table 2B, 2A or 1 or an increased level of expression of at least 1 gene from Table 2B, 2A or 1.

The invention provides a method of treating cancer comprising administration of a modulator of an immune checkpoint, such as an antagonist of an inhibitory immune checkpoint and/or an agonist of a stimulatory immune checkpoint, in combination with a DNA damage therapeutic agent, to a subject, characterised in that a sample from the subject, prior to administration, displays a positive combined test score derived from the determined expression levels of at least 2 genes from Table 2B, 2A or 1 or an increased level of expression of at least 1 gene from Table 2B, 2A or 1. The a modulator of an immune checkpoint, such as antagonist of an inhibitory immune checkpoint and/or the agonist of a stimulatory immune checkpoint, and the DNA damage therapeutic agent can be administered simultaneously, separately or sequentially to the subject, The methods of treating cancer may comprise determining the expression level of any of the genes or sets of genes described herein.

The invention provides a modulator of an immune checkpoint, such as an antagonist of an inhibitory immune checkpoint and/or an agonist of a stimulatory immune checkpoint for use in the treatment of cancer in a subject wherein, prior to administration of the antagonist and/or agonist, a sample from the subject displays a positive combined test score derived from the determined expression levels of at least 2 genes from Table 2B, 2A or 1 or an increased level of expression of at least 1 gene from Table 2B, 2A or 1.

The invention provides a modulator of an immune checkpoint, such as an antagonist of an inhibitory immune checkpoint and/or an agonist of a stimulatory immune checkpoint for use in the treatment of cancer in a subject wherein, prior to administration of the antagonist and/or agonist, a sample from the subject displays a positive combined test score derived from the determined expression levels of at least 2 genes from Table 2B, 2A or 1 or an increased level of expression of at least 1 gene from Table 2B, 2A or 1, and wherein the antagonist and/or agonist is administered in combination with a DNA damage therapeutic agent. The modulator of an immune checkpoint, such as antagonist of an inhibitory immune checkpoint and/or the agonist of a stimulatory immune checkpoint, and the DNA damage therapeutic agent can be administered simultaneously, separately or sequentially to the subject, The invention provides a modulator of an immune checkpoint, such as an antagonist of an inhibitory immune checkpoint in combination with a DNA damage therapeutic agent and/or an agonist of a stimulatory immune checkpoint in combination with a DNA damage therapeutic agent for use in the treatment of cancer in a subject wherein, prior to administration of the antagonist and/or agonist and DNA damage therapeutic agent, a sample from the subject displays a positive combined test score derived from the determined expression levels of at least 2 genes from Table 2B, 2A or 1 or an increased level of expression of at least 1 gene from Table 2B, 2A or 1. The a modulator of an immune checkpoint, such as antagonist of an inhibitory immune checkpoint and/or the agonist of a stimulatory immune checkpoint, and the DNA damage therapeutic agent can be for simultaneous, separate or sequential use in the treatment of cancer in the subject, The genes for which the expression level is determined may be any of the genes or sets of genes described herein.

The subject may be selected for treatment according to any of the methods described herein.

The sample may comprise cancer cells. The sample may be a tissue sample e.g. a fixed and embedded tissue sample.

The cancer may be selected from leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer or head and neck cancer.

The inhibitory immune checkpoint may be a regulatory pathway, or a molecule in such a pathway, that inhibits an immune response. The inhibitory immune checkpoint may be a polypeptide expressed by B-cells and/or T-cells. The inhibitory immune checkpoint may be an inhibitory receptor. The inhibitory immune checkpoint may be a membrane receptor. Preferably, the inhibitory immune checkpoint is an inhibitory membrane receptor. The ligand of the inhibitory immune checkpoint may be membrane bound or soluble.

The inhibitory immune checkpoint may be selected from A2AR, B7-H3 (CD276), B7-H4 (VTCN1), BTLA (CD272), CTLA-4 (CD152), IDO, KIR, LAG3, PD-1/PD-L1, TIM-3 and VISTA. In some embodiments, the inhibitory immune checkpoint is not PD-1/PD-L1. In some embodiments, the immune checkpoint is IDO.

The antagonist of an inhibitory immune checkpoint may amplify an antigen-specific B-cell and/or T-cell response. The antagonist of an inhibitory immune checkpoint may inhibit the interaction between an inhibitory receptor and its ligand. The antagonist of an inhibitory immune checkpoint may be selected from an antibody and an inhibitory nucleic acid molecule.

The antibody may be of monoclonal or polyclonal origin. Fragments and derivative antibodies may also be utilised, to include without limitation Fab fragments, ScFv, single domain antibodies, nanoantibodies, heavy chain antibodies, aptamers etc. which retain peptide-specific binding function and these are included in the definition of "antibody". Such antibodies are useful in the practice of the invention. Methods for generating specific antibodies are known to those skilled in the art. Antibodies may be of human or non-human origin (e.g. rodent, such as rat or mouse) and be humanized etc. according to known techniques (Jones et al., Nature (1986) May 29-June 4; 321(6069):522-5; Roguska et al., Protein Engineering, 1996, 9(10):895-904; and Studnicka et al., Humanizing Mouse Antibody Frameworks While Preserving 3-D Structure. Protein Engineering, 1994, Vol. 7, pg 805).

The inhibitory nucleic acid molecule may be single stranded or double stranded. Examples of inhibitory nucleic acid molecules include antisense nucleic acid, RNAi, siRNA, shRNA, miRNA, shmiRNA, or derivatives or precursors thereof.

The antagonist of an inhibitory immune checkpoint may be selected from MGA271 (targets B7-H3), ipilimumab (Yervoy—targets CTLA-4), indoximod (targets IDO pathway), NLG919 (targets IDO pathway), lirilumab (targets KIR), IMP321 (targets LAG3), BMS-986016 (targets LAG3), CT-011 (PD-1 blockade), nivolumab/BMS-936558 (PD-1 blockade), BMS-936559 (PDL1 blockade) and pembrolizumab (Keytruda—targets PD-1). Preferably, the antagonist is not pembrolizumab. Further antagonists include MGB453 (targets TIM-3), LAG525 (targets LAG-3) and PDR001 (PD1 Blockade).

The stimulatory immune checkpoint may be a regulatory pathway, or a molecule in such a pathway, that activates an immune response. The stimulatory immune checkpoint may be a polypeptide expressed by B-cells and/or T-cells. The stimulatory immune checkpoint may be a membrane receptor. The stimulatory immune checkpoint may be a co-stimulatory receptor. The co-stimulatory receptor may be a T-cell co-stimulatory receptor or a B-cell co-stimulatory receptor. The ligand of the stimulatory immune checkpoint may be membrane bound or soluble.

The stimulatory immune checkpoint may be selected from CD27, CD28, CD40, CD122, CD137, OX40, GITR and ICOS.

The agonist of a stimulatory immune checkpoint may amplify an antigen-specific B-cell and/or T-cell response. The agonist of a stimulatory immune checkpoint may increase the interaction between a co-stimulatory receptor and its ligand. The agonist of a stimulatory immune checkpoint may comprise a ligand molecule that binds to a (co-)stimulatory receptor. The agonist of a stimulatory immune checkpoint may be selected from an antibody (as described herein), a lipocalin and a cytokine.

The lipocalin may be a molecule that incorporates a lipocalin, or a fragment or derivative of a lipocalin. Such molecules which retain the function of acting as an agonist of a stimulatory immune checkpoint are included in the definition of "lipocalin".

The cytokine may be a molecule that incorporates a cytokine, or a fragment or derivative of a cytokine. Such molecules which retain the function of acting as an agonist of a stimulatory immune checkpoint are included in the definition of "cytokine".

The agonist of a stimulatory immune checkpoint may be selected from CDX-1127 (agonist of CD27), NKTR-214 (agonist of CD122), BMS-663513 (agonist of CD137), TRX518 (agonist of GITR), CP-870893 (CD40 agonist), MEDI0562, MEDI6469 and MEDI6383 (OX40 agonists).

The DNA damage therapeutic agent may be selected from a DNA damaging agent, a DNA repair targeted therapy, an inhibitor of DNA damage signalling, an inhibitor of DNA damage induced cell cycle arrest and an inhibitor of a process indirectly leading to DNA damage.

The DNA damaging agent may be selected from an alkylating agent, a topoisomerase inhibitor and radiation. The alkylating agent may be selected from a platinum containing agent, cyclophosphamide and busulphan. The platinum containing agent may be selected from cisplatin, carboplatin and oxaliplatin. The topoisomerase inhibitor may be selected from a topoisomerase I inhibitor and a topoisomerase II inhibitor. The topoisomerase I inhibitor may be selected from irinotecan and topotecan. The topisomerase II inhibitor may be selected from etoposide and an anthracycline. The anthracycline may be selected from doxorubicin and epirubicin. The radiation may be ionising radiation The DNA repair targeted therapy may be selected from an inhibitor of Non-homologous end-joining, an inhibitor of homologous recombination, an inhibitors of nucleotide excision repair, an inhibitor of base excision repair and an inhibitor of the Fanconi anemia pathway. The inhibitor of Non-homologous end-joining may be selected from a DNA-PK inhibitor, Nu7441 and NU7026. The inhibitor of base excision repair may be selected from a PARP inhibitor, AG014699, AZD2281, ABT-888, MK4827, BSI-201, INO-1001, TRC-102, an APEX 1 inhibitor, an APEX 2 inhibitor and a Ligase III inhibitor.

The inhibitor of DNA damage signalling may be selected from an ATM inhibitor, a CHK 1 inhibitor and a CHK 2 inhibitor. The ATM inhibitor may be selected from CP466722 and KU-55933. The CHK 1 inhibitor may be selected from XL-844, UCN-01, AZD7762 and PF00477736. The CHK 2 inhibitor may be selected from XL-844, AZD7762 and PF00477736.

The inhibitor of DNA damage induced cell cycle arrest may be selected from a Wee1 kinase inhibitor and a CDC25a, b or c inhibitor.

The inhibitor of a process indirectly leading to DNA damage may be selected from a histone deacetylase inhibitor and a heat shock protein inhibitor.

The heat shock protein inhibitor may be selected from geldanamycin and AUY922.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

The articles "a" and "an" are used herein to refer to one or to more than one (i.e., to at least one) of the grammatical object of the article. By way of example, "an element" means one element or more than one element, unless explicitly indicated to the contrary.

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individual's response to a foreign compound or drug. Agents or modulators which have a stimulatory or inhibitory effect on expression of a marker of the invention can be administered to individuals to treat (prophylactically or therapeutically) cancer in a patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a marker of the invention in an individual can be determined to thereby select appropriate agent(s) for therapeutic or prophylactic treatment of the individual.

The invention is directed to a unique collection of gene or gene product markers (hereinafter referred to as "biomarkers") expressed in a cancer tissue. In different aspects, this biomarker list may form the basis of a single parameter or multiparametric predictive test that could be delivered using methods known in the art such as microarray, Q-PCR, sequencing (e.g. RNA seq), immunohistochemistry, ELISA or other technologies that can quantify mRNA or protein expression.

The present invention also relates to kits and methods that are useful for prognosis following cytotoxic chemotherapy or selection of specific treatments for cancer. Methods are provided such that when some or all of the transcripts are over or under-expressed, the expression profile indicates responsiveness or resistance to immune checkpoint therapies, such as antagonists of an inhibitory immune checkpoint and/or agonists of a stimulatory immune checkpoint. These kits and methods employ gene or gene product markers that are differentially expressed in tumors of patients with cancer. In one embodiment of the invention, the expression profiles of these biomarkers are correlated with clinical outcome (response or survival) in archival tissue samples under a statistical method or a correlation model to create a database or model correlating expression profile with responsiveness to one or more immune checkpoint therapies, such as antagonists of an inhibitory immune checkpoint and/or agonists of a stimulatory immune checkpoint, optionally in combination with DNA-damage therapeutic agents. The predictive model may then be used to predict the responsiveness in a patient whose responsiveness to the immune checkpoint therapies, such as antagonists of an inhibitory immune checkpoint and/or agonists of a stimulatory immune checkpoint is unknown. In many other embodiments, a patient population can be divided into at least two classes based on patients' clinical outcome, prognosis, or responsiveness to immune checkpoint therapies, such as antagonists of an inhibitory immune checkpoint and/or agonists of a stimulatory immune checkpoint, and the biomarkers are substantially correlated with a class distinction between these classes of patients. The biological pathways described herein are common to cancer as a disease, similar to grade and stage, and as such, the classifiers and methods are not limited to a single cancer disease type.

Predictive Marker Panels/Expression Classifiers

A unique collection of biomarkers as a genetic classifier expressed in a cancer tissue is provided that is useful in determining responsiveness or resistance to therapeutic agents, such as immune checkpoint therapies, such as antagonists of an inhibitory immune checkpoint and/or agonists of a stimulatory immune checkpoint, used to treat cancer. Such a collection may be termed a "marker panel", "expression classifier", or "classifier".

Some biomarkers useful in the present methods are identified in Table 1. These biomarkers are identified as having predictive value to determine a patient response to a therapeutic agent, or lack thereof. Their expression correlates with the response to an agent, and more specifically, immune checkpoint therapies, such as antagonists of an inhibitory immune checkpoint and/or agonists of a stimulatory immune checkpoint, optionally in combination with a DNA-damage therapeutic agent. By examining the expression of a collection of the identified biomarkers in a tumor, it is possible to determine which therapeutic agent or combination of agents will be most likely to reduce the growth rate of a cancer, and in some embodiments, breast or ovarian cancer cells. By examining a collection of identified transcript gene or gene product markers, it is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

TABLE 1A

| Sense genes (166) | | Antisense of known genes (24) | | SEQ ID |
|---|---|---|---|---|
| Gene Symbol | EntrezGene ID | Almac Gene ID | Almac Gene symbol | NO: |
| ABCA12 | 26154 | | N/A | |
| ALDH3B2 | 222 | | N/A | |
| APOBEC3G | 60489 | | N/A | |
| APOC1 | 341 | | N/A | |
| APOL6 | 80830 | | N/A | |
| ARHGAP9 | 64333 | | N/A | |
| BAMBI | 25805 | | N/A | |
| BIK | 638 | | N/A | |
| BIRC3 | 330 | AS1_BIRC3 | Hs127799.0C7n9_at | 1 |
| BTN3A3 | 10384 | | N/A | |
| C12orf48 | 55010 | | N/A | |
| C17orf28 | 283987 | | N/A | |
| C1orf162 | 128346 | | N/A | |
| C1orf64 | 149563 | | N/A | |
| C1QA | 712 | | N/A | |
| C21orf70 | 85395 | | N/A | |
| C22orf32 | 91689 | | N/A | |
| C6orf211 | 79624 | | N/A | |
| CACNG4 | 27092 | | N/A | |
| CCDC69 | 26112 | | N/A | |
| CCL5 | 6352 | | N/A | |
| CCNB2 | 9133 | | N/A | |
| CCND1 | 595 | | N/A | |
| CCR7 | 1236 | | N/A | |
| CD163 | 9332 | | N/A | |
| CD2 | 914 | | N/A | |
| CD22 | 933 | | N/A | |
| CD24 | 100133941 | | N/A | |
| CD274 | 29126 | | N/A | |
| CD3D | 915 | | N/A | |
| CD3E | 916 | | N/A | |
| CD52 | 1043 | | N/A | |
| CD53 | 963 | | N/A | |
| CD79A | 973 | | N/A | |
| CDH1 | 999 | | N/A | |
| CDKN3 | 1033 | | N/A | |

TABLE 1A-continued

| Sense genes (166) | | Antisense of known genes (24) | | SEQ ID NO: |
|---|---|---|---|---|
| Gene Symbol | EntrezGene ID | Almac Gene ID | Almac Gene symbol | |
| CECR1 | 51816 | | N/A | |
| CHEK1 | 1111 | | N/A | |
| CKMT1B | 1159 | | N/A | |
| CMPK2 | 129607 | | N/A | |
| CNTNAP2 | 26047 | | N/A | |
| COX16 | 51241 | | N/A | |
| CRIP1 | 1396 | | N/A | |
| CXCL10 | 3627 | | N/A | |
| CXCL9 | 4283 | | N/A | |
| CYBB | 1536 | | N/A | |
| CYP2B6 | 1555 | | N/A | |
| DDX58 | 23586 | | N/A | |
| DDX60L | 91351 | | N/A | |
| ERBB2 | 2064 | | N/A | |
| ETV7 | 51513 | | N/A | |
| FADS2 | 9415 | | N/A | |
| FAM26F | 441168 | | N/A | |
| FAM46C | 54855 | | N/A | |
| FASN | 2194 | | N/A | |
| FBP1 | 2203 | | N/A | |
| FBXO2 | 26232 | | N/A | |
| FKBP4 | 2288 | | N/A | |
| FLJ40330 | 645784 | | N/A | |
| FYB | 2533 | | N/A | |
| GBP1 | 2633 | | N/A | |
| GBP4 | 115361 | | N/A | |
| GBP5 | 115362 | AS1_GBP5 | BRMX.5143C1n2_at | 2 |
| GIMAP4 | 55303 | | N/A | |
| GLRX | 2745 | | N/A | |
| GLUL | 2752 | | N/A | |
| GVIN1 | 387751 | | N/A | |
| H2AFJ | 55766 | | N/A | |
| HGD | 3081 | | N/A | |
| HIST1H2BK | 85236 | | N/A | |
| HIST3H2A | 92815 | | N/A | |
| HLA-DOA | 3111 | | N/A | |
| HLA-DPB1 | 3115 | | N/A | |
| HMGB2 | 3148 | | N/A | |
| HMGB3 | 3149 | | N/A | |
| HSP90AA1 | 3320 | | N/A | |
| IDO1 | 3620 | | N/A | |
| IFI27 | 3429 | | N/A | |
| IFI44 | 10561 | | N/A | |
| IFI44L | 10964 | AS1_IFI44L | BRSA.1606C1n4_at | 3 |
| IFI6 | 2537 | | N/A | |
| IFIH1 | 64135 | | N/A | |
| IGJ | 3512 | AS1_IGJ | BRIH.1231C2n2_at | 4 |
| IKZF1 | 10320 | | N/A | |
| IL10RA | 3587 | | N/A | |
| IL2RG | 3561 | | N/A | |
| IL7R | 3575 | | N/A | |
| IMPAD1 | 54928 | | N/A | |
| IQGAP3 | 128239 | AS1_IQGAP3 | BRAD.30779_s_at | 5 |
| IRF1 | 3659 | | N/A | |
| ISG15 | 9636 | | N/A | |
| ITGAL | 3683 | | N/A | |
| KIAA1467 | 57613 | | N/A | |
| KIF20A | 10112 | | N/A | |
| KITLG | 4254 | | N/A | |
| KLRK1 | 22914 | | N/A | |
| KRT19 | 3880 | | N/A | |
| LAIR1 | 3903 | | N/A | |
| LCP1 | 3936 | | N/A | |
| LOC100289702 | 100289702 | | N/A | |
| LOC100294459 | 100294459 | AS1_LOC100294459 | BRSA.396C1n2_at | 6 |
| LOC150519 | 150519 | | N/A | |
| LOC439949 | 439949 | | N/A | |
| LYZ | 4069 | | N/A | |
| MAL2 | 114569 | | N/A | |
| MGC29506 | 51237 | | N/A | |
| MIAT | 440823 | | N/A | |
| MS4A1 | 931 | | N/A | |
| MX1 | 4599 | AS1_MX1 | BRMX.2948C3n7_at | 7 |
| NAPSB | 256236 | | N/A | |

TABLE 1A-continued

| Sense genes (166) | | Antisense of known genes (24) | | SEQ ID NO: |
|---|---|---|---|---|
| Gene Symbol | EntrezGene ID | Almac Gene ID | Almac Gene symbol | |
| NCKAP1L | 3071 | | N/A | |
| NEK2 | 4751 | | N/A | |
| NLRC3 | 197358 | | N/A | |
| NLRC5 | 84166 | | N/A | |
| NPNT | 255743 | | N/A | |
| NQO1 | 1728 | | N/A | |
| OAS2 | 4939 | | N/A | |
| OAS3 | 4940 | | N/A | |
| PAQR4 | 124222 | | N/A | |
| PARP14 | 54625 | | N/A | |
| PARP9 | 83666 | | N/A | |
| PIK3CG | 5294 | | N/A | |
| PIM2 | 11040 | | N/A | |
| PLEK | 5341 | | N/A | |
| POU2AF1 | 5450 | | N/A | |
| PP14571 | 100130449 | | N/A | |
| PPP2R2C | 5522 | | N/A | |
| PSMB9 | 5698 | | N/A | |
| PTPRC | 5788 | | N/A | |
| RAC2 | 5880 | | N/A | |
| RAMP1 | 10267 | | N/A | |
| RARA | 5914 | | N/A | |
| RASSF7 | 8045 | | N/A | |
| RSAD2 | 91543 | | N/A | |
| RTP4 | 64108 | | N/A | |
| SAMD9 | 54809 | | N/A | |
| SAMD9L | 219285 | | N/A | |
| SASH3 | 54440 | | N/A | |
| SCD | 6319 | | N/A | |
| SELL | 6402 | | N/A | |
| SIX1 | 6495 | AS1_SIX1 | Hs539969.0C4n3_at | 8 |
| SLAMF7 | 57823 | | N/A | |
| SLC12A2 | 6558 | | N/A | |
| SLC9A3R1 | 9368 | AS1_SLC9A3R1 | Hs396783.3C1n4_at | 9 |
| SPOCK2 | 9806 | | N/A | |
| SQLE | 6713 | | N/A | |
| ST20 | 400410 | | N/A | |
| ST6GALNAC2 | 10610 | | N/A | |
| STAT1 | 6772 | AS1_STAT1 | BRMX.13670C1n2_at | 10 |
| STRA13 | 201254 | | N/A | |
| SUSD4 | 55061 | | N/A | |
| SYT12 | 91683 | | N/A | |
| TAP1 | 6890 | | N/A | |
| TBC1D10C | 374403 | | N/A | |
| TNFRSF13B | 23495 | | N/A | |
| TNFSF10 | 8743 | | N/A | |
| TOB1 | 10140 | AS1_TOB1 | BRAD.30243_at | 11 |
| TOM1L1 | 10040 | | N/A | |
| TRIM22 | 10346 | | N/A | |
| UBD | 10537 | AS1_UBD | BRMX.941C2n2_at | 12 |
| UBE2T | 29089 | | N/A | |
| UCK2 | 7371 | | N/A | |
| USP18 | 11274 | | N/A | |
| VNN2 | 8875 | | N/A | |
| XAF1 | 54739 | | N/A | |
| ZWINT | 11130 | | N/A | |
| | | AS1_C1QC | BRMX.4154C1n3_s_at | 13 |
| | | AS1_C2orf14 | BRAD.39498_at | 14 |
| | | AS1_EPSTI1 | BRAD.34868_s_at | 15 |
| | | AS1_GALNT6 | 5505575.0C1n42_at | 16 |
| | | AS1_HIST1H4H | BREM.1442_at | 17 |
| | | AS1_HIST2H4B | BRHP.827_s_at | 18 |
| | | AS2_HIST2H4B | BRRS.18322_s_at | 19 |
| | | AS3_HIST2H4B | BRRS.18792_s_at | 20 |
| | | AS1_KIAA1244 | Hs632609.0C1n37_at | 21 |
| | | AS1_LOC100287927 | Hs449575.0C1n22_at | 22 |
| | | AS1_LOC100291682 | BRAD.18827_s_at | 23 |
| | | AS1_L0C100293679 | BREM.2466_s_at | 24 |

TABLE 1B

Novel genes

| Gene symbol | SEQ ID NO: |
| --- | --- |
| BRAD.2605_at | 25 |
| BRAD.33618_at | 26 |
| BRAD.36579_s_at | 27 |
| BRAD1_5440961_s_at | 28 |
| BRAD1_66786229_s_at | 29 |
| BREM.2104_at | 30 |
| BRAG_AK097020.1_at | 31 |
| BRAD.20415_at | 32 |
| BRAD.29668_at | 33 |
| BRAD.30228_at | 34 |
| BRAD.34830_at | 35 |
| BRAD.37011_s_at | 36 |
| BRAD.37762_at | 37 |
| BRAD.40217_at | 38 |
| BRAD1_4307876_at | 39 |
| BREM.2505_at | 40 |
| Hs149363.0CB4n5_s_at | 41 |
| Hs172587.9C1n9_at | 42 |
| Hs271955.16C1n9_at | 43 |
| Hs368433.18C1n6_at | 44 |
| Hs435736.0C1n27_s_at | 45 |
| Hs493096.15C1n6_at | 46 |
| Hs493096.2C1n15_s_at | 47 |
| Hs592929.0CB2n8_at | 48 |
| Hs79953.0C1n23_at | 49 |
| BRMX.2377C1n3_at | 50 |

All or a portion of the biomarkers recited in Table 1 may be used in a predictive biomarker panel. For example, biomarker panels selected from the biomarkers in Table 1 can be generated using the methods provided herein and can comprise between one, and all of the biomarkers set forth in Table 1 and each and every combination in between (e.g., four selected biomarkers, 16 selected biomarkers, 74 selected biomarkers, etc.). In some embodiments, the predictive biomarker set comprises at least 5, 10, 20, 40, 60, 100, 150, 200, or 300 or more biomarkers. In other embodiments, the predictive biomarker set comprises no more than 5, 10, 20, 40, 60, 100, 150, 200, 300, 400, 500, 600 or 700 biomarkers. In some embodiments, the predictive biomarker set includes a plurality of biomarkers listed in Table 1. In some embodiments the predictive biomarker set includes at least about 1%, about 5%, about 10%, about 20%, about 30%, about 40%, about 50%, about 60%, about 70%, about 80%, about 90%, about 95%, about 96%, about 97%, about 98%, or about 99% of the biomarkers listed in Table 1. Selected predictive biomarker sets can be assembled from the predictive biomarkers provided using methods described herein and analogous methods known in the art. In one embodiment, the biomarker panel contains all 203 biomarkers in Table 1. In another embodiment, the biomarker panel contains 40 or 44 biomarkers in Table 1 or 2.

Predictive biomarker sets may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug or drug class. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("decisive function") is compared with a pre-determined reference point or value. The comparison with the reference point or value may be used to diagnose, or predict a clinical condition or outcome.

As described above, one of ordinary skill in the art will appreciate that the biomarkers included in the classifier provided in Table 1 will carry unequal weights in a classifier for responsiveness or resistance to a therapeutic agent. Therefore, while as few as one sequence may be used to diagnose or predict an outcome such as responsiveness to therapeutic agent, the specificity and sensitivity or diagnosis or prediction accuracy may increase using more sequences.

As used herein, the term "weight" refers to the relative importance of an item in a statistical calculation. The weight of each biomarker in a gene expression classifier may be determined on a data set of patient samples using analytical methods known in the art.

In one embodiment the biomarker panel is directed to the 40 biomarkers detailed in Table 2A with corresponding ranks and weights detailed in the table or alternative rankings and weightings, depending, for example, on the disease setting. In another embodiment, the biomarker panel is directed to the 44 biomarkers detailed in Table 2B with corresponding ranks and weights detailed in the table or alternative rankings and weightings, depending, for example, on the disease setting. Tables 2A and 2B rank the biomarkers in order of decreasing weight in the classifier, defined as the rank of the average weight in the compound decision score function measured under cross-validation. Table 2C present the probe sets that represent the genes in Table 2A and 2B with reference to their sequence ID numbers. Table 2D presents the antisense probe sequences that were present on the array for the genes in the signatures.

TABLE 2A

Gene IDs and EntrezGene IDs for 40-gene DDRD classifier model with associated ranking and weightings
DDRD classifier 40 gene model

| Rank | Genes Symbol | EntrezGene ID | Weights |
| --- | --- | --- | --- |
| 1 | GBP5 | 115362 | 0.022389581 |
| 2 | CXCL10 | 3627 | 0.021941734 |
| 3 | IDO1 | 3620 | 0.020991115 |
| 4 | MX1 | 4599 | 0.020098675 |
| 5 | IFI44L | 10964 | 0.018204957 |
| 6 | CD2 | 914 | 0.018080661 |
| 7 | PRAME | 23532 | 0.016850837 |
| 8 | ITGAL | 3683 | 0.016783359 |
| 9 | LRP4 | 4038 | −0.015129969 |
| 10 | SP140L | 93349 | 0.014646025 |
| 11 | APOL3 | 80833 | 0.014407174 |
| 12 | FOSB | 2354 | −0.014310521 |
| 13 | CDR1 | 1038 | −0.014209848 |
| 14 | RSAD2 | 91543 | 0.014177132 |
| 15 | TSPAN7 | 7102 | −0.014111562 |
| 16 | RAC2 | 5880 | 0.014093627 |
| 17 | FYB | 2533 | 0.01400475 |
| 18 | KLHDC7B | 113730 | 0.013298413 |
| 19 | GRB14 | 2888 | 0.013031204 |
| 20 | KIF26A | 26153 | −0.012942351 |
| 21 | CD274 | 29126 | 0.012651964 |

TABLE 2A-continued

Gene IDs and EntrezGene IDs for 40-gene DDRD classifier
model with associated ranking and weightings
DDRD classifier 40 gene model

| Rank | Genes Symbol | EntrezGene ID | Weights |
|---|---|---|---|
| 22 | CD109 | 135228 | −0.012239425 |
| 23 | ETV7 | 51513 | 0.011787297 |
| 24 | MFAP5 | 8076 | −0.011480443 |
| 25 | OLFM4 | 10562 | −0.011130113 |
| 26 | PI15 | 51050 | −0.010904326 |
| 27 | FAM19A5 | 25817 | −0.010500936 |
| 28 | NLRC5 | 84166 | 0.009593449 |
| 29 | EGR1 | 1958 | −0.008947963 |
| 30 | ANXA1 | 301 | −0.008873991 |
| 31 | CLDN10 | 9071 | −0.008165127 |
| 32 | ADAMTS4 | 9507 | −0.008109892 |
| 33 | ESR1 | 2099 | 0.007524594 |
| 34 | PTPRC | 5788 | 0.007258669 |
| 35 | EGFR | 1956 | −0.007176203 |
| 36 | NAT1 | 9 | 0.006165534 |
| 37 | LATS2 | 26524 | −0.005951091 |
| 38 | CYP2B6 | 1555 | 0.005838391 |
| 39 | PPP1R1A | 5502 | −0.003898835 |
| 40 | TERF1P1 | 348567 | 0.002706847 |

TABLE 2B

Gene IDs and EntrezGene IDs for 44-gene DDRD classifier
model with associated ranking and weightings
DDRD Classifier-44 Gene Model (NA:genomic sequence)

| Rank | Gene symbol | EntrezGene ID | Weight |
|---|---|---|---|
| 1 | CXCL10 | 3627 | 0.023 |
| 2 | MX1 | 4599 | 0.0226 |
| 3 | IDO1 | 3620 | 0.0221 |
| 4 | IFI44L | 10964 | 0.0191 |
| 5 | CD2 | 914 | 0.019 |
| 6 | GBP5 | 115362 | 0.0181 |
| 7 | PRAME | 23532 | 0.0177 |
| 8 | ITGAL | 3683 | 0.0176 |
| 9 | LRP4 | 4038 | −0.0159 |
| 10 | APOL3 | 80833 | 0.0151 |
| 11 | CDR1 | 1038 | −0.0149 |
| 12 | FYB | 2533 | −0.0149 |
| 13 | TSPAN7 | 7102 | 0.0148 |
| 14 | RAC2 | 5880 | −0.0148 |
| 15 | KLHDC7B | 113730 | 0.014 |
| 16 | GRB14 | 2888 | 0.0137 |
| 17 | AC138128.1 | N/A | −0.0136 |
| 18 | KIF26A | 26153 | −0.0136 |
| 19 | CD274 | 29126 | 0.0133 |
| 20 | CD109 | 135228 | −0.0129 |
| 21 | ETV7 | 51513 | 0.0124 |
| 22 | MFAP5 | 8076 | −0.0121 |
| 23 | OLFM4 | 10562 | −0.0117 |
| 24 | PI15 | 51050 | −0.0115 |
| 25 | FOSB | 2354 | −0.0111 |
| 26 | FAM19A5 | 25817 | 0.0101 |
| 27 | NLRC5 | 84166 | −0.011 |
| 28 | PRICKLE1 | 144165 | −0.0089 |
| 29 | EGR1 | 1958 | −0.0086 |
| 30 | CLDN10 | 9071 | −0.0086 |
| 31 | ADAMTS4 | 9507 | −0.0085 |
| 32 | SP140L | 93349 | 0.0084 |
| 33 | ANXA1 | 301 | −0.0082 |
| 34 | RSAD2 | 91543 | 0.0081 |
| 35 | ESR1 | 2099 | 0.0079 |
| 36 | IKZF3 | 22806 | 0.0073 |
| 37 | OR2I1P | 442197 | 0.007 |
| 38 | EGFR | 1956 | −0.0066 |
| 39 | NAT1 | 9 | 0.0065 |
| 40 | LATS2 | 26524 | −0.0063 |
| 41 | CYP2B6 | 1555 | 0.0061 |
| 42 | PTPRC | 5788 | 0.0051 |
| 43 | PPP1R1A | 5502 | −0.0041 |
| 44 | AL137218.1 | N/A | −0.0017 |

TABLE 2C

Probe set IDs and SEQ Numbers for genes
contained in 40- and 44-gene signature
Probe set IDs and SEQ Numbers for genes
contained in 40 and 44 gene signature

| Gene Symbol | Probe Set ID | SEQ ID NO. |
|---|---|---|
| FYB | BRAD.10849_at | 83 |
| CLDN10 | BRAD.10890_at | 84 |
| PPP1R1A | BRAD.11026_at | 85 |
| PI15 | BRAD.12809_at | 86 |
| MFAP5 | BRAD.14326_s_at | 87 |
| ESR1 | BRAD.15436_s_at | 88 |
| FYB | BRAD.15833_s_at | 89 |
| ESR1 | BRAD.19080_s_at | 90 |
| TERF1P1 | BRAD.2707_at | 91 |
| PRICKLE1 | BRAD.27716_s_at | 92 |
| LATS2 | BRAD.28628_s_at | 93 |
| IKZF3 | BRAD.28643_at | 94 |
| MX1 | BRAD.28663_s_at | 95 |
| CD274 | BRAD.29038_at | 96 |
| FAM19A5 | BRAD.30917_at | 97 |
| LATS2 | BRAD.31470_at | 98 |
| EGFR | BRAD.32716_at | 99 |
| EGFR | BRAD.33042_at | 100 |
| EGFR | BRAD.33341_at | 101 |
| ANXA1 | BRAD.33405_at | 102 |
| EGFR | BRAD.33431_at | 103 |
| KLHDC7B | BRAD.35695_at | 104 |
| IKZF3 | BRAD.35710_at | 105 |
| PTPRC | BRAD.37907_at | 106 |
| TERF1P1 | BRAD.40353_at | 107 |
| EGFR | BRAD.40654_s_at | 108 |
| FYB | BRAD.4701_at | 109 |
| PTPRC | BRAD.5967_at | 110 |
| EGFR | BRAD.7701_at | 111 |
| ESR1 | BREM.1048_at | 112 |
| EGFR | BREM.1129_at | 113 |
| NAT1 | BREM.1226_at | 114 |
| FOSB | BREM.1262_at | 115 |
| OR2I1P | BREM.130_at | 116 |
| ADAMTS4 | BREM.1689_s_at | 117 |
| CYP2B6 | BREM.2334_at | 118 |
| EGFR | BREM.2382_at | 119 |
| ETV7 | BREM.532_at | 120 |
| ANXA1 | BRHP.106_s_at | 121 |
| ESR1 | BRIH.10647C1n2_at | 122 |
| EGFR | BRIH.1453C1n2_at | 123 |
| EGR1 | BRIH.1518C1n4_at | 124 |
| ANXA1 | BRIH.2770C3n31_at | 125 |
| NAT1 | BRIH.365C1n2_at | 126 |
| IFI44L | BRIH.5410C1n7_at | 127 |
| MX1 | BRIH.5478C1n2_s_at | 128 |
| ESR1 | BRIH.5650C1n2_at | 129 |
| CD109 | BRIH.5952C1n2_s_at | 130 |
| CXCL10 | BRIH.7359C1n3_s_at | 131 |
| FYB | BRIHRC.10930C1n2_s_at | 132 |
| AC138128.1 | BRMX.13731C1n18_at | 133 |
| TERF1P1 | BRMX.25436C1n2_at | 134 |
| GBP5 | BRMX.25712C1n2_at | 135 |
| EGR1 | BRMX.3079C1n3_at | 136 |
| EGR1 | BRMX.3079C2n3_at | 137 |
| ESR1 | BRPD.10690C1n5_at | 138 |
| FYB | BRPD.4019C1n3_s_at | 139 |
| GBP5 | BRPD.5301C1n2_s_at | 140 |

TABLE 2C-continued

Probe set IDs and SEQ Numbers for genes contained in 40- and 44-gene signature
Probe set IDs and SEQ Numbers for genes contained in 40 and 44 gene signature

| Gene Symbol | Probe Set ID | SEQ ID NO. |
|---|---|---|
| NLRC5 | BRRS.12588_at | 141 |
| GBP5 | BRRS.13369_s_at | 142 |
| RSAD2 | BRRS.13576_at | 143 |
| PTPRC | BRRS.13647_at | 144 |
| PTPRC | BRRS.13648_s_at | 145 |
| CD109 | BRRS.13767_at | 146 |
| SP140L | BRRS.13859_at | 147 |
| KLHDC7B | BRRS.13881_at | 148 |
| APOL3 | BRRS.14465_s_at | 149 |
| PRICKLE1 | BRRS.15053_at | 150 |
| CLDN10 | BRRS.16228_s_at | 151 |
| EGFR | BRRS.16746_s_at | 152 |
| EGFR | BRRS.16747_at | 153 |
| PRAME | BRRS.16948_s_at | 154 |
| TERF1P1 | BRRS.17863_s_at | 155 |
| TERF1P1 | BRRS.17909_s_at | 156 |
| AL137218.1 | BRRS.18137_at | 157 |
| KIF26A | BRRS.18652_s_at | 158 |
| FYB | BRRS.2573_s_at | 159 |
| CXCL10 | BRRS.2644_at | 160 |
| CD2 | BRRS.2783_s_at | 161 |
| EGR1 | BRRS.2935_at | 162 |
| IDO1 | BRRS.3099_at | 163 |
| ITGAL | BRRS.3131_at | 164 |
| LRP4 | BRRS.3220_at | 165 |
| MX1 | BRRS.3319_at | 166 |
| MX1 | BRRS.3319_s_at | 167 |
| RAC2 | BRRS.3645_s_at | 168 |
| MFAP5 | BRRS.4126_s_at | 169 |
| NAT1 | BRRS.455_at | 170 |
| CDR1 | BRRS.4562_at | 171 |
| ANXA1 | BRRS.487_s_at | 172 |
| GRB14 | BRRS.4891_s_at | 173 |
| TSPAN7 | BRRS.4996_at | 174 |
| CYP2B6 | BRRS.524_s_at | 175 |
| ADAMTS4 | BRRS.5356_at | 176 |
| EGFR | BRRS.5451_at | 177 |
| OLFM4 | BRRS.6371_at | 178 |
| FOSB | BRRS.6611_at | 179 |
| PPP1R1A | BRRS.6619_at | 180 |
| PPP1R1A | BRRS.6619-22_at | 181 |
| IFI44L | BRRS.6684_at | 182 |
| CD274 | BRRS.7616_at | 183 |
| LATS2 | BRRS.7901_at | 184 |
| ESR1 | BRRS.81_at | 185 |
| ESR1 | BRRS.81-22_at | 186 |
| FAM19A5 | BRRS.8480_s_at | 187 |
| PI15 | BRRS.8711_at | 188 |
| ETV7 | BRRS.8900_s_at | 189 |
| EGR1 | BRSA.1686C1n5_at | 190 |
| RAC2 | BRSA.8072C1n2_s_at | 191 |
| SP140L | Hs369056.20C1n2_at | 192 |
| EGFR | Hs488293.0CB1n69_at | 193 |
| ANXA1 | Hs494173.0CB4n15_at | 194 |
| GBP5 | Hs513726.0C2n39_s_at | 195 |
| TERF1P1 | Hs514006.0C1n8_at | 196 |
| TERF1P1 | Hs522202.0C1n6_at | 197 |
| PRICKLE1 | Hs524348.0CB1n97_at | 198 |
| PRICKLE1 | Hs524348.2C1n5_s_at | 199 |
| NLRC5 | Hs528836.0C1n3_s_at | 200 |
| TERF1P1 | Hs591893.1C1n4_s_at | 201 |
| RSAD2 | Hs7155.0CB1n102_at | 202 |

TABLE 2D

Almac IDs and Almac Gene symbol and SEQ ID numbers for antisense probe sets in 40-gene signature
(D) Almac IDs and Almac Gene symbol and SEQ ID numbers for antisense probe sets in 40 gene signature

| Gene Symbol | EntrezGene ID (40) | Almac Gene ID (32) | Almac Gene symbol | SEQ ID NO: |
|---|---|---|---|---|
| ADAMTS4 | 9507 | | | |
| ANXA1 | 301 | | | |
| ANXA1 | 301 | AS1_ANXA1 | BRAD.33405_at | 51 |
| APOL3 | 80833 | | | |
| CD109 | 135228 | | | |
| CD2 | 914 | | | |
| CD274 | 29126 | | | |
| CD274 | 29126 | AS1_CD274 | Hs584242.2C1n64_at | 52 |
| CDR1 | 1038 | | | |
| CDR1 | 1038 | AS1_CDR1 | BRRS1RC_NM_004065_at | 53 |
| CLDN10 | 9071 | | | |
| CLDN10 | 9071 | AS1_CLDN10 | BRRS.8182_at | 54 |
| CXCL10 | 3627 | | | |
| CXCL10 | 3627 | AS1_CXCL10 | BRMX.13815C1n5_at | 55 |
| CYP2B6 | 1555 | | | |
| EGFR | 1956 | | | |
| EGFR | 1956 | AS1_EGFR | BRMX.2637C1n26_at | 56 |
| EGFR | 1956 | AS2_EGFR | BRAD.36737_at | 57 |
| EGFR | 1956 | AS3_EGFR | BRAD.3853_at | 58 |
| EGFR | 1956 | AS4_EGFR | BRAD1_19760734_at | 59 |
| EGR1 | 1958 | | | |
| EGR1 | 1958 | AS1_EGR1 | BRMX.2797C4n2_at | 60 |
| ESR1 | 2099 | | | |
| ESR1 | 2099 | AS1_ESR1 | BRMX.10399C1n5_at | 61 |
| ESR1 | 2099 | AS2_ESR1 | BRMX.8912C1n3_at | 62 |
| ETV7 | 51513 | | | |
| FAM19A5 | 25817 | | | |
| FOSB | 2354 | | | |

TABLE 2D-continued

Almac IDs and Almac Gene symbol and SEQ ID numbers
for antisense probe sets in 40-gene signature
(D) Almac IDs and Almac Gene symbol and SEQ ID numbers
for antisense probe sets in 40 gene signature

| Gene Symbol | EntrezGene ID (40) | Almac Gene ID (32) | Almac Gene symbol | SEQ ID NO: |
|---|---|---|---|---|
| FOSB | 2354 | AS1_FOSB | BRMX.13731C1n18_at | 63 |
| FYB | 2533 | | | |
| FYB | 2533 | AS1_FYB | BRAD.25947_at | 64 |
| GBP5 | 115362 | | | |
| GBP5 | 115362 | AS1_GBP5 | BRMX.5143C1n2(2)_at | 65 |
| GRB14 | 2888 | | | |
| IDO1 | 3620 | | | |
| IFI44L | 10964 | | | |
| IFI44L | 10964 | AS1_IFI44L | Hs633116.0C1n30_at | 66 |
| IFI44L | 10964 | AS2_IFI44L | BRSA.1606C1n4(2)_at | 67 |
| ITGAL | 3683 | | | |
| ITGAL | 3683 | AS1_ITGAL | BRAD.41047_at | 68 |
| ITGAL | 3683 | AS2_ITGAL | BRAD.4420_at | 69 |
| KIF26A | 26153 | | | |
| KLHDC7B | 113730 | | | |
| KLHDC7B | 113730 | AS1_KLHDC7B | Hs137007.0C1n9_at | 70 |
| LATS2 | 26524 | | | |
| LATS2 | 26524 | AS1_LATS2 | BRSA.18050C1n3_at | 71 |
| LRP4 | 4038 | | | |
| MFAP5 | 8076 | | | |
| MX1 | 4599 | | | |
| MX1 | 4599 | AS1_MX1 | BRMX.2948C3n7(2)_at | 72 |
| MX1 | 4599 | AS2_MX1 | Hs43047.0C4n40_at | 73 |
| MX1 | 4599 | AS2_MX1 | Hs926.1C10n7_at | 74 |
| NAT1 | 9 | | | |
| NLRC5 | 84166 | | | |
| NLRC5 | 84166 | AS1_NLRC5 | Hs528836.0CB6n98_s_at | 75 |
| OLFM4 | 10562 | | | |
| OLFM4 | 10562 | AS1_OLFM4 | BRMX.7284C1n6_at | 76 |
| PI15 | 51050 | | | |
| PI15 | 51050 | AS1_PI15 | BRAD1_19751014_at | 77 |
| PPP1R1A | 5502 | | | |
| PRAME | 23532 | | | |
| PTPRC | 5788 | | | |
| RAC2 | 5880 | | | |
| RAC2 | 5880 | AS1_RAC2 | BRMX.13502C1n6_at | 78 |
| RSAD2 | 91543 | | | |
| SP140L | 93349 | | | |
| SP140L | 93349 | AS1_SP140L | BRMX.1111C4n3_at | 79 |
| SP140L | 93349 | AS2_SP140L | Hs369056.9C26n3_at | 80 |
| TERF1P1 | 348567 | | | |
| TERF1P1 | 348567 | AS1_TERF1P1 | BRMX.24432C1n2_at | 81 |
| TERF1P1 | 348567 | AS2_TERF1P1 | BRRS.17773_at | 82 |
| TSPAN7 | 7102 | | | |

In different embodiments, subsets of the biomarkers listed in Table 2A and Table 2B may be used in the methods described herein. These subsets include but are not limited to biomarkers ranked 1-2, 1-3, 1-4, 1-5, 1-10, 1-20, 1-30, 1-40, 1-44, 6-10, 11-15, 16-20, 21-25, 26-30, 31-35, 36-40, 36-44, 11-20, 21-30, 31-40, and 31-44 in Table 2A or Table 2B. In one aspect, therapeutic responsiveness is predicted in an individual by conducting an assay on a biological sample from the individual and detecting biomarker values that each correspond to at least one of the biomarkers GBP5, CXCL10, IDO1 and MX1 and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. In some embodiments, when referring to a biomarker of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, the biomarker comprises an mRNA of CXCL10, IDO1, CD2, GBP5, PRAME, ITGAL, LRP4, APOL3, CDR1, FYB, TSPAN7, RAC2, KLHDC7B, GRB14, AC138128.1, KIF26A, CD274, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, or AL137218.1, respectively. In further or other embodiments, when referring to a biomarker of MX1, GBP5, IF144L, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, the biomarker comprises an antisense transcript of MX1, IF144L, GBP5, BIRC3, IGJ, IQGAP3, LOC100294459, SIX1, SLC9A3R1, STAT1, TOB1, UBD, C1QC, C2orf14, EPSTI, GALNT6, HIST1H4H, HIST2H4B, KIAA1244, LOC100287927, LOC100291682, or LOC100293679, respectively.

In a further aspect, therapeutic responsiveness is predicted, or a cancer diagnosis is indicated, in an individual by conducting an assay on a biological sample from the individual and detecting biomarker values that each correspond to the biomarkers GBP5, CXCL10, IDO1 and MX1 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36. In a further aspect, therapeutic responsiveness is predicted, or a cancer diagnosis is indicated, in an individual by conducting an assay on a biological sample from the individual and detecting biomarker values that each correspond to the biomarker GBP5 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39. In a further aspect, therapeutic responsiveness is predicted, or a cancer diagnosis is indicated, in an individual by conducting an assay on a biological sample from the individual and detecting biomarker values that each correspond to the biomarker MX-1 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38 or 39.

In a further aspect, therapeutic responsiveness is predicted, or a cancer diagnosis is indicated, in an individual by conducting an assay on a biological sample from the individual and detecting biomarker values that each correspond to at least two of the biomarkers CXCL10, MX1, IDO1 and IF144L and at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarkers CXCL10, MX1, IDO1 and IF144L and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. In a further aspect, therapeutic responsiveness is predicted, or a cancer diagnosis is indicated, in an individual by conducting an assay on a biological sample from the individual and detecting biomarker values that each correspond to the biomarker CXCL10 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker MX1 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IDO1 and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43. In a further aspect, therapeutic responsiveness is predicted, or a cancer diagnosis is indicated, in an individual by conducting an assay on a biological sample from the individual and detecting biomarker values that each correspond to the biomarker IF144L and one of at least N additional biomarkers selected from the list of biomarkers in Table 2B, wherein N equals 1, 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42 or 43.

In other embodiments, the probes listed in Table 2C (SEQ ID NOs:83-202), or subsets thereof, may be used in the methods described herein. These subsets include but are not limited to a subset of SEQ ID NOs corresponding to one or more of GBP5, CXCL10, IDO1, MX1, IF1441, CD2, PRAME, ITGAL, LRP4, and APOL3. In other embodiments, the probes correspond to all of the biomarkers CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1. It should be understood that each subset can include multiple probes directed to the same biomarker. For example, the probes represented by SEQ ID NOs: 135, 140, 142 and 195 are all directed to GBP5. Accordingly, a subset containing probes directed or corresponding to GBP5 includes one or more of SEQ ID NOs: 135, 140, 142 and 195. A subset containing probes directed to or corresponding to CXCL10 includes one or more of SEQ ID NOs: 131 and 160.

In other embodiments, specific nucleic acid amplification assays (e.g. PCR, such as qPCR) may be used to determine the expression level of one or more of the genes or sets of genes described herein. The expression level(s) of one or more of the genes may be determined using primers (primer pairs) and/or probes that hybridize with the sequence of the one or more genes. Exemplary primer pairs and probes are provided in Table 2E for each of the genes of the 44-gene DDRD classifier model. The primer pairs and/or probes provided for each gene may be used alone or two or more of the primer pairs and/or probes may be used in combination in accordance with any of the sets of genes described herein. For example, the primer pairs and/or probes provided in Table 2E may be used to determine the expression level of any of the gene signatures provided in Tables 3-45. Exemplary PCR assays are summarized in Table 2E for each of the genes of the 44-gene DDRD classifier model. The PCR assay provided for each gene may be used alone or two or more of the assays may be used in combination in accordance with any of the sets of genes described herein. For example, the PCR assays provided in the table may be used to determine the expression level of any of the gene signatures provided in Tables 3-45.

TABLE 2E

PCR assays designed for each of the 44 genes listed in Table 2B

| GenBank ID | Gene Symbol | Assay ID | Forward Primer ID | Forward Primer SEQ ID NO | Forward Primer ABI Tm (° C.) | Reverse Primer ID | Reverse Primer SEQ ID NO | Reverse Primer ABI Tm (° C.) | Probe ID | Probe SEQ ID NO | Probe ABI Tm (° C.) |
|---|---|---|---|---|---|---|---|---|---|---|---|
| NM_002164 | IDO1 | IDO_A1 | IDO_F1 | 203 | 56.80 | IDO_R1 | 204 | 56.30 | IDO_P1 | 205 | 62.00 |
| NM_001767 | CD2 | CD2_A1 | CD2_F1 | 206 | 58.20 | CD2_R1 | 207 | 57.80 | CD2_P1 | 208 | 64.90 |
| NM_052942 | GBP5 | GBP5_A1 | GBP5_F1 | 209 | 57.00 | GBP5_R1 | 210 | 58.10 | GBP5_P1 | 211 | 64.30 |
| NM_206953 | PRAME | PRAME_A1 | PRAME_F1 | 212 | 58.40 | PRAME_R1 | 213 | 58.40 | PRAME_P1 | 214 | 64.00 |
| NM_002209 | ITGAL | ITGAL_A1 | ITGAL_F1 | 215 | 59.20 | ITGAL_R1 | 216 | 58.30 | ITGAL_P1 | 217 | 66.10 |
| NM_002334 | LRP4 | LRP4_A1 | LRP4_F1 | 218 | 57.20 | LRP4_R1 | 219 | 58.50 | LRP4_P | 220 | 63.80 |
| NM_145640 | APOL3 | APOL3_A1 | APOL3_F1 | 221 | 57.10 | APOL3_R1 | 222 | 57.90 | APOL3_P1 | 223 | 63.10 |
| NM_004065 | CDR1 | CDR1_A1 | CDR1_F1 | 224 | 58.30 | CDR1_R1 | 225 | 57.90 | CDR1_P1 | 226 | 63.80 |
| NM_001465 | FYB | FYB_A1 | FYB_F1 | 227 | 59.10 | FYB_R1 | 228 | 59.20 | FYB_P1 | 229 | 64.70 |
| NM_004615 | TSPAN7 | TSPAN7_A1 | TSPAN7_F1 | 230 | 58.00 | TSPAN7_R1 | 231 | 57.40 | TSPAN7_P1 | 232 | 63.20 |
| NM_002872 | RAC2 | RAC2_A1 | RAC2_F1 | 233 | 59.10 | RAC2_R1 | 234 | 58.70 | RAC2_P1 | 235 | 64.20 |
| NM_138433 | KLHDC7B | KLHDC7B_A1 | KLHDC7B_F1 | 236 | 59.40 | KLHDC7B_R1 | 237 | 59.70 | KLHDC7B_P1 | 238 | 66.50 |
| NM_044490 | GRB14 | GRB14_A1 | GRB14_F1 | 239 | 57.70 | GRB14_R1 | 240 | 57.30 | GRB14_P1 | 241 | 62.70 |
| NM_015656 | KIF26A | KIF26A_A1 | KIF26A_F1 | 242 | 58.40 | KIF26A_R1 | 243 | 59.40 | KIF26A_P1 | 244 | 66.80 |
| NM_014143 | CD274 | CD274_A1 | CD274_F1 | 245 | 58.60 | CD274_R1 | 246 | 57.50 | CD274_P1 | 247 | 65.80 |
| NM_133493 | CD109 | CD109_A1 | CD109_F1 | 248 | 59.60 | CD109_R1 | 249 | 58.70 | CD109_P1 | 250 | 67.10 |
| NM_016135 | ETV7 | ETV7_A1 | ETV7_F1 | 251 | 58.90 | ETV7_R1 | 252 | 59.20 | ETV7_P1 | 253 | 65.70 |
| NM_003480 | MFAP5 | MFAP5_A1 | MFAP5_F1 | 254 | 58.80 | MFAP5_R1 | 255 | 59.40 | MFAP5_P1 | 256 | 64.90 |
| NM_006418 | OLFM4 | OLFM4_A1 | OLFM4_F1 | 257 | 57.70 | OLFM4_R1 | 258 | 58.60 | OLFM4_P1 | 259 | 63.60 |
| NM_015886 | PI15 | PI15_A1 | PI15_F1 | 260 | 58.20 | PI15_R1 | 261 | 58.60 | PI15_P1 | 262 | 64.20 |
| NM_006732 | FOSB | FOSB_A1 | FOSB_F1 | 263 | 59.30 | FOSB_R1 | 264 | 59.40 | FOSB_P1 | 265 | 66.80 |
| NM_001565 | CXCL10 | CXCL10_A1 | CXCL10_F1 | 266 | 63.87 | CXCL10_R1 | 267 | 63.23 | CXCL10_P1 | 268 | 72.36 |
| NM_001144925.2 | MX1 | MX1_A1 | MX1_F1 | 269 | 61.41 | MX1_R1 | 270 | 61.01 | MX1_P1 | 271 | 72.48 |
| NM_001166049.1 | IFI44L | IFI44L_A1 | IFI44L_F1 | 272 | 65.75 | IFI44L_R1 | 273 | 65.12 | IFI44L_P1 | 274 | 69.81 |
| NM_001166049.1 | AC138128.1 | AC138128.1_A1 | AC138128.1_F1 | 275 | 60.48 | AC138128.1_R1 | 276 | 64.46 | AC138128.1_P1 | 277 | 72.44 |
| NM_001082967.2 | FAM19A5 | FAM19A5_A1 | FAM19A5_F1 | 278 | 64.30 | FAM19A5_R1 | 279 | 61.45 | FAM19A5_P1 | 280 | 73.11 |
| NM_032206.4 | NLRC5 | NLRC5_A1 | NLRC5_F1 | 281 | 62.55 | NLRC5_R1 | 282 | 62.69 | NLRC5_P1 | 283 | 69.77 |
| NM_001144881.1 | PRICKLE1 | PRICKLE1_A1 | PRICKLE1_F1 | 284 | 68.01 | PRICKLE1_R1 | 285 | 65.53 | PRICKLE1_P1 | 286 | 70.66 |
| NM_001964.2 | EGR1 | EGR1_A1 | EGR1_F1 | 287 | 61.27 | EGR1_R1 | 288 | 61.27 | EGR1_P1 | 289 | 68.60 |
| NM_001160100.1 | CLDN10 | CLDN10_A1 | CLDN10_F1 | 290 | 68.19 | CLDN10_R1 | 291 | 62.50 | CLDN10_P1 | 292 | 68.19 |
| NM_005099.4 | ADAMTS4 | ADAMTS4_A1 | ADAMTS4_F1 | 293 | 63.69 | ADAMTS4_R1 | 294 | 63.82 | ADAMTS4_P1 | 295 | 71.38 |
| NM_001308162.1 | SP140L | SP140L_A1 | SP140L_F1 | 296 | 60.61 | SP140L_R1 | 297 | 62.67 | SP140L_P1 | 298 | 72.17 |
| NM_000700.2 | ANXA1 | ANXA1_A1 | ANXA1_F1 | 299 | 64.80 | ANXA1_R1 | 300 | 64.81 | ANXA1_P1 | 301 | 72.90 |
| NM_080657.4 | RSAD2 | RSAD2_A1 | RSAD2_F1 | 302 | 63.44 | RSAD2_R1 | 303 | 63.00 | RSAD2_P1 | 304 | 70.95 |
| NM_000125.3 | ESR1 | ESR1_A1 | ESR1_F1 | 305 | 61.54 | ESR1_R1 | 306 | 64.65 | ESR1_P1 | 307 | 70.06 |
| NM_001257408.1 | IKZF3 | IKZF3_A1 | IKZF3_F1 | 308 | 62.37 | IKZF3_R1 | 309 | 64.92 | IKZF3_P1 | 310 | 69.53 |
| NT_167248.2 | OR2I1P | OR2I1P_A1 | OR2I1P_F1 | 353 | N/A | OR2I1P_R1 | 354 | 58.13 | OR2I1P_P1 | 355 | 67.43 |
| NM_005228.3 | EGFR | EGFR_A1 | EGFR_F1 | 311 | 62.20 | EGFR_R1 | 312 | 62.13 | EGFR_P1 | 313 | 70.85 |
| NM_000662.7 | NAT1 | NAT1_A1 | NAT1_F1 | 314 | 60.92 | NAT1_R1 | 315 | 62.70 | NAT1_P1 | 316 | 70.40 |
| NM_014572.2 | LATS2 | LATS2_A1 | LATS2_F1 | 317 | 60.44 | LATS2_R1 | 318 | 60.54 | LATS2_P1 | 319 | 71.63 |
| NM_000767.4 | CYP2B6 | CYP2B6_A1 | CYP2B6_F1 | 320 | 64.52 | CYP2B6_R1 | 321 | 62.64 | CYP2B6_P1 | 322 | 73.80 |
| NM_001267798 | PTPRC | PTPRC_A1 | PTPRC_F1 | 323 | 62.95 | PTPRC_R1 | 324 | 62.81 | PTPRC_P1 | 325 | 70.74 |
| NM_006741.3 | PPP1R1A | PPP1R1A_A1 | PPP1R1A_F1 | 326 | 62.77 | PPP1R1A_R1 | 327 | 66.34 | PPP1R1A_P1 | 328 | 69.55 |
| NR_003366.2 | AL137218.1 | AL137218.1_A1 | AL137218.1_F1 | 356 | 57.17 | AL137218.1_R1 | 357 | 56.40 | AL137218.1_P1 | 358 | 67.23 |

It should be noted that the complement of each sequence described herein may be employed as appropriate (e.g. for designing hybridizing probes and/or primers, including primer pairs).

Additional gene signatures representing selections of the 44 gene signature are described herein and are applicable to all aspects of the invention. The additional gene signatures are set forth in Tables 3-45, together with suitable weight and bias scores that may be adopted when calculating the final signature score (as further described herein). The k value for each signature can be set once the threshold for defining a positive signature score has been determined, as would be readily appreciated by the skilled person. Similarly, the rankings for each gene in the signature can readily be determined by reviewing the weightings attributed to each gene (where a larger weight indicates a higher ranking in the signature—see Tables 2A and 2B for the rank order in respect of the 40 and 44 gene signatures, respectively).

Whilst Tables 3-45 provide an exemplary weight and bias for each gene in each signature, it will be appreciated that the gene signatures provided by these tables are not limited to the particular weights and biases given. Weight values may indicate the directionality of expression that is measured to indicate a positive signature score according to the invention. Thus, a positive weight indicates that an increase in gene expression contributes to a positive signature score/identification of DDRD biology and vice versa.

Suitable probes and probesets to investigate the expression of the genes included in Tables 3-45 are provided in Table 2C and Table 2D. In addition, suitable PCR assays to investigate the expression of the genes included in Tables 3-45 are provided in Table 2E.

TABLE 3

One gene signature

| Gene Names | Weight | Bias |
|---|---|---|
| CXCL10 | 0.137044 | 2.03931 |

TABLE 4

Two gene signature

| Gene Names | Weight | Bias |
|---|---|---|
| CXCL10 | 0.081638 | 2.03931 |
| MX1 | 0.080192 | 3.43549 |

TABLE 5

Three gene signature

| Gene Names | Weight | Bias |
|---|---|---|
| CXCL10 | 0.058512 | 2.03931 |
| IDO1 | 0.055977 | 0.725702 |
| MX1 | 0.057475 | 3.43549 |

TABLE 6

Four gene signature

| Gene Names | Weight | Bias |
|---|---|---|
| CXCL10 | 0.048331 | 2.03931 |
| IDO1 | 0.046238 | 0.725702 |
| IFI44L | 0.0401 | 1.17581 |
| MX1 | 0.047475 | 3.43549 |

TABLE 7

Five gene signature

| Gene Names | Weight | Bias |
|---|---|---|
| CD2 | 0.034275 | 4.09036 |
| CXCL10 | 0.041595 | 2.03931 |
| IDO1 | 0.039792 | 0.725702 |
| IFI44L | 0.034511 | 1.17581 |
| MX1 | 0.040858 | 3.43549 |

TABLE 8

Six gene signature

| Gene Names | Weight | Bias |
|---|---|---|
| CD2 | 0.030041 | 4.09036 |
| CXCL10 | 0.036456 | 2.03931 |
| GBP5 | 0.028552 | 1.39771 |
| IDO1 | 0.034877 | 0.725702 |
| IFI44L | 0.030247 | 1.17581 |
| MX1 | 0.03581 | 3.43549 |

TABLE 9

Seven gene signature

| Gene Names | Weight | Bias |
|---|---|---|
| CD2 | 0.025059 | 4.09036 |
| CXCL10 | 0.03041 | 2.03931 |
| GBP5 | 0.023817 | 1.39771 |
| IDO1 | 0.029093 | 0.725702 |
| IFI44L | 0.025231 | 1.17581 |
| MX1 | 0.029872 | 3.43549 |
| PRAME | 0.023355 | 2.2499 |

TABLE 10

Eight gene signature

| Gene Names | Weight | Bias |
|---|---|---|
| CD2 | 0.02446 | 4.09036 |
| CXCL10 | 0.029683 | 2.03931 |
| GBP5 | 0.023247 | 1.39771 |
| IDO1 | 0.028397 | 0.725702 |
| IFI44L | 0.024628 | 1.17581 |
| ITGAL | 0.022705 | 3.21615 |
| MX1 | 0.029157 | 3.43549 |
| PRAME | 0.022796 | 2.2499 |

TABLE 11

Nine gene signature

| Gene Names | Weight | Bias |
|---|---|---|
| CD2 | 0.023997 | 4.09036 |
| CXCL10 | 0.029122 | 2.03931 |
| GBP5 | 0.022807 | 1.39771 |
| IDO1 | 0.02786 | 0.725702 |
| IFI44L | 0.024162 | 1.17581 |
| ITGAL | 0.022275 | 3.21615 |
| LRP4 | −0.02008 | 0.306454 |
| MX1 | 0.028606 | 3.43549 |
| PRAME | 0.022365 | 2.2499 |

TABLE 12

Ten gene signature

| Gene Names | Weight | Bias |
|---|---|---|
| APOL3 | 0.017969 | 2.20356 |
| CD2 | 0.02255 | 4.09036 |
| CXCL10 | 0.027366 | 2.03931 |
| GBP5 | 0.021432 | 1.39771 |
| IDO1 | 0.02618 | 0.725702 |
| IFI44L | 0.022705 | 1.17581 |
| ITGAL | 0.020932 | 3.21615 |
| LRP4 | −0.01887 | 0.306454 |
| MX1 | 0.026881 | 3.43549 |
| PRAME | 0.021017 | 2.2499 |

TABLE 13

Eleven gene signature

| Gene Names | Weight | Bias |
|---|---|---|
| APOL3 | 0.018313 | 2.20356 |
| CD2 | 0.022983 | 4.09036 |
| CDR1 | −0.01806 | 4.79794 |
| CXCL10 | 0.027891 | 2.03931 |
| GBP5 | 0.021844 | 1.39771 |
| IDO1 | 0.026683 | 0.725702 |
| IFI44L | 0.023141 | 1.17581 |
| ITGAL | 0.021334 | 3.21615 |
| LRP4 | −0.01923 | 0.306454 |
| MX1 | 0.027397 | 3.43549 |
| PRAME | 0.02142 | 2.2499 |

TABLE 14

Twelve gene signature

| Gene Names | Weight | Bias |
|---|---|---|
| APOL3 | 0.017235 | 2.20356 |
| CD2 | 0.021629 | 4.09036 |
| CDR1 | −0.017 | 4.79794 |
| CXCL10 | 0.026248 | 2.03931 |
| FYB | 0.016949 | 1.56179 |
| GBP5 | 0.020557 | 1.39771 |
| IDO1 | 0.025111 | 0.725702 |
| IFI44L | 0.021778 | 1.17581 |
| ITGAL | 0.020077 | 3.21615 |
| LRP4 | −0.0181 | 0.306454 |
| MX1 | 0.025783 | 3.43549 |
| PRAME | 0.020158 | 2.2499 |

TABLE 15

Thirteen gene signature

| Gene Names | Weight | Bias |
|---|---|---|
| APOL3 | 0.017102 | 2.20356 |
| CD2 | 0.021463 | 4.09036 |
| CDR1 | −0.01687 | 4.79794 |
| CXCL10 | 0.026046 | 2.03931 |
| FYB | 0.016819 | 1.56179 |
| GBP5 | 0.020399 | 1.39771 |
| IDO1 | 0.024918 | 0.725702 |
| IFI44L | 0.02161 | 1.17581 |
| ITGAL | 0.019923 | 3.21615 |
| LRP4 | −0.01796 | 0.306454 |
| MX1 | 0.025585 | 3.43549 |
| PRAME | 0.020003 | 2.2499 |
| TSPAN7 | −0.01675 | 1.65843 |

TABLE 16

Fourteen gene signature

| Gene Names | Weight | Bias |
|---|---|---|
| APOL3 | 0.016213 | 2.20356 |
| CD2 | 0.020347 | 4.09036 |
| CDR1 | −0.01599 | 4.79794 |
| CXCL10 | 0.024692 | 2.03931 |
| FYB | 0.015945 | 1.56179 |
| GBP5 | 0.019338 | 1.39771 |
| IDO1 | 0.023622 | 0.725702 |
| IFI44L | 0.020487 | 1.17581 |
| ITGAL | 0.018887 | 3.21615 |
| LRP4 | −0.01703 | 0.306454 |
| MX1 | 0.024255 | 3.43549 |
| PRAME | 0.018963 | 2.2499 |
| RAC2 | 0.01586 | 3.03644 |
| TSPAN7 | −0.01588 | 1.65843 |

TABLE 17

Fifteen gene signature

| Gene Names | Weight | Bias |
|---|---|---|
| APOL3 | 0.015496 | 2.20356 |
| CD2 | 0.019447 | 4.09036 |
| CDR1 | −0.01528 | 4.79794 |
| CXCL10 | 0.023599 | 2.03931 |
| FYB | 0.015239 | 1.56179 |
| GBP5 | 0.018482 | 1.39771 |
| IDO1 | 0.022577 | 0.725702 |
| IFI44L | 0.01958 | 1.17581 |
| ITGAL | 0.018051 | 3.21615 |
| KLHDC7B | 0.014303 | 1.43954 |
| LRP4 | −0.01627 | 0.306454 |
| MX1 | 0.023181 | 3.43549 |
| PRAME | 0.018124 | 2.2499 |
| RAC2 | 0.015158 | 3.03644 |
| TSPAN7 | −0.01518 | 1.65843 |

TABLE 18

Sixteen gene signature

| Gene Names | Weight | Bias |
|---|---|---|
| APOL3 | 0.016001 | 2.20356 |
| CD2 | 0.020081 | 4.09036 |

TABLE 18-continued

Sixteen gene signature

| Gene Names | Weight | Bias |
|---|---|---|
| CDR1 | −0.01578 | 4.79794 |
| CXCL10 | 0.024369 | 2.03931 |
| FYB | 0.015736 | 1.56179 |
| GBP5 | 0.019085 | 1.39771 |
| GRB14 | 0.014473 | 0.269629 |
| IDO1 | 0.023313 | 0.725702 |
| IFI44L | 0.020219 | 1.17581 |
| ITGAL | 0.01864 | 3.21615 |
| KLHDC7B | 0.014769 | 1.43954 |
| LRP4 | −0.0168 | 0.306454 |
| MX1 | 0.023937 | 3.43549 |
| PRAME | 0.018715 | 2.2499 |
| RAC2 | 0.015653 | 3.03644 |
| TSPAN7 | −0.01567 | 1.65843 |

TABLE 19

Seventeen gene signature

| Gene Names | Weight | Bias |
|---|---|---|
| AC138128.1 | −0.01406 | 1.4071 |
| APOL3 | 0.015604 | 2.20356 |
| CD2 | 0.019583 | 4.09036 |
| CDR1 | −0.01539 | 4.79794 |
| CXCL10 | 0.023765 | 2.03931 |
| FYB | 0.015346 | 1.56179 |
| GBP5 | 0.018612 | 1.39771 |
| GRB14 | 0.014114 | 0.269629 |
| IDO1 | 0.022735 | 0.725702 |
| IFI44L | 0.019718 | 1.17581 |
| ITGAL | 0.018178 | 3.21615 |
| KLHDC7B | 0.014403 | 1.43954 |
| LRP4 | −0.01639 | 0.306454 |
| MX1 | 0.023344 | 3.43549 |
| PRAME | 0.018251 | 2.2499 |
| RAC2 | 0.015265 | 3.03644 |
| TSPAN7 | −0.01528 | 1.65843 |

TABLE 20

Eighteen gene signature

| Gene Names | Weight | Bias |
|---|---|---|
| AC138128.1 | −0.01401 | 1.4071 |
| APOL3 | 0.015556 | 2.20356 |
| CD2 | 0.019522 | 4.09036 |
| CDR1 | −0.01534 | 4.79794 |
| CXCL10 | 0.023691 | 2.03931 |
| FYB | 0.015298 | 1.56179 |
| GBP5 | 0.018554 | 1.39771 |
| GRB14 | 0.01407 | 0.269629 |
| IDO1 | 0.022665 | 0.725702 |
| IFI44L | 0.019656 | 1.17581 |
| ITGAL | 0.018121 | 3.21615 |
| KIF26A | −0.01397 | 2.05036 |
| KLHDC7B | 0.014359 | 1.43954 |
| LRP4 | −0.01634 | 0.306454 |
| MX1 | 0.023271 | 3.43549 |
| PRAME | 0.018194 | 2.2499 |
| RAC2 | 0.015217 | 3.03644 |
| TSPAN7 | −0.01524 | 1.65843 |

TABLE 21

Nineteen gene signature

| Gene Names | Weight | Bias |
|---|---|---|
| AC138128.1 | −0.01338 | 1.4071 |
| APOL3 | 0.014853 | 2.20356 |
| CD2 | 0.01864 | 4.09036 |
| CD274 | 0.013043 | 1.37297 |
| CDR1 | −0.01465 | 4.79794 |
| CXCL10 | 0.02262 | 2.03931 |
| FYB | 0.014607 | 1.56179 |
| GBP5 | 0.017716 | 1.39771 |
| GRB14 | 0.013434 | 0.269629 |
| IDO1 | 0.02164 | 0.725702 |
| IFI44L | 0.018768 | 1.17581 |
| ITGAL | 0.017302 | 3.21615 |
| KIF26A | −0.01334 | 2.05036 |
| KLHDC7B | 0.01371 | 1.43954 |
| LRP4 | −0.0156 | 0.306454 |
| MX1 | 0.022219 | 3.43549 |
| PRAME | 0.017372 | 2.2499 |
| RAC2 | 0.014529 | 3.03644 |
| TSPAN7 | −0.01455 | 1.65843 |

TABLE 22

Twenty gene signature

| Gene Names | Weight | Bias |
|---|---|---|
| AC138128.1 | −0.0137 | 1.4071 |
| APOL3 | 0.015205 | 2.20356 |
| CD109 | −0.01292 | 0.947671 |
| CD2 | 0.019081 | 4.09036 |
| CD274 | 0.013352 | 1.37297 |
| CDR1 | −0.015 | 4.79794 |
| CXCL10 | 0.023156 | 2.03931 |
| FYB | 0.014953 | 1.56179 |
| GBP5 | 0.018135 | 1.39771 |
| GRB14 | 0.013752 | 0.269629 |
| IDO1 | 0.022153 | 0.725702 |
| IFI44L | 0.019212 | 1.17581 |
| ITGAL | 0.017712 | 3.21615 |
| KIF26A | −0.01366 | 2.05036 |
| KLHDC7B | 0.014034 | 1.43954 |
| LRP4 | −0.01597 | 0.306454 |
| MX1 | 0.022746 | 3.43549 |
| PRAME | 0.017783 | 2.2499 |
| RAC2 | 0.014874 | 3.03644 |
| TSPAN7 | −0.01489 | 1.65843 |

TABLE 23

Twenty one gene signature

| Gene Names | Weight | Bias |
|---|---|---|
| AC138128.1 | −0.01327 | 1.4071 |
| APOL3 | 0.014725 | 2.20356 |
| CD109 | −0.01251 | 0.947671 |
| CD2 | 0.018479 | 4.09036 |
| CD274 | 0.012931 | 1.37297 |
| CDR1 | −0.01452 | 4.79794 |
| CXCL10 | 0.022425 | 2.03931 |
| ETV7 | 0.012047 | 1.46783 |
| FYB | 0.014481 | 1.56179 |
| GBP5 | 0.017563 | 1.39771 |
| GRB14 | 0.013318 | 0.269629 |
| IDO1 | 0.021453 | 0.725702 |
| IFI44L | 0.018606 | 1.17581 |
| ITGAL | 0.017153 | 3.21615 |
| KIF26A | −0.01323 | 2.05036 |

TABLE 23-continued

Twenty one gene signature

| Gene Names | Weight | Bias |
|---|---|---|
| KLHDC7B | 0.013591 | 1.43954 |
| LRP4 | −0.01546 | 0.306454 |
| MX1 | 0.022028 | 3.43549 |
| PRAME | 0.017222 | 2.2499 |
| RAC2 | 0.014404 | 3.03644 |
| TSPAN7 | −0.01442 | 1.65843 |

TABLE 24

Twenty two gene signature

| Gene Names | Weight | Bias |
|---|---|---|
| AC138128.1 | −0.01326 | 1.4071 |
| APOL3 | 0.014714 | 2.20356 |
| CD109 | −0.0125 | 0.947671 |
| CD2 | 0.018466 | 4.09036 |
| CD274 | 0.012921 | 1.37297 |
| CDR1 | −0.01451 | 4.79794 |
| CXCL10 | 0.022409 | 2.03931 |
| ETV7 | 0.012038 | 1.46783 |
| FYB | 0.014471 | 1.56179 |
| GBP5 | 0.01755 | 1.39771 |
| GRB14 | 0.013309 | 0.269629 |
| IDO1 | 0.021438 | 0.725702 |
| IFI44L | 0.018593 | 1.17581 |
| ITGAL | 0.017141 | 3.21615 |
| KIF26A | −0.01322 | 2.05036 |
| KLHDC7B | 0.013582 | 1.43954 |
| LRP4 | −0.01545 | 0.306454 |
| MFAP5 | −0.01172 | 2.69918 |
| MX1 | 0.022012 | 3.43549 |
| PRAME | 0.01721 | 2.2499 |
| RAC2 | 0.014394 | 3.03644 |
| TSPAN7 | −0.01441 | 1.65843 |

TABLE 25

Twenty three gene signature

| Gene Names | Weight | Bias |
|---|---|---|
| AC138128.1 | −0.01361 | 1.4071 |
| APOL3 | 0.015108 | 2.20356 |
| CD109 | −0.01284 | 0.947671 |
| CD2 | 0.018961 | 4.09036 |
| CD274 | 0.013268 | 1.37297 |
| CDR1 | −0.0149 | 4.79794 |
| CXCL10 | 0.02301 | 2.03931 |
| ETV7 | 0.012361 | 1.46783 |
| FYB | 0.014858 | 1.56179 |
| GBP5 | 0.018021 | 1.39771 |
| GRB14 | 0.013666 | 0.269629 |
| IDO1 | 0.022013 | 0.725702 |
| IFI44L | 0.019091 | 1.17581 |
| ITGAL | 0.0176 | 3.21615 |
| KIF26A | −0.01357 | 2.05036 |
| KLHDC7B | 0.013946 | 1.43954 |
| LRP4 | −0.01587 | 0.306454 |
| MFAP5 | −0.01204 | 2.69918 |
| MX1 | 0.022602 | 3.43549 |
| OLFM4 | −0.01167 | 0.636684 |
| PRAME | 0.017671 | 2.2499 |
| RAC2 | 0.01478 | 3.03644 |
| TSPAN7 | −0.0148 | 1.65843 |

TABLE 26

Twenty four gene signature

| Gene Names | Weight | Bias |
|---|---|---|
| AC138128.1 | −0.01365 | 1.4071 |
| APOL3 | 0.015148 | 2.20356 |
| CD109 | −0.01287 | 0.947671 |
| CD2 | 0.01901 | 4.09036 |
| CD274 | 0.013302 | 1.37297 |
| CDR1 | −0.01494 | 4.79794 |
| CXCL10 | 0.023069 | 2.03931 |
| ETV7 | 0.012393 | 1.46783 |
| FYB | 0.014897 | 1.56179 |
| GBP5 | 0.018068 | 1.39771 |
| GRB14 | 0.013701 | 0.269629 |
| IDO1 | 0.02207 | 0.725702 |
| IFI44L | 0.019141 | 1.17581 |
| ITGAL | 0.017646 | 3.21615 |
| KIF26A | −0.01361 | 2.05036 |
| KLHDC7B | 0.013982 | 1.43954 |
| LRP4 | −0.01591 | 0.306454 |
| MFAP5 | −0.01207 | 2.69918 |
| MX1 | 0.022661 | 3.43549 |
| OLFM4 | −0.0117 | 0.636684 |
| PI15 | −0.01146 | 0.335476 |
| PRAME | 0.017717 | 2.2499 |
| RAC2 | 0.014818 | 3.03644 |
| TSPAN7 | −0.01484 | 1.65843 |

TABLE 27

Twenty five gene signature

| Gene Names | Weight | Bias |
|---|---|---|
| AC138128.1 | −0.01342 | 1.4071 |
| APOL3 | 0.014899 | 2.20356 |
| CD109 | −0.01266 | 0.947671 |
| CD2 | 0.018698 | 4.09036 |
| CD274 | 0.013084 | 1.37297 |
| CDR1 | −0.0147 | 4.79794 |
| CXCL10 | 0.022691 | 2.03931 |
| ETV7 | 0.01219 | 1.46783 |
| FOSB | −0.01093 | 1.85886 |
| FYB | 0.014653 | 1.56179 |
| GBP5 | 0.017771 | 1.39771 |
| GRB14 | 0.013476 | 0.269629 |
| IDO1 | 0.021708 | 0.725702 |
| IFI44L | 0.018827 | 1.17581 |
| ITGAL | 0.017357 | 3.21615 |
| KIF26A | −0.01338 | 2.05036 |
| KLHDC7B | 0.013753 | 1.43954 |
| LRP4 | −0.01565 | 0.306454 |
| MFAP5 | −0.01187 | 2.69918 |
| MX1 | 0.022289 | 3.43549 |
| OLFM4 | −0.01151 | 0.636684 |
| PI15 | −0.01128 | 0.335476 |
| PRAME | 0.017426 | 2.2499 |
| RAC2 | 0.014575 | 3.03644 |
| TSPAN7 | −0.01459 | 1.65843 |

TABLE 28

Twenty six gene signature

| Gene Names | Weight | Bias |
|---|---|---|
| AC138128.1 | −0.01339 | 1.4071 |
| APOL3 | 0.014858 | 2.20356 |
| CD109 | −0.01262 | 0.947671 |
| CD2 | 0.018647 | 4.09036 |
| CD274 | 0.013048 | 1.37297 |

TABLE 28-continued

Twenty six gene signature

| Gene Names | Weight | Bias |
|---|---|---|
| CDR1 | −0.01465 | 4.79794 |
| CXCL10 | 0.022629 | 2.03931 |
| ETV7 | 0.012157 | 1.46783 |
| FAM19A5 | −0.01083 | 0.413683 |
| FOSB | −0.0109 | 1.85886 |
| FYB | 0.014613 | 1.56179 |
| GBP5 | 0.017723 | 1.39771 |
| GRB14 | 0.013439 | 0.269629 |
| IDO1 | 0.021649 | 0.725702 |
| IFI44L | 0.018775 | 1.17581 |
| ITGAL | 0.017309 | 3.21615 |
| KIF26A | −0.01335 | 2.05036 |
| KLHDC7B | 0.013715 | 1.43954 |
| LRP4 | −0.0156 | 0.306454 |
| MFAP5 | −0.01184 | 2.69918 |
| MX1 | 0.022228 | 3.43549 |
| OLFM4 | −0.01148 | 0.636684 |
| PI15 | −0.01125 | 0.335476 |
| PRAME | 0.017379 | 2.2499 |
| RAC2 | 0.014535 | 3.03644 |
| TSPAN7 | −0.01455 | 1.65843 |

TABLE 29

Twenty seven gene signature

| Gene Names | Weight | Bias |
|---|---|---|
| AC138128.1 | −0.01316 | 1.4071 |
| APOL3 | 0.014603 | 2.20356 |
| CD109 | −0.01241 | 0.947671 |
| CD2 | 0.018326 | 4.09036 |
| CD274 | 0.012824 | 1.37297 |
| CDR1 | −0.0144 | 4.79794 |
| CXCL10 | 0.022239 | 2.03931 |
| ETV7 | 0.011947 | 1.46783 |
| FAM19A5 | −0.01064 | 0.413683 |
| FOSB | −0.01071 | 1.85886 |
| FYB | 0.014361 | 1.56179 |
| GBP5 | 0.017417 | 1.39771 |
| GRB14 | 0.013208 | 0.269629 |
| IDO1 | 0.021276 | 0.725702 |
| IFI44L | 0.018452 | 1.17581 |
| ITGAL | 0.017011 | 3.21615 |
| KIF26A | −0.01312 | 2.05036 |
| KLHDC7B | 0.013479 | 1.43954 |
| LRP4 | −0.01534 | 0.306454 |
| MFAP5 | −0.01164 | 2.69918 |
| MX1 | 0.021845 | 3.43549 |
| NLRC5 | 0.009724 | 2.26863 |
| OLFM4 | −0.01128 | 0.636684 |
| PI15 | −0.01105 | 0.335476 |
| PRAME | 0.017079 | 2.2499 |
| RAC2 | 0.014285 | 3.03644 |
| TSPAN7 | −0.0143 | 1.65843 |

TABLE 30

Twenty eight gene signature

| Gene Names | Weight | Bias |
|---|---|---|
| AC138128.1 | −0.01326 | 1.4071 |
| APOL3 | 0.014712 | 2.20356 |
| CD109 | −0.0125 | 0.947671 |
| CD2 | 0.018464 | 4.09036 |
| CD274 | 0.01292 | 1.37297 |
| CDR1 | −0.01451 | 4.79794 |

TABLE 30-continued

Twenty eight gene signature

| Gene Names | Weight | Bias |
|---|---|---|
| CXCL10 | 0.022407 | 2.03931 |
| ETV7 | 0.012037 | 1.46783 |
| FAM19A5 | −0.01072 | 0.413683 |
| FOSB | −0.01079 | 1.85886 |
| FYB | 0.014469 | 1.56179 |
| GBP5 | 0.017548 | 1.39771 |
| GRB14 | 0.013307 | 0.269629 |
| IDO1 | 0.021436 | 0.725702 |
| IFI44L | 0.018591 | 1.17581 |
| ITGAL | 0.017139 | 3.21615 |
| KIF26A | −0.01322 | 2.05036 |
| KLHDC7B | 0.01358 | 1.43954 |
| LRP4 | −0.01545 | 0.306454 |
| MFAP5 | −0.01172 | 2.69918 |
| MX1 | 0.02201 | 3.43549 |
| NLRC5 | 0.009797 | 2.26863 |
| OLFM4 | −0.01137 | 0.636684 |
| PI15 | −0.01114 | 0.335476 |
| PRAME | 0.017208 | 2.2499 |
| PRICKLE1 | −0.00864 | 1.77018 |
| RAC2 | 0.014392 | 3.03644 |
| TSPAN7 | −0.01441 | 1.65843 |

TABLE 31

Twenty nine gene signature

| Gene Names | Weight | Bias |
|---|---|---|
| AC138128.1 | −0.01307 | 1.4071 |
| APOL3 | 0.014506 | 2.20356 |
| CD109 | −0.01232 | 0.947671 |
| CD2 | 0.018204 | 4.09036 |
| CD274 | 0.012739 | 1.37297 |
| CDR1 | −0.01431 | 4.79794 |
| CXCL10 | 0.022092 | 2.03931 |
| EGR1 | −0.00827 | 2.18651 |
| ETV7 | 0.011868 | 1.46783 |
| FAM19A5 | −0.01057 | 0.413683 |
| FOSB | −0.01064 | 1.85886 |
| FYB | 0.014266 | 1.56179 |
| GBP5 | 0.017302 | 1.39771 |
| GRB14 | 0.01312 | 0.269629 |
| IDO1 | 0.021135 | 0.725702 |
| IFI44L | 0.01833 | 1.17581 |
| ITGAL | 0.016898 | 3.21615 |
| KIF26A | −0.01303 | 2.05036 |
| KLHDC7B | 0.013389 | 1.43954 |
| LRP4 | −0.01523 | 0.306454 |
| MFAP5 | −0.01156 | 2.69918 |
| MX1 | 0.021701 | 3.43549 |
| NLRC5 | 0.009659 | 2.26863 |
| OLFM4 | −0.01121 | 0.636684 |
| PI15 | −0.01098 | 0.335476 |
| PRAME | 0.016966 | 2.2499 |
| PRICKLE1 | −0.00852 | 1.77018 |
| RAC2 | 0.01419 | 3.03644 |
| TSPAN7 | −0.01421 | 1.65843 |

TABLE 32

Thirty gene signature

| Gene Names | Weight | Bias |
|---|---|---|
| AC138128.1 | −0.01326 | 1.4071 |
| APOL3 | 0.014722 | 2.20356 |
| CD109 | −0.01251 | 0.947671 |

TABLE 32-continued

Thirty gene signature

| Gene Names | Weight | Bias |
|---|---|---|
| CD2 | 0.018476 | 4.09036 |
| CD274 | 0.012928 | 1.37297 |
| CDR1 | −0.01452 | 4.79794 |
| CLDN10 | −0.00834 | −0.34464 |
| CXCL10 | 0.022421 | 2.03931 |
| EGR1 | −0.00839 | 2.18651 |
| ETV7 | 0.012045 | 1.46783 |
| FAM19A5 | −0.01073 | 0.413683 |
| FOSB | −0.0108 | 1.85886 |
| FYB | 0.014478 | 1.56179 |
| GBP5 | 0.01756 | 1.39771 |
| GRB14 | 0.013316 | 0.269629 |
| IDO1 | 0.02145 | 0.725702 |
| IFI44L | 0.018603 | 1.17581 |
| ITGAL | 0.01715 | 3.21615 |
| KIF26A | −0.01323 | 2.05036 |
| KLHDC7B | 0.013589 | 1.43954 |
| LRP4 | −0.01546 | 0.306454 |
| MFAP5 | −0.01173 | 2.69918 |
| MX1 | 0.022024 | 3.43549 |
| NLRC5 | 0.009803 | 2.26863 |
| OLFM4 | −0.01137 | 0.636684 |
| PI15 | −0.01114 | 0.335476 |
| PRAME | 0.017219 | 2.2499 |
| PRICKLE1 | −0.00864 | 1.77018 |
| RAC2 | 0.014402 | 3.03644 |
| TSPAN7 | −0.01442 | 1.65843 |

TABLE 33

Thirty one gene signature

| Gene Names | Weight | Bias |
|---|---|---|
| AC138128.1 | −0.01339 | 1.4071 |
| ADAMTS4 | −0.00837 | 1.95693 |
| APOL3 | 0.014864 | 2.20356 |
| CD109 | −0.01263 | 0.947671 |
| CD2 | 0.018654 | 4.09036 |
| CD274 | 0.013053 | 1.37297 |
| CDR1 | −0.01466 | 4.79794 |
| CLDN10 | −0.00842 | −0.34464 |
| CXCL10 | 0.022638 | 2.03931 |
| EGR1 | −0.00847 | 2.18651 |
| ETV7 | 0.012161 | 1.46783 |
| FAM19A5 | −0.01083 | 0.413683 |
| FOSB | −0.0109 | 1.85886 |
| FYB | 0.014618 | 1.56179 |
| GBP5 | 0.017729 | 1.39771 |
| GRB14 | 0.013444 | 0.269629 |
| IDO1 | 0.021657 | 0.725702 |
| IFI44L | 0.018782 | 1.17581 |
| ITGAL | 0.017316 | 3.21615 |
| KIF26A | −0.01335 | 2.05036 |
| KLHDC7B | 0.01372 | 1.43954 |
| LRP4 | −0.01561 | 0.306454 |
| MFAP5 | −0.01184 | 2.69918 |
| MX1 | 0.022236 | 3.43549 |
| NLRC5 | 0.009898 | 2.26863 |
| OLFM4 | −0.01148 | 0.636684 |
| PI15 | −0.01125 | 0.335476 |
| PRAME | 0.017385 | 2.2499 |
| PRICKLE1 | −0.00873 | 1.77018 |
| RAC2 | 0.014541 | 3.03644 |
| TSPAN7 | −0.01456 | 1.65843 |

TABLE 34

Thirty two gene signature

| Gene Names | Weight | Bias |
|---|---|---|
| AC138128.1 | −0.01332 | 1.4071 |
| ADAMTS4 | −0.00832 | 1.95693 |
| APOL3 | 0.014789 | 2.20356 |
| CD109 | −0.01256 | 0.947671 |
| CD2 | 0.01856 | 4.09036 |
| CD274 | 0.012987 | 1.37297 |
| CDR1 | −0.01459 | 4.79794 |
| CLDN10 | −0.00838 | −0.34464 |
| CXCL10 | 0.022523 | 2.03931 |
| EGR1 | −0.00843 | 2.18651 |
| ETV7 | 0.0121 | 1.46783 |
| FAM19A5 | −0.01078 | 0.413683 |
| FOSB | −0.01085 | 1.85886 |
| FYB | 0.014544 | 1.56179 |
| GBP5 | 0.01764 | 1.39771 |
| GRB14 | 0.013377 | 0.269629 |
| IDO1 | 0.021548 | 0.725702 |
| IFI44L | 0.018688 | 1.17581 |
| ITGAL | 0.017228 | 3.21615 |
| KIF26A | −0.01329 | 2.05036 |
| KLHDC7B | 0.013651 | 1.43954 |
| LRP4 | −0.01553 | 0.306454 |
| MFAP5 | −0.01178 | 2.69918 |
| MX1 | 0.022124 | 3.43549 |
| NLRC5 | 0.009848 | 2.26863 |
| OLFM4 | −0.01143 | 0.636684 |
| PI15 | −0.01119 | 0.335476 |
| PRAME | 0.017298 | 2.2499 |
| PRICKLE1 | −0.00868 | 1.77018 |
| RAC2 | 0.014467 | 3.03644 |
| SP140L | 0.00825 | 0.550538 |
| TSPAN7 | −0.01449 | 1.65843 |

TABLE 35

Thirty three gene signature

| Gene Names | Weight | Bias |
|---|---|---|
| AC138128.1 | −0.01348 | 1.4071 |
| ADAMTS4 | −0.00842 | 1.95693 |
| ANXA1 | −0.0081 | 2.00146 |
| APOL3 | 0.014961 | 2.20356 |
| CD109 | −0.01271 | 0.947671 |
| CD2 | 0.018776 | 4.09036 |
| CD274 | 0.013138 | 1.37297 |
| CDR1 | −0.01476 | 4.79794 |
| CLDN10 | −0.00848 | −0.34464 |
| CXCL10 | 0.022785 | 2.03931 |
| EGR1 | −0.00853 | 2.18651 |
| ETV7 | 0.01224 | 1.46783 |
| FAM19A5 | −0.0109 | 0.413683 |
| FOSB | −0.01097 | 1.85886 |
| FYB | 0.014713 | 1.56179 |
| GBP5 | 0.017845 | 1.39771 |
| GRB14 | 0.013532 | 0.269629 |
| IDO1 | 0.021798 | 0.725702 |
| IFI44L | 0.018905 | 1.17581 |
| ITGAL | 0.017428 | 3.21615 |
| KIF26A | −0.01344 | 2.05036 |
| KLHDC7B | 0.01381 | 1.43954 |
| LRP4 | −0.01571 | 0.306454 |
| MFAP5 | −0.01192 | 2.69918 |
| MX1 | 0.022381 | 3.43549 |
| NLRC5 | 0.009962 | 2.26863 |
| OLFM4 | −0.01156 | 0.636684 |
| PI15 | −0.01132 | 0.335476 |
| PRAME | 0.017498 | 2.2499 |

TABLE 35-continued

Thirty three gene signature

| Gene Names | Weight | Bias |
|---|---|---|
| PRICKLE1 | −0.00878 | 1.77018 |
| RAC2 | 0.014635 | 3.03644 |
| SP140L | 0.008345 | 0.550538 |
| TSPAN7 | −0.01465 | 1.65843 |

TABLE 36

Thirty four gene signature

| Gene Names | Weight | Bias |
|---|---|---|
| AC138128.1 | −0.01334 | 1.4071 |
| ADAMTS4 | −0.00834 | 1.95693 |
| ANXA1 | −0.00802 | 2.00146 |
| APOL3 | 0.014812 | 2.20356 |
| CD109 | −0.01258 | 0.947671 |
| CD2 | 0.018589 | 4.09036 |
| CD274 | 0.013007 | 1.37297 |
| CDR1 | −0.01461 | 4.79794 |
| CLDN10 | −0.00839 | −0.34464 |
| CXCL10 | 0.022558 | 2.03931 |
| EGR1 | −0.00844 | 2.18651 |
| ETV7 | 0.012118 | 1.46783 |
| FAM19A5 | −0.0108 | 0.413683 |
| FOSB | −0.01086 | 1.85886 |
| FYB | 0.014567 | 1.56179 |
| GBP5 | 0.017667 | 1.39771 |
| GRB14 | 0.013397 | 0.269629 |
| IDO1 | 0.021581 | 0.725702 |
| IFI44L | 0.018716 | 1.17581 |
| ITGAL | 0.017255 | 3.21615 |
| KIF26A | −0.01331 | 2.05036 |
| KLHDC7B | 0.013672 | 1.43954 |
| LRP4 | −0.01556 | 0.306454 |
| MFAP5 | −0.0118 | 2.69918 |
| MX1 | 0.022159 | 3.43549 |
| NLRC5 | 0.009863 | 2.26863 |
| OLFM4 | −0.01144 | 0.636684 |
| PI15 | −0.01121 | 0.335476 |
| PRAME | 0.017324 | 2.2499 |
| PRICKLE1 | −0.0087 | 1.77018 |
| RAC2 | 0.01449 | 3.03644 |
| RSAD2 | 0.007894 | 1.44894 |
| SP140L | 0.008262 | 0.550538 |
| TSPAN7 | −0.01451 | 1.65843 |

TABLE 37

Thirty five gene signature

| Gene Names | Weight | Bias |
|---|---|---|
| AC138128.1 | −0.0137 | 1.4071 |
| ADAMTS4 | −0.00856 | 1.95693 |
| ANXA1 | −0.00823 | 2.00146 |
| APOL3 | 0.015208 | 2.20356 |
| CD109 | −0.01292 | 0.947671 |
| CD2 | 0.019085 | 4.09036 |
| CD274 | 0.013355 | 1.37297 |
| CDR1 | −0.015 | 4.79794 |
| CLDN10 | −0.00862 | −0.34464 |
| CXCL10 | 0.023161 | 2.03931 |
| EGR1 | −0.00867 | 2.18651 |
| ESR1 | 0.007943 | 0.851213 |
| ETV7 | 0.012442 | 1.46783 |
| FAM19A5 | −0.01108 | 0.413683 |
| FOSB | −0.01115 | 1.85886 |
| FYB | 0.014956 | 1.56179 |

TABLE 37-continued

Thirty five gene signature

| Gene Names | Weight | Bias |
|---|---|---|
| GBP5 | 0.018139 | 1.39771 |
| GRB14 | 0.013755 | 0.269629 |
| IDO1 | 0.022157 | 0.725702 |
| IFI44L | 0.019216 | 1.17581 |
| ITGAL | 0.017716 | 3.21615 |
| KIF26A | −0.01366 | 2.05036 |
| KLHDC7B | 0.014037 | 1.43954 |
| LRP4 | −0.01597 | 0.306454 |
| MFAP5 | −0.01212 | 2.69918 |
| MX1 | 0.022751 | 3.43549 |
| NLRC5 | 0.010127 | 2.26863 |
| OLFM4 | −0.01175 | 0.636684 |
| PI15 | −0.01151 | 0.335476 |
| PRAME | 0.017787 | 2.2499 |
| PRICKLE1 | −0.00893 | 1.77018 |
| RAC2 | 0.014877 | 3.03644 |
| RSAD2 | 0.008105 | 1.44894 |
| SP140L | 0.008483 | 0.550538 |
| TSPAN7 | −0.0149 | 1.65843 |

TABLE 38

Thirty six gene signature

| Gene Names | Weight | Bias |
|---|---|---|
| AC138128.1 | −0.01359 | 1.4071 |
| ADAMTS4 | −0.00849 | 1.95693 |
| ANXA1 | −0.00816 | 2.00146 |
| APOL3 | 0.015081 | 2.20356 |
| CD109 | −0.01281 | 0.947671 |
| CD2 | 0.018926 | 4.09036 |
| CD274 | 0.013244 | 1.37297 |
| CDR1 | −0.01487 | 4.79794 |
| CLDN10 | −0.00855 | −0.34464 |
| CXCL10 | 0.022968 | 2.03931 |
| EGR1 | −0.0086 | 2.18651 |
| ESR1 | 0.007876 | 0.851213 |
| ETV7 | 0.012338 | 1.46783 |
| FAM19A5 | −0.01099 | 0.413683 |
| FOSB | −0.01106 | 1.85886 |
| FYB | 0.014831 | 1.56179 |
| GBP5 | 0.017988 | 1.39771 |
| GRB14 | 0.01364 | 0.269629 |
| IDO1 | 0.021973 | 0.725702 |
| IFI44L | 0.019056 | 1.17581 |
| IKZF3 | 0.007318 | −0.58991 |
| ITGAL | 0.017568 | 3.21615 |
| KIF26A | −0.01355 | 2.05036 |
| KLHDC7B | 0.01392 | 1.43954 |
| LRP4 | −0.01584 | 0.306454 |
| MFAP5 | −0.01202 | 2.69918 |
| MX1 | 0.022561 | 3.43549 |
| NLRC5 | 0.010042 | 2.26863 |
| OLFM4 | −0.01165 | 0.636684 |
| PI15 | −0.01141 | 0.335476 |
| PRAME | 0.017639 | 2.2499 |
| PRICKLE1 | −0.00885 | 1.77018 |
| RAC2 | 0.014753 | 3.03644 |
| RSAD2 | 0.008038 | 1.44894 |
| SP140L | 0.008412 | 0.550538 |
| TSPAN7 | −0.01477 | 1.65843 |

TABLE 39

Thirty seven gene signature

| Gene Names | Weight | Bias |
|---|---|---|
| AC138128.1 | −0.01342 | 1.4071 |
| ADAMTS4 | −0.00838 | 1.95693 |
| ANXA1 | −0.00806 | 2.00146 |
| APOL3 | 0.014896 | 2.20356 |
| CD109 | −0.01265 | 0.947671 |
| CD2 | 0.018694 | 4.09036 |
| CD274 | 0.013081 | 1.37297 |
| CDR1 | −0.01469 | 4.79794 |
| CLDN10 | −0.00844 | −0.34464 |
| CXCL10 | 0.022686 | 2.03931 |
| EGR1 | −0.00849 | 2.18651 |
| ESR1 | 0.00778 | 0.851213 |
| ETV7 | 0.012187 | 1.46783 |
| FAM19A5 | −0.01086 | 0.413683 |
| FOSB | −0.01092 | 1.85886 |
| FYB | 0.014649 | 1.56179 |
| GBP5 | 0.017767 | 1.39771 |
| GRB14 | 0.013473 | 0.269629 |
| IDO1 | 0.021703 | 0.725702 |
| IFI44L | 0.018823 | 1.17581 |
| IKZF3 | 0.007228 | −0.58991 |
| ITGAL | 0.017353 | 3.21615 |
| KIF26A | −0.01338 | 2.05036 |
| KLHDC7B | 0.01375 | 1.43954 |
| LRP4 | −0.01564 | 0.306454 |
| MFAP5 | −0.01187 | 2.69918 |
| MX1 | 0.022284 | 3.43549 |
| NLRC5 | 0.009919 | 2.26863 |
| OLFM4 | −0.01151 | 0.636684 |
| OR2I1P | 0.00685 | −1.30235 |
| PI15 | −0.01127 | 0.335476 |
| PRAME | 0.017422 | 2.2499 |
| PRICKLE1 | −0.00875 | 1.77018 |
| RAC2 | 0.014572 | 3.03644 |
| RSAD2 | 0.007939 | 1.44894 |
| SP140L | 0.008309 | 0.550538 |
| TSPAN7 | −0.01459 | 1.65843 |

TABLE 40

Thirty eight gene signature

| Gene Names | Weight | Bias |
|---|---|---|
| AC138128.1 | −0.01345 | 1.4071 |
| ADAMTS4 | −0.0084 | 1.95693 |
| ANXA1 | −0.00808 | 2.00146 |
| APOL3 | 0.014924 | 2.20356 |
| CD109 | −0.01268 | 0.947671 |
| CD2 | 0.01873 | 4.09036 |
| CD274 | 0.013106 | 1.37297 |
| CDR1 | −0.01472 | 4.79794 |
| CLDN10 | −0.00846 | −0.34464 |
| CXCL10 | 0.022729 | 2.03931 |
| EGFR | −0.00649 | −0.17669 |
| EGR1 | −0.00851 | 2.18651 |
| ESR1 | 0.007795 | 0.851213 |
| ETV7 | 0.01221 | 1.46783 |
| FAM19A5 | −0.01088 | 0.413683 |
| FOSB | −0.01095 | 1.85886 |
| FYB | 0.014677 | 1.56179 |
| GBP5 | 0.017801 | 1.39771 |
| GRB14 | 0.013499 | 0.269629 |
| IDO1 | 0.021745 | 0.725702 |
| IFI44L | 0.018858 | 1.17581 |
| IKZF3 | 0.007242 | −0.58991 |
| ITGAL | 0.017386 | 3.21615 |
| KIF26A | −0.01341 | 2.05036 |
| KLHDC7B | 0.013776 | 1.43954 |
| LRP4 | −0.01567 | 0.306454 |
| MFAP5 | −0.01189 | 2.69918 |

TABLE 40-continued

Thirty eight gene signature

| Gene Names | Weight | Bias |
|---|---|---|
| MX1 | 0.022327 | 3.43549 |
| NLRC5 | 0.009938 | 2.26863 |
| OLFM4 | −0.01153 | 0.636684 |
| OR2I1P | 0.006863 | −1.30235 |
| PI15 | −0.0113 | 0.335476 |
| PRAME | 0.017456 | 2.2499 |
| PRICKLE1 | −0.00876 | 1.77018 |
| RAC2 | 0.0146 | 3.03644 |
| RSAD2 | 0.007954 | 1.44894 |
| SP140L | 0.008325 | 0.550538 |
| TSPAN7 | −0.01462 | 1.65843 |

TABLE 41

Thirty nine gene signature

| Gene Names | Weight | Bias |
|---|---|---|
| AC138128.1 | −0.01356 | 1.4071 |
| ADAMTS4 | −0.00847 | 1.95693 |
| ANXA1 | −0.00815 | 2.00146 |
| APOL3 | 0.015054 | 2.20356 |
| CD109 | −0.01279 | 0.947671 |
| CD2 | 0.018892 | 4.09036 |
| CD274 | 0.01322 | 1.37297 |
| CDR1 | −0.01485 | 4.79794 |
| CLDN10 | −0.00853 | −0.34464 |
| CXCL10 | 0.022926 | 2.03931 |
| EGFR | −0.00654 | −0.17669 |
| EGR1 | −0.00858 | 2.18651 |
| ESR1 | 0.007862 | 0.851213 |
| ETV7 | 0.012316 | 1.46783 |
| FAM19A5 | −0.01097 | 0.413683 |
| FOSB | −0.01104 | 1.85886 |
| FYB | 0.014805 | 1.56179 |
| GBP5 | 0.017955 | 1.39771 |
| GRB14 | 0.013616 | 0.269629 |
| IDO1 | 0.021933 | 0.725702 |
| IFI44L | 0.019022 | 1.17581 |
| IKZF3 | 0.007305 | −0.58991 |
| ITGAL | 0.017536 | 3.21615 |
| KIF26A | −0.01352 | 2.05036 |
| KLHDC7B | 0.013895 | 1.43954 |
| LRP4 | −0.01581 | 0.306454 |
| MFAP5 | −0.012 | 2.69918 |
| MX1 | 0.02252 | 3.43549 |
| NAT1 | 0.006442 | −0.79732 |
| NLRC5 | 0.010024 | 2.26863 |
| OLFM4 | −0.01163 | 0.636684 |
| OR2I1P | 0.006922 | −1.30235 |
| PI15 | −0.01139 | 0.335476 |
| PRAME | 0.017607 | 2.2499 |
| PRICKLE1 | −0.00884 | 1.77018 |
| RAC2 | 0.014726 | 3.03644 |
| RSAD2 | 0.008023 | 1.44894 |
| SP140L | 0.008397 | 0.550538 |
| TSPAN7 | −0.01474 | 1.65843 |

TABLE 42

Forty gene signature

| Gene Names | Weight | Bias |
|---|---|---|
| AC138128.1 | −0.01357 | 1.4071 |
| ADAMTS4 | −0.00848 | 1.95693 |
| ANXA1 | −0.00815 | 2.00146 |
| APOL3 | 0.015057 | 2.20356 |

TABLE 42-continued

Forty gene signature

| Gene Names | Weight | Bias |
|---|---|---|
| CD109 | −0.01279 | 0.947671 |
| CD2 | 0.018896 | 4.09036 |
| CD274 | 0.013223 | 1.37297 |
| CDR1 | −0.01485 | 4.79794 |
| CLDN10 | −0.00853 | −0.34464 |
| CXCL10 | 0.022931 | 2.03931 |
| EGFR | −0.00654 | −0.17669 |
| EGR1 | −0.00858 | 2.18651 |
| ESR1 | 0.007864 | 0.851213 |
| ETV7 | 0.012319 | 1.46783 |
| FAM19A5 | −0.01097 | 0.413683 |
| FOSB | −0.01104 | 1.85886 |
| FYB | 0.014808 | 1.56179 |
| GBP5 | 0.017959 | 1.39771 |
| GRB14 | 0.013619 | 0.269629 |
| IDO1 | 0.021938 | 0.725702 |
| IFI44L | 0.019026 | 1.17581 |
| IKZF3 | 0.007306 | −0.58991 |
| ITGAL | 0.01754 | 3.21615 |
| KIF26A | −0.01353 | 2.05036 |
| KLHDC7B | 0.013898 | 1.43954 |
| LATS2 | −0.00622 | 0.486251 |
| LRP4 | −0.01581 | 0.306454 |
| MFAP5 | −0.012 | 2.69918 |
| MX1 | 0.022525 | 3.43549 |
| NAT1 | 0.006444 | −0.79732 |
| NLRC5 | 0.010026 | 2.26863 |
| OLFM4 | −0.01163 | 0.636684 |
| OR2I1P | 0.006924 | −1.30235 |
| PI15 | −0.0114 | 0.335476 |
| PRAME | 0.017611 | 2.2499 |
| PRICKLE1 | −0.00884 | 1.77018 |
| RAC2 | 0.014729 | 3.03644 |
| RSAD2 | 0.008025 | 1.44894 |
| SP140L | 0.008399 | 0.550538 |
| TSPAN7 | −0.01475 | 1.65843 |

TABLE 43

Forty one gene signature

| Gene Names | Weight | Bias |
|---|---|---|
| AC138128.1 | −0.01374 | 1.4071 |
| ADAMTS4 | −0.00859 | 1.95693 |
| ANXA1 | −0.00826 | 2.00146 |
| APOL3 | 0.015253 | 2.20356 |
| CD109 | −0.01296 | 0.947671 |
| CD2 | 0.019143 | 4.09036 |
| CD274 | 0.013395 | 1.37297 |
| CDR1 | −0.01504 | 4.79794 |
| CLDN10 | −0.00864 | −0.34464 |
| CXCL10 | 0.02323 | 2.03931 |
| CYP2B6 | 0.006181 | 0.921835 |
| EGFR | −0.00663 | −0.17669 |
| EGR1 | −0.00869 | 2.18651 |
| ESR1 | 0.007966 | 0.851213 |
| ETV7 | 0.01248 | 1.46783 |
| FAM19A5 | −0.01112 | 0.413683 |
| FOSB | −0.01119 | 1.85886 |
| FYB | 0.015001 | 1.56179 |
| GBP5 | 0.018194 | 1.39771 |
| GRB14 | 0.013797 | 0.269629 |
| IDO1 | 0.022224 | 0.725702 |
| IFI44L | 0.019274 | 1.17581 |
| IKZF3 | 0.007402 | −0.58991 |
| ITGAL | 0.017769 | 3.21615 |
| KIF26A | −0.0137 | 2.05036 |
| KLHDC7B | 0.014079 | 1.43954 |
| LATS2 | −0.0063 | 0.486251 |
| LRP4 | −0.01602 | 0.306454 |

TABLE 43-continued

Forty one gene signature

| Gene Names | Weight | Bias |
|---|---|---|
| MFAP5 | −0.01215 | 2.69918 |
| MX1 | 0.022819 | 3.43549 |
| NAT1 | 0.006528 | −0.79732 |
| NLRC5 | 0.010157 | 2.26863 |
| OLFM4 | −0.01178 | 0.636684 |
| OR2I1P | 0.007014 | −1.30235 |
| PI15 | −0.01154 | 0.335476 |
| PRAME | 0.01784 | 2.2499 |
| PRICKLE1 | −0.00896 | 1.77018 |
| RAC2 | 0.014921 | 3.03644 |
| RSAD2 | 0.00813 | 1.44894 |
| SP140L | 0.008509 | 0.550538 |
| TSPAN7 | −0.01494 | 1.65843 |

TABLE 44

Forty two gene signature

| Gene Names | Weight | Bias |
|---|---|---|
| AC138128.1 | −0.01365 | 1.4071 |
| ADAMTS4 | −0.00853 | 1.95693 |
| ANXA1 | −0.0082 | 2.00146 |
| APOL3 | 0.015146 | 2.20356 |
| CD109 | −0.01287 | 0.947671 |
| CD2 | 0.019008 | 4.09036 |
| CD274 | 0.013301 | 1.37297 |
| CDR1 | −0.01494 | 4.79794 |
| CLDN10 | −0.00858 | −0.34464 |
| CXCL10 | 0.023067 | 2.03931 |
| CYP2B6 | 0.006138 | 0.921835 |
| EGFR | −0.00658 | −0.17669 |
| EGR1 | −0.00863 | 2.18651 |
| ESR1 | 0.00791 | 0.851213 |
| ETV7 | 0.012392 | 1.46783 |
| FAM19A5 | −0.01104 | 0.413683 |
| FOSB | −0.01111 | 1.85886 |
| FYB | 0.014895 | 1.56179 |
| GBP5 | 0.018065 | 1.39771 |
| GRB14 | 0.013699 | 0.269629 |
| IDO1 | 0.022067 | 0.725702 |
| IFI44L | 0.019138 | 1.17581 |
| IKZF3 | 0.00735 | −0.58991 |
| ITGAL | 0.017644 | 3.21615 |
| KIF26A | −0.01361 | 2.05036 |
| KLHDC7B | 0.01398 | 1.43954 |
| LATS2 | −0.00626 | 0.486251 |
| LRP4 | −0.01591 | 0.306454 |
| MFAP5 | −0.01207 | 2.69918 |
| MX1 | 0.022658 | 3.43549 |
| NAT1 | 0.006482 | −0.79732 |
| NLRC5 | 0.010085 | 2.26863 |
| OLFM4 | −0.0117 | 0.636684 |
| OR2I1P | 0.006965 | −1.30235 |
| PI15 | −0.01146 | 0.335476 |
| PRAME | 0.017715 | 2.2499 |
| PRICKLE1 | −0.00889 | 1.77018 |
| PTPRC | 0.005152 | −1.11824 |
| RAC2 | 0.014816 | 3.03644 |
| RSAD2 | 0.008072 | 1.44894 |
| SP140L | 0.008449 | 0.550538 |
| TSPAN7 | −0.01484 | 1.65843 |

TABLE 45

Forty three gene signature

| Gene Names | Weight | Bias |
|---|---|---|
| AC138128.1 | −0.01364 | 1.4071 |
| ADAMTS4 | −0.00852 | 1.95693 |
| ANXA1 | −0.0082 | 2.00146 |
| APOL3 | 0.015139 | 2.20356 |
| CD109 | −0.01286 | 0.947671 |
| CD2 | 0.018999 | 4.09036 |
| CD274 | 0.013295 | 1.37297 |
| CDR1 | −0.01493 | 4.79794 |
| CLDN10 | −0.00858 | −0.34464 |
| CXCL10 | 0.023056 | 2.03931 |
| CYP2B6 | 0.006135 | 0.921835 |
| EGFR | −0.00658 | −0.17669 |
| EGR1 | −0.00863 | 2.18651 |
| ESR1 | 0.007907 | 0.851213 |
| ETV7 | 0.012386 | 1.46783 |
| FAM19A5 | −0.01103 | 0.413683 |
| FOSB | −0.0111 | 1.85886 |
| FYB | 0.014889 | 1.56179 |
| GBP5 | 0.018057 | 1.39771 |
| GRB14 | 0.013693 | 0.269629 |
| IDO1 | 0.022057 | 0.725702 |
| IFI44L | 0.01913 | 1.17581 |
| IKZF3 | 0.007346 | −0.58991 |
| ITGAL | 0.017636 | 3.21615 |
| KIF26A | −0.0136 | 2.05036 |
| KLHDC7B | 0.013974 | 1.43954 |
| LATS2 | −0.00625 | 0.486251 |
| LRP4 | −0.0159 | 0.306454 |
| MFAP5 | −0.01206 | 2.69918 |
| MX1 | 0.022648 | 3.43549 |
| NAT1 | 0.006479 | −0.79732 |
| NLRC5 | 0.010081 | 2.26863 |
| OLFM4 | −0.0117 | 0.636684 |
| OR2I1P | 0.006962 | −1.30235 |
| PI15 | −0.01146 | 0.335476 |
| PPP1R1A | −0.0041 | 1.76371 |
| PRAME | 0.017707 | 2.2499 |
| PRICKLE1 | −0.00889 | 1.77018 |
| PTPRC | 0.00515 | −1.11824 |
| RAC2 | 0.01481 | 3.03644 |
| RSAD2 | 0.008069 | 1.44894 |
| SP140L | 0.008445 | 0.550538 |
| TSPAN7 | −0.01483 | 1.65843 |

Measuring Gene Expression Using Classifier Models

A variety of methods have been utilized in an attempt to identify biomarkers and diagnose disease. For protein-based markers, these include two-dimensional electrophoresis, mass spectrometry, and immunoassay methods. For nucleic acid markers, these include mRNA expression profiles, microRNA profiles, FISH, serial analysis of gene expression (SAGE), methylation profiles, and large-scale gene expression arrays.

When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is one that is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression.

Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143, 854; 5,288,644; 5,324,633; 5,432,049; 5,470,710; 5,492, 806; 5,503,980; 5,510,270; 5,525,464; 5,547,839; 5,580, 732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Creating a Biomarker Expression Classifier

In one embodiment, the relative expression levels of biomarkers in a cancer tissue are measured to form a gene expression profile. The gene expression profile of a set of biomarkers from a patient tissue sample is summarized in the form of a compound decision score and compared to a score threshold that is mathematically derived from a training set of patient data. The score threshold separates a patient group based on different characteristics such as, but not limited to, responsiveness/non-responsiveness to treatment. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. The threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc. Using a linear classifier on the normalized data to make a diagnostic or prognostic call (e.g. responsiveness or resistance to therapeutic agent) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is above the score threshold (decision function positive) or below (decision function negative).

Effectively, this means that the data space, i.e. the set of all possible combinations of biomarker expression values, is split into two mutually exclusive halves corresponding to different clinical classifications or predictions, e.g. one corresponding to responsiveness to a therapeutic agent and the other to resistance. In the context of the overall classifier, relative over-expression of a certain biomarker can either increase the decision score (positive weight) or reduce it (negative weight) and thus contribute to an overall decision of, for example, responsiveness or resistance to a therapeutic agent.

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In a preferred embodiment of the present method, Partial Least Squares Discriminant Analysis (PLS-DA) is used for determining the weights. (L. Ståhle, S. Wold, J. Chemom. 1 (1987) 185-196; D. V. Nguyen, D. M. Rocke, Bioinformatics 18 (2002) 39-50). Other methods for performing the classification, known to those skilled in the art, may also be with the methods described herein when applied to the transcripts of a cancer classifier.

Different methods can be used to convert quantitative data measured on these biomarkers into a prognosis or other predictive use. These methods include, but not limited to methods from the fields of pattern recognition (Duda et al. Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998).

In a training step, a set of patient samples for both responsiveness/resistance cases are measured and the prediction method is optimised using the inherent information from this training data to optimally predict the training set or a future sample set. In this training step, the used method is trained or parameterised to predict from a specific intensity pattern to a specific predictive call. Suitable transformation or pre-processing steps might be performed with the measured data before it is subjected to the prognostic method or algorithm.

In a preferred embodiment of the invention, a weighted sum of the pre-processed intensity values for each transcript is formed and compared with a threshold value optimised on the training set (Duda et al. Pattern Classification, $2^{nd}$ ed., John Wiley, New York 2001). The weights can be derived by a multitude of linear classification methods, including but not limited to Partial Least Squares (PLS, (Nguyen et al., 2002, Bioinformatics 18 (2002) 39-50)) or Support Vector Machines (SVM, (Schölkopf et al. Learning with Kernels, MIT Press, Cambridge 2002)).

In another embodiment of the invention, the data is transformed non-linearly before applying a weighted sum as described above. This non-linear transformation might include increasing the dimensionality of the data. The non-linear transformation and weighted summation might also be performed implicitly, e.g. through the use of a kernel function. (Schölkopf et al. Learning with Kernels, MIT Press, Cambridge 2002).

In another embodiment of the invention, a new data sample is compared with two or more class prototypes, being either real measured training samples or artificially created prototypes. This comparison is performed using suitable similarity measures, for example, but not limited to Euclidean distance (Duda et al. Pattern Classification, 2nd ed., John Wiley, New York 2001), correlation coefficient (Van't Veer, et al. 2002, Nature 415:530) etc. A new sample is then assigned to the prognostic group with the closest prototype or the highest number of prototypes in the vicinity.

In another embodiment of the invention, decision trees (Hastie et al., The Elements of Statistical Learning, Springer, New York 2001) or random forests (Breiman, Random Forests, Machine Learning 45:5 2001) are used to make a prognostic call from the measured intensity data for the transcript set or their products.

In another embodiment of the invention neural networks (Bishop, Neural Networks for Pattern Recognition, Clarendon Press, Oxford 1995) are used to make a prognostic call from the measured intensity data for the transcript set or their products.

In another embodiment of the invention, discriminant analysis (Duda et al., Pattern Classification, $2^{nd}$ ed., John Wiley, New York 2001), comprising but not limited to linear, diagonal linear, quadratic and logistic discriminant analysis, is used to make a prognostic call from the measured intensity data for the transcript set or their products.

In another embodiment of the invention, Prediction Analysis for Microarrays (PAM, (Tibshirani et al., 2002, Proc. Natl. Acad. Sci. USA 99:6567-6572)) is used to make a prognostic call from the measured intensity data for the transcript set or their products.

In another embodiment of the invention, Soft Independent Modelling of Class Analogy (SIMCA, (Wold, 1976, Pattern Recogn. 8:127-139)) is used to make a predictive call from the measured intensity data for the transcript set or their products.

Therapeutic Agents

As described above, the methods described herein permit the classification of a patient as responsive or non-responsive to a therapeutic agent that targets tumors with increased immune signaling associated with abnormal DNA repair. In particular, the therapeutic agents may be immune checkpoint therapies, such as antagonists of an inhibitory immune checkpoint and/or agonists of a stimulatory immune checkpoint. In some embodiments, the inhibitory immune checkpoint is selected from A2AR, B7-H3 (CD276), B7-H4 (VTCN1), BTLA (CD272), CTLA-4 (CD152), IDO, KIR, LAG3, PD-1/PD-L1, TIM-3 and VISTA. In some embodiments, the inhibitory immune checkpoint is not PD-1/PD-L1. In some embodiments, the inhibitory immune checkpoint is IDO. In some embodiments, the antagonist of an inhibitory immune checkpoint is selected from an antibody and an inhibitory nucleic acid molecule as defined herein. In some embodiments, the antagonist of an inhibitory immune checkpoint is selected from MGA271 (targets B7-H3), ipilimumab (Yervoy—targets CTLA-4), indoximod (targets IDO pathway), NLG919 (targets IDO pathway), lirilumab (targets KIR), IMP321 (targets LAG3), BMS-986016 (targets LAG3), CT-011 (PD-1 blockade), nivolumab/BMS-936558 (PD-1 blockade), BMS-936559 (PDL1 blockade) and pembrolizumab (Keytruda—targets PD-1), optionally wherein the antagonist is not pembrolizumab. In some embodiments, the stimulatory immune checkpoint is selected from CD27, CD28, CD40, CD122, CD137, OX40, GITR and ICOS. In some embodiments, the agonist of a stimulatory immune checkpoint is selected from an antibody, a lipocalin and a cytokine, as defined herein. In some embodiments, the agonist of a stimulatory immune checkpoint is selected from CDX-1127 (agonist of CD27), NKTR-214 (agonist of CD122), BMS-663513 (agonist of CD137), TRX518 (agonist of GITR), CP-870893 (CD40 agonist), MEDI0562, MEDI6469 and MEDI6383 (OX40 agonists).

In some embodiments, the immune checkpoint therapies, such as antagonists of an inhibitory immune checkpoint and/or agonists of a stimulatory immune checkpoint may be administered in combination with a "DNA-damage therapeutic agent". As used herein "DNA-damage therapeutic agent" includes agents known to damage DNA directly, agents that prevent DNA damage repair, agents that inhibit DNA damage signaling, agents that inhibit DNA damage induced cell cycle arrest, and agents that inhibit processes indirectly leading to DNA damage. Some current such therapeutics used to treat cancer include, but are not limited to, the following DNA-damage therapeutic agents.

1) DNA damaging agents:
   a. Alkylating agents (platinum containing agents such as cisplatin, carboplatin, and oxaliplatin; cyclophosphamide; busulphan).
   b. Topoisomerase I inhibitors (irinotecan; topotecan)
   c. Topisomerase II inhibitors (etoposide;anthracylcines such as doxorubicin and epirubicin)
   d. Ionising radiation
2) DNA repair targeted therapies
   a. Inhibitors of Non-homologous end-joining (DNA-PK inhibitors, Nu7441, NU7026)
   b. Inhibitors of homologous recombination
   c. Inhibitors of nucleotide excision repair
   d. Inhibitors of base excision repair (PARP inhibitors, AG014699, AZD2281, ABT-888, MK4827, BSI-201, INO-1001, TRC-102, APEX 1 inhibitors, APEX 2 inhibitors, Ligase III inhibitors
   e. Inhibitors of the Fanconi anemia pathway
3) Inhibitors of DNA damage signalling
   a. ATM inhibitors (CP466722, KU-55933)
   b. CHK 1 inhibitors (XL-844, UCN-01, AZD7762, PF00477736)
   c. CHK 2 inhibitors (XL-844, AZD7762, PF00477736)
4) Inhibitors of DNA damage induced cell cycle arrest
   a. Wee1 kinase inhibitors
   b. CDC25a, b or c inhibitors 5) Inhibition of processes indirectly leading to DNA damage
   a. Histone deacetylase inhibitors
   b. Heat shock protein inhibitors (geldanamycin, AUY922), Diseases and Tissue Sources The predictive classifiers described herein are useful for determining responsiveness or resistance to a therapeutic agent for treating cancer. The biological pathway described herein is a feature of cancer itself, similar to grade and stage, and as such, is not limited to a single cancer disease type. Therefore, the collection of genes or gene products may be used to predict responsiveness of cancer therapeutics across different cancer types in different tissues. In one embodiment, this collection of genes or gene products is useful for evaluating both breast and ovarian cancer tumors.

As used herein, cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, head and neck cancer and the like.

In one embodiment, the methods described herein refer to cancers that are treated with chemotherapeutic agents of the classes immune checkpoint therapies, such as antagonists of an inhibitory immune checkpoint and/or agonists of a stimulatory immune checkpoint, optionally in combination with DNA damaging agents, DNA repair target therapies, inhibitors of DNA damage signalling, inhibitors of DNA damage induced cell cycle arrest and inhibition of processes indirectly leading to DNA damage, (i.e. "DNA-damage therapeutic agent" as the term is used herein).

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

In such cases, the target cells may be tumor cells, for example colon cancer cells or stomach cancer cells. The target cells are derived from any tissue source, including human and animal tissue, such as, but not limited to, a newly obtained sample, a frozen sample, a biopsy sample, a sample of bodily fluid, a blood sample, preserved tissue such as a paraffin-embedded fixed tissue sample (i.e., a tissue block), or cell culture.

Methods and Kits

Kits for Gene Expression Analysis

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a biomarker expression analysis, such as reagents for performing RT-PCR, qPCR, northern blot, proteomic analysis, or immunohistochemistry to determine expression levels of biomarkers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below.

The kits featured herein can also include an instruction sheet describing how to perform the assays for measuring biomarker expression. The instruction sheet can also include instructions for how to determine a reference cohort, including how to determine expression levels of biomarkers in the reference cohort and how to assemble the expression data to establish a reference for comparison to a test patient. The instruction sheet can also include instructions for assaying biomarker expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The kits featured herein can also contain software necessary to infer a patient's likelihood of having a positive response to a specific therapeutic agent from the biomarker expression.

a) Gene Expression Profiling Methods

Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')2 fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for predicting responsiveness of a cancer therapeutic agent, where the methods comprise detecting, in a biological sample from an individual, at least N biomarker values that each correspond to a biomarker selected from the group consisting of the biomarkers provided in Tables 1 or 2, wherein a classification, as described in detail below, using the biomarker values indicates whether the individual will be responsive to a therapeutic agent. While certain of the described predictive biomarkers are useful alone for predicting responsiveness to a therapeutic agent, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays"). Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 cm$^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

d) Sequencing

Gene expression may also be determined using sequencing methods, which include the various next generation sequencing technologies. In specific embodiments RNAseq may be utilized.

Clinical Uses

In some embodiments, methods are provided for identifying and/or selecting a cancer patient who is responsive to a therapeutic regimen. In particular, the methods are directed to identifying or selecting a cancer patient who is responsive to a therapeutic regimen that includes administering immune checkpoint therapies, such as antagonists of an inhibitory immune checkpoint and/or agonists of a stimulatory immune checkpoint, optionally in combination with an agent that directly or indirectly damages DNA. Methods are also provided for identifying a patient who is non-responsive to a therapeutic regimen. These methods typically include determining the level of expression of a collection of predictive markers in a patient's tumor (primary, metastatic or other derivatives from the tumor such as, but not limited to, blood, or components in blood, urine, saliva and other bodily fluids)(e.g., a patient's cancer cells), comparing the level of expression to a reference expression level, and identifying whether expression in the sample includes a pattern or profile of expression of a selected predictive biomarker or biomarker set which corresponds to response or non-response to therapeutic agent.

In some embodiments a method of predicting responsiveness of an individual to immune checkpoint therapies, such as antagonists of an inhibitory immune checkpoint and/or agonists of a stimulatory immune checkpoint, optionally in combination with a DNA-damage therapeutic agent, comprises the following steps: obtaining a test sample from the individual; measuring expression levels of one or more biomarkers in the test sample, wherein the one or more biomarkers are selected from the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and responsiveness; and comparing the test score to the threshold score; wherein responsiveness is predicted when the test score exceeds the threshold score. One of ordinary skill in the art can determine an appropriate threshold score, and appropriate biomarker weightings, using the teachings provided herein including the teachings of Example 1.

In other embodiments, the method of predicting responsiveness of an individual to immune checkpoint therapies, such as antagonists of an inhibitory immune checkpoint and/or agonists of a stimulatory immune checkpoint, optionally in combination with a DNA-damage therapeutic agent comprises measuring the expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1. The method may comprise deriving a test score that captures the expression levels; providing a threshold score comprising information correlating the test score and responsiveness; and comparing the test score to the threshold score; wherein responsiveness is predicted when the test score exceeds the threshold score. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a likelihood that the individual will be responsive to immune checkpoint therapies, such as antagonists of an inhibitory immune checkpoint and/or agonists of a stimulatory immune checkpoint, optionally in combination with a DNA-damage therapeutic agent.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways, for instance, the size of a tumor or the expression of tumor markers appropriate for that tumor type may be measured.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or the expression of tumor markers appropriate for that tumor type may be measured. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor, including patient quality of life, degree of metastases, etc.

An application of this test will predict end points including, but not limited to, overall survival, progression free survival, radiological response, as defined by RECIST, complete response, partial response, stable disease and serological markers such as, but not limited to, PSA, CEA, CA125, CA15-3 and CA19-9.

Alternatively, non-array based methods for detection, quantification and qualification of RNA, DNA or protein within a sample of one or more nucleic acids or their biological derivatives such as encoded proteins may be employed, including quantitative PCR (QPCR), enzyme-linked immunosorbent assay (ELISA) or immunohistochemistry (IHC) and the like.

After obtaining an expression profile from a sample being assayed, the expression profile is compared with a reference or control profile to make a diagnosis regarding the therapy responsive phenotype of the cell or tissue, and therefore host, from which the sample was obtained. The terms "reference" and "control" as used herein in relation to an expression profile mean a standardized pattern of gene or gene product expression or levels of expression of certain biomarkers to be used to interpret the expression classifier of a given patient and assign a prognostic or predictive class. The reference or control expression profile may be a profile that is obtained from a sample known to have the desired phenotype, e.g., responsive phenotype, and therefore may be a positive reference or control profile. In addition, the reference profile may be from a sample known to not have the desired phenotype, and therefore be a negative reference profile.

If quantitative PCR is employed as the method of quantitating the levels of one or more nucleic acids, this method quantifies the PCR product accumulation through measurement of fluorescence released by a dual-labeled fluorogenic probe (i.e. TaqMan® probe).

In certain embodiments, the obtained expression profile is compared to a single reference profile to obtain information regarding the phenotype of the sample being assayed. In yet other embodiments, the obtained expression profile is compared to two or more different reference profiles to obtain more in depth information regarding the phenotype of the assayed sample. For example, the obtained expression profile may be compared to a positive and negative reference profile to obtain confirmed information regarding whether the sample has the phenotype of interest.

The comparison of the obtained expression profile and the one or more reference profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the one or more reference profiles, which similarity information is employed to determine the phenotype of the sample being assayed. For example, similarity with a positive control indicates that the assayed sample has a responsive phenotype similar to the responsive reference sample. Likewise, similarity with a negative control indicates that the assayed sample has a non-responsive phenotype to the non-responsive reference sample.

The level of expression of a biomarker can be further compared to different reference expression levels. For example, a reference expression level can be a predetermined standard reference level of expression in order to evaluate if expression of a biomarker or biomarker set is informative and make an assessment for determining whether the patient is responsive or non-responsive. Additionally, determining the level of expression of a biomarker can be compared to an internal reference marker level of expression which is measured at the same time as the biomarker in order to make an assessment for determining whether the patient is responsive or non-responsive. For example, expression of a distinct marker panel which is not comprised of biomarkers of the invention, but which is known to demonstrate a constant expression level can be assessed as an internal reference marker level, and the level of the biomarker expression is determined as compared to the reference. In an alternative example, expression of the selected biomarkers in a tissue sample which is a non-tumor sample can be assessed as an internal reference marker level. The level of expression of a biomarker may be determined as having increased expression in certain aspects. The level of expression of a biomarker may be determined as having decreased expression in other aspects. The level of expression may be determined as no informative change in expression as compared to a reference level. In still other aspects, the level of expression is determined against a pre-determined standard expression level as determined by the methods provided herein.

The invention is also related to guiding conventional treatment of patients. Patients in which the diagnostics test reveals that they are responders to the immune checkpoint therapies, such as antagonists of an inhibitory immune checkpoint and/or agonists of a stimulatory immune checkpoint, optionally in combination with, can be administered with that therapy and both patient and oncologist can be confident that the patient will benefit. Patients that are designated non-responders by the diagnostic test can be identified for alternative therapies which are more likely to offer benefit to them.

The invention further relates to selecting patients for clinical trials where novel drugs of the class of immune checkpoint therapies, such as antagonists of an inhibitory immune checkpoint and/or agonists of a stimulatory immune checkpoint, optionally in combination with. Enrichment of trial populations with potential responders will facilitate a more thorough evaluation of that drug under relevant criteria.

The invention still further relates to methods of diagnosing patients as having a cancer with increased innate immune response associated with a DNA damage response deficiency (DDRD). DDRD is defined herein as any condition wherein a cell or cells of the patient have a reduced ability to repair DNA damage, which reduced ability is a causative factor in the development or growth of a tumor. The DDRD diagnosis may be associated with a mutation in the Fanconi anemia/BRCA pathway. The DDRD diagnosis may also be associated with breast cancer or ovarian cancer. These methods of diagnosis comprise the steps of obtaining a test sample from the individual; measuring expression levels of one or more biomarkers in the test sample, wherein the one or more biomarkers are selected from Table 2B, 2A or 1A, including the group consisting of CXCL10, MX1, IDO1, IF144L, CD2, GBP5, PRAME, ITGAL, LRP4, and APOL3; deriving a test score that captures the expression levels; providing a threshold score comprising information correlating the test score and a diagnosis of the cancer; and comparing the test score to the threshold score; wherein the individual is determined to have the cancer when the test score exceeds the threshold score. One of ordinary skill in the art can determine an appropriate threshold score, and appropriate biomarker weightings, using the teachings provided herein including the teachings of Example 1.

In other embodiments, the methods of diagnosing patients as having developing a cancer with increased innate immune response associated with DDRD comprise measuring expression levels of one or more biomarkers in the test sample, wherein the one or more biomarkers are selected from the group consisting of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1. The method may comprise deriving a test score that captures the expression levels; providing a threshold score comprising information correlating the test score and a diagnosis of the cancer; and comparing the test score to the threshold score; wherein the individual is determined to have the cancer when the test score exceeds the threshold score. Tables 2A and 2B provide exemplary gene signatures (or gene classifiers) wherein the biomarkers consist of 40 or 44 of the gene products listed therein, respectively, and wherein a threshold score is derived from the individual gene product weightings listed therein. In one of these embodiments wherein the biomarkers consist of the 44 gene products listed in Table 2B, and the biomarkers are associated with the weightings provided in Table 2B, a test score that exceeds a threshold score of 0.3681 indicates a diagnosis of cancer or of being susceptible to developing a cancer.

The invention is also defined in the following numbered clauses:

1. A method for predicting responsiveness to an antagonist of an inhibitory immune checkpoint and/or an agonist of a stimulatory immune checkpoint comprising:
determining the expression level of at least one gene selected from Table 2B, 2A or 1 in a sample from the subject wherein the determined expression level is used to predict responsiveness to an antagonist of an inhibitory immune checkpoint and/or an agonist of a stimulatory immune checkpoint.

2. The method of clause 1 wherein an increased expression level of the at least one gene predicts responsiveness to an antagonist of an inhibitory immune checkpoint and/or an agonist of a stimulatory immune checkpoint.

3. The method of clause 1 or 2 which comprises determining the expression level of at least 2 of the genes and the determined expression levels are used to generate a combined test score, wherein a positive combined test score (generally above threshold, but may be equal to or above threshold) predicts responsiveness to an antagonist of an inhibitory immune checkpoint and/or an agonist of a stimulatory immune checkpoint.

4. The method of any preceding clause which comprises:
(i) deriving a combined test score that captures the expression levels;
(ii) providing a threshold score comprising information correlating the combined test score and responsiveness;
(iii) and comparing the combined test score to the threshold score; wherein responsiveness is predicted when the combined test score exceeds the threshold score.

5. The method of any preceding clause which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

6. The method of any preceding clause which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

7. The method of any preceding clause which comprises determining the expression level of at least 12 genes selected from Table 1.

8. The method of any preceding clause which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

9. The method of any preceding clause which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

10. The method of any of clauses 1 to 4 which comprises determining the expression level of each of the genes from any one of Tables 4 to 45.

11. The method of any preceding clause wherein the weight values for each gene are as set out in Table 2B, or wherein the weight and/or bias values for each gene are as set out in any one of Tables 3 to 45.

12. The method of any preceding clause which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

13. The method of any preceding clause wherein determining the expression level employs at least one primer or primer pair from Table 2E and/or at least one probe from Table 2E.

14. A method for predicting responsiveness to an antagonist of an inhibitory immune checkpoint and/or an agonist of a stimulatory immune checkpoint in combination with a DNA damage therapeutic agent comprising:
determining the expression level of at least one gene selected from Table 2B, 2A or 1 in a sample from the subject wherein the determined expression level is used to predict responsiveness to an antagonist of an inhibitory immune checkpoint and/or an agonist of a stimulatory immune checkpoint in combination with a DNA damage therapeutic agent.

15. The method of clause 14 wherein an increased expression level of the at least one gene predicts responsiveness to an antagonist of an inhibitory immune checkpoint and/or an agonist of a stimulatory immune checkpoint in combination with a DNA damage therapeutic agent.

16. The method of clause 14 or 15 which comprises determining the expression level of at least 2 of the genes and the determined expression levels are used to generate a combined test score, wherein a positive combined test score (generally above threshold, but may be equal to or above threshold) predicts responsiveness to an antagonist of an inhibitory immune checkpoint and/or an agonist of a stimulatory immune checkpoint in combination with a DNA damage therapeutic agent.

17. The method of any of clauses 14 to 16 which comprises:
(i) deriving a combined test score that captures the expression levels;
(ii) providing a threshold score comprising information correlating the combined test score and responsiveness;
(iii) and comparing the combined test score to the threshold score; wherein responsiveness is predicted when the combined test score exceeds the threshold score.

18. The method of any of clauses 14 to 17 which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

19. The method of any of clauses 14 to 18 which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

20. The method of any of clauses 14 to 19 which comprises determining the expression level of at least 12 genes selected from Table 1.

21. The method of any of clauses 14 to 20 which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

22. The method of any of clauses 14 to 21 which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

23. The method of any of clauses 14 to 17 which comprises determining the expression level of each of the genes from any one of Tables 4 to 45.

24. The method of any of clauses 14 to 23 wherein the weight values for each gene are as set out in Table 2B, or wherein the weight and/or bias values for each gene are as set out in any one of Tables 3 to 45.

25. The method of any of clauses 14 to 24 which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

26. The method of any of clauses 14 to 25 wherein determining the expression level employs at least one primer or primer pair from Table 2E and/or at least one probe from Table 2E.

27. A method for identifying a cancer that can be effectively treated with an antagonist of an inhibitory immune checkpoint and/or an agonist of a stimulatory immune checkpoint comprising: determining the expression level of at least one gene selected from Table 2B, 2A or 1 in a sample from the subject wherein the determined expression level is used to identify a cancer that can be effectively treated with an antagonist of an inhibitory immune checkpoint and/or an agonist of a stimulatory immune checkpoint.

28. The method of clause 27 wherein an increased expression level of the at least one gene identifies a cancer that can be effectively treated with an antagonist of an inhibitory immune checkpoint and/or an agonist of a stimulatory immune checkpoint.

29. The method of clause 27 or 28 which comprises determining the expression level of at least 2 genes and the determined expression levels are used to generate a combined test score, wherein a positive combined test score (generally above threshold, but may be equal to or above threshold) identifies a cancer that can be effectively treated with an antagonist of an inhibitory immune checkpoint and/or an agonist of a stimulatory immune checkpoint.

30. The method of any of clauses 27 to 29 which comprises:
(i) deriving a combined test score that captures the expression levels;
(ii) providing a threshold score comprising information correlating the combined test score and responsiveness;

(iii) and comparing the combined test score to the threshold score; wherein a cancer that can be effectively treated is identified when the combined test score exceeds the threshold score.

31. The method of any of clauses 27 to 30 which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

32. The method of any of clauses 27 to 31 which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

33. The method of any one of clauses 27 to 32 which comprises determining the expression level of at least 12 genes selected from Table 1.

34. The method of any of clauses 27 to 33 which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

35. The method of any of clauses 27 to 34 which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

36. The method of any of clauses 27 to 30 which comprises determining the expression level of each of the genes from any one of Tables 4 to 45.

37. The method of any of clauses 27 to 36 wherein the weight values for each gene are as set out in Table 2B, or wherein the weight and/or bias values for each gene are as set out in any one of Tables 3 to 45.

38. The method of any of clauses 27 to 37 which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

39. The method of any of clauses 27 to 38 wherein determining the expression level employs at least one primer or primer pair from Table 2E and/or at least one probe from Table 2E.

40. A method for identifying a cancer that can be effectively treated with an antagonist of an inhibitory immune checkpoint and/or an agonist of a stimulatory immune checkpoint in combination with a DNA damage therapeutic agent comprising:

determining the expression level of at least one gene selected from Table 2B, 2A or 1 in a sample from the subject wherein the determined expression level is used to identify a cancer that can be effectively treated with an antagonist of an inhibitory immune checkpoint and/or an agonist of a stimulatory immune checkpoint in combination with a DNA damage therapeutic agent.

41. The method of clause 40 wherein an increased expression level of the at least one gene identifies a cancer that can be effectively treated with an antagonist of an inhibitory immune checkpoint and/or an agonist of a stimulatory immune checkpoint in combination with a DNA damage therapeutic agent.

42. The method of clause 40 or 41 which comprises determining the expression level of at least 2 of the genes and the determined expression levels are used to generate a combined test score, wherein a positive combined test score (generally above threshold, but may be equal to or above threshold) identifies a cancer that can be effectively treated with an antagonist of an inhibitory immune checkpoint and/or an agonist of a stimulatory immune checkpoint in combination with a DNA damage therapeutic agent.

43. The method of any of clauses 40 to 42 which comprises:
(i) deriving a combined test score that captures the expression levels;
(ii) providing a threshold score comprising information correlating the combined test score and responsiveness;
(iii) and comparing the combined test score to the threshold score; wherein a cancer that can be effectively treated is identified when the combined test score exceeds the threshold score.

44. The method of any of clauses 40 to 43 which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

45. The method of any of clauses 40 to 44 which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

46. The method of any of clauses 40 to 45 which comprises determining the expression level of at least 12 genes selected from Table 1.

47. The method of any of clauses 40 to 46 which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

48. The method of any of clauses 40 to 47 which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

49. The method of any of clauses 40 to 43 which comprises determining the expression level of each of the genes from any one of Tables 4 to 45.

50. The method of any of clauses 40 to 49 wherein the weight values for each gene are as set out in Table 2B, or wherein the weight and/or bias values for each gene are as set out in any one of Tables 3 to 45.

51. The method of any of clauses 40 to 50 which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

52. The method of any preceding clause wherein determining the expression level employs at least one primer or primer pair from Table 2E and/or at least one probe from Table 2E.

53. A method for selecting treatment for a cancer comprising:
determining the expression level of at least one gene selected from Table 2B, 2A or 1 in a sample from the subject wherein the determined expression level is used to select an antagonist of an inhibitory immune checkpoint and/or an agonist of a stimulatory immune checkpoint for use in treatment of the cancer.

54. The method of clause 53 wherein an increased expression level of the at least one gene is used to select an antagonist of an inhibitory immune checkpoint and/or an agonist of a stimulatory immune checkpoint for use in treatment of the cancer.

55. The method of clause 53 or 54 which comprises determining the expression level of at least 2 of the genes and the determined expression levels are used to generate a combined test score, wherein a positive combined test score (generally above threshold, but may be equal to or above threshold) is used to select an antagonist of an inhibitory immune checkpoint and/or an agonist of a stimulatory immune checkpoint for use in treatment of the cancer.

56. The method of any of clauses 53 to 55 further comprising treating the cancer using the selected antagonist and/or agonist.

57. The method of any of clauses 53 to 56 which comprises:
(i) deriving a combined test score that captures the expression levels;
(ii) providing a threshold score comprising information correlating the combined test score and responsiveness;
(iii) and comparing the combined test score to the threshold score; wherein an antagonist of an inhibitory immune checkpoint and/or an agonist of a stimulatory immune checkpoint is selected for use when the combined test score exceeds the threshold score.

58. The method of any of clauses 53 to 57 which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

59. The method of any of clauses 53 to 58 which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

60. The method of any of clauses 53 to 59 which comprises determining the expression level of at least 12 genes selected from Table 1.

61. The method of any of clauses 53 to 60 which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

62. The method of any of clauses 53 to 61 which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

63. The method of any of clauses 53 to 57 which comprises determining the expression level of each of the genes from any one of Tables 4 to 45.

64. The method of any of clauses 53 to 63 wherein the weight values for each gene are as set out in Table 2B, or wherein the weight and/or bias values for each gene are as set out in any one of Tables 3 to 45.

65. The method of any of clauses 53 to 64 which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

66. The method of any of clauses 53 to 65 wherein determining the expression level employs at least one primer or primer pair from Table 2E and/or at least one probe from Table 2E.

67. A method for selecting treatment for a cancer comprising:
determining the expression level of at least one gene selected from 2B, 2A or 1 in a sample from the subject wherein the determined expression level is used to select an antagonist of an inhibitory immune checkpoint and/or an agonist of a stimulatory immune checkpoint, in combination with a DNA damage therapeutic agent, for use in treatment of the cancer.

68. The method of clause 67 wherein an increased expression level of the at least one gene is used to select an antagonist of an inhibitory immune checkpoint and/or an agonist of a stimulatory immune checkpoint, in combination with a DNA damage therapeutic agent, for use in treatment of the cancer.

69. The method of clause 67 or 68 which comprises determining the expression level of at least 2 of the genes and the determined expression levels are used to generate a combined test score, wherein a positive combined test score (generally above threshold, but may be equal to or above threshold) is used to select an antagonist of an inhibitory immune checkpoint and/or an agonist of a stimulatory immune checkpoint, in combination with a DNA damage therapeutic agent, for use in treatment of the cancer.

70. The method of any of clauses 67 to 69 further comprising treating the cancer using the selected antagonist and/or agonist, in combination with a DNA damage therapeutic agent.

71 The method of any of clauses 67 to 70 which comprises:
(i) deriving a combined test score that captures the expression levels;
(ii) providing a threshold score comprising information correlating the combined test score and responsiveness;
(iii) and comparing the combined test score to the threshold score; wherein an antagonist of an inhibitory immune checkpoint and/or an agonist of a stimulatory immune checkpoint in combination with a DNA damage therapeutic agent is selected for use when the combined test score exceeds the threshold score.

72. The method of any of clauses 67 to 71 which comprises determining the expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

73. The method of any of clauses 67 to 72 which comprises determining the expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

74. The method of any of clauses 67 to 73 which comprises determining the expression level of at least 12 genes selected from Table 1.

75. The method of any of clauses 67 to 74 which comprises determining the expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

76. The method of any of clauses 67 to 75 which comprises determining the expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

77. The method of any of clauses 67 to 71 which comprises determining the expression level of each of the genes from any one of Tables 4 to 45.

78. The method of any of clauses 67 to 77 wherein the weight values for each gene are as set out in Table 2B, or wherein the weight and/or bias values for each gene are as set out in any one of Tables 3 to 45.

79. The method of any of clauses 67 to 78 which comprises determining the expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

80. The method of any of clauses 67 to 79 wherein determining the expression level employs at least one primer or primer pair from Table 2E and/or at least one probe from Table 2E.

81. The method of any preceding clause wherein the combined test score (or "signature score") is derived according to the formula:

$$SignatureScore = \sum_i w_i \times (ge_i - b_i) + k$$

Where $w_i$ is a weight for each gene, $b_i$ is a gene-specific bias, $ge_i$ is the gene expression after pre-processing, and k is a constant offset.

82. A method of treating cancer comprising administration of an antagonist of an inhibitory immune checkpoint and/or an agonist of a stimulatory immune checkpoint to a subject, characterised in that a sample from the subject, prior to administration, displays a positive combined test score derived from the determined expression levels of at least 2 genes from Table 2B, 2A or 1 or an increased level of expression of at least 1 gene from Table 2B, 2A or 1.

83. A method of treating cancer comprising administration of an antagonist of an inhibitory immune checkpoint and/or an agonist of a stimulatory immune checkpoint, in combination with a DNA damage therapeutic agent, to a subject, characterised in that a sample from the subject, prior to administration, displays a positive combined test score derived from the determined expression levels of at least 2 genes from Table 2B, 2A or 1 or an increased level of expression of at least 1 gene from Table 2B, 2A or 1.

84. An antagonist of an inhibitory immune checkpoint and/or an agonist of a stimulatory immune checkpoint for use in the treatment of cancer in a subject wherein, prior to administration of the antagonist and/or agonist, a sample from the subject displays a positive combined test score derived from the determined expression levels of at least 2 genes from Table 2B, 2A or 1 or an increased level of expression of at least 1 gene from Table 2B, 2A or 1.

85. An antagonist of an inhibitory immune checkpoint and/or an agonist of a stimulatory immune checkpoint for use in the treatment of cancer in a subject wherein, prior to administration of the antagonist and/or agonist, a sample from the subject displays a positive combined test score derived from the determined expression levels of at least 2 genes from Table 2B, 2A or 1 or an increased level of expression of at least 1 gene from Table 2B, 2A or 1, and wherein the antagonist and/or agonist is administered in combination with a DNA damage therapeutic agent.

86. An antagonist of an inhibitory immune checkpoint in combination with a DNA damage therapeutic agent and/or an agonist of a stimulatory immune checkpoint in combination with a DNA damage therapeutic agent for use in the treatment of cancer in a subject wherein, prior to administration of the antagonist and/or agonist and DNA damage therapeutic agent, a sample from the subject displays a positive combined test score derived from the determined expression levels of at least 2 genes from Table 2B, 2A or 1 or an increased level of expression of at least 1 gene from Table 2B, 2A or 1.

87. The method of clause 82 or 83, or the antagonist and/or agonist for use of any of clauses 84 to 86, wherein the combined test score (or "signature score") is derived according to the formula:

$$SignatureScore = \sum_{i} w_i \times (ge_i - b_i) + k$$

Where $w_i$ is a weight for each gene, $b_i$ is a gene-specific bias, $ge_i$ is the gene expression after pre-processing, and k is a constant offset.

88. The method of any of clauses 82, 83 or 87, or the antagonist and/or agonist for use of any of clauses 84 to 87, wherein the combined test score is derived from the determined expression level of at least 6 genes selected from CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

89. The method of any of clauses 82, 83, 87 or 88, or the antagonist and/or agonist for use of any of clauses 84 to 88, wherein the combined test score is derived from the determined expression level of at least 1 gene selected from CD2, ITGAL, PTPRC, CXCL10 and IDO1, together with at least one further gene selected from MX1, IF144L, GBP5, PRAME, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PPP1R1A, and AL137218.1.

90. The method of any of clauses 82, 83 or 87 to 89, or the antagonist and/or agonist for use of any of clauses 84 to 89, wherein the combined test score is derived from the determined expression level of at least 12 genes selected from Table 1.

91. The method of any of clauses 82, 83 or 87 to 90, or the antagonist and/or agonist for use of any of clauses 84 to 90, wherein the combined test score is derived from the determined expression level of at least 1 gene selected from CD2, ITGAL, PTPRC, CXCL10, IDO1, CD3D, HLA-DPB1, CXCL9, CCL5, STAT1, IL2RG, CD3E, IRF1, IKZF3 and IGJ together with at least one further gene selected from (the remaining genes in) Table 1 or together with at least one further gene from the (remaining genes in) Table 2B (the 44 gene panel).

92. The method of any of clauses 82, 83 or 87 to 91, or the antagonist and/or agonist for use of any of clauses 84 to 91, wherein the combined test score is derived from the determined expression level of each of CXCL10, MX1, IDO1, IF144L, CD2, GBP5, PRAME, ITGAL, LRP4, APOL3, CDR1, FYB, TSPAN7, RAC2, KLHDC7B, GRB14, AC138128.1, KIF26A, CD274, CD109, ETV7, MFAP5, OLFM4, PI15, FOSB, FAM19A5, NLRC5, PRICKLE1, EGR1, CLDN10, ADAMTS4, SP140L, ANXA1, RSAD2, ESR1, IKZF3, OR2I1P, EGFR, NAT1, LATS2, CYP2B6, PTPRC, PPP1R1A, and AL137218.1.

93. The method of any of clauses 82, 83 or 87, or the antagonist and/or agonist for use of any of clauses 84 to 87, wherein the combined test score is derived from the determined expression level of the genes from any one of Tables 4 to 45.

94. The method of any of clauses 82, 83 or 87 to 93, or the antagonist and/or agonist for use of any of clauses 84 to 93, wherein the weight values for each gene are as set out in Table 2B, or wherein the weight and/or bias values for each gene are as set out in any one of Tables 3 to 45.

95. The method of any of clauses 82, 83 or 87 to 94, or the antagonist and/or agonist for use of any of clauses 84 to 94, wherein the combined test score is derived from the determined expression level of at least one, up to all, of CCL5, CXCL9 and CXCL10 together with at least one further gene selected from (the remaining genes in) Table 1 or together with at least one further gene from the (remaining genes in) Table 2B (the 44 gene panel).

96. The method of any of clauses 82, 83 or 87 to 95, or the antagonist and/or agonist for use of any of clauses 84 to 95, wherein the expression levels are determined using at least one primer or primer pair from Table 2E and/or at least one probe from Table 2E.

97. The method of any one of clauses 82, 83 or 87 to 96, or the antagonist and/or agonist for use of any of clauses 84 to 96, wherein the subject is selected for treatment according to a method as described in any one of clauses 1 to 81.

98. The method of any of clauses 1 to 83 or 87 to 97, or the antagonist and/or agonist for use of any of clauses 84 to 97, wherein the sample comprises cancer cells.

99. The method of any of clauses 1 to 83 or 87 to 98, or the antagonist and/or agonist for use of any of clauses 84 to 98, wherein the sample is a tissue sample.

100. The method of clause 99, or the antagonist and/or agonist for use of clause 99, wherein the tissue sample is a fixed and embedded tissue sample.

101. The method of any of clauses 1 to 83 or 87 to 100, or the antagonist and/or agonist for use of any of clauses 84 to 100, wherein the cancer is selected from leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer or head and neck cancer.

102. The method of any of clauses 1 to 83 or 87 to 101, or the antagonist and/or agonist for use of any of clauses 84 to 101, wherein the inhibitory immune checkpoint is selected from A2AR, B7-H3 (CD276), B7-H4 (VTCN1), BTLA (CD272), CTLA-4 (CD152), IDO, KIR, LAG3, PD-1/PD-L1, TIM-3 and VISTA, optionally wherein the inhibitory immune checkpoint is not PD-1/PD-L1.

103. The method of any of clauses 1 to 83 or 87 to 102, or the antagonist and/or agonist for use of any of clauses 84 to 102, wherein the antagonist of an inhibitory immune checkpoint is selected from an antibody and an inhibitory nucleic acid molecule.

104. The method of any of clauses 1 to 83 or 87 to 103, or the antagonist and/or agonist for use of any of clauses 84 to 103, wherein the antagonist of an inhibitory immune checkpoint is selected from MGA271 (targets B7-H3), ipilimumab (Yervoy—targets CTLA-4), indoximod (targets IDO pathway), NLG919 (targets IDO pathway), lirilumab (targets KIR), IMP321 (targets LAG3), BMS-986016 (targets LAG3), CT-011 (PD-1 blockade), nivolumab/BMS-936558 (PD-1 blockade), BMS-936559 (PDL1 blockade) and pembrolizumab (Keytruda—targets PD-1), optionally wherein the antagonist is not pembrolizumab; and/or wherein the antagonist of an inhibitory immune checkpoint is selected from MGB453 (targets TIM-3), LAG525 (targets LAG-3) and PDR001 (PD1 Blockade).

105. The method of any of clauses 1 to 83 or 87 to 104, or the antagonist and/or agonist for use of any of clauses 84 to 104, wherein the stimulatory immune checkpoint is selected from CD27, CD28, CD40, CD122, CD137, OX40, GITR and ICOS.

106. The method of any of clauses 1 to 83 or 87 to 105, or the antagonist and/or agonist for use of any of clauses 84 to 105, wherein the agonist of a stimulatory immune checkpoint is selected from an antibody, a lipocalin and a cytokine.

107. The method of any of clauses 1 to 83 or 87 to 106, or the antagonist and/or agonist for use of any of clauses 84 to 106, wherein the agonist of a stimulatory immune checkpoint is selected from CDX-1127 (agonist of CD27), NKTR-214 (agonist of CD122), BMS-663513 (agonist of CD137), TRX518 (agonist of GITR), CP-870893 (CD40 agonist), MEDI0562, MEDI6469 and MEDI6383 (OX40 agonists).

108. The method of any of clauses 1 to 83 or 87 to 107, or the antagonist and/or agonist for use of any of clauses 84 to 107, wherein the DNA damage therapeutic agent is selected from a DNA damaging agent, a DNA repair targeted therapy, an inhibitor of DNA damage signalling, an inhibitor of DNA damage induced cell cycle arrest and an inhibitor of a process indirectly leading to DNA damage.

109. The method of clause 108, or the antagonist and/or agonist for use of clause 108, wherein the DNA damaging agent is selected from an alkylating agent, a topoisomerase inhibitor and radiation.

110. The method of clause 109, or the antagonist and/or agonist for use of clause 109, wherein the alkylating agent is selected from a platinum containing agent, cyclophosphamide and busulphan.

111. The method of clause 110, or the antagonist and/or agonist for use of clause 110, wherein the platinum containing agent is selected from cisplatin, carboplatin and oxaliplatin.

112. The method of clause 109, or the antagonist and/or agonist for use of clause 109, wherein the topoisomerase inhibitor is selected from a topoisomerase I inhibitor and a topoisomerase II inhibitor.

113. The method of clause 112, or the antagonist and/or agonist for use of clause 112, wherein the topoisomerase I inhibitor is selected from irinotecan and topotecan.

114. The method of clause 112, or the antagonist and/or agonist for use of clause 112, wherein the topisomerase II inhibitor is selected from etoposide and an anthracycline.

115. The method of clause 114, or the antagonist and/or agonist for use of clause 114, wherein the anthracycline is selected from doxorubicin and epirubicin.

116. The method of clause 109, or the antagonist and/or agonist for use of clause 109, wherein the radiation is ionising radiation 117. The method of any of clauses 108 to 116, or the antagonist and/or agonist for use of any of clauses 108 to 116, wherein the DNA repair targeted therapy is selected from an inhibitor of Non-homologous end-joining, an inhibitor of homologous recombination, an inhibitors of nucleotide excision repair, an inhibitor of base excision repair and an inhibitor of the Fanconi anemia pathway.

118. The method of clause 117, or the antagonist and/or agonist for use of clause 117, wherein the inhibitor of Non-homologous end-joining is selected from a DNA-PK inhibitor, Nu7441 and NU7026.

119. The method of clause 117, or the antagonist and/or agonist for use of clause 117, wherein the inhibitor of base excision repair is selected from a PARP inhibitor, AG014699, AZD2281, ABT-888, MK4827, BSI-201, INO-1001, TRC-102, an APEX 1 inhibitor, an APEX 2 inhibitor and a Ligase III inhibitor.

120. The method of any of clauses 108 to 119, or the antagonist and/or agonist for use of any of clauses 108 to 119, wherein the inhibitor of DNA damage signalling is selected from an ATM inhibitor, a CHK 1 inhibitor and a CHK 2 inhibitor.

121. The method of clause 120, or the antagonist and/or agonist for use of clause 120, wherein the ATM inhibitor is selected from CP466722 and KU-55933.

122. The method of clause 120, or the antagonist and/or agonist for use of clause 120, wherein the CHK 1 inhibitor is selected from XL-844, UCN-01, AZD7762 and PF00477736.

123. The method of clause 120, or the antagonist and/or agonist for use of clause 120, wherein the CHK 2 inhibitor is selected from XL-844, AZD7762 and PF00477736.

124. The method of any of clauses 108 to 123, or the antagonist and/or agonist for use of any of clauses 108 to 123, wherein the inhibitor of DNA damage induced cell cycle arrest is selected from a Wee1 kinase inhibitor and a CDC25a, b or c inhibitor.

125. The method of any of clauses 108 to 124, or the antagonist and/or agonist for use of any of clauses 108 to 124, wherein the inhibitor of a process indirectly leading to DNA damage is selected from a histone deacetylase inhibitor and a heat shock protein inhibitor.

126. The method of clause 125, or the antagonist and/or agonist for use of clause 125, wherein the heat shock protein inhibitor is selected from geldanamycin and AUY922.

127. A method as described herein with reference to the accompanying figures.

The following examples are offered by way of illustration and not by way of limitation.

EXAMPLES

Example 1

Tissue Processing, Hierarchical Clustering, Subtype Identification and Classifier Development Tumor Material The genes determined to be useful in the present methods (Table 2) were identified from gene expression analysis of a cohort of 107 macrodissected breast tumor FFPE tissue samples sourced from the Mayo Clinic Rochester. Ethical approval for this study was obtained from the Institutional Review Board and the Office of Research Ethics Northern Ireland.

This cohort of samples can be further described as follows:

- 47 samples were wild-type for BRCA1 and BRCA2 i.e. expressed biologically functional BRCA1 and BRCA2 proteins. These samples shall henceforth be referred to as sporadic controls.
- 31 samples were BRCA1 mutant i.e. did not express biologically functional BRCA1 protein.
- 29 samples were BRCA2 mutant i.e. did not express biologically functional BRCA2 protein.

Gene Expression Profiling

Total RNA was extracted from the macrodissected FFPE tumor samples using the Roche High Pure RNA Paraffin Kit (Roche Diagnostics GmbH, Mannheim, Germany). Total RNA was amplified using the NuGEN WT-Ovation™ FFPE System (NuGEN Technologies Inc., San Carlos, Calif., USA). The amplified single-stranded cDNA was then fragemented and biotin labeled using the FL-Ovation™ cDNA Biotin Module V2 (NuGEN Technologies Inc.). It was then hybridized to the Almac Breast Cancer DSA™ The Almac's Breast Cancer DSA™ research tool has been optimised for analysis of FFPE tissue samples, enabling the use of valuable archived tissue banks. The Almac Breast Cancer DSA™ research tool is an innovative microarray platform that represents the transcriptome in both normal and cancerous breast tissues. Consequently, the Breast Cancer DSA™ provides a comprehensive representation of the transcriptome within the breast disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MASS pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end of a polynucleotide. Therefore standard Affymetrix RNA quality measures were adapted—for housekeeping genes intensities of 3' end probesets along with ratios of 3' end probeset intensity to the average background intensity were used in addition to usual 3'/5' ratios. Hybridization controls were checked to ensure that their intensities and present calls conform to the requirements specified by Affymetrix.

Tumor samples from the BRCA1/2 mutant and sporadic control training set were split into 2 datasets based on the transcript levels of ESR1 (Estrogen receptor 1). mRNA expression level $E_{avg}$ for each sample was determined by the average expression of all ESR1 probe sets (BRAD.15436_s_at, BRAD.19080_s_at, BREM.1048_at, BRIH.10647C1n2_at, BRIH.5650C1n2_at, BRPD.10690C1n5_at, BRRS.81_at and BRRS.81-22_at). The mRNA median expression ($E_{med.all}$) was calculated for all samples. Samples were considered ER positive when $E_{avg} - E_{med.all} > 0.5$ and ER negative when $E_{avg} - E_{med.all} < 0.5$.

Pre-processing was performed in expression console v1.1 with Robust Multi-array Analysis (RMA) (Irizarry et al., 2003) resulting in 2 data matrices of ER positive and ER negative samples composed of 56 and 51 samples respectively. An additional transformation was performed to remove the variance associated with array quality as described by Alter (Alter et al., 2000).

Feature Selection

A combined background & variance filter was applied to each data matrix to identify the most variable probesets. The background filter is based on the selection of probe sets with expression E and expression variance $var_E$ above the thresholds defined by background standard deviation $\sigma Bg$ (from the Expression Console software) and quantile of the standard normal distribution $z_a$ at a specified significance a probesets were kept if:

$$E > \log_2((z_a \sigma_{Bg})); \log_2((var_E) > 2[\log_2(\sigma_{Bg}) - E - \log_2(\log(2))]$$

where the significance threshold was $a = 6.3 \cdot 10^{-5}$, see Table 1 for the list of selected probesets and their gene annotations.

Hierarchical Clustering Analysis

Figure 1B:
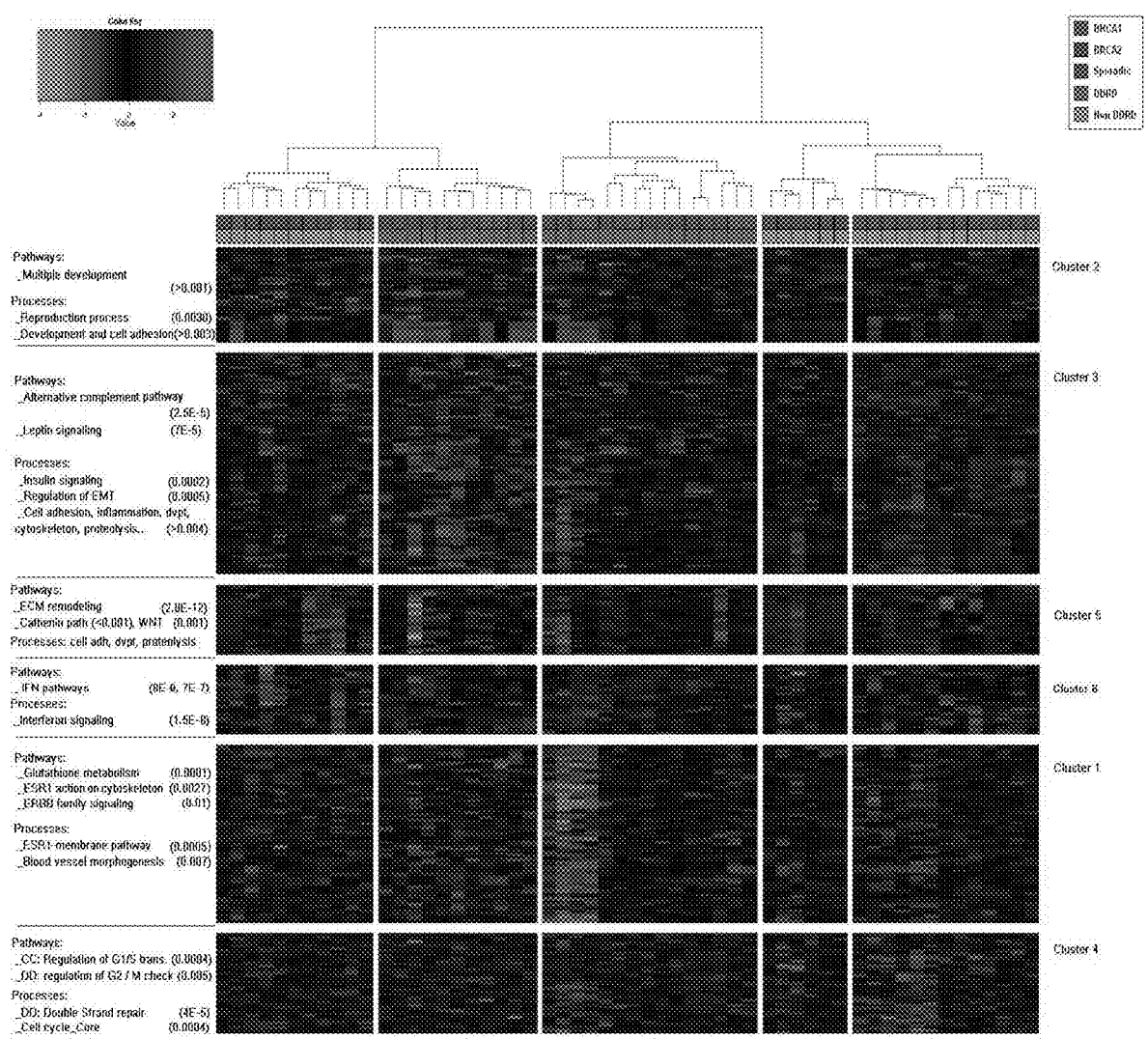

Hierarchical clustering techniques were applied to microarray data from 199 epithelial serous ovarian tumors analysed using the Ovarian Cancer DSA™ (disease specific array) platform (FIG. 1). Raw expression data was preprocessed using the standard Robust Multichip Algorithm (RMA) procedure.

Non-biological systematic variance in the data set was identified and removed. Those probesets whose expression levels varied significantly from tumor to tumor were identified. These probesets formed the intrinsic list.

2-D cluster analysis (tumor, probeset) was performed to establish tumor relationships based on the intrinsic list. Hierarchical agglomerative clustering was applied (Pearson correlation distance and Ward's linkage). Optimal partition number was selected using the GAP index (Tibshirani et al., 2002, J. R. Stat. Soc., 63:411-423). All probesets available in the subclusters were mapped to genes names.

Functional Analysis of Gene Clusters

To establish the functional significance of the probeset clusters, probesets were mapped to genes (Entrez gene ID) and an enrichment analysis, based on the hypergeometric function (False Discovery Rate applied (Benjamini and Hochberg, 1995, J. R. Stat. Soc. 57:289:300)), was performed. Over-representation of biological processes and pathways were analysed for each gene group generated by the hierarchical clustering for both ER-positive and ER-negative samples using Metacore™ single experiment analysis workflow from GeneGo®. Antisense probesets were excluded from the analysis. Hypergeometric p-values were assessed for each enriched functional entity class. Functional entity classes with the highest p-values were selected as representative of the group and a general functional category representing these functional entities was assigned to the gene clusters based on significance of representation (i.e. p-value).

Genes in clusters enriched for the IFN/DD general functional terms were grouped into a DNA-damage responsedeficiency (DDRD) sample group and used for the classifier generation. The sample clusters from ER-positive and ER-negative datasets represented by the IFN/DD general functional terms were selected for classification and labelled as DDRD. Those not represented by these functional terms were labelled as non-DDRD.

Classifier Development at a Probeset Level

Following the identification of a class of tumors that form the DDRD subgroup, computational classification of these tumors vs. all the others in the tumor cohort (non-DDRD) was performed, with reference to the functional DDRD gene list (Table 1), to identify a refined gene classification model that classifies the DDRD subgroup. This was evaluated using all combinations of the following options (a total of 18):

Three sample sets
    Combined sample set of ER-negative and ER-positive samples (combined sample set)
    ER-negative samples alone
    ER-positive samples alone Two feature sets
  Full feature list with 75% variance/intensity filtering and forced inclusion of the DDRD list. Here 75% of the probesets with the lowest combined variance and intensity were removed, based on the average rank of both. When used, the term "Varint" refers to this option.
  DDRD list only. When used, the term "List only" refers to this option.
Three classification algorithms
  PLS (Partial Least Squares) (de Jong, 1993)
  SDA (Shrinkage Discriminate Analysis)(Ahdesmaki and Strimmer, 2010)
  DSDA (Diagonal SDA)(Ahdesmaki and Strimmer, 2010)

The AUC was used to assess the performance of the different models. Iterative Feature Elimination (IFE) was implemented throughout the development of each model, where the maximum AUC was the main criteria in selecting an optimal number of features over cross validation. In cases where there was no visible AUC difference across features, the minimum feature length was selected.

Classifier Development at a Gene Level

To facilitate validation of the classifier across multiple array platforms, the selected probeset classifier was regenerated at the gene level. A redevelopment of the probeset classifier at a gene level required two separate steps:
  1. The expression intensities of the unique genes in the probeset classifier were estimated from the median of the probesets mapping to each gene, excluding anti-sense probesets.
  2. The classifier parameters used for classification were re-estimated A threshold was chosen based on the maximum sensitivity and specificity over all cross validation predictions.

Similarly the gene level defined expression intensities for the 10 top genes (or any number of features present in current 44 gene signature) could be used to re-develop the classifier based on only these 10 genes (or any number of features present in current 44 gene signature) by re-estimating classification parameters in cross-validation in the training data set as well as to re-establish the threshold by assessing and maximising the sensitivity and specificity obtained from all cross-validation predictions. The methodology would be similar to the method used when working from a larger feature set (described above) except there will be no feature selection involved: the features will remain the same but will be assigned new weights.

Calculating Classifier Scores for Validation Data Sets

Public Datasets

The datasets used in for this analysis are namely: FAC1 [GEO accession number GSE20271, (Tabchy et al., 2010)], FAC2 [GEO accession number GSE22093, (Iwamoto et al., 2011)], FEC [GEO accession number GSE6861, (Bonnefoi et al., 2007)], T/FAC1 [http://bioinformatics.mdanderson.org/pubdata.html, (Hess et al., 2006)], T/FAC2 [GEO accession number GSE16716, (Lee et al., 2010)] and T/FAC3 [GEO accession number GSE20271, (Tabchy et al., 2010)]. It must be noted that there is an overlap in 31 samples between the FAC1 and FAC2 datasets. These samples were removed from the FAC2 dataset and as such were only included once in the combined analysis of the FAC1, FAC2 and FEC datasets. In addition, sample GSM508092 was removed from FAC1 as it is a metastatic lymph node sample.

All datasets were pre-processed using RMA (Irizarry et al., 2003). For each validation set, the probesets that map to the classifier genes were determined, excluding anti-sense probesets (if applicable). Annotation for Affymetrix X3P and U133A arrays are available from the Affymetrix website. The median intensity over all probesets mapping to each gene in the classifier was calculated, resulting in a gene intensity matrix. The classifier was then applied to this data matrix to produce a classifier score/prediction for each sample.

Calculating Performance Metrics

To calculate NPV and PPV, the prevalence of each end point (BRCA status/Response) was estimated using the proportions of each class in the corresponding data set.

Univariate and Multivariate analysis

Univariate and multivariate analysis was carried out to assess respectively the association between the DDRD classifier and response, and to determine if the association, if any, was independent to known clinical predictors. The p-values presented Table 47, for univariate analysis were calculated using logistic regression in MATLAB. For the multivariate analysis we used step-wise logistic regression (Dupont, 2009), where the p-values represent the log-likelihood of the variable. The log-likelihood is a measure of the importance of the variable's fit to the model, thus highlighting it's independence as a predictor relative to the other predictors. In both univariate and multivariate analysis, a p-value<0.05 was used as the criterion for significance. Furthermore, samples with unknown clinical factors were excluded in this assessment.

Results

Selection of Samples for Classifier Generation

The objective of this study was to characterize at a transcriptomic level a set of genes that would be capable of determining responsiveness or resistance of a pathogenic cell to DNA-damage therapeutic agents. With this in mind, those samples within the Almac breast cancer dataset that best represented this biology were to be selected and compared to the remaining samples for classifier generation (see next section). It was decided that the samples from sample cluster two within the ER−ve sample set were the most relevant samples for this selection as these showed the greatest proportion of BRCA mutant samples (64%) and they exhibited the most dominant biology (IFN/immune response). From within the ER+ve sample set, the samples from sample cluster two and three were selected as these sample clusters had 73% and 67% BRCA mutant tumors respectively. In addition, the most dominant biology within these clusters was related to cell cycle, DNA damage response and IFN/immune response. Immune signaling and cell-cycle pathways have been reported to be modulated in response to DNA-damage (Jackson, S. P., and Bartek, J., Nature 461, 1071-1078 (2009); Rodier, F., et al., Nat Cell Biol 11, 973-979 (2009); Xu, Y., Nat Rev Immunol6, 261-270 (2006), and these subgroups were combined to form a putative DDRD subgroup. Those samples within cluster two of the ER−ve sample set (described below) and clusters two and three of the ER+ve sample set (described below) were class labelled DDRD (DNA damage response deficient) (see FIG. 1A) whilst the samples within sample clusters one and three of the ER−ve sample set and sample clusters one, four, five and six of the ER+ve sample set were class labeled non-DDRD (see FIG. 1B).

ER−ve sample set: Within the ER−ve sample set, the hierarchical cluster analysis defined three sample clusters and six probeset cluster groups. Probeset cluster three was identified as the most significant biology within the ER−ve sample set and was enriched for interferon and immune response signaling.

ER+ve sample set: Within the ER+ve sample set, the hierarchical analysis defined six sample groups and six probeset cluster groups. Probeset cluster five was identified as the most significant biology within the ER+ve sample set and was enriched for extracellular matrix remodeling. The next most significant probeset cluster within the ER+ve sample set is probeset cluster six and again was enriched for interferon and immune response signaling.

Development and Validation of the DDRD Classifier Model

Following the identification of a class of tumors, that form the DDRD subgroup, computational classification of these tumors vs. all others in the tumor cohort with reference to the functional DDRD (IFN/DNA damage) gene list was performed to identify a refined gene classification model, which classifies the DDRD subgroup.

The classification pipeline was used to derive a model using the set of combined ER−ve and ER+ve breast cancer samples. The classification pipeline has been developed in accordance with commonly accepted good practice [MAQC Consortium, Nat Biotechnol 2010]. The process will, in parallel: 1) derive gene classification models from empirical data; and 2) assess the classification performance of the models, both under cross-validation. The performance and success of the classifier generation depends on a number of parameters that can be varied, for instance the choice of classification method or probe set filtering. Taking this into account, two feature sets were evaluated (i) the full feature list with 75% variance/intensity filtering (with forced inclusion of the DDRD (IFN/DNA damage) list, Table 1) and (ii) the DDRD (IFN/DNA damage) list only; and three classification algorithms were evaluated, namely PLS (Partial Least Squares); SDA (Shrinkage Discriminate Analysis) and DSDA (Diagonal SDA). Iterative Feature Elimination (IFE) was used throughout model development, which is an iterative procedure removing a fraction of the worst-ranked features at each iteration; stopping when only a minimum number of features remain. The Area under the Receiver Operating Characteristics Curve (AUC-ROC), denoted AUC, was used to assess the classification performance, as this measure is independent of cut-off between groups and prevalence rates in the data. It is also one of the recognized measurements of choice for classification performance. As such, the best number of features for each model was chosen based on the average AUC under cross-validation.

A cross comparison of the models was made, by first selecting the best number of features for each model based on the highest average AUC, and then using box-plots to visualize the performance for each model. This is demonstrated in FIG. 2. From left to right, the first three plots represent the PLS, SDA and DSDA classifiers respectively that were developed using an initial filtering of probe sets to remove 75% with the lowest average variance and intensity (forcing the inclusion of the gene list). The next three plots respectively represent the PLS, SDA and DSDA classifiers developed using the DDRD (IFN/DNA damage) list only.

Figure 2:
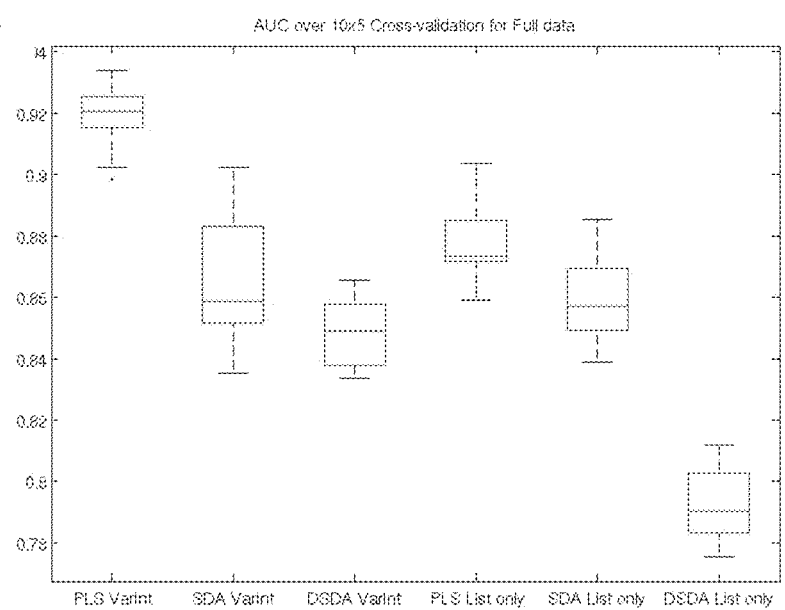
FIG. 2 provides a diagram of box plots comparing the AUC performance of each classification model under 10 repeats of 5-fold cross validation for (A) the combined sample set, (B) the ER-negative sample set and (C) the ER-positive sample set. (D) Sensitivity plus specificity plot of the cross validation predictions used to select threshold. The maximum sensitivity plus specificity is 1.682 with a corresponding signature score of ~0.37.
Figure 2:
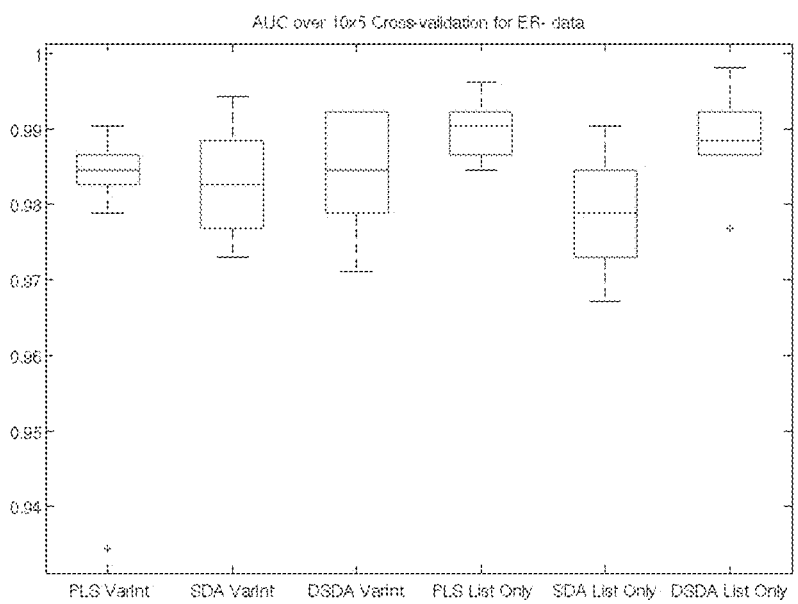

From FIG. 2, it is clear that the PLS Varint' classification model, comprising 53 probe sets, is the highest performing model, with a significantly higher AUC than the majority of the other 5 models. This model was then taken forward to the next phase for validation on independent external data sets, to assess the ability of the DDRD classification scores to stratify patients with respect to response and prognosis.

A non-orthodox approach to validating the classification model was taken, due to the fact that the validation data sets where either public or internal data with different array platforms. Commonly used approaches are not designed to be applicable to alternative array platforms, and as such a phased approach for classification model development and independent validation was followed:

1. Phase I—Model generation at the probe set level, selecting the best model under cross validation for classifying the DDRD subgroup (described previously)
2. Phase II—Transformation of the probe set level classification model to a gene level classification model
3. Phase III—Validation of re-developed gene classification model using external data sets Having selected a candidate model to progress to the validation stage, this model needed to be re-built at the gene level (Phase II). This involved mapping the probe sets in the classification model to the gene level and recalculating the weights for each gene. The 53 probe sets in the selected model mapped to 40 genes listed in Table 2A and subsequently mapped to 44 genes listed in Table 2B when the accuracy of the annotation pipeline was improved through further analysis.

In the re-development of the gene classification model, to ensure that all information relating to the gene is used, the median intensity of all probe sets associated with each gene (Table 2C) is used as the gene expression value. This was calculated for all samples, resulting in a gene expression data matrix, as opposed to a probe set expression data matrix that was used in Phase I for model development and selection. To stabilize the intensities across different batches, the median of all probe sets for each sample was subtracted from the corresponding intensity of each gene for that sample.

New weights were calculated for each gene using PLS regression, resulting in the final gene classifier models (40-gene and 44-gene classifier models) that may be used for validation on external data sets from different array platforms (Phase III).

In Phase III, the validation of the classifier using data sets that may be from other array platforms, the following steps were taken:

1. The probe sets that map to the genes in the classifier are determined, excluding anti-sense probe sets (if applicable)
2. The median intensity over all probe sets relating to each gene in the classifier is calculated resulting in a reduced gene intensity matrix
   a. If no probe sets exist for the gene on the particular array platform, the observed average from the training data will be used as a replacement
3. The median value of all probe sets for each sample is calculated and subtracted from the reduced gene intensity matrix
4. The value for each gene is multiplied by the "weight" of that gene in the signature.
5. The values obtained in point 4 for each of the genes in the signature are added together to produce a signature score for that sample.
6. The classifier produces a score for each sample, which can then be used to stratify patients from say, more likely to respond to less likely to respond.

Example 2

In Silico Validation of the 44-Gene DDRD Classifier Model

The performance of the 44-gene DDRD classifier model was validated by the Area Under the ROC (Receiver Operator Characteristic) Curve (AUC) within the original Almac breast dataset and three independent datasets. The AUC is a statistic calculated on the observed disease scale and is a measure of the efficacy of prediction of a phenotype using a classifier model pray et. al., PLoS Genetics Vol 6, 1-9). An AUC of 0.5 is typical of a random classifier, and an AUC of 1.0 would represent perfect separation of classes. Therefore, in order to determine if the 44-gene DDRD classifier model is capable of predicting response to, and selecting patients for, standard breast and ovarian cancer therapeutic drug classes, including DNA damage causing agents and DNA repair targeted therapies, the hypothesis is that the AUCs following application within these datasets should be above 0.5 with the lowest confidence interval also above 0.5.

Assessment of 44-Gene Classifier Model's Ability to Separate BRCA Mutant from Sporadic Tumors The classifier scores for predicting DDRD status were utilized to assess the ability of the model to separate BRCA mutant samples from sporadic samples. This analysis was performed to assess the relationships between the classifier model and BRCA mutation status. BRCA mutant tumors display a high degree of genomic instability due to a deficiency in DNA damage response by virtue of the loss of functional BRCA1/2. As such, the hypothesis is that the DDRD classifier models should be able to separate BRCA mutant samples from BRCA wildtype sporadic samples.

Figure 3:
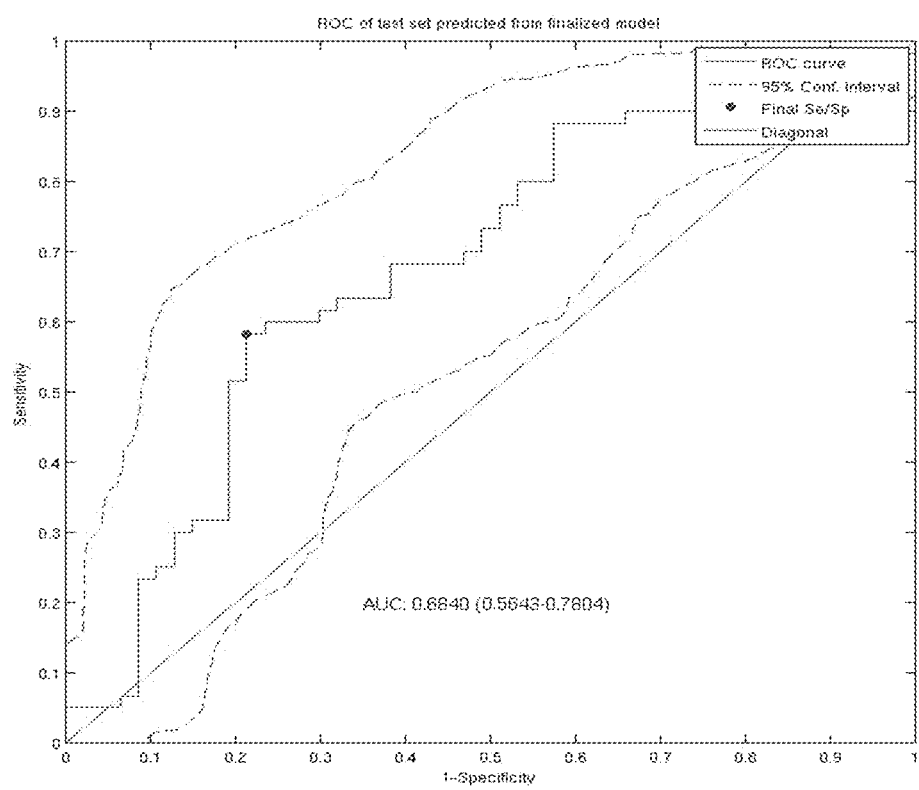
FIG. 3 provides a diagram of a ROC curve of the classification performance for predicting BRCA status using the 44-gene classifier model, estimated by cross validation. The AUC is ~0.68 following application the classifier model. The 95% confidence limits have been estimated from bootstrap with 1000 iterations.

FIG. 3 shows that the 44-gene classifier models separate the BRCA mutants from the sporadic samples with an AUC of ~0.68, where the lower confidence interval is ~0.56 for both models (Table 46A); showing that the performance is significantly better than a random classifier. As such, this analysis confirms that the 44-gene DDRD classifier model is capable of identifying samples with high genomic instability due to an inability to repair DNA damage.

Application of Classifier Model to Independent Microarray Clinical Datasets

Independent Breast Microarray Clinical Datasets (1) Assessment of the 44-Gene DDRD Classifier Model's Predictive Power to DNA-Damaging Chemotherapy To assess the ability of the 44-gene DDRD classifier model to predict response to DNA-damaging chemotherapeutics, it was applied to data combined from three publicly available datasets. In each study, breast cancer patients were treated with neoadjuvant 5-fluorouracil, anthracycline, and cyclophosphamide-based regimens, drugs that directly damage DNA. The first (Tabchy et al., 2010) and second (Iwamoto et al., 2011) datasets had response data for 87 and 50 ER-positive and ER-negative primary breast tumor samples respectively following neoadjuvant treatment with fluorouracil, doxorubicin and cyclophosphamide (FAC). The third dataset (Bonnefoi et al., Lancet Oncol 8, 1071-1078(2007)) had response data for 66 ER-negative primary breast tumor samples following neoadjuvant 5-fluorouracil, epirubicin and cyclophosphamide (FEC) treatment. Each study used pathological complete response (pCR) or residual disease (RD) as endpoints. As each dataset was relatively small, the data was combined to increase the power of the analysis.

Figure 4:
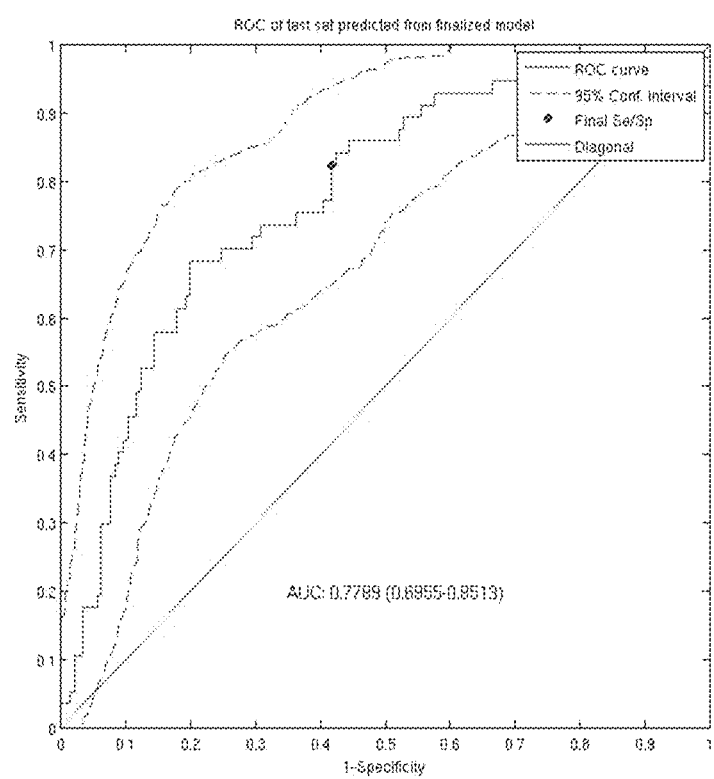
FIG. 4 provides a diagram of a ROC curve of the classification performance of the 44-gene classifier model in a combined analysis of three independent datasets: FEC, FAC1 and FAC2 (Bonnefoi et al., 2007; Iwamoto et al., J Natl Cancer Inst 103, 264-272 (2011); Lee, J. K., et al. Clin Cancer Res 16, 711-718 (2010) for predicting response to anthracycline-based chemotherapy. The AUC is ~0.78 following application of the classifier model. The 95% confidence limits have been estimated from bootstrap with 1000 iterations.

The analysis revealed that that the 44-gene DDRD classifier model was significantly associated with response to anthracycline-based chemotherapy (relative risk (RR)=4.13, CI=1.94-9.87; AUC=0.78, CI=0.70-0.85, P=0.001; Table 46B, FIG. 4). The negative predictive value (NPV) of the classifier was considerably higher than the positive predictive value (PPV) (0.90 versus 0.44, Table 46B), indicating that DDRD-negative tumors were unlikely to respond to DNA-damaging chemotherapy.

Stepwise logistic regression was used to determine the ability of the 44-gene DDRD classifier model to predict response in the combined datasets when adjusting for clinical variables (Table 47). The 44-gene DDRD classifier model was determined to be the most significant clinical variable in univariate analysis. Multivariate analysis confirmed that the 44-gene DDRD classifier model's predictive value was independent of stage, grade and notably ER status.

Negativity for estrogen, progesterone and HER2 receptors has been suggested as a biomarker of abnormal DDR and thus response to DNA-damaging and DNA repair targeted therapies (Foulkes et al., 2010). However, this approach excludes the 20% of BRCA1 and the 40% of BRCA2 mutant tumors that are reported to be ER-positive (Foulkes et al., 2004; Tung et al., 2010). In contrast, by virtue of the analysis approach we adopted, the 44-gene DDRD classifier detects the DDRD subgroup in both ER-positive and ER-negative tumors, as validated by the multivariate analysis of the 44-gene DDRD classifier's predictive value within the combined analysis of FEC and FAC datasets, demonstrating its independence from ER status. Clinically, this is an important aspect of the translational application of the DDRD classifier as it suggests it can be applied to all breast cancer patients, irrespective of ER status, to determine their predicted responsiveness to DNA-damaging therapeutics.

Figure 5:
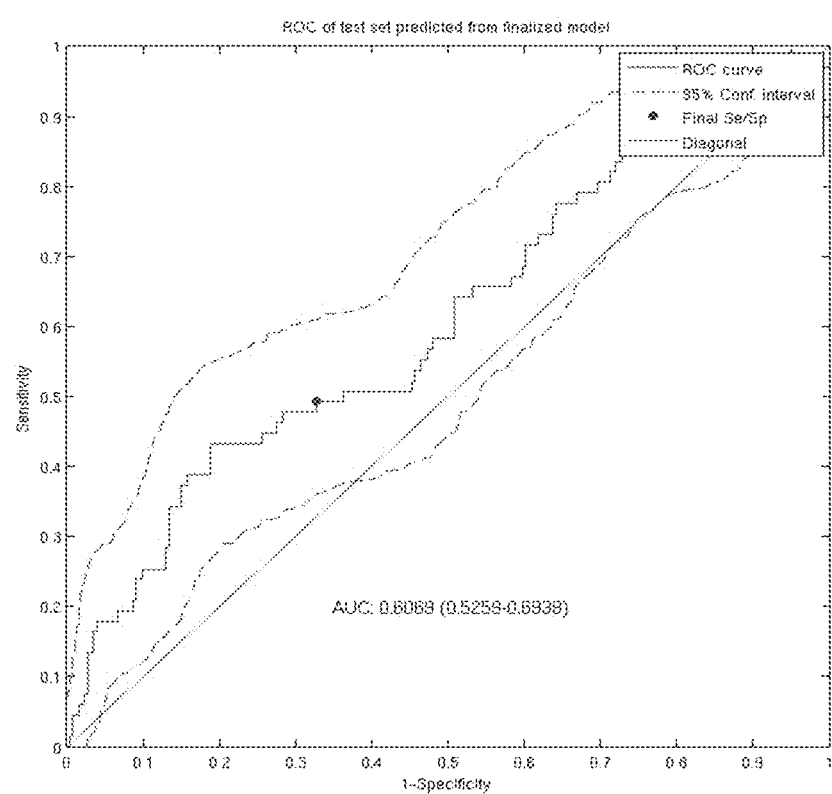
FIG. 5 provides a diagram of a ROC curve of the classification performance of the 44-gene classifier model in a combined analysis of three independent datasets for response in T/FAC treated samples (Hess et al., J Clin Oncol 24, 4236-4244 (2006); Lee et al., 2010; Tabchy, A., et al. Clin Cancer Res 16, 5351-5361 (2010). The AUC is ~0.61 following application of the classifier model respectively. The 95% confidence limits were determined using 1000 bootstrap iterations.

(2) Assessment of 44-Gene DDRD Classifier Model's Predictive Power to Taxane-Containing Chemotherapy Regimens The ability of the 44-gene DDRD classifier model to predict response to chemotherapy regimens that contained non-DNA-damaging agents such as taxanes was assessed. Data was combined from 3 datasets with response data following neoadjuvant treatment with paclitaxel and FAC (T/FAC) for 321 primary breast cancer patients, where response was defined as pCR (Hess et al., 2006; Lee et al., 2010; Tabchy et al., 2010). Whilst the 44-gene DDRD classifier model was both associated with response (AUC=0.61, CI=~0.52-0.69, Table 46B, FIG. 5), this performance was significantly reduced compared to that within the FAC/FEC only treated samples. In addition, multivariate analysis indicated the DDRD classifier was not independent from other clinical parameters (P=0.21) in its ability to predict response to T/FAC (Table 47). This suggests that the subgroup detected by the DDRD classifier is more sensitive to DNA-damaging only regimens rather than regimens also containing anti-microtubule agents.

Independent Ovarian Microarray Clinical Datasets

Figure 6:
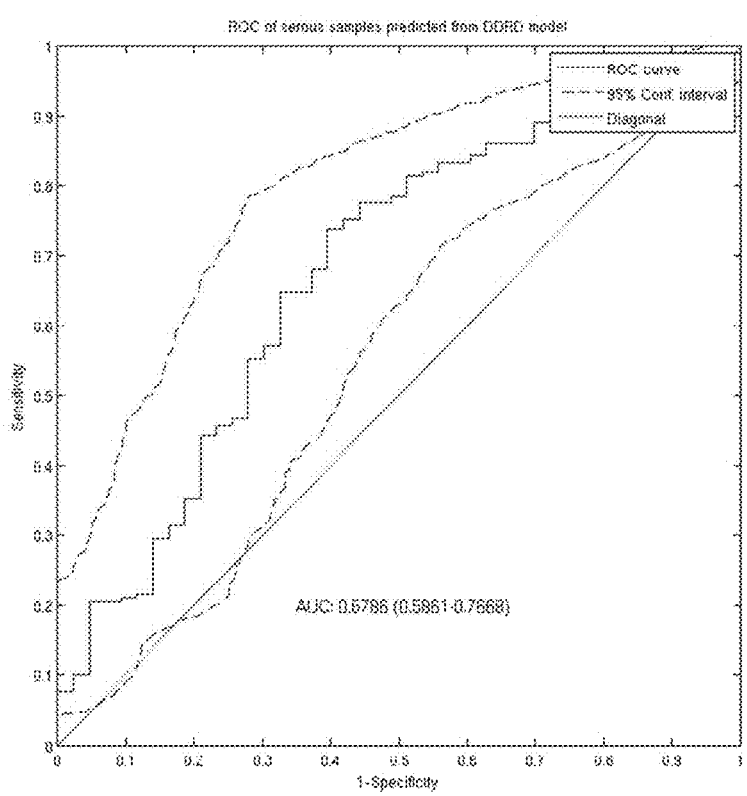
FIG. 6 provides a diagram of a ROC curve of the classification performance of the 44-gene classifier model within 259 serous ovarian cancer samples for response in platinum and taxol treated samples from the in-house Almac Diagnostics ovarian dataset. The AUC is ~0.68 following application of the classifier model. The 95% confidence limits were determined using 1000 bootstrap iterations.

It was decided to explore the performance of the 44-gene DDRD classifier model in another disease area. As such, the performance of the classifier models was assessed within a set of 259 FFPE primary ovarian cancer samples with serous histology. These samples were from patients that received either adjuvant platinum treatment or adjuvant platinum and taxane treatment and were profiled on the Ovarian cancer DSA™. Response data was determined by RESIST and/or the serum marker CA125 levels. Applying the 44-gene DDRD classifier model to these samples proved to separate the responders from the non-responders significantly, with an AUC of ~0.68 and a lower confidence limit of approx 0.59 (FIG. 6). The 44-gene DDRD classifier model detects dysfunction of the Fanconi Anemia/BRCA pathway.

Figure 7:
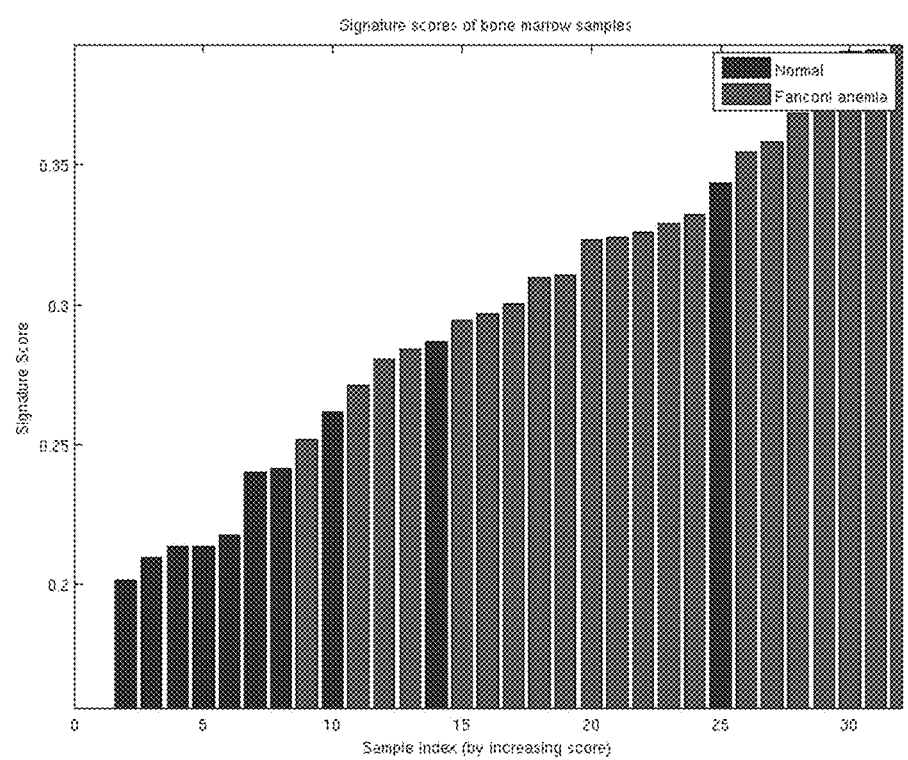
FIG. 7 provides a histogram representation of the 44-gene DDRD classifier scores in bone marrow samples taken from healthy donors and patients with Fanconi Anaemia mutations. The AUC is 0.90 following application of the classifier model. The 95% confidence limits were determined using 1000 bootstrap iterations.

The Fanconi anemia/BRCA (FA/BRCA) pathway, which includes BRCA1 and BRCA2, plays an integral role in DNA repair and can be lost in breast cancer either due to mutation or epigenetic silencing (Kennedy and D'Andrea, 2006). It was therefore determined if the 44-gene DDRD classifier model could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf, S. M., et al., Blood 114, 5290-5298 (2009). The 44-gene DDRD classifier model significantly distinguished between the FA/BRCA mutant and normal samples with an AUC of 0.90 (CI=0.76-1.00, P<0.001, FIG. 7), demonstrating a strong correlation between the DDRD classifier and dysfunction of the FA/BRCA pathway through multiple mechanisms.

Summary of in Silico Validation of 44-Gene DDRD Classifier Model

The in silico validation of the 44-gene DDRD classifier model has shown the following:
  (a) The 44-gene DDRD classifier model is able to significantly separate BRCA mutant breast tumor samples from wildtype BRCA (sporadic) breast tumor samples. This implies that the DDRD classifier model is capable of detecting biology related to tumors with a high level of genomic instability, such as BRCA mutant tumors. These tumors typically respond better to DNA damaging chemotherapeutic regimens.
  (b) The 44-gene DDRD classifier model is able to significantly separate defined responders (those that demonstrated pCR) from the non-responders (those that did not demonstrate pCR) in a combination of three independent breast datasets following neoadjuvant treatment with FAC and FEC (Bonnefoi et al., 2007; Iwamoto et al., 2011; Tabchy et al., 2010) and T/FAC (Hess et al., 2006; Lee et al., 2010; Tabchy et al., 2010). The 44-gene DDRD classifier model was found to be independent of other clinical factors and the most significant independent predictor of response in the FAC/FEC combined analysis. These studies were carried out using fresh frozen (FF) samples and using two different microarray platforms, namely the Affymetrix X3P microarray and the Affymetrix U133A microarray. These results validate the performance of the 44-gene DDRD classifier model within independent breast datasets utilizing a different sample material (FF instead of FFPE) and utilizing microarray data from two different microarray platforms.
  (c) The 44-gene DDRD classifier model is able to significantly separate responders from non-responders within an independent Almac ovarian dataset following adjuvant treatment with platinum or platinum/taxane based therapy. This data was generated using FFPE samples profiled upon the Almac Ovarian DSA™.
  (d) The 44-gene DDRD classifier model is able to significantly distinguish between FA/BRCA mutant and normal samples using bone marrow tissue samples, demonstrating a strong correlation between the DDRD classifier and dysfunction of the FA/BRCA pathway through multiple mechanisms.

In summary, the DDRD classifier model has been independently validated and demonstrated robustness in performance across three different disease areas (breast, ovarian and FA), demonstrated ability to separate responders from non-responders to four different chemotherapeutic regimens (FAC, FEC, T/FAC and platinum/taxane) in two different sample types (FFPE and FF) utilizing data from four different microarray platforms (Almac Breast DSA™ and Almac Ovarian DSA™, Affymetrix X3P microarray and Affymetrix U133A microarray). It has been demonstrated that the DDRD is an independent predictor of response to DNA-damage therapeutic agents and can predict mutations in the FA/BRCA pathways. This plasticity and repeatability of performance implies that the biology identified within the DDRD subgroup identified via the 44-gene classifier model is significantly and robustly related to predicting response to DNA damage causing agents and as such supports the claim of this invention which is to identify a subtype that can be used to predict response to, and select patients for, standard breast and ovarian cancer therapeutic drug classes, including drugs that damage DNA directly, damage DNA indirectly or inhibit normal DNA damage signaling and/or repair processes.

TABLE 46

Performance metrics and independence assessment of the 44-gene DDRD classifier model in breast datasets

| Dataset | No. | Treatment | Clinical Outcome | AUC (CI) | ACC (CI) | SENS (CI) | SPEC (CI) | PPV (CI) | NPV (CI) | RR (CI) |
|---|---|---|---|---|---|---|---|---|---|---|
| (A) Prediction of BRCA mutation status using the 44-gene DDRD classifier model | | | | | | | | | | |
| Training | 107 | N/A | BRCA mutant V wildtype | 0.68 (0.56-0.78) | 0.70 (0.57-0.76) | 0.58 (0.48-0.65) | 0.79 (0.64-0.86) | 0.78 (0.63-0.85) | 0.60 (0.49-0.65) | 1.93 (1.23-2.55) |
| (B) Prediction of pCR using 44-gene DDRD classifier model | | | | | | | | | | |
| FAC1 FAC2 and FEC | 203 | FEC and FAC | pCR V RD | 0.78 (0.70-0.85) | 0.76 (0.64-0.83) | 0.82 (0.69-0.92) | 0.58 (0.52-0.62) | 0.44 (0.36-0.48) | 0.90 (0.81-0.95) | 4.13 (1.94-9.87) |
| T/FAC | 321 | T/FAC | pCR V RD | 0.61 (0.53-0.69) | 0.53 (0.43-0.62) | 0.49 (0.38-0.60) | 0.67 (0.64-0.70) | 0.29 (0.22-0.35) | 0.83 (0.80-0.87) | 1.72 (1.05-2.65 |

Numbers in brackets denote the 95% confidence limits from +/− 2SD from cross-validation (A) or bootstrapping with 1000 repeats (B).
AUC = Area Under the Receiver Operating Characteristics Curve;
ACC = Accuracy;
SENS = Sensitivity;
SPEC = Specificity;
PPV = Positive Predictive value;
NPV = Negative Predictive Value;
RR = Relative Risk,
pCR = pathological complete response,
RD = residual disease.

TABLE 47

Univariate and Multivariate Analysis of the 44-gene
DDRD classifier model
Comparison of the 44-gene DDRD classifier model
to standard pathological parameters in
independent validation sets. The predictive value of
the DDRD classifier model as well
as significant clinical parameters were
evaluated in a univariate and multivariate
analysis using logistic regression models with
p-values coming from a log-likelihood test.
Univariate and Multivariate Analysis of the
44-gene DDRD classifier model

| FAC1, FAC2 and FEC Variable | Univariate P value | Multivariate P value |
|---|---|---|
| DDRD classifier | 0.0000 | 0.0014 |
| ER | 0.0004 | 0.0249 |
| Stage | 0.0459 | 0.0492 |
| Grade | 0.0100 | 0.0468 |
| T/FAC Variable | Univariate P value | Multivariate P value |
| DDRD classifier | 0.0129 | 0.2100 |
| ER | 0.0000 | 0.0000 |
| Stage | 0.3626 | 0.0359 |
| Grade | 0.0000 | 0.0115 |

Example 3

In Vitro Validation of the 44-Gene DDRD Classifier Model

In order to assess the biology underlying the genes contained within the 44-gene classifier model, a number of studies were carried out in vitro using a panel of breast cell-lines.

Methods

Maintenance of Cell-Lines

The HCC1937 parental, HCC1937-EV and HCC1937-BR cell-lines were kindly donated by Professor Paul Harkin from Queen's University College Belfast (QUB). The cell-lines were routinely maintained in RPMI-1640 medium supplemented with 50 U penicillin/ml, 50 µg streptomycin/ml, 2 mM glutamine, 1 mM Sodium Pyruvate and 20% (v/v) fetal bovine serum (FBS). The HCC1937-EV and HCC937-BR cell-lines also required 0.2 ml/mg geneticin. Cell-lines were cultured at 37° C. with a humidified atmosphere of 5% $CO_2$.

Clonogenic Assays—Determination of PARP-1 Inhibitor Sensitivity

For measurement of sensitivity to PARP-1 inhibitor (KU0058948), exponentially growing cells were seeded into 6-well plates. Twenty-four hours following seeding the cells were exposed to medium containing increasing doses of drug. Cell medium was replenished every 4-5 days. After 12-14 days the cells were fixed in methanol, stained with crystal violet and counted. The percentage survival of control for a given dose was calculated as the plating efficiencies for that dose divided by the plating efficiencies of vehicle-treated cells. Survival curves and half maximal inhibitory concentration ($IC_{50}$) values were calculated using GraphPad Prism.

Cell Viability Assay—Determination of Cisplatin Sensitivity

For measurement of sensitivity to cisplatin, exponentially growing cells were seeded into 96-well plates. 24 hours following seeding the cells were exposed to medium containing increasing doses of cisplatin. Cells were incubated in the presence of drug for 96 hours following which time the viability of the cells was assessed using the Promega CellTitre-Glo luminescent cell viability assay. The sensitivity of the cells was calculated as the percentage of vehicle (DMSO) control. Survival curves and half maximal inhibitory concentration ($IC_{50}$) values were calculated using GraphPad Prism.

Results

The DDRD Subgroup can be Identified within Breast Cancer Cell-Line Models

A preclinical model system was used to confirm that the 44-gene DDRD classifier was a measure of abnormal DDR. The HCC1937 breast cancer cell-line is DDRD due to a BRCA1 mutation (Tomlinson et al., 1998). The 44-gene classifier was applied to HCC1937 empty vector control cells (HCC1937-EV) and HCC1937 cells in which BRCA1 functionality was corrected (HCC1937-BR) (FIG. 8A). The DDRD 44-gene classifier score was found to be higher within HCC1937-EV relative to HCC1937-BR cells, with average scores of 0.5111 and 0.1516 respectively (FIG. 8B). Consistent with the DDRD 44-gene classifier scores, the HCC1937 BRCA1 mutant cell-line was more sensitive to the PARP-1 inhibitor KU0058948 (FIG. 8C) and cisplatin (FIG. 8D) relative to the BRCA1 corrected cell-line. These preclinical data suggest that the DDRD 44-gene classifier measures immune signalling in DDRD-positive tumor cells and correlates with response to both a DNA-damaging agent (cisplatin) and a DNA repair targeted agent (PARP-1 inhibitor).

The DDRD 44-Gene Classifier Detects Dysfunction of the Fanconi Anemia/BRCA Pathway The Fanconi anemia/BRCA (FA/BRCA) pathway, which includes BRCA1 and BRCA2, plays an integral role in DNA repair and can be lost in breast cancer either due to mutation or epigenetic silencing (Kennedy, R. D., and D'Andrea, A. D., J Clin Oncol 24, 3799-3808 (2006)). It was determined if the DDRD 44-gene classifier could detect abrogation of members of this pathway in addition to BRCA1 and BRCA2. A public dataset was identified with microarray data generated from the bone marrow of 21 FA patients carrying a range of mutations in the FA/BRCA pathway and 11 healthy controls with a functional FA/BRCA pathway (Vanderwerf et al., 2009). The DDRD 44-gene classifier significantly distinguished between the FA/BRCA mutant and normal samples with an AUC of 0.90 (CI=0.76-1.00, P<0.001), demonstrating a strong correlation between the DDRD classifier and dysfunction of the FA/BRCA pathway through multiple mechanisms.

Conclusion

The DDRD 44-gene classifier score was significantly higher in the BRCA1 mutant, and thus DDRD, HCC1937 breast cancer cell-line relative to an isogenic BRCA1 corrected cell-line. As the 44-gene classifier score correlates with DDR dysfunction within these cells, it demonstrates that the immune signalling detected by the DDRD classifier is intrinsic to the cell and not a function of lymphocytic infiltrate. BRCA1 and BRCA2 represent part of the FA/BRCA DDR network, which contains a number of other proteins that have been reported to be mutant or under-expressed in approximately 33% of breast cancer (Kennedy, R. D., and D'Andrea, A. D., J Clin Oncol 24, 3799-3808 (2006). As described previously, the DDRD 44-gene classifier significantly separated bone marrow samples from patients with FA mutations from normal controls. This suggests that the DDRD classifier is capable of detecting any abnormality within the pathway rather than specifically BRCA1 or BRCA2 dysfunction. It is possible that the DDRD 44-gene classifier may identify tumors with DDR-deficiency due to other mechanisms such as PTEN loss, cell-cycle checkpoint dysfunction or increased reactive oxygen species due to metabolic disturbance. Due to constitutive DNA-damage, these tumors are likely to respond to DNA repair targeted therapies such as PARP-1 or CHK1/2 inhibitors.

Example 4

Endogenous and Exogenous DNA Damage Activates Expression of Innate Immune Genes Via the cGAS-STING Pathway Methodologies
Immunohistochemistry All immunohistochemistry was using the Ventana Discovery®-XT Automated Stainer. Immunohistochemical application was performed on 4 µm sections taken from FFPE blocks. Sections for IHC were cut at 4 µm on a rotary microtome, dried at 37° C. overnight and then used for IHC assays. A Tissue MicroArray of a previously described cohort of 191 N0-N1 ER positive and ER negative FFPE breast tumour samples was scored in triplicate for immune expression analysis. CD4 (4612, M7310, Dako) was diluted 1:50, and CD8 (C8/1446, M7103, Dako) was diluted 1:50 to enable visualisation of immune cell infiltrate. CD274 (PDL1) (Roche, SP142) was diluted 1:40 and an 8 minute amplification step using the OptiView Amplification Kit (Roche). A semi-quantitative scoring system was employed for CD4 and CD8 characterisation. Briefly, a score of 3 indicates strong CD4 or CD8 expression, 2 indicates moderate expression and 1 low or weak expression. If there was absence of CD4 or CD8 expression the score 0 was applied. Scores were determined by two independent observers for both the stromal and intratumoral component of cores visualized on TMA. For CD274 (PDL1) previously published cut offs of >1% and >5% were used for scoring positive cores on TMA. CD274 (PDL1) staining was investigated in both the tumour and stroma of cores.

Reverse siRNA Transfection siRNA oligonucleotides (MWG Eurofins) were resuspended to a concentration of 100 µM according to the manufacturer's instructions. The following sequences were used for siRNA:

```
STING_a    5' CAGCGGCUGUAUAUUCUCCUCCCUU 3'
STING_b    5' GGUCAUAUUACAUCGGAUAUU 3'
TBK1_a     5' GGAAAUAUCAUGCGUGUUAUU 3'
TBK1_b     5' UGGUGCAGCUAGAGAAUUAUU 3'
IRF3_a     5' CCUCUGAGAACCCACUGAAUU 3'
IRF3_b     5' GGACAAUCCCACUCCCUUCUU 3'
cGAS_a     5' AGAGAAAUGUUGCAGGAAAUU 3'
cGAS_b     5' CAGCUUCUAAGAUGCUGUCAAAGUU 3'
BRCA1_a    5' CCUAUCGGAAGAAGGCAAGUU 3'
BRCA1_b    5' CAUACAGCUUCAUAAAUAAUU 3'
BRCA2_a    5' GGACACAAUUACAACUAAAUU 3'
BRCA2_b    5' GGAGGAAUAUCGUAGGUAAUU 3'
FancD2_a   5' GCAGAUUCAUGAAGAGAAAUU 3'
FancD2_b   5' GGUUAAAGCACAUUGUAGAUU 3'
```

In a 6 well plate, 20 µl of 2 µM siRNA stock was resuspended in 500 µl 1:100 Optimem:Lipofectamine® RNAiMax (Life Technologies), incubated for 5 minutes at room temperature. This was then incubated for 20 minutes at room temperature, during which time cells were trypsinised and counted using a Countess Automated Cell Counter (Life Technologies). Cells were then resuspended in antibiotic free medium to a concentration determined to yield 50% confluency at 24 hours with 1.5 ml of cell suspension added to each plate. Media was changed at 24 hours, and drug treatment added at this point if indicated. Cells were then incubated for a further 48 hours before harvesting RNA and protein.

Quantitative Real-Time PCR (qRT-PCR)

Reverse transcription was performed using the First Strand cDNA synthesis kit (Roche). 500 ng of RNA was reverse transcribed according to manufacturer's instructions. Exon-spanning qPCR primers were designed using Roche Universal Probe Library Assay Design Centre and were used at a concentration of 0.5 µM. The following primer sequences were used:

```
CXCL10
Forward 5' GGC CAT CAA GAA TTT ACT GAA AGC AGC A 3'
Reverse 5' TCT GTG TGG TCC ATC CTT GGA A 3'

CCL5
Forward 5' TGC CCA CAT CAA GGA GTA TTT 3'
Reverse 5' CTT TCG GGT GAC AAA GAC G 3'

IDO1
Forward 5' CAT CTG CAA ATC GTG ACT AAG 3'
Reverse 5' CAG TCG ACA CAT TAA CCT TCC TTC 3'

PDL1
Forward 5' GGC ATC CAA GAT ACA AAC TCA AAG A 3'
Reverse 5' AGT TCC AAT GCT GGA TTA CGT CT 3'

PUM1 (Housekeeping gene)
Forward 5' CCA GAA AGC TCT TGA GTT TAT TCC 3'
Reverse 5' CAT CTA GTT CCC GAA CCA TCT C 3'
```

To preform absolute quantification from qPCR, we used a standard curve method. The efficiency of each primer set was derived from the standard curve using the following equation:

$$E = 10\textasciicircum(-1/\text{slope})$$

The product of Reverse Transcription was diluted 1:10 in Nuclease Free Water (NFW). Each 10 µl PCR reaction, consisted of 0.5 µl of 10 µM Forward primer, 0.5 µl of 10 µM Reverse primer, 5 µl of 2× LightCycler® 480 SYBR Green I Master mix (Roche), 1.5 µl NFW and 2.5 µl diluted Reverse Transcription product. These 10 µl reactions were pipetted into wells of a LightCycler® 480 multiwell 96 plate (Roche), the plate was then sealed using clear adhesive film (Roche). The plate was placed into the LightCycler® 480 (Roche) and run with the following protocol. (95° C. for 10 mins, 45 cycles of; 95° C. for 15 secs, 55° C. for 30 secs and 72° C. for 30 secs, finishing with a melt curve for confirmation of primer specificity. All qPCR data was analysed using the LightCycler® 480 software provided by Roche. For analysis, the Cp value from a technical duplicate was calculated and the relative amount of a gene was calculated Cp value to an in-run standard curve. Each mean value was then normalised to the mean concentration of the housekeeping gene PUM1 within the corresponding sample, by dividing the concentration of the target gene by the concentration of the house keeping gene. Relative expression refers to the gene expression levels that have been normalised to the housekeeping gene and made relative to the associated control samples. From these normalized values, the fold changes for each gene were calculated and the average of three individual fold changes were derived from three independent experimental triplicates. The unpaired, two-tailed students T-test available on GraphPad Prism 5.0 software was used to detect statistical significance.

Western Blotting

Adherent cells formed whole cell lysates suspended in RIPA buffer containing phosphatase and protease inhibitors (Roche Inhibitor cocktails, Germany). Lysates were then spun to eliminate cell debris. Protein was quantified using the BCA Assay (Pierce, Rockford, Ill., USA) according to manufacturer's instructions using a plate reader. Equal amounts of protein per sample was prepared in mercaptoethanol protein loading buffer and separated by size using a gradient 4-12% Bolt® Tris-Bis plus polyacrylamide gel (Life Technologies, Thermo Fisher Scientific Inc.) or a gradient 3-8% NuPAGE® Novex® Tris-acetate gel (for BRCA1 only; Life Technologies, Thermo Fisher Scientific Inc.) and transferred to a PVDF 0.45 µm membrane (Immoblion-P, Millipore) by electroblotting. For investigation of PDL1 expression, the membranes were blocked in 3% BSA/TBST and probed overnight with ant-PDL1 antibody (catalogue no. #13684, Cell Signalling, Technology, MA, USA) diluted 1:500 in 3% BSA/TBST. For the investigation of BRCA1 (HPA034966, Sigma Aldrich), Lamin B1 (ab16048, Abcam), cGAS (HPA031700, Sigma Aldrich), Histone H3 (ab1791, Abcam), MHC class I/HLA A/HLA B (ab134189, Abcam), and HLA G (ab52455, Abcam), membranes were blocked in 3% non-fat milk/TBST and probed overnight with antibody diluted 1:1000 in 3% milk/TBST. For the investigation of IDO1 expression (catalogue no. #12006, Cell Signalling Technology), membranes were blocked in 5% BSA/TBST and probed overnight with antibody diluted 1:500 in 5% BSA/TBST. For loading controls, membranes were blocked in 3% Milk/TBST and probed with anti-β-actin (Sigma Aldrich) diluted 1:10,000 in 3% Milk/TBST or Vinculin (sc-73614, Santa Cruz) diluted 1:2000 in 3% Milk/TBST before the appropriate HRP-conjugated secondary was added. Results were then visualized and recorded using Luminata Crescendo Western HRP substrate (Millipore, UK) and an alpha imager.

Invasion Assay

To test the invasive properties of cell secretions, conditioned media was collected from indicated cell lines with and without transfected knockdowns. Cells were seeded and/or treated on day 0, media was changed to Optimem on day 1 and collected on day 3. Media was then centrifuged at 800 g for 5 minutes to remove cellular debris. Invasion assays were performed using Corning® Transwell® polycarbonate membrane 5 µm 24 well cell culture inserts (Sigma, MO, USA). PBMCs were counted, and resuspended in Optimem 0.5% BSA at a density of $5 \times 10^6$ cells/ml. 100 µl of cell suspension was placed in the top chamber of the transwell plate equating to $5 \times 10^5$ cells. 600 µl of conditioned media was placed in the bottom chamber and the assay was incubated for 16 hours. After 16 hours, 100 µl of media from the bottom chamber was removed and a CellTiter-Glo® (Promega, PA, USA) assay was performed per manufacturer's instructions. Invaded cell numbers were derived from a standard curve generated with the CellTiter-Glo® assay and samples of cells counted with a countess (Life technologies, Paisley, UK).

Cytotoxicity

The cytotoxic effects of lymphocytes on cancer cells was measured using LIVE/DEAD® Cell-Mediated Cytotoxicity Kit (Life technologies, Paisley, UK.) RKO parental and Fanc G cells were trypsinised, counted and stained with green-fluorescent membrane stain DiOC18 in PBS at a concentration of 2 µl of stain per ml. Cells were incubated with the stain for 20 minutes at 37° C. before being seeded into 12 well plates at a density of $1 \times 10^5$ cells per well and left to adhere overnight. The next day PMBCs were counted and added to RKO cell cultures at the ratios indicated. For 1:1 ratio $1 \times 10^5$ PBMCs were added, for 5:1 ratio $5 \times 10^5$ PBMCs were added. The co-cultures were incubated for 4 hours before cells were collected for analysis by flow cytometry. A BD FACSCalibur™ (BD Biosciences, CA, USA) was used for the analysis of samples and Flow Jo software was used for data analysis. Cells were treated with interferon-γ at a concentration of 20 ng/ml for 16 hours. Cells were treated with LEAF purified anti-human CD274 (Clone 29E.2A3) antibody (BioLegend, CA, USA) at a concentration of 100 µg/ml for 16 hours prior to addition of PBMCs.

Small Molecule Inhibitors & Chemotherapeutic Agents

For analysis of effects of ATM, ATR and DNAPK on cytokine expression, cells were seeded in six well plates at ~60% confluency. Following incubation overnight, small molecule inhibitors of ATM (Ku60019, Selleck Chem) at a dose of 1 µm, ATR (ETP46464, Selleck Chem) at a dose of 5 µm and DNAPK (Nu7441, Selleck Chem) at a dose of 5 µm were added. At 24 hours, RNA and protein samples were obtained for analysis. For analysis of the effects of DNA damaging agents and paclitaxel on cytokine expression, cells were seeded in six well plates at ~60% confluency. Following incubation overnight, $IC_{50}$ doses of Cisplatin and Paclitaxel (obtained from fresh Pharmacy stock) and Hydroxyurea (Sigma Aldrich) were added for 24 hours to 48 hours. At the appropriate timepoint, RNA and protein samples were obtained for analysis.

Cell Cycle Analysis

Cells were trypsinised and fixed in 70% ethanol, incubated with RNase A and propidium iodide (PI) and analysed using a BD FACSCalibur™ (BD Biosciences, CA, USA). Data was analysed using Flow Jo software to perform cell cycle analysis.

Immunoprecipitation

Whole cell lysates were prepared and quantified as in the Western Blotting section. For immunoprecipitation, 500 pg of protein was rotated at 4° C. overnight with 2 pg of TBK1 (sc-52957, Santa Cruz Biotechnology) or IRF3 (Catalogue no. #4302, Cell Signalling Technology). Appropriate secondary anti-mouse or anti-rabbit Dynabeads® (Invitrogen) were pre-washed with RIPA buffer and equal amounts added to samples. Following rotation for 2 hours at 4° C., samples were washed with RIPA, using the Dynamag Magnetic Rack. Samples were then boiled at 95° C. for 15 minutes in NuPAGE LDS sample buffer (Life Technologies) and NuPAGE Reducing Agent (Life Technologies). Equal amounts of reduced samples were separated by size using a gradient 4-12% Bolt® Tris-Bis plus polyacrylamide gel (Life Technologies, Thermo Fisher Scientific Inc). Western blotting procedure was followed as described previously.

Membranes were blocked for 1 hour at room temperature in 5% BSA/TBST and probed with either pTBK1 (Ser172) (Catalogue no. #5483, Cell Signalling Technology) or pIRF3 (Ser396) (Catalogue no. #4947, Cell Signalling Technology) overnight at 4° C. Membranes were then probed with appropriate HRP-conjugated secondary (Anti-rabbit IgG, Catalogue no. #7074, Cell Signalling Technology for pTBK1; Anti-rabbit Light Chain Specific IgG, 211-032-171, Jackson ImmunoResearch Laboratories Inc. for pIRF3). Results were then visualized and recorded using Luminata Crescendo Western HRP substrate (Millipore, UK) and an alpha imager.

Cell Fractionation

Cells were fractionated using Buffer A (10 mM Hepes pH7.4; 1.5 nM $MgCl_2$, 10 mM NaCl, 0.1% NP-40, Protease and Phosphatase inhibitors) and Buffer C (10 mM Hepes pH7.4; 1.5 nM $MgCl_2$, 420 mM NaCl, 0.1% NP-40, Protease and Phosphatase inhibitors). Cells were cultured at ~70% confluency. Cells were then removed in PBS using a cell scraper and transferred to an Eppendorf. Following centrifugation at 1000 rpm at 4° C. for 5 minutes, cell pellets were resuspended in 350 μl Buffer A. Cells were lysed on ice for twenty minutes, following which samples were centrifuged at 12000 rpm for 2 minutes. Supernatants were removed, and spun a further two times at 12000 rpm for 2 minutes. The supernatant (cytoplasmic fraction) was carefully removed and stored at −80° C. until quantification using the BCA Assay (Pierce, Rockford, Ill., USA) according to manufacturer's instructions using a plate reader. The remaining pellet was washed ×1 in Buffer A, then centrifuged at 12000 rpm for 2 minutes. The pellet was resuspended in Buffer C, lysed on ice for 10 minutes and sonicated at 20K cycles/second for 30 seconds. Samples were then centrifuged at 12000 rpm for two minutes to remove debris, and supernatant (nuclear fraction) stored at −80° C. until quantification as described above.

Co-Immunoprecipitation

Cytoplasmic fractions were prepared as described above. 500 pg of protein was rotated at 4° C. overnight with 2 μg of Histone H3 antibody (ab1791, Abcam) resuspended in Pierce IP Lysis Buffer (Thermo Scientific). Secondary anti-rabbit Dynabeads® (Invitrogen) were pre-washed with Pierce IP Lysis Buffer and equal amounts added to samples. Following rotation for 2 hours at 4° C., samples were washed with Pierce IP Lysis Buffer, using the Dynamag Magnetic Rack. Samples were then boiled at 95° C. for 15 minutes in NuPAGE LDS sample buffer (Life Technologies) and NuPAGE Reducing Agent (Life Technologies). Equal amounts of reduced samples were separated by size using a gradient 4-12% Bolt® Tris-Bis plus polyacrylamide gel (Life Technologies, Thermo Fisher Scientific Inc). Western blotting procedure was followed as described previously. Membranes were blocked for 1 hour at room temperature in 5% BSA/TBST and probed with cGAS antibody (HPA031700, Sigma Aldrich) in 5% BSA/TBST at 4° C. overnight. Membranes were probed with HRP-conjugated secondary (Anti-rabbit IgG, Catalogue no. #7074, Cell Signalling Technology). Results were then visualized and recorded using Luminata Crescendo Western HRP substrate (Millipore, UK) and an alpha imager.

Results

CD4+ and CD8+ T Lymphocytes are Associated with DDRD Assay Positive Tumours.

Figure 9B:
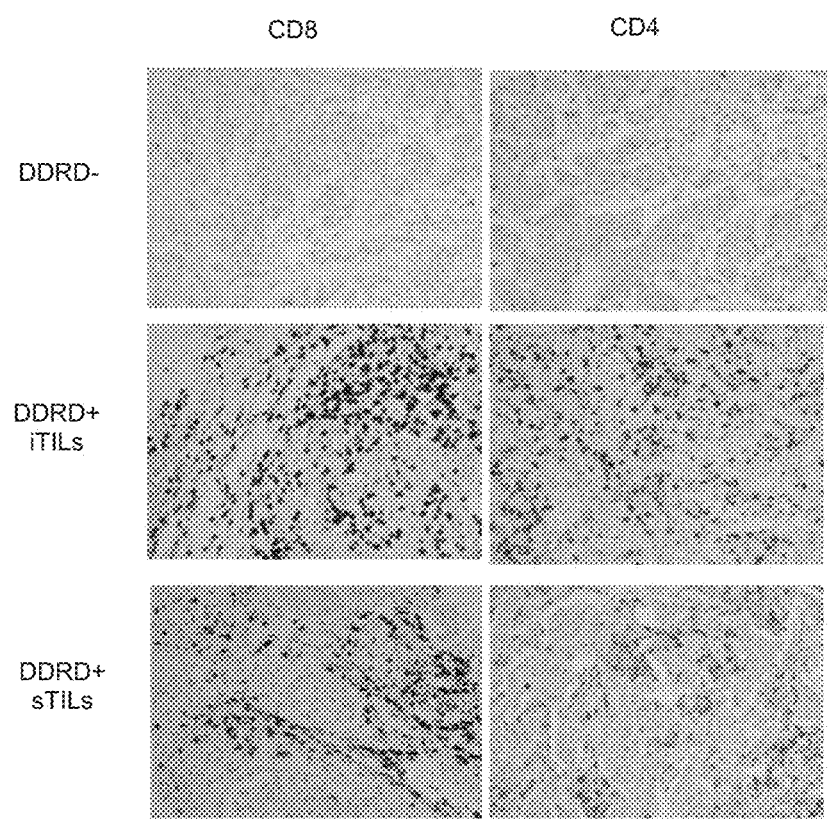
FIG. 9 provides a table and images showing that DDRD Tumours are Associated with Lymphocytic Infiltration.

As we had observed up-regulation of interferon-related genes including T-cell specific ligands in DDRD tumors, we asked if these were associated with a T cell immune response. The presence of intratumoral CD4+ and CD8+ T lymphocytes have previously been described as prognostic in breast cancer. The presence of intratumoral and stromal CD4+ and CD8+ T lymphocytes was assessed by IHC using a semi-quantitative score between 0-3 whereby a higher score represents a greater number of T lymphocytes present. A total cohort of 191 N0-N1 ER positive and ER negative breast scored as DDRD positive or negative using the DDRD assay. A significant association of both CD4+ and CD8+ intratumoral tumour infiltrating lymphocytes (iTILs) and stromal tumour infiltrating lymphocytes (sTILs) with DDRD positivity was identified (FIG. 9). This is demonstrated by the increased proportion of tumour sample cores with a greater IHC score within the DDRD positive CD8+ (DDRD pos CD8) and DDRD positive CD4+(DDRD pos CD4) populations (p<0.0001) (FIG. 9A). The association between CD4+ and CD8+T-lymphocytes and DDRD positivity was confirmed by the IHC images whereby an increased staining intensity is indicative of a greater presence of iTILs and sTILS within the tumours (FIG. 98).

Chemokine Production is Associated with DNA Damage Repair Deficiency.

Figure 10A:
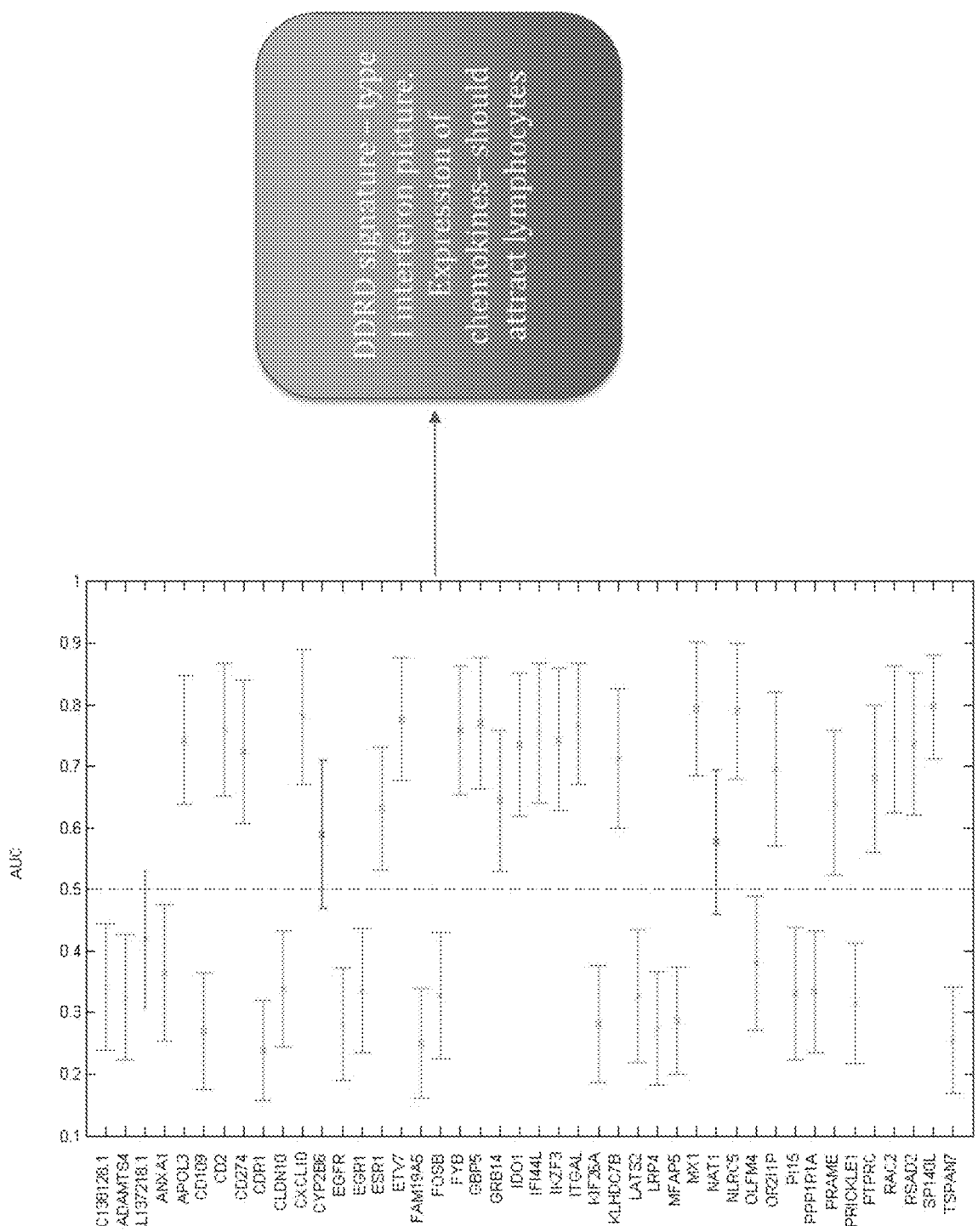
FIG. 10 shows a DDRD subtype, a type I interferon picture.
Figure 10B:
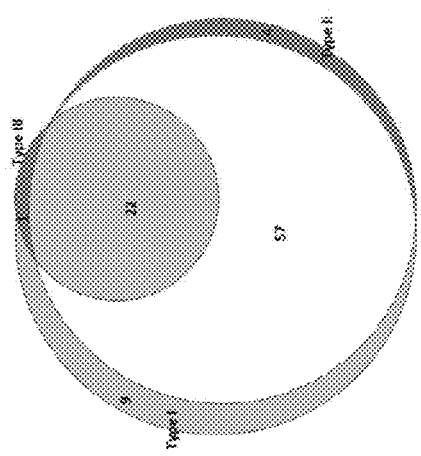

CXCL10 is the most discriminating gene in the DDRD assay, and has previously been reported as a prognostic factor in breast cancer[1]. CCL5 (RANTES) was identified as the top differentially expressed gene in DDRD positive ER negative tumours (Table 48). The majority of differentially expressed genes were identified as interferon responsive indicated by an area under curve (AUC) greater than 0.5. This is in keeping with a chemokine rich inflammatory tumour microenvironment (FIG. 10A). Further interferome analysis of the differentially expressed genes showed that 53.1% of these genes were interferon driven with a predominant association with Type I interferons (FIG. 108). The CXCL10/CXCR3 axis has been reported as key for the chemotaxis of CD4+ and CD8+ T lymphocytes to sites of inflammation[2]. CXCL10 and CCL5 overexpression are associated with the presence of CD8+ lymphocytes in melanoma, gastric and colorectal cancers[3-5]. We therefore sought to identify the mechanism of production of these key chemokines, CXCL10 and CCL5, in DNA damage repair deficient tumours.

TABLE 48

Differentially Expressed Genes in ER negative DDRD positive tumors (FC > 3)

| | Gene Symbol | Gene ID | Mean DDRD neg | Mean DDRD pos | p-value | Fold-Change | Fold-Change Description |
|---|---|---|---|---|---|---|---|
| 1 | IFI44L | 10964 | −0.41495 | 1.37672 | 6.11E-13 | −3.46216 | DDRD neg down vs DDRD pos |
| 2 | IDO1 | 3620 | −0.260724 | 1.46939 | 2.18E-12 | −3.31754 | DDRD neg down vs DDRD pos |
| 3 | GBP5 | 115362 | −0.313374 | 1.42788 | 2.96E-12 | −3.34325 | DDRD neg down vs DDRD pos |

TABLE 48-continued

Differentially Expressed Genes in ER negative DDRD positive tumors (FC > 3)

| | Gene Symbol | Gene ID | Mean DDRD neg | Mean DDRD pos | p-value | Fold-Change | Fold-Change Description |
|---|---|---|---|---|---|---|---|
| 4 | CCL5 | 6352 | −0.460764 | 1.26706 | 1.71E−11 | −3.31227 | DDRD neg down vs DDRD pos |
| 5 | ART3 | 419 | −0.40557 | 1.29577 | 4.67E−11 | −3.25203 | DDRD neg down vs DDRD pos |
| 6 | DDX60 | 55601 | −0.199854 | 1.44622 | 5.19E−11 | −3.12981 | DDRD neg down vs DDRD pos |
| 7 | XAF1 | 54739 | −0.274869 | 1.39532 | 5.75E−11 | −3.18257 | DDRD neg down vs DDRD pos |
| 8 | GBP5 | 115362 | −0.33513 | 1.33699 | 1.03E−10 | −3.18682 | DDRD neg down vs DDRD pos |
| 9 | GBP5 | 115362 | −0.358814 | 1.29533 | 2.59E−10 | −3.14737 | DDRD neg down vs DDRD pos |
| 10 | CD274 | 29126 | −0.397379 | 1.26159 | 2.60E−10 | −3.15791 | DDRD neg down vs DDRD pos |
| 11 | GABBR1 /// UBD | 2550 /// 10537 | −0.372545 | 1.28096 | 2.88E−10 | −3.14596 | DDRD neg down vs DDRD pos |
| 12 | PSMB9 | 5698 | −0.301324 | 1.33198 | 3.82E−10 | −3.10222 | DDRD neg down vs DDRD pos |
| 13 | TNFSF13B | 10673 | −0.260167 | 1.35947 | 4.29E−10 | −3.07297 | DDRD neg down vs DDRD pos |
| 14 | CCL5 | 6352 | −0.507855 | 1.13341 | 5.06E−10 | −3.11939 | DDRD neg down vs DDRD pos |
| 15 | ISG15 | 9636 | −0.30543 | 1.31872 | 5.71E−10 | −3.0826 | DDRD neg down vs DDRD pos |
| 16 | — | — | −0.343938 | 1.28446 | 6.48E−10 | −3.0917 | DDRD neg down vs DDRD pos |
| 17 | STAT1 | 6772 | −0.388005 | 1.24196 | 7.59E−10 | −3.09505 | DDRD neg down vs DDRD pos |
| 18 | — | — | −0.222883 | 1.36652 | 9.16E−10 | −3.00925 | DDRD neg down vs DDRD pos |
| 19 | IFI44L | 10964 | −0.472957 | 1.14736 | 1.16E−09 | −3.07443 | DDRD neg down vs DDRD pos |
| 20 | STAT1 | 6772 | −0.331983 | 1.27178 | 1.51E−09 | −3.03936 | DDRD neg down vs DDRD pos |
| 21 | PSMB9 | 5698 | −0.312228 | 1.28678 | 1.57E−09 | −3.02935 | DDRD neg down vs DDRD pos |
| 22 | STAT1 | 6772 | −0.397685 | 1.20857 | 1.83E−09 | −3.04461 | DDRD neg down vs DDRD pos |
| 23 | CD3G | 917 | −0.543926 | 1.05165 | 2.03E−09 | −3.02216 | DDRD neg down vs DDRD pos |
| 24 | STAT1 | 6772 | −0.495509 | 1.10127 | 2.44E−09 | −3.02466 | DDRD neg down vs DDRD pos |
| 25 | GBP4 | 115361 | −0.414399 | 1.18384 | 2.50E−09 | −3.02774 | DDRD neg down vs DDRD pos |
| 26 | SAMD9L | 219285 | −0.339994 | 1.25098 | 2.51E−09 | −3.01252 | DDRD neg down vs DDRD pos |
| 27 | EPSTI1 | 94240 | −0.356971 | 1.23204 | 2.91E−09 | −3.00843 | DDRD neg down vs DDRD pos |
| 28 | PARP14 | 54625 | −0.373931 | 1.21386 | 3.24E−09 | −3.00589 | DDRD neg down vs DDRD pos |
| 29 | OAS2 | 4939 | −0.394501 | 1.1948 | 3.26E−09 | −3.00904 | DDRD neg down vs DDRD pos |

Figure 8:
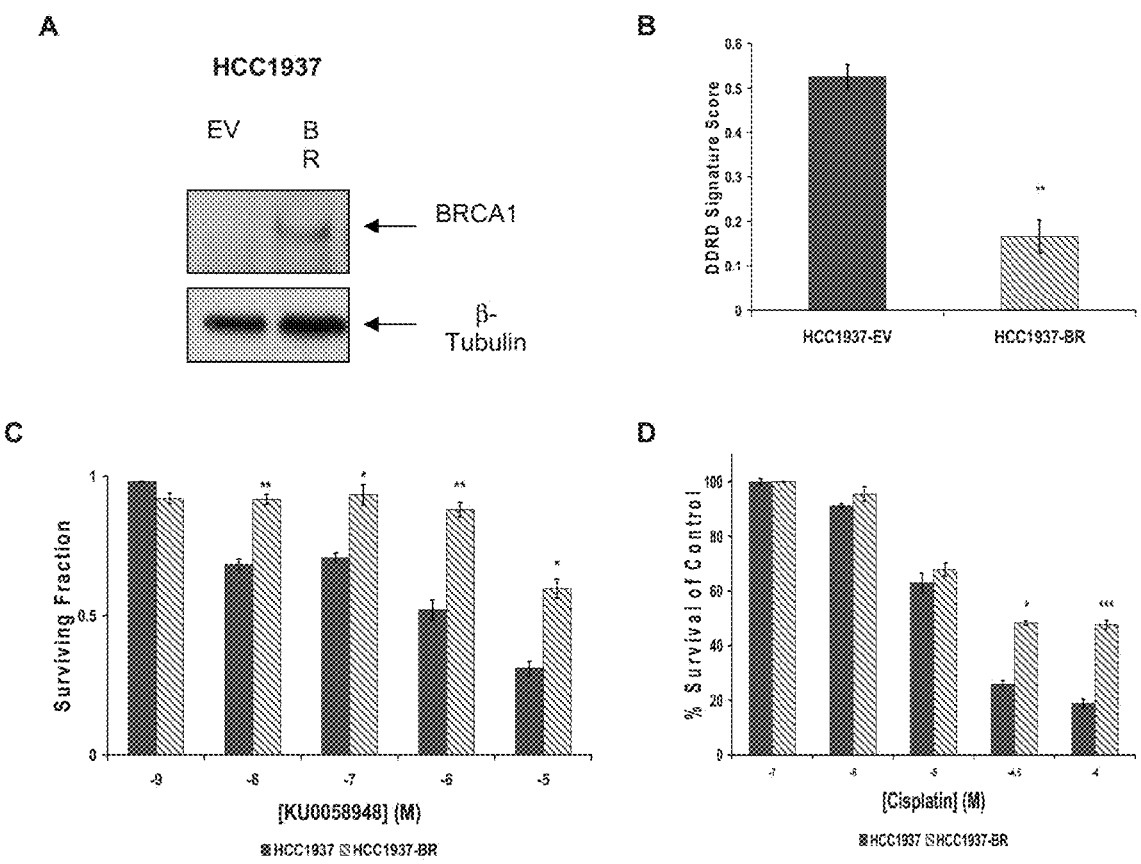
FIG. 8 provides a figure correlating the 44-gene classifier model with therapeutic response in BRCA1 mutant and wildtype cell-lines. (A) Western blot analysis confirming increased expression of BRCA1 in the HCC1937-BR cells compared with the HCC1937-EV cells. (B) Mean 44-gene model (DDRD) classifier score (±SEM) within the control vector-only transfected HCC1937 (HCC1937-EV) and HCC1937 with returned exogenous expression of BRCA1 (HCC1937-BR) cell-lines. Histogram representation of cell-viability of HCC1937 parental and HCC1937-BR cells under constant exposure to a range of concentrations of PARP inhibitor KU0058948 (C) and cisplatin (D).
Figure 11:
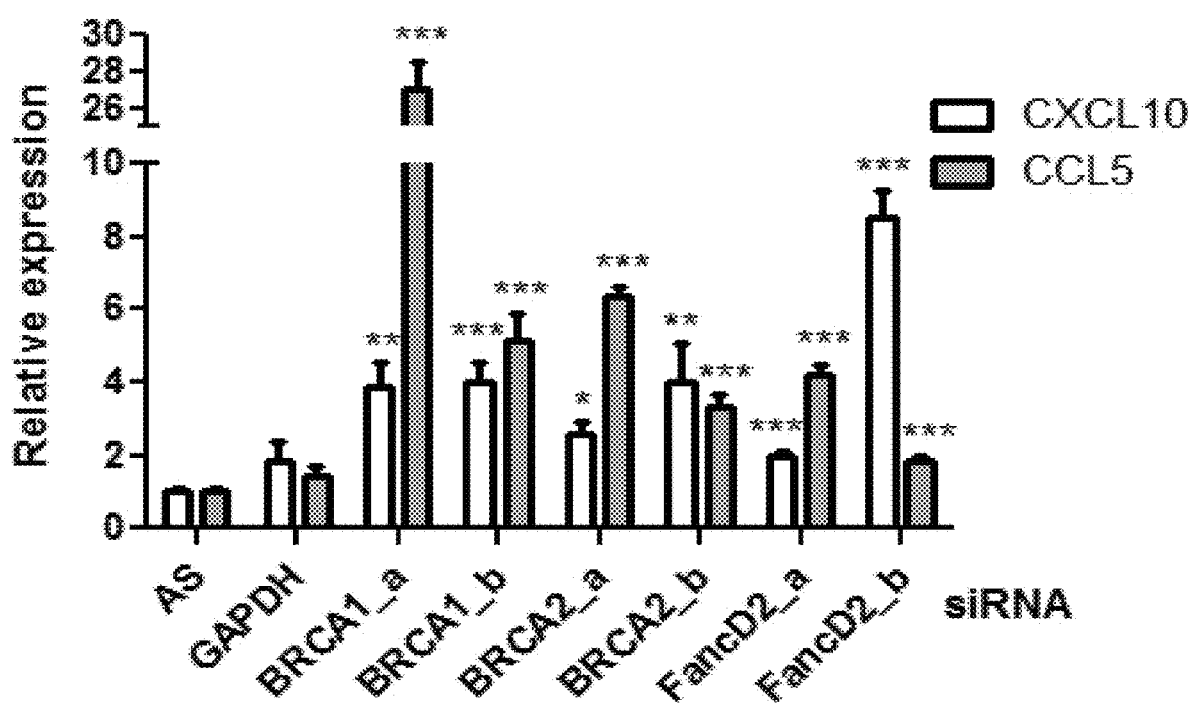
FIG. 11 provides a graph showing that DNA damage induces Expression of Chemokines (and other DDRD assay genes). Statistical significance of the data is indicated with * signifying a p value of <0.05,  a p value of <0.01 and * a p value of <0.001.
Figure 12A:
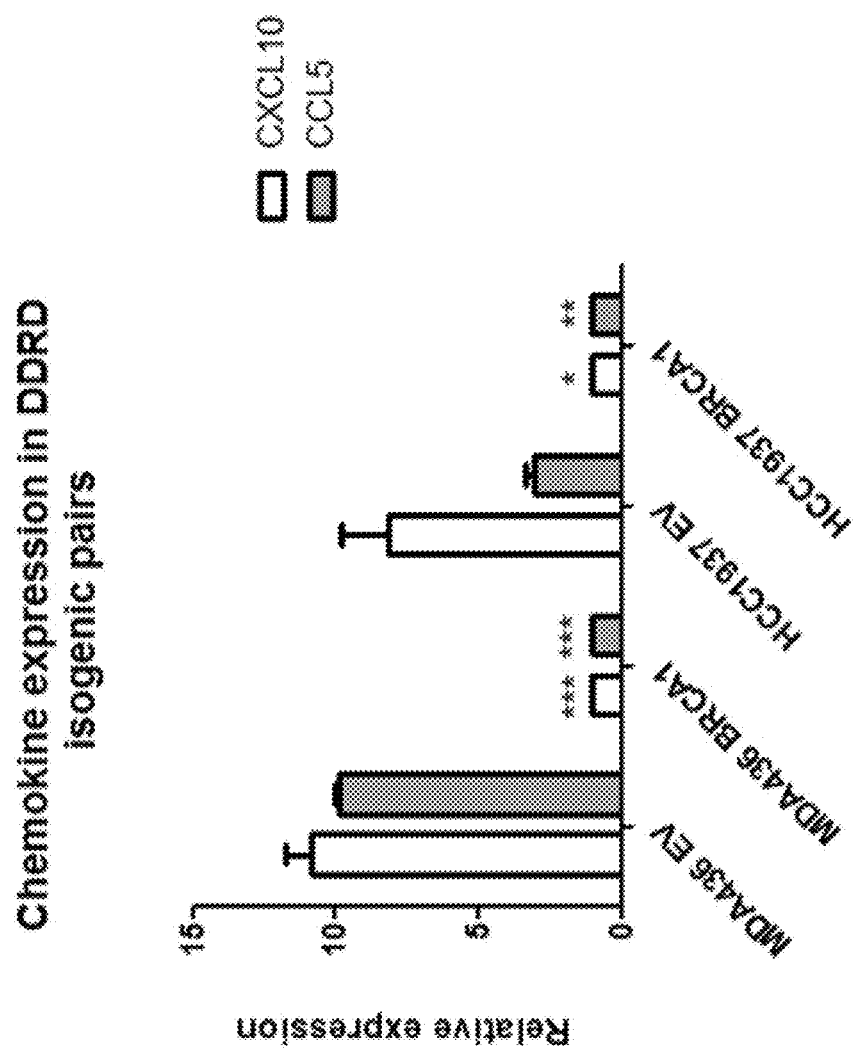
FIG. 12 provides a graph and images showing that correction of DNA Repair Defect Reduces Expression of Chemokines (and other DDRD assay genes).
Figure 12B:
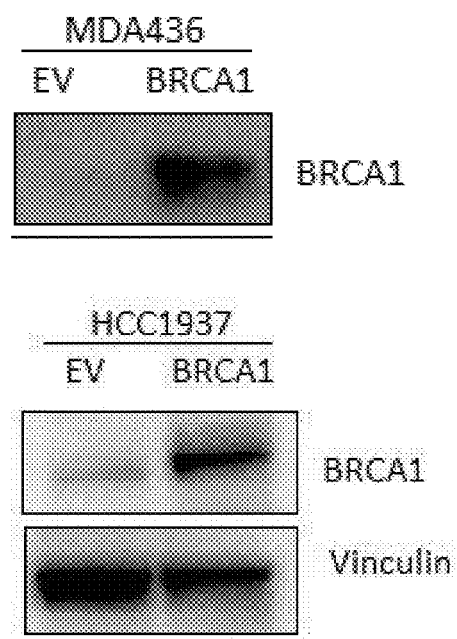
Figure 13:
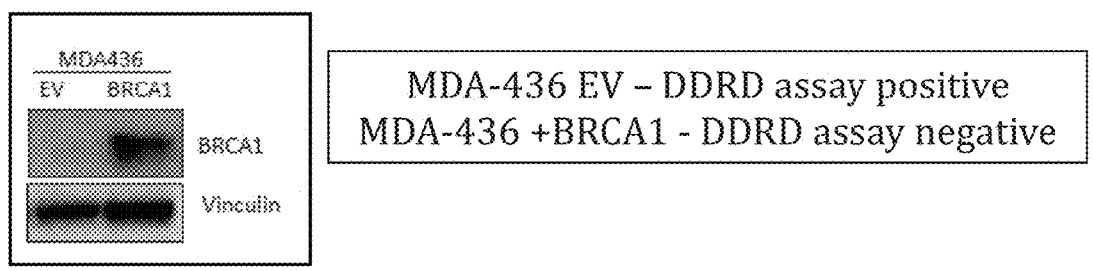
FIG. 13 shows that DDRD Positive Cells release chemokines into conditioned medium that attract lymphocytes.
Figure 13:
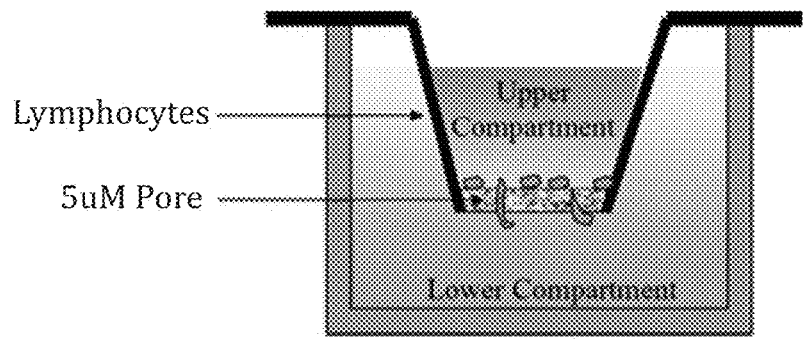
Figure 13:
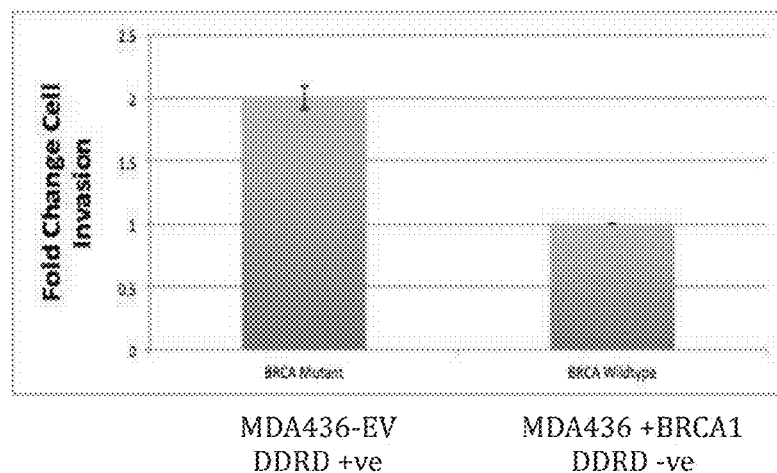
Figure 13:
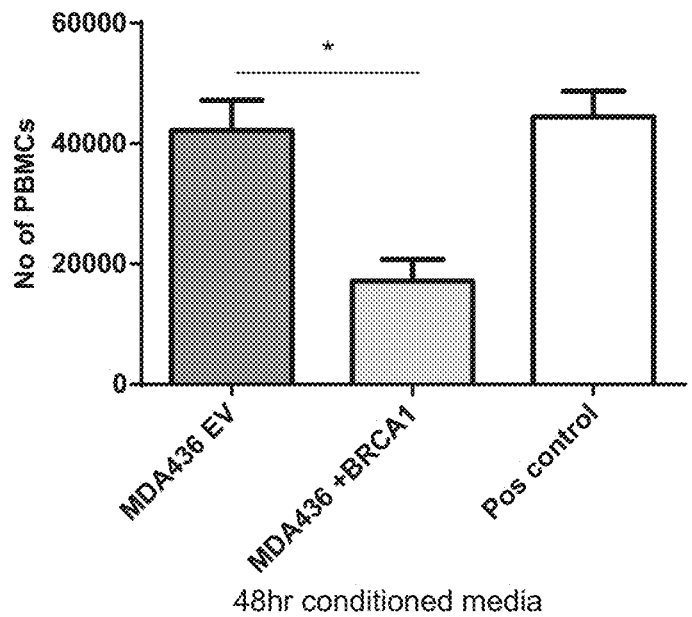
Figure 13:
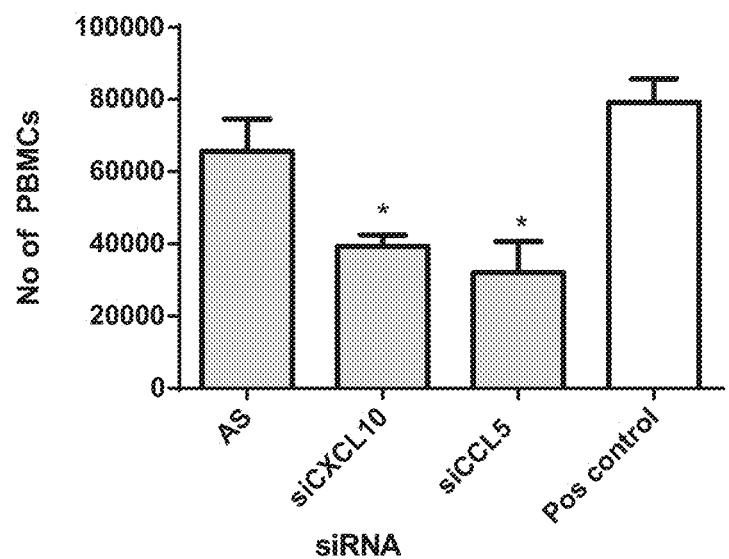

We next asked if a loss in DNA damage response may result in the observed DDRD assay immune response. We inhibited BRCA1, BRCA2 and FANCD2 function using siRNA knockdown constructs in T47D cells to address the role of intrinsic DNA damage repair deficiency and therein DDRD biology in the chemokine production. CXCL10 and CCL5 were identified as significantly upregulated in response to loss of DNA repair proteins. The increased relative expression of CXCL10 and CCL5 upon inhibiting BRCA1 (using BRCA1_a/b siRNAs), BRCA2 (using BRCA2_c/d siRNAs) and FANCC (FancC_1/2 siRNAs) compared to the control scrambled sequence siRNA (AS) in T47D cells confirmed that DNA damage induced the expression of chemokines (FIG. 11). Using isogenic cell lines, HCC1937 EV (DDRD Pos) and HCC1937+BRCA1 (DDRD Neg); and MDA-436 EV (DDRD Pos) and MDA-436+ BRCA1 (DDRD Neg), we again observed significant upregulation of CXCL10 and CCL5 in the DNA damage repair deficient cells compared to their repair-corrected line. Therefore FIG. 12A displays that upon correction of the DNA repair defect through the re-expression of BRCA1, the relative expression of both CXCL10 and CCL5 was significantly reduced (FIG. 12A). Western blotting confirms the protein expression of BRCA1 in both the corrected cell line models compared to the empty vector (EV) paired equivalent (FIG. 12B). To address if the upregulation of CXCL10 and CCL5 contributed to lymphocytic infiltration, we used a migration assay of activated peripheral blood mononuclear cells (PBMCs) with conditioned media from MDA436-EV and +BRCA1 cells (FIGS. 13A & 8). After co-culture for four hours, we observed a significant increase in the migration of PBMCs to conditioned media from the DNA damage repair deficient line. The MDA436-EV which are DDRD positive (DDRD+ ve) displayed a greater fold change in cell invasion compared to the corrected cell line pair expressing BRCA1 which are DDRD negative (DDRD-ve) (FIG. 13C) (p<0.001). Therefore endogenous DNA damage repair deficiency causes chemokine production and the subsequent immune cell infiltration. The MDA436-EV which are DDRD positive (DDRD+ ve) displayed a greater fold change in cell invasion compared to the corrected cell line pair expressing BRCA1 which are DDRD negative (DDRD-ve) (FIG. 13D) (p<0.001). Additionally, siRNA mediated knockdown of CXCL10 and CCL5 reduced PBMC migration, indicating their importance for lymphocytic infiltration (p<0.05; FIG. 13E).

Chemokine Expression is Controlled in a Cell Cycle Specific Manner.

Figure 14:
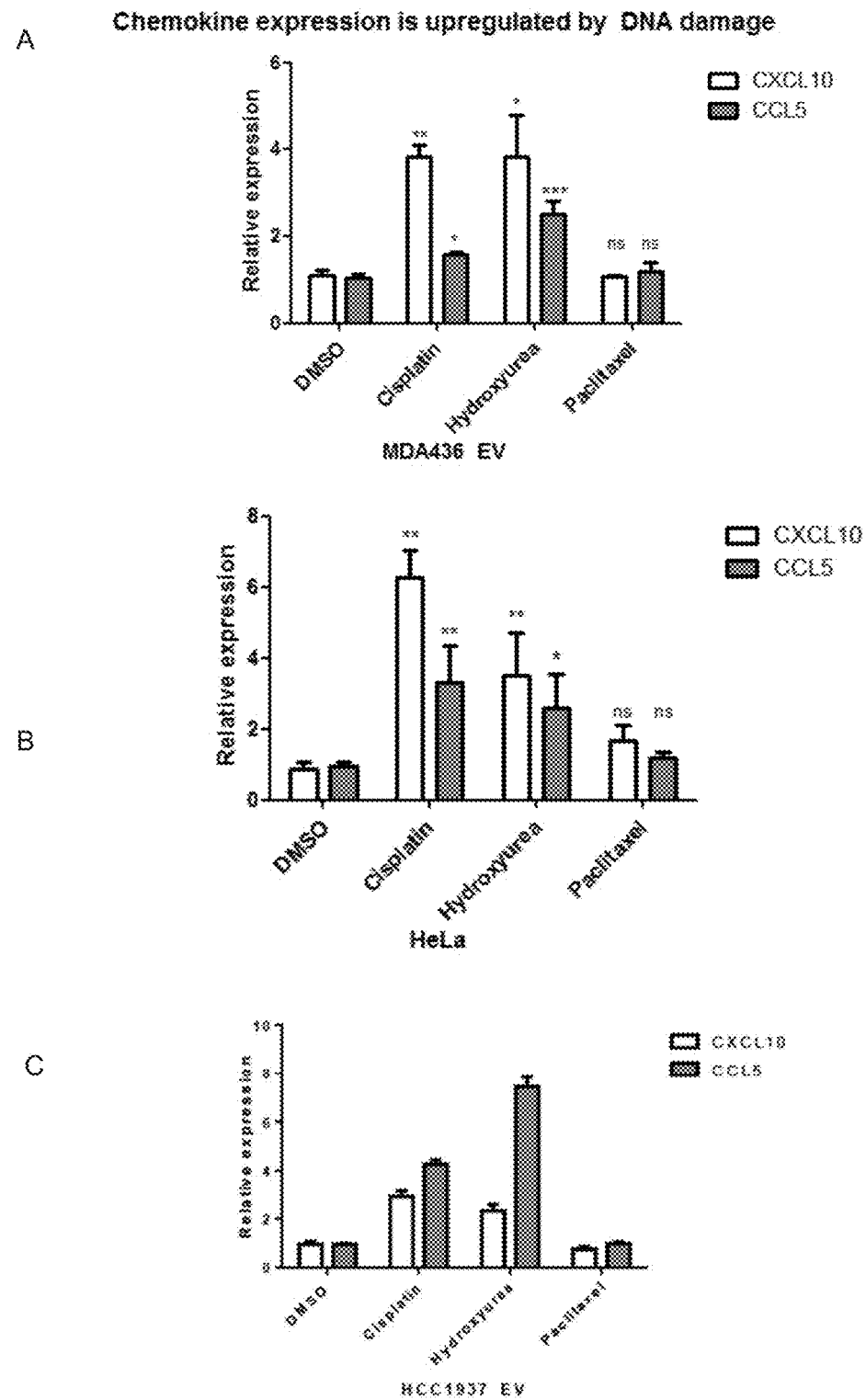
FIG. 14 provides graphs showing that DDRD Gene Expression is Induced by DNA Damaging Agents.
Figure 15A:
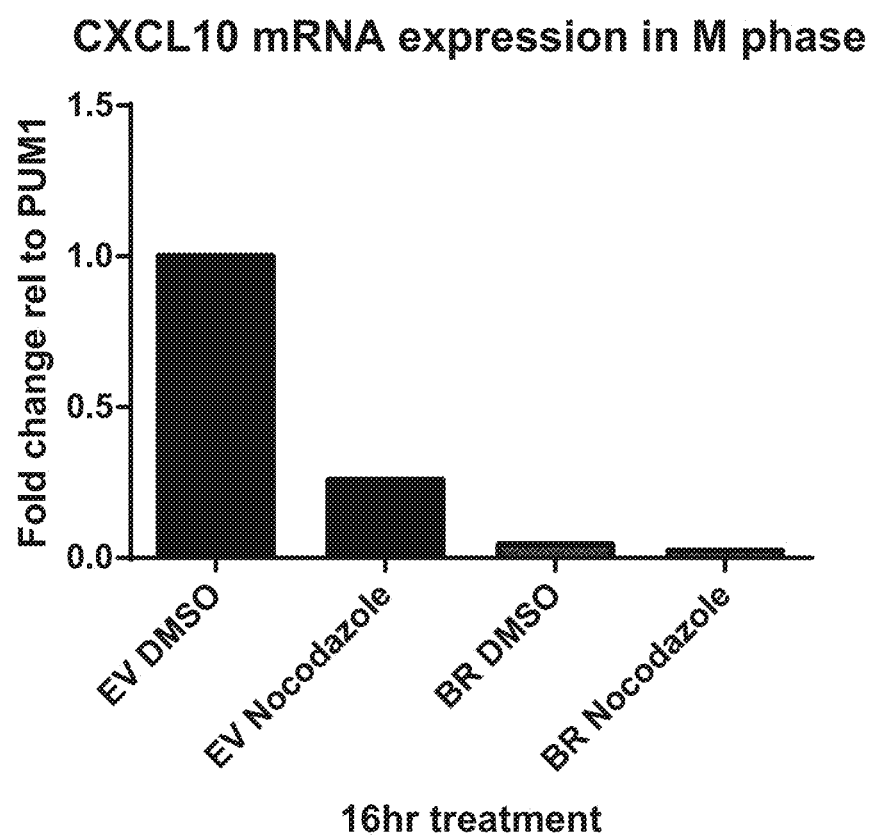
FIG. 15 provides graphs showing that expression of DDRD Signature Genes is Cell Cycle Regulated.
Figure 15B:
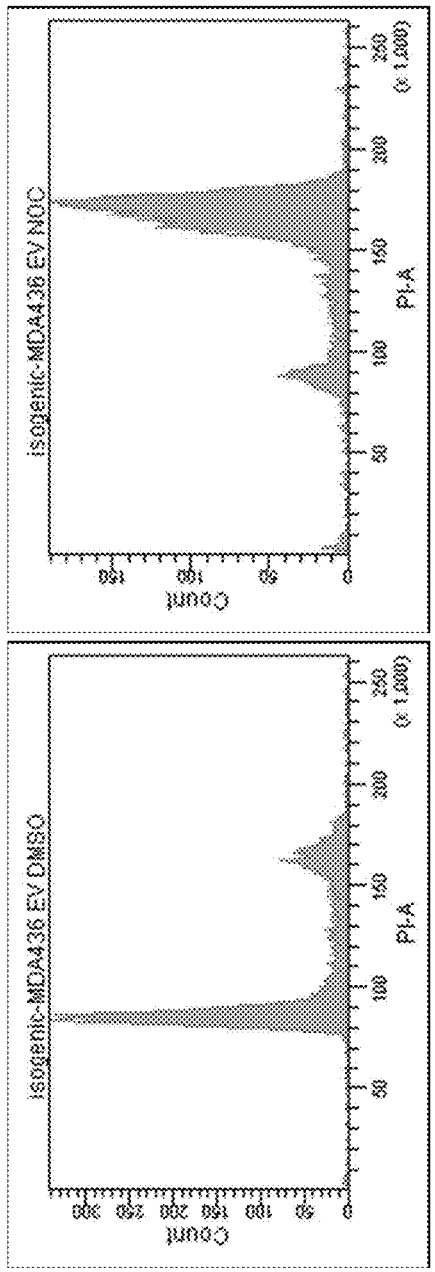
Figure 15B:
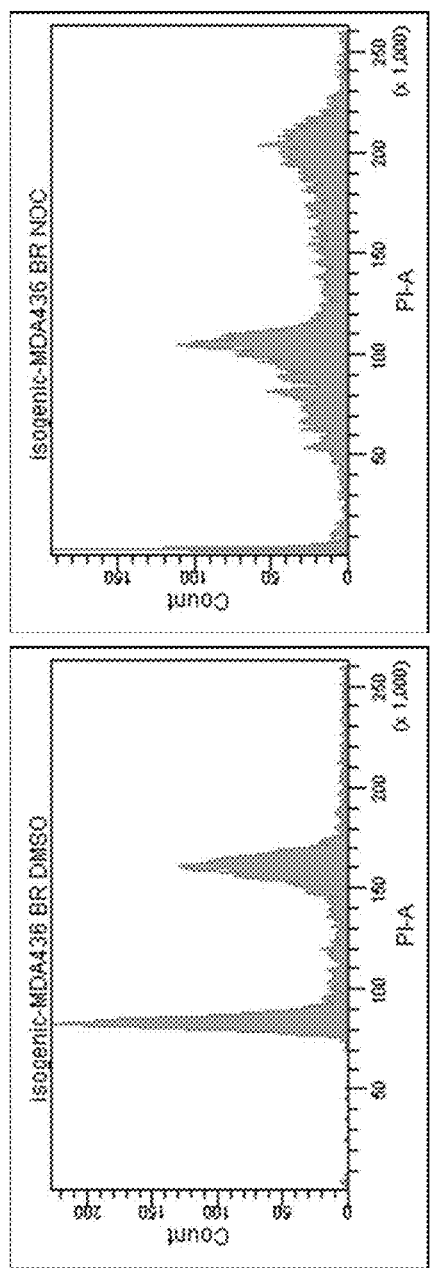

HeLa, HCC1937 EV and MDA-MB-436 EV cells were treated with IC-50 doses of DNA damaging agents Cisplatin and Hydroxyurea, and the microtubule-stabilising agent Paclitaxel. As demonstrated by the increased relative expression compared to DMSO control, upregulation of CXCL10 and CCL5 expression was stimulated in all cell lines following treatment with cisplatin and hydroxyurea. However, CXCL10 and CCL5 expression was not significantly increased with Paclitaxel treatment in either cell line model (FIG. 14). Treatment with cisplatin and hydroxyurea resulted in an increased proportion of cells in S phase (FIG. 14). However, treatment with a further anti-mitotic agent, Nocodazole caused an arrest in the M phase of cell cycle as observed by the reduced mRNA expression of CXCL10 (FIG. 15A). The block in M phase was confirmed by the changes in the cell cycle profile shown in FIG. 15 (FIG. 15B). Together these data support an S-phase specific signal for activation of the immune response to DNA damage.

Chemokine Expression is Independent of DNA Damage Sensors ATM, ATR and DNAPK.

Figure 16:
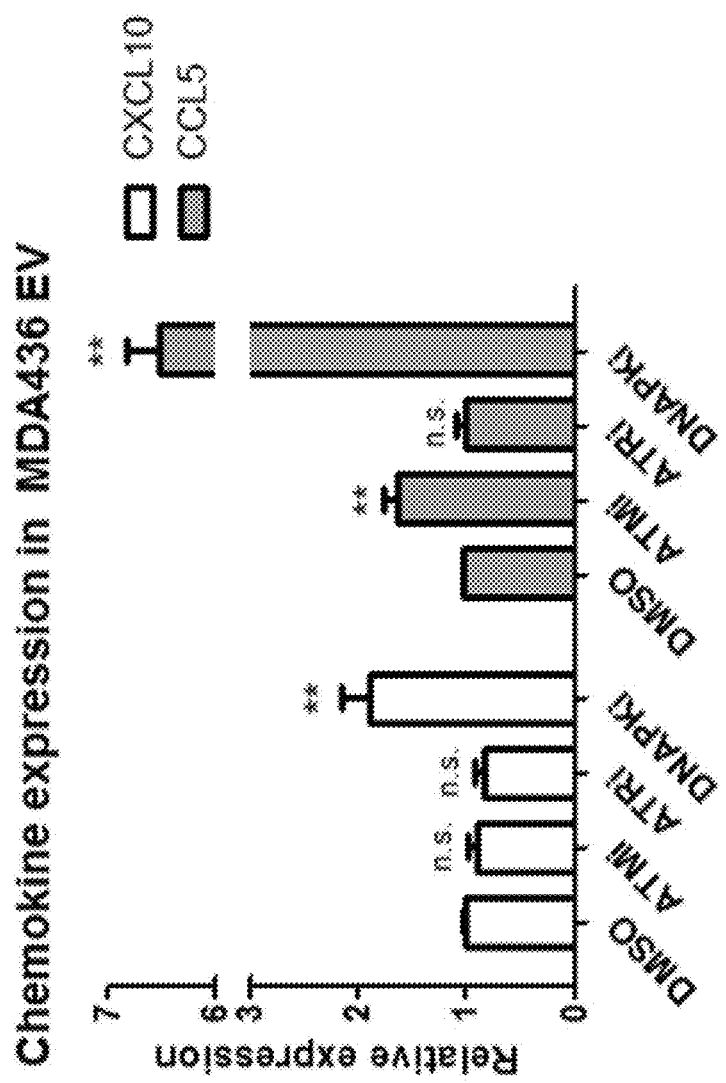
FIG. 16 provides a graph showing that DDRD gene expression is Independent of Classic DNA Damage Sensors ATM, ATR & DNAPK.

The kinases Ataxia Telangiectasia Mutated (ATM), ATM- and RAD3 related (ATR), and DNA-dependent protein kinase catalytic subunit (DNA-PKcs) are activated in response to DNA damage. Activation of ATM has previously been reported to result in the upregulation of immune genes suggesting that ATM may be required for chemokine production in response to DNA damage repair deficiency[6]. We treated DDRD positive cells (MDA-MB-436 EV) with small molecule inhibitors of ATM (Ku60019), ATR (ETP-46464) and DNAPK (Nu7440). No significant decreases in CXCL10 and CCL5 chemokine production were identified upon treatment with ATM inhibitors (ATMi), ATR inhibitors (ATRi) or DNAPK inhibitors (DNAPKi) compared to the DMSO control (FIG. 16). However, inhibition of DNAPK (DNAPKi) significantly increased CXCL10 and CCL5 chemokine expression levels compared to the DMSO control (FIG. 16). Together these data indicate that these DNA damage response kinases are not required for the interferon response to endogenous DNA damage repair deficiency.

The STING/TBK1/IRF3 Pathway is Constitutively Active in DDRD Tumour Cells.

Figure 17A:
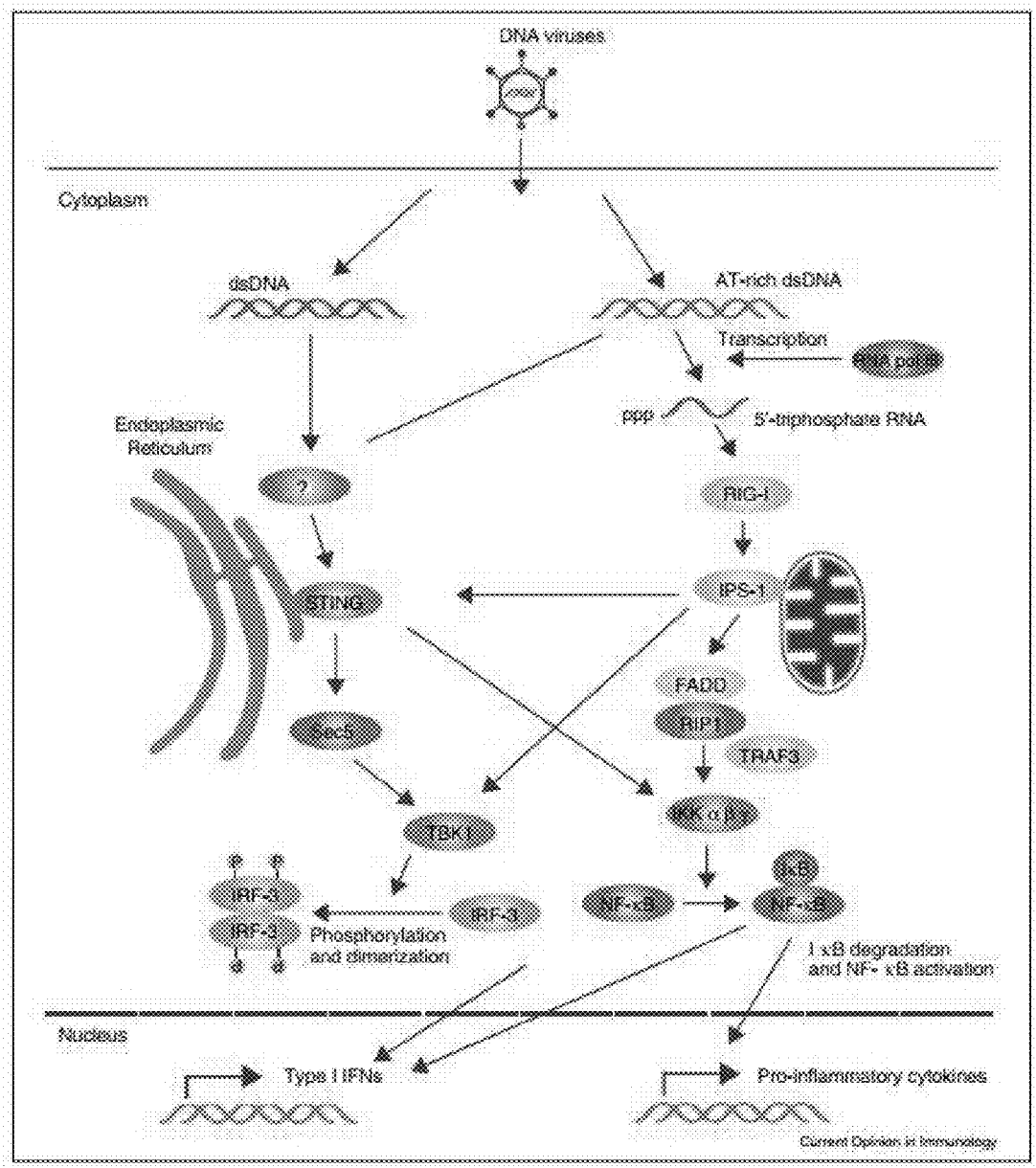
FIG. 17 shows that the STING activated innate Immune Pathway is related to DDRD Signature Genes.
Figure 17B:
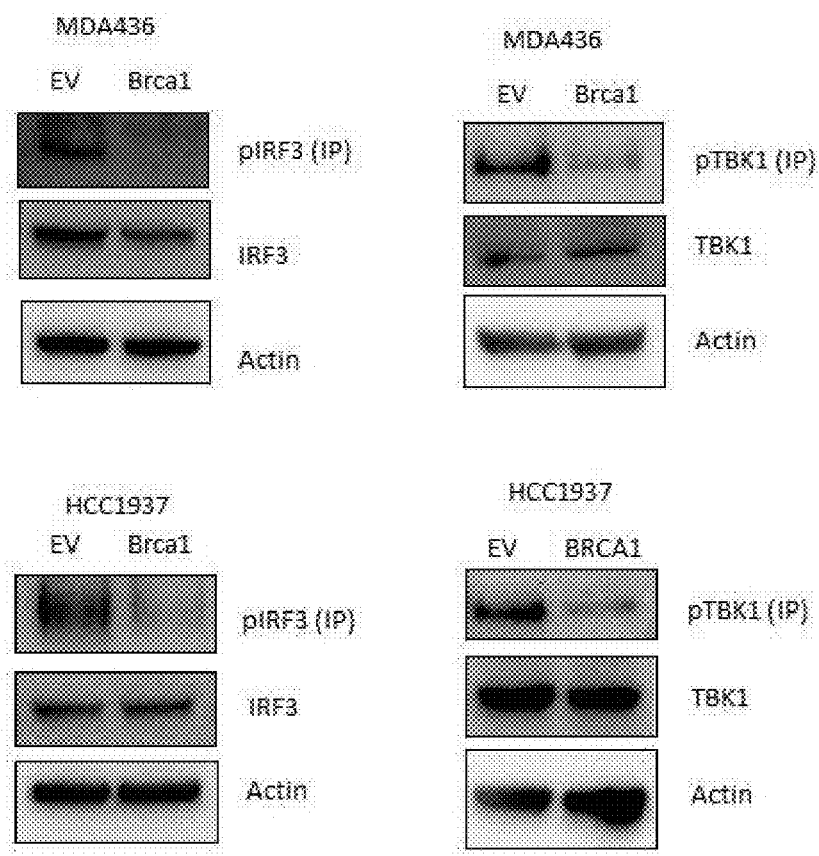
Figure 17C:
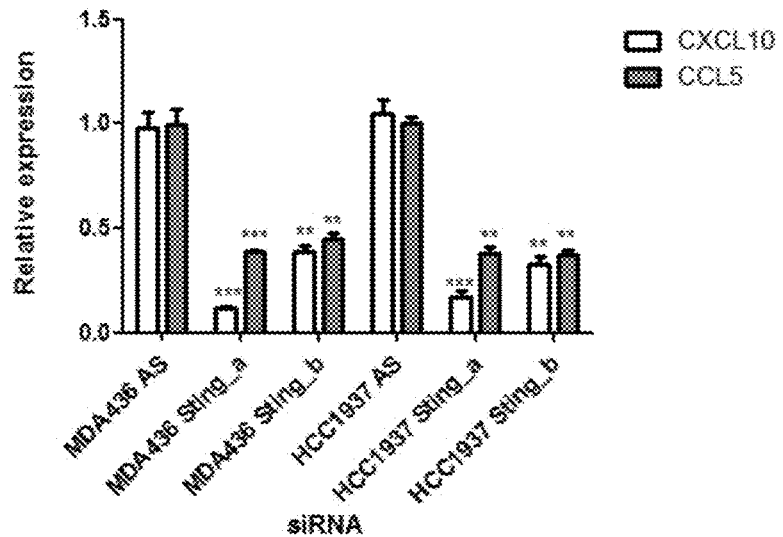
Figure 17C:
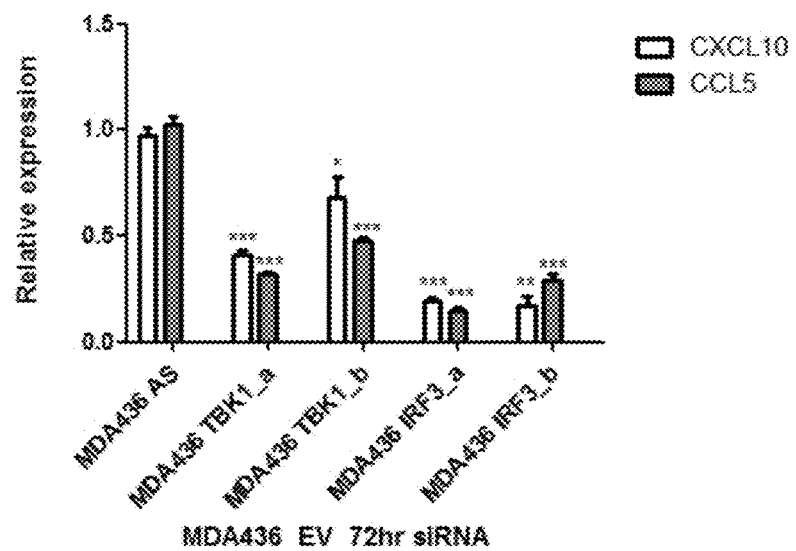

Next we performed a transcription factor analysis to identify those that could activate genes upregulated in DDRD tumours. IRFs (Interferon Regulatory Factors) gene targets were significantly enriched within this list. In addition, stimulation of the innate immune pathway STING/TBK1/IRF3 (FIG. 17A) has been reported as a driver of CXCL10 expression[7]. IRF3 is recognised to be active in response to DNA damaging agents[8], therefore we hypothesised that IRF3 would be active in DDRD positive cells. Supporting this we observed enhanced phosphorylation of IRF3 (pIRF3) from whole cell lysates of BRCA1-deficenct cells MDA-436 EV and HCC1937 EV compared to their BRCA1 corrected isogenic line (MDA-436+BRCA1 and HCC1937+BRCA1) (FIG. 17B). Similarly, TBK1 was constructively phosphorylation was observed in the repair deficient cells (EV) compared to the repair corrected DDRD negative cell lines (BRCA1) (FIG. 17B). Using siRNA mediated knockdown, we inhibited the function of STING (Sting_a/b), TBK1 (TBK1_a/b) and IRF3 (IRF3_a/b) in both MDA-436 and HCC1937 cells. When compared to the control (AS), the knockdown of STING, TBK1 and IRF3 significantly reduced the relative expression of both CXCL10 and CCL5 (FIG. 17C).

These data demonstrates the requirement of STING, TBK1 and IRF3 for the immune response to DNA damage response deficiency.

Endogenous or Exogenous DNA Damage Results in an Increase in Cytosolic DNA

Figure 18A:
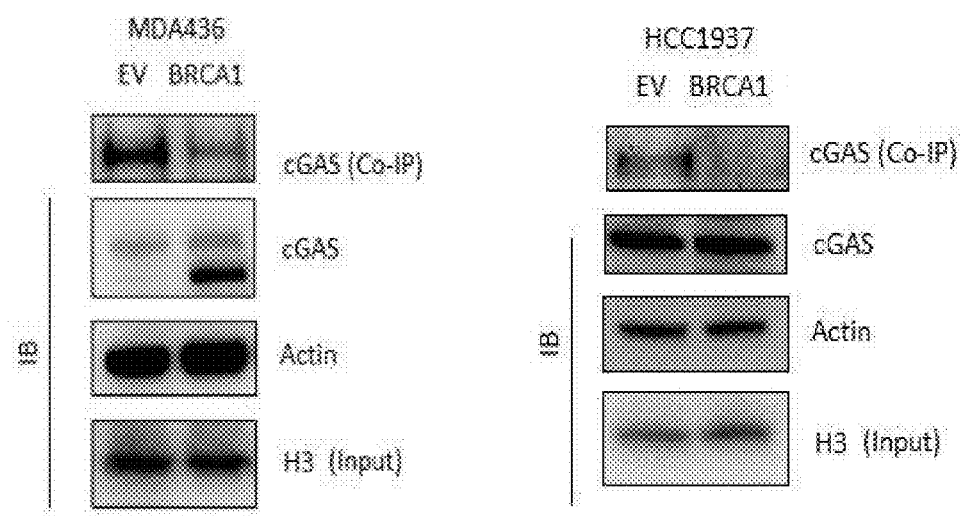
FIG. 18 provides images and a graph showing that the cytosolic DNA sensor is activated by DNA damage and is required for DDRD signalling.
Figure 18B:
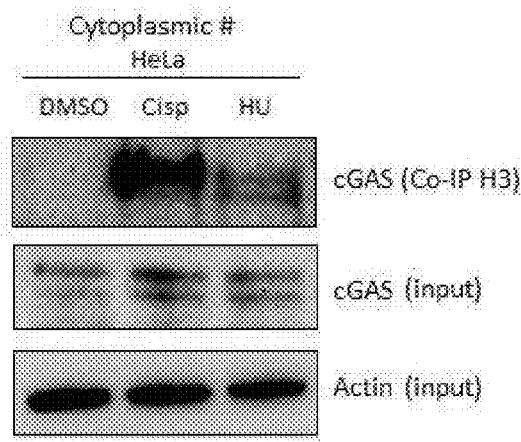
Figure 18C:
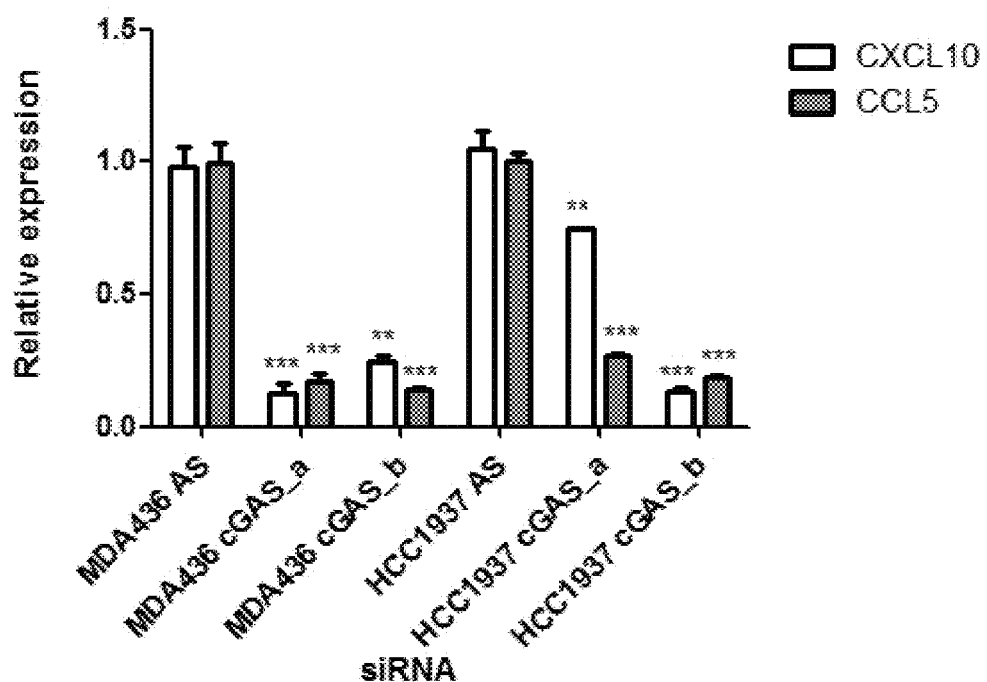

The cytosolic DNA sensor cGAS has been described as the most potent activator of the STING pathway. We therefore asked if it cytosolic DNA was associated with observed immune response to S phase specific DNA damages. Using co-immunoprecipitation (co-IP), we identified cGAS as bound to Histone H3 in the cytosolic fraction of DDRD positive cells MDA-436 EV and HCC1937 (FIG. 18A, top panel of blots). Binding of double stranded DNA to cGAS results in activation of STING via cGAMP, and immune gene expression. Additionally, in HeLa cells treated with Cisplatin (Cisp) or Hydroxyurea (HU), co-IP showed that cGAS was again bound to Histone H3. The binding of cGAS to Histone H3 was not observed in the DMSO treated control (FIG. 18B, top panel of blots). Abrogation of cGAS function using siRNA mediated knockdown constructs (cGAS_a/b) in both MDA-436 and HCC1937 cells, resulted in significant reduction in both CXCL10 and CCL5 chemokine relative expression levels in the context of endogenous DDRD, and in response to DNA damaging agents (FIG. 18C). Therefore, cGAS is required for expression of chemokines from the tumour cell in response to DNA damage.

Cytosolic DNA is Present in Response to Endogenous and Exogenous DNA Damage.

Figure 19A:
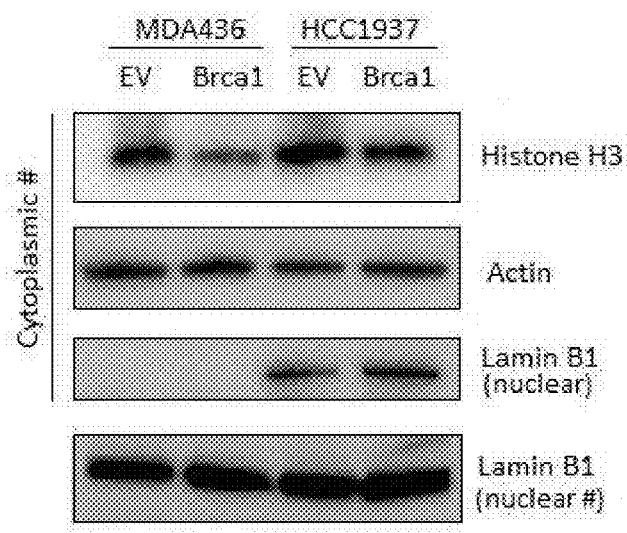
FIG. 19 provides images showing that S Phase DNA Damage Increases Cytoplasmic DNA.
Figure 19B:
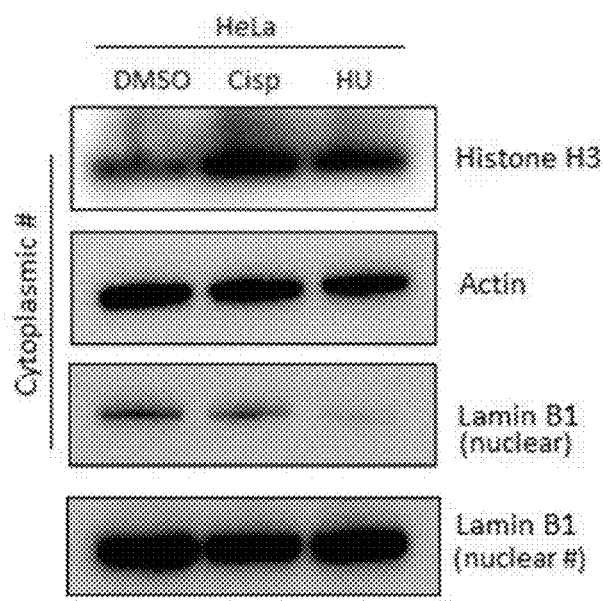
Figure 19C:
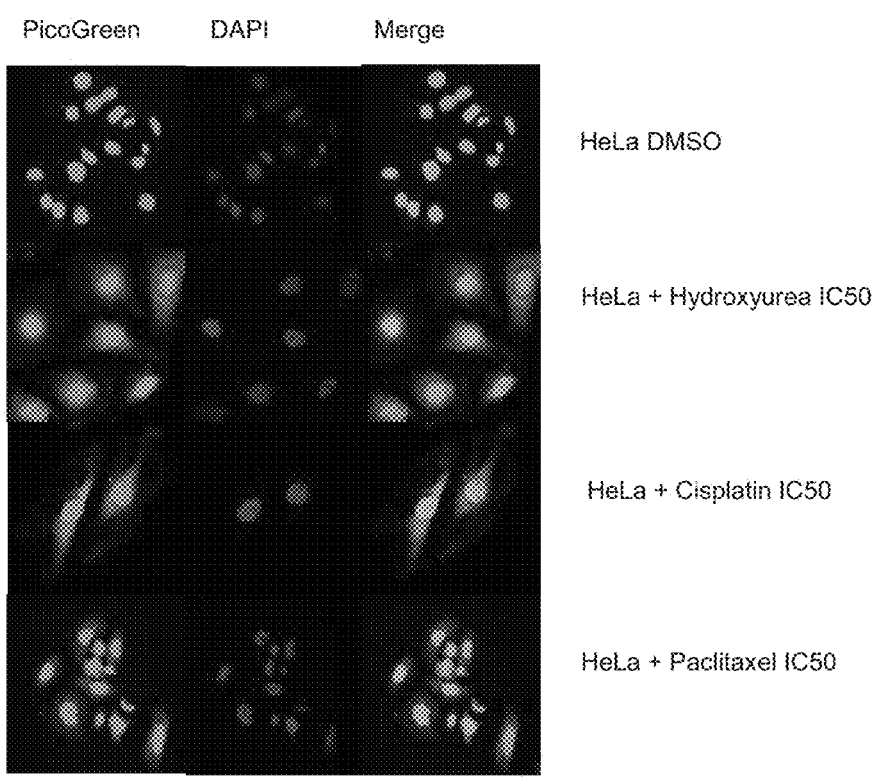

We probed cytosolic fractions of DDRD positive cells MDA-436-EV and +BRCA1, and HCC1937-EV and +BRCA1 cells for the presence of Histone H3, and found Histone H3 protein expression was increased in the repair deficient lines (EV) (FIG. 19A, top panel of blots). We also confirmed increased Histone H3 protein levels in response to DNA damage in HeLa cells treated with Cisplatin (Cisp) and Hydroxyurea (HU) compared to DMSO control treatment (FIG. 19B, top panel of blots). PicoGreen fluorescent staining was used to detect double-stranded DNA (ds-DNA). HeLa cells treated with $IC_{50}$ doses of DNA damaging agents Cisplatin (HeLa+Cisplatin $IC_{50}$) and Hydroxyurea (HeLa+Hydroxyurea $IC_{50}$) revealed increased cytosolic DNA when examined by confocal microscopy. This increase in cytosolic DNA was however not observed in response to treatment with Paclitaxel (HeLa+Paclitaxel $IC_{50}$) (FIG. 19C).

DDRD Positive Tumours are Associated with Expression of PDL1.

Figure 20B:
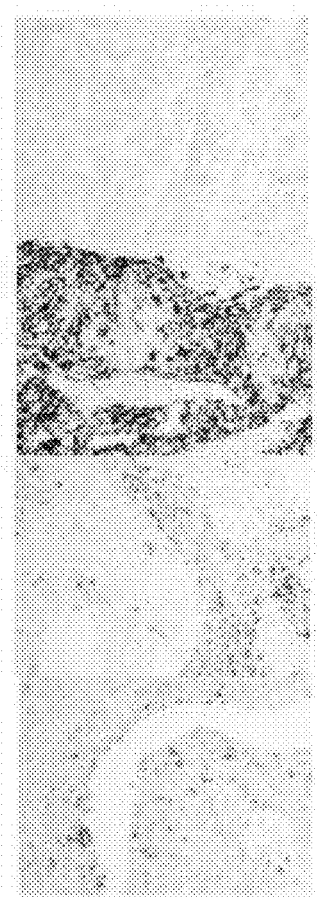
FIG. 20 provides a table and images showing that DDRD+ shows significant levels of PD-L1 in breast cancer samples.

The apparent paradox of upregulation of chemoattractants and subsequent lymphocytic infiltration in DDRD positive tumours is potentially explained by the upregulation of the immune checkpoint target PDL1. This target is known to cause lymphocyte exhaustion and effectively switches off the immune cytotoxic response to the cancer cells. Using the Roche SP142 antibody to PDL1 we performed IHC analysis on the original cohort of breast tumours previously scored for CD4+ and CD8+T lymphocytic infiltration. Previously reported cut-offs of >1% and >5% were used to define PDL1 positivity, for both infiltrating tumour immune cell and tumour cell PDL1 expression[10] (FIG. 20). Significant association of PDL1 expression at both the predefined cut offs was identified within DDRD positive tumours displayed by the 46.2% and 21.5% positivity for tumour populations positive for both DDRD (DDRD pos) and PDL1 (PDL1 pos) at >1% and >5% respectively (p<0.0001, p=0.0004) (FIG. 20A, tumour). In addition, infiltrating immune cell PDL1 positivity was also associated with DDRD positivity as demonstrated by the 75.4% and 40% positivity for lymphocytes at both>1% and >5% respectively (p<0.0001) (FIG. 20A, lymphocytes). Immunohistochemistry staining confirms strong PDL1 expression within the tumour, with additional PDL1 expression with lymphocytic infiltration as depicted by the staining patterns and intensities (FIG. 20B). In sum, both tumour cell PDL1 positivity and infiltrating immune cell PDL1 expression were significantly associated with DDRD positivity (FIG. 20).

Figure 21:
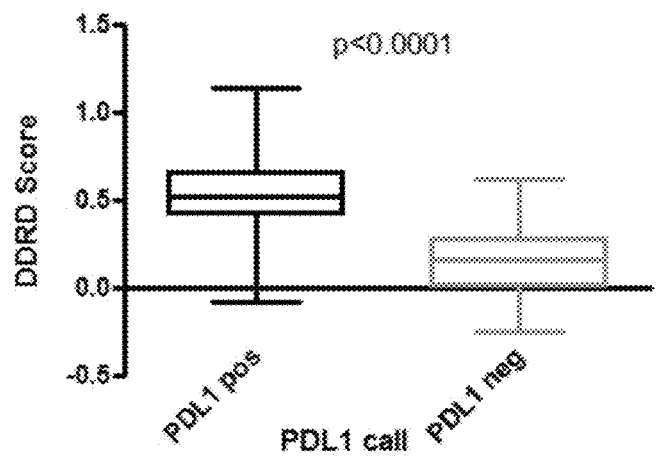
FIG. 21 provides graphs showing that PDL1 positive tumours have active DDRD signalling.
Figure 21:
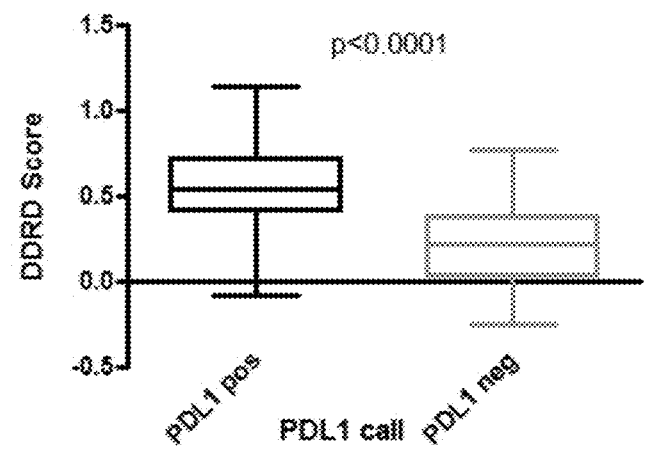

Additionally, the tumours were analysed based on their DDRD scores which assigns each tumour sample to a DDRD positive or DDRD negative subgroup based on the cut-off values within the defined gene signature. The DDRD scores of the PDL1 positive cohort (PDL1 pos) based on the aggregate tumour and lymphocyte staining using the predefined>1% and >5% cut offs demonstrated significantly higher DDRD scores than PDL1 negative cohort (PDL1 neg) (p<0.001) (FIG. 21). This data suggests that PDL1 protein expression is associated with a positive DDRD assay result and likewise PDL1 positive tumours have active DDRD signalling.

Figure 22:
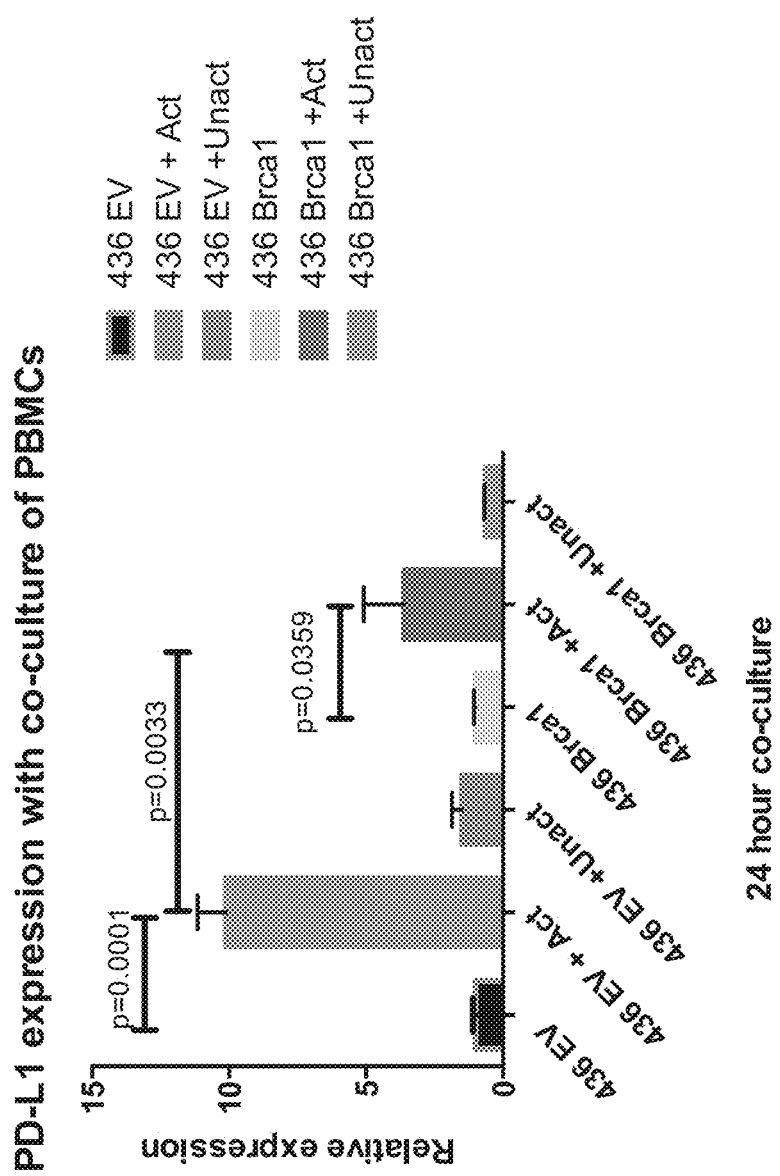
FIG. 22 provides a graph showing that PDL1 expression is increased by co-culture with lymphocytes, specifically in DDRD+ models.

DNA Damage Repair Deficient Cell Lines are Primed to Express PDL1 in Response to Co-Culture with PBMCs MDA-436 EV and MDA-436+BRCA1 cells (repair corrected) were co-cultured with activated PBMCs. Within the co-culture, PDL1 relative expression levels were significantly upregulated in both repair deficient cells (436 EV+Act) (p=0.0001) and BRCA1 repair corrected MDA-436 cells (436 BRCA1+Act) (p=0.0359). Moreover, the increased levels of PDL1 expression was more enhanced in DDRD positive cell models in co-culture (436 EV+Act) compared to the DDRD negative cells (436 BRCA1+Act) (p=0.0033) (FIG. 22). Therefore, PDL1 expression is increased by co-culture with lymphocytes, specifically in DDRD positive models.

DNA Damage Induces Expression of PDL1

Figure 23:
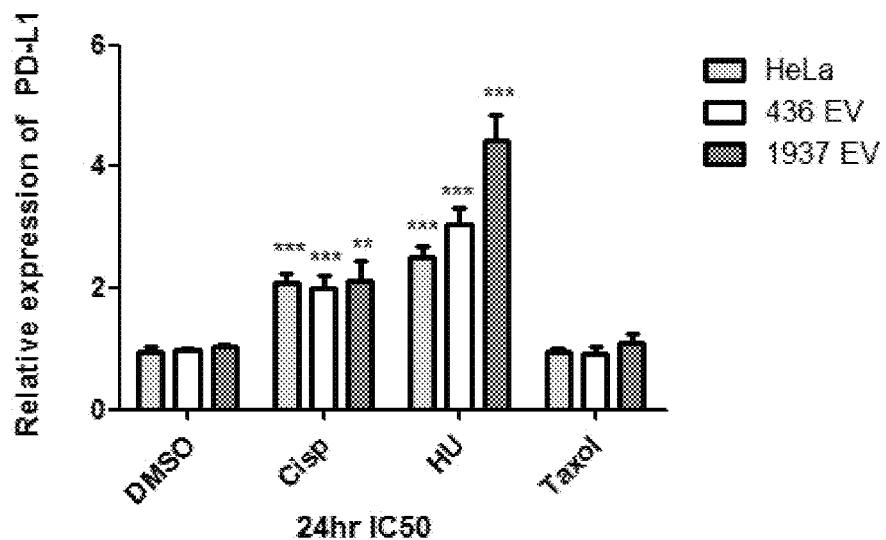
FIG. 23 provides a graph and images showing that PDL1 Expression is Increased by DNA damage. Statistical significance of the data is indicated with * signifying a p value of <0.05,  a p value of <0.01 and * a p value of <0.001.
Figure 23:
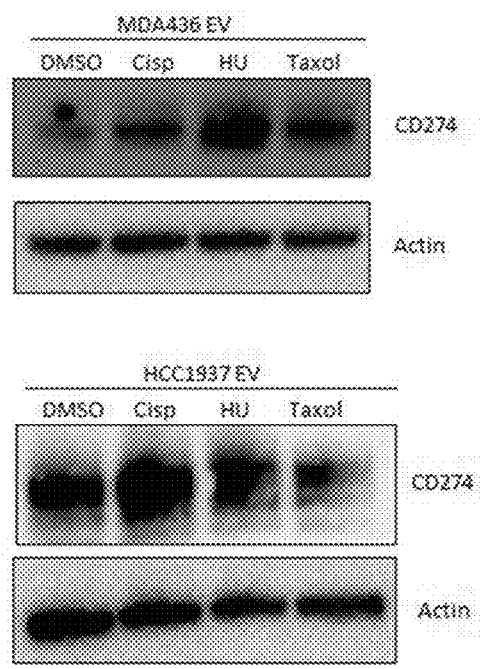

Treatment of HHC1937 EV, MDA-MB436 EV and HeLa cells treated with the DNA damaging Cisplatin (Cisp) or Hydroxyurea (HU) but not Paclitaxel induce expression of CD274 (PDL1) through Q-PCR analysis (FIG. 23A). This effect was confirmed at the protein level through western blot analysis (FIG. 23B).

Other Potential Immune Checkpoint Targets are Activated in Response to DNA Damage.

Figure 24:
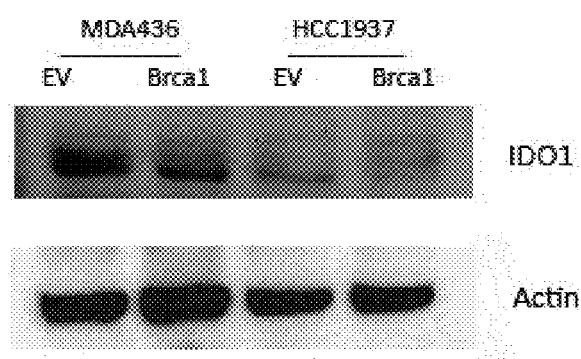
FIG. 24 provides an image showing that alternative immune checkpoint target IDO1 expression is increased by genomic instability.
Figure 25:
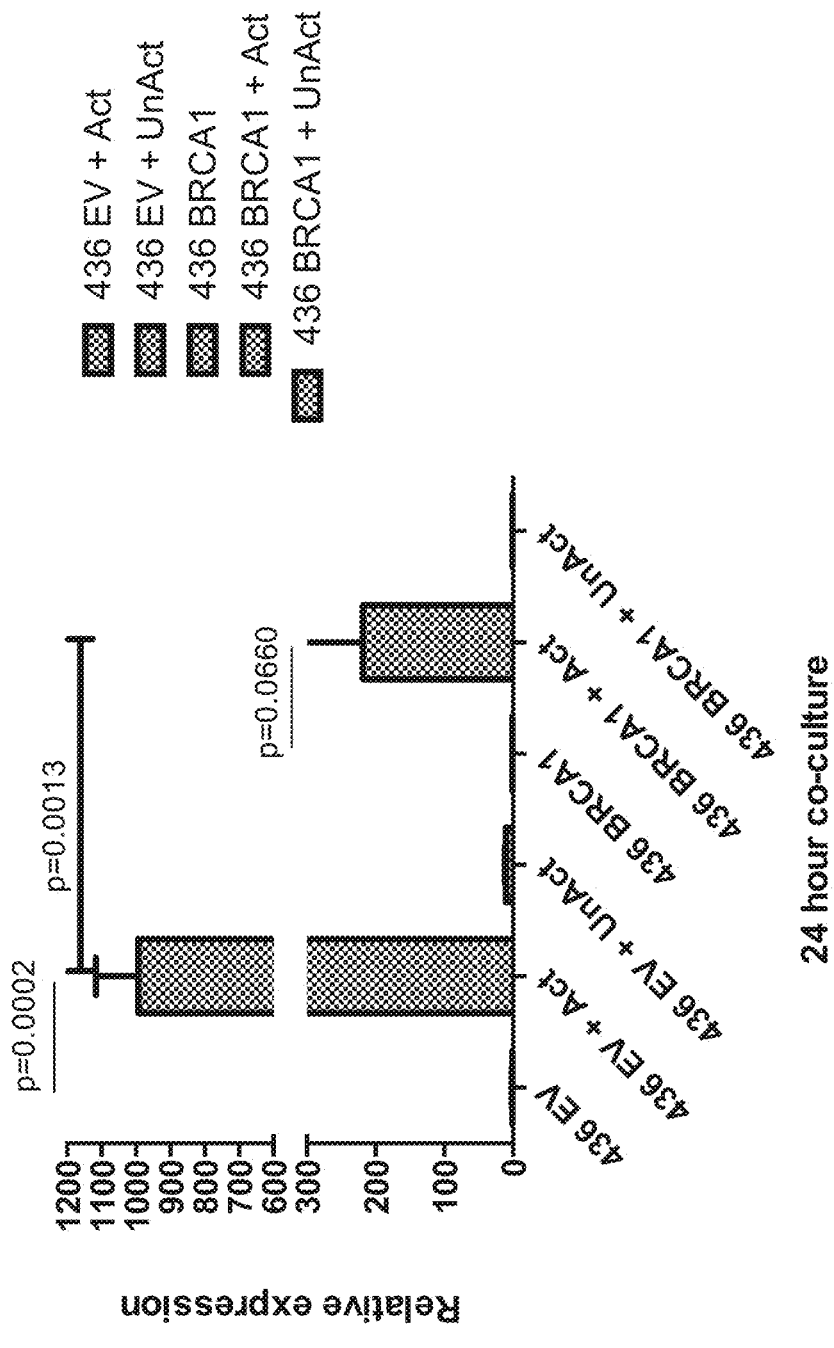
FIG. 25 provides a graph showing that IDO1 expression is increased by co-culture with lymphocytes, specifically in DDRD+ models FIG. 26 provides a graph showing that DDRD+ cells are protected from lymphocyte mediated cytotoxicity.

To determine the involvement of other potential immune checkpoint targets, we checked the protein expression of the alternative immune checkpoint target IDO1 in MDA-436 and HCC1937 isogenic cell line pairs. Accordingly DDRD positive cells (MDA-436 EV and HCC1937 EV) demonstrated increased IDO1 protein levels in comparison to corrected DDRD negative isogenic pairs (MDA-436+ BRCA1 and HCC1937+BRCA1) (FIG. 24, top panel of blot). Furthermore, within co-culture with lymphocytes, IDO1 relative expression levels were significantly upregulated in both repair deficient cells (436 EV+Act) (p=0.0002) and BRCA1 repair corrected MDA-436 cells (436 BRCA1+ Act) (p=0.0660). Moreover, the increased levels of IDO1 expression was more enhanced in DDRD positive cell models in co-culture (436 EV+Act) compared to the DDRD negative cells (436 BRCA1+Act) (p=0.0013) (FIG. 25). Therefore, similarly to PDL1, IDO1 expression is also increased by co-culture with lymphocytes, specifically in DDRD positive models.

DDRD+ Cells are Protected from Lymphocyte Mediated Cytotoxicity.

Figure 26:
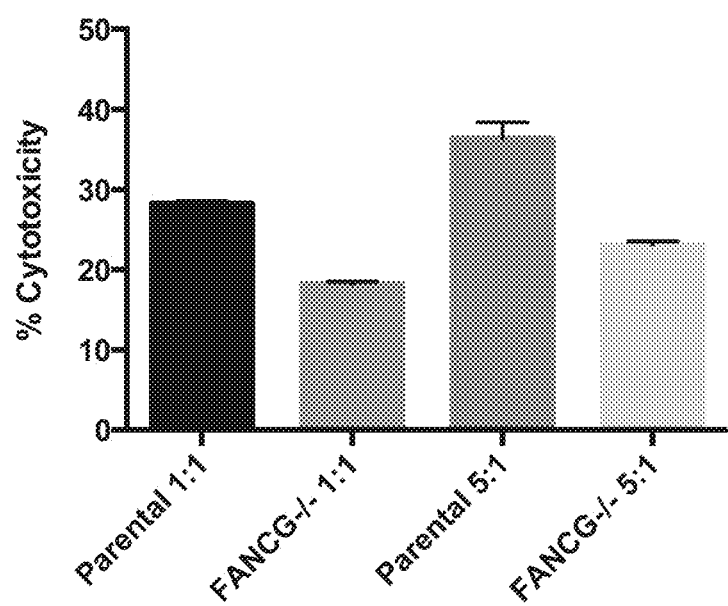
Figure 27:
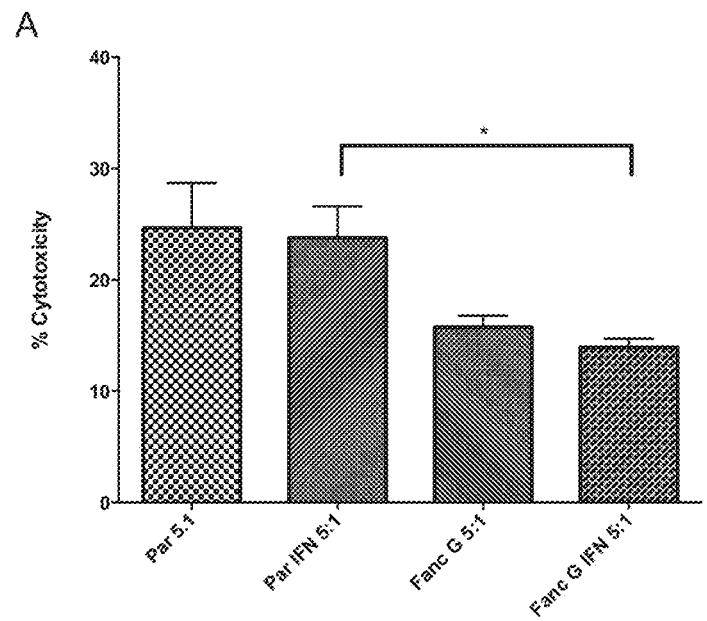
FIG. 27 provides graphs and an image showing that IFN-γ drives PDL-1 expression in DDRD+ and protects against PBMC mediated cytotoxicity.
Figure 27:
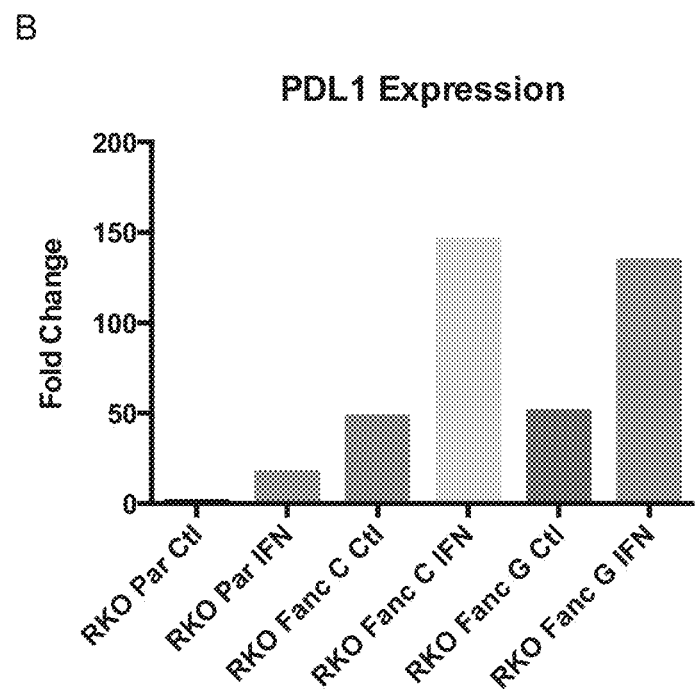

PBMCs were co-cultured with RKO Parental and RKO FANCG−/− for 4 hours and labelled with 5-(6)-carboxyfluorescein diacetate succinimidyl ester (CFSE) to label the cancer cells, in combination with 7-AAD to label the dead cancer cells and PBMCs. The RKO FANCG−/− at both ratios (FANCG−/− 1:1 and FANCG−/− 5:1) demonstrated reduced lymphocyte mediated toxicity compared to the RKO Parental cells (Parental 1:1 and Parental 5:1), as shown by the lower percentage of cytotoxicity. This reduction in toxicity is consistent with the expression of PDL1 in these cells. It is apparent that DDRD positive cells exhibit protection against lymphocyte mediated toxicity (FIG. 26). Furthermore pre-treatment of the cancer cells with Interferon-γ (Fanc G IFN 5:1) extends the differential cytotoxicity between the RKO FANCG−/− and RKO Parental cells (p-value<0.05) (FIG. 27A). In addition, treatment of RKO cells with Interferon-γ significantly increases PDL1 gene expression levels, as demonstrated by the difference in fold change of RKO Par IFN, RKO Fanc C IFN and RKO Fanc G IFN (FIG. 27B). The enhanced PDL1 levels upon Interferon-γ pre-treatment were confirmed at the protein level by western blotting (RKO Par IFN and RKO Fanc G IFN) (FIG. 27C, top panel). Taken together these data suggest that DDRD positive cells substantially overexpress PDL1 which protects the DDRD positive cells from lymphocyte mediated cell death.

Blockade of PDL1 Function Reverses DDRD Resistance to Lymphocyte Mediated Cytotoxicity.

Figure 28:
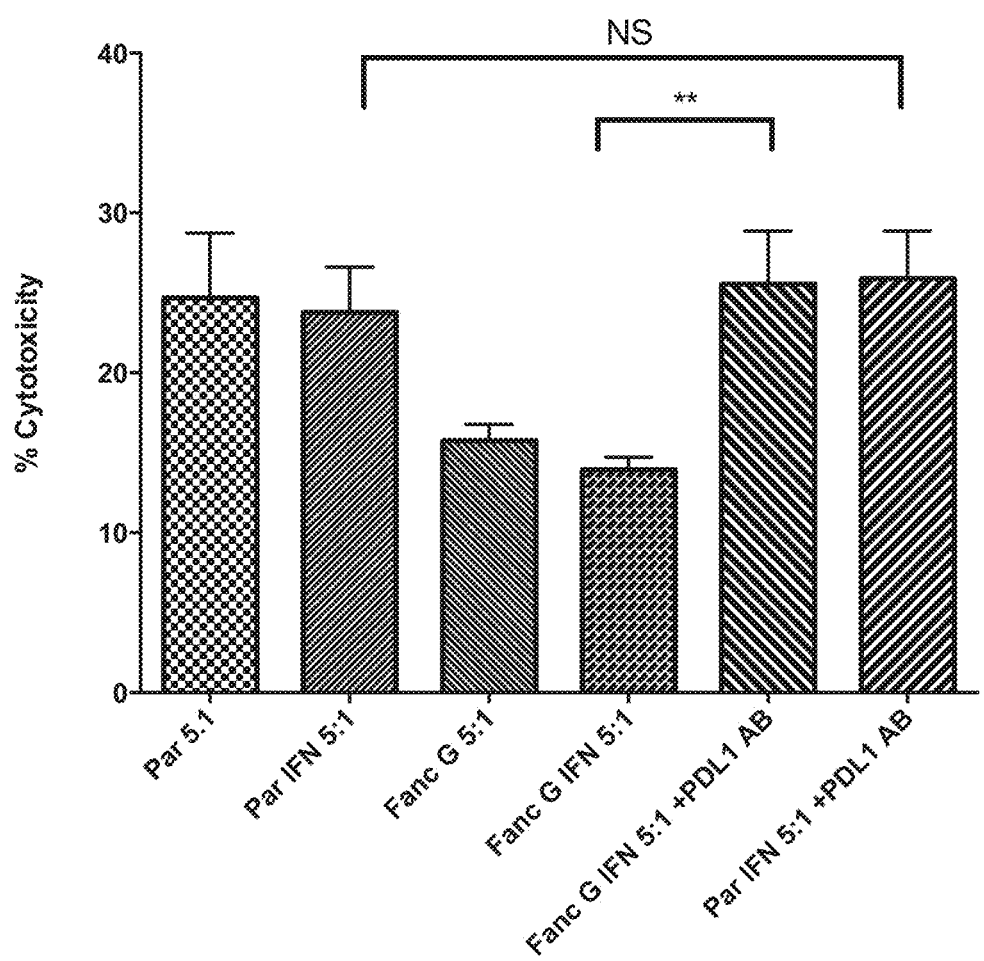
FIG. 28 provides a graph showing that a blocking antibody to PDL-1 reverses resistance to PBMC mediated cytotoxicity in DDRD+ cells alone.

To further assess the protective properties against lymphocyte mediated toxicity, a PDL1 blocking antibody was introduced to inhibit PDL1 function. Pre-treatment of RKO Parental cells and RKO FANCG−/− cells with Interferon-γ in combination with the PDL1 blocking antibody prior to cytotoxicity assays using PMBCs resulted in significantly more cytotoxicity in the DDRD positive RKO FANCG−/−. This was demonstrated by the enhanced percentage cytotoxicity of Fanc G treated with both Interferon-γ and PDL1 antibody (Fanc G IFN 5:1+PDL1 AB) in comparison to Fanc G with Interferon-γ alone (Fanc G IFN 5:1) (p<0.01) (FIG. 28). Of note, no significant difference in cytotoxicity was observed between the Parental RKO treated with IFN (Par IFN 5:1) and the Parental RKO treated with a combination of IFN and PDL1 antibody (Par IFN 5:1+PDL1 AB) (FIG. 28).

The DDRD Subtype has Upregulation of Multiple Immune Checkpoint Targets in Multiple Indications.

To assess if other immune checkpoint targets were upregulated and therefore protected DDRD positive tumours from immune mediated cytotoxicity, we performed differential gene expression analysis of two breast cancer datasets[11], a publically available colorectal cancer dataset[12] and a melanoma dataset[13]. In each instance hierarchal clustering using DDRD genes identified from the breast cancer discovery cohort were used to define class labels. A number of additional immune checkpoint targets including PDL1, IDO1, LAG3, HAVCR2 and CTLA4 were upregulated in DDRD positive tumours when compared to DDRD negative tumours (Table 49). A number of these immune checkpoint genes have therapeutic targets identified towards them.

TABLE 49

DDRD positive tumors have increased expression of multiple immune checkpoint targets

| Gene ID | Alias | BC Discovery ER Negative | BC Discovery All samples | BC Validation All samples | CRC (E-GEOD-39582 Marisa) | Melanoma (GSE19293_Augustine) |
|---|---|---|---|---|---|---|
| CD274 | PDL1 | 3.16 | 1.74 | 1.90 | 3.3 | 4.20 |
| IDO1 |  | 3.32 | 3.04 | 3.58 | 4.62 | 2.82 |
| LAG3 |  | 2.89 | NA | NA | 1.82 | 2.98 |
| HAVCR2 | TIM-3 | 2.43 | 2.36 | 1.68 | 1.83 | 2.79 |
| CD80 |  | 2.03 | NA | NA | NA | 1.78 |
| CD86 |  | 2.52 | 1.57 | NA | 2.26 | 3.38 |
| CTLA4 |  | 2.55 | 1.50 | NA | 1.65 | 3.54 |
| MHC Class 1 | HLA-DRA | 2.38 | 1.73 | 1.87 | 4.25 | 4.77 |
|  | HLA-DPA1 | 2.25 | 1.75 | 1.74 | 3.91757 | 4.55 |

Figure 29:
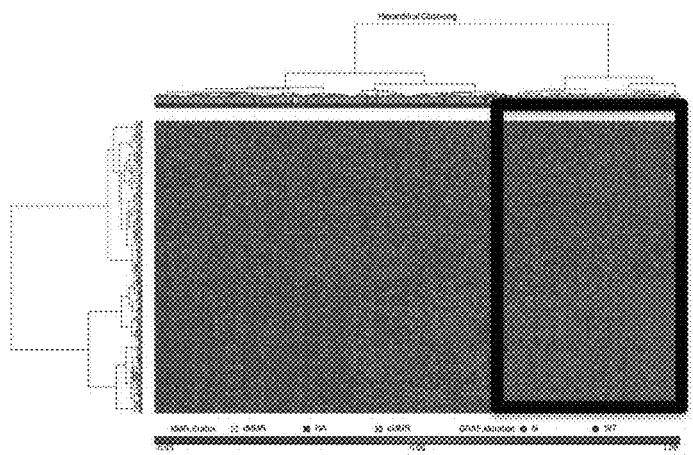
FIG. 29 shows that DDRD identifies MSI colorectal samples.
Figure 29:
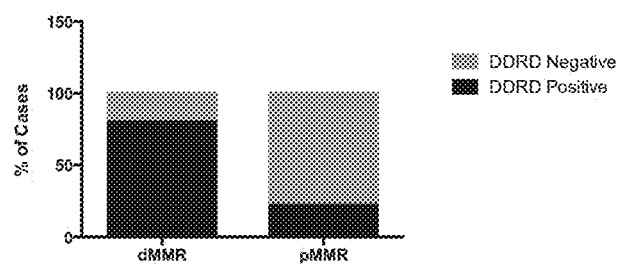

The DDRD Biology is Significantly Enriched in Microsatellite Instable (MSI) Colorectal Cancers To date the only known genetic stratification for response to PDL1 inhibition is Microsatellite Instability (MSI)[14], which results from impaired DNA mismatch repair (MMR). We hypothesised that the DDRD biology would represent MSI cancers and could be used as an improved stratification tool. We performed semi-supervised clustering on a public gene expression dataset using an intrinsic DDRD biology derived from the breast cancer analysis (Mayo clinic data, Marisa dataset). This process identified a group of colorectal samples with activation of the DDRD biology and was highly enriched in MSI tumours (FIG. 29A, outlined within the box). Of this identified group, specifically 80% of the MSI tumours were present within the DDRD positive group as indicated by the percentage of cases with deficient MMR (dMMR) (FIG. 298). Separately analysis of a cohort of stage II colorectal cancer samples which we have previously profiled[15] demonstrated that samples with known MSI status (MSI-H) had significantly higher DDRD scores than microsatellite stable (MSS) samples (p>0.05) (FIG. 29C).

Figure 30:
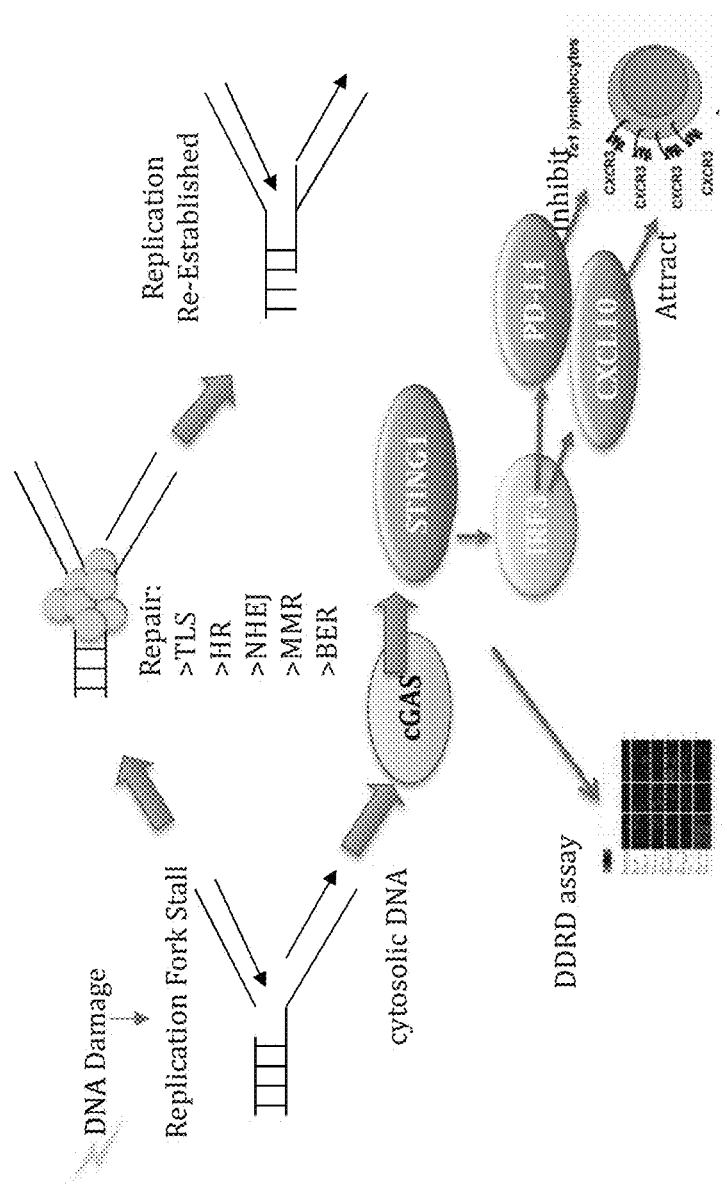
FIG. 30 illustrates a model of a DNA damage pathway.

Our current model, intrinsic or extrinsic DNA damage causes an accumulation of cytosolic DNA, this leads to activation of the innate immune STING mediated pathway which is responsible for chemokine production resulting in an inflammatory microenvironment in DNA damage repair deficient breast tumors. Expression of PD-L1 is also associated with tumors deficient in DNA damage repair and prevents T cell mediated cytotoxicity (FIG. 30).

Discussion

The DDRD molecular subtype represents tumours that have loss of function of the FA/BRCA pathway, the primary response mechanism to DNA damage and stalled DNA replication in the S-phase of the cell cycle. Our new data suggest that in the absence of a functional FA/BRCA pathway or as a result of exogenous S phase DNA damage, there is a mechanism through which an accumulation of cytosolic DNA activates the STING/TBK1/IRF3 innate immune response.

Previous studies have suggested that genomic instability may activate immune signalling through the production of neoantigens[3]. Our model proposes cytosolic DNA as an important immune-stimulating factor in response to DNA damage in the S phase of the cell cycle. This immune signal arises from the epithelial component of the cell and does not require immune recognition of abnormal proteins. Although it is unclear why S-phase DNA damage should result in cytosolic DNA we hypothesize that this may be a by-product of replication fork processing. Indeed there is some evidence that the cell may actively export DNA fragments from the nucleus, possibly to prevent misincorporation into genomic DNA[16]. Normally cytosolic DNA is processed by cytoplasmic DNase II, however it may be that this mechanism is overwhelmed by a failure to respond to endogenous DNA damage or following exogenous DNA damage thereby triggering the cGAS-mediated innate immune response. Indeed, a similar activation of the STING pathway in response to an abnormal accumulation of cytosolic DNA has been observed in the disease Systemic Lupus Erythramatosis (SLE)[17].

Our DDRD gene assay contains 2 immune checkpointing genes that represent therapeutic targets, PD-L1 and IDO1. Inhibition of the PD1/PD-L1 axis has resulted in dramatic responses in a subset of patients with advanced solid tumors including melanoma and non-small cell lung cancer[18]. Importantly, our observation that DDRD positive tumours associate with PD-L1 expression provides a rationale for exploration of immune checkpoint treatments in this molecular subgroup. Using isolated lymphocytes we have demonstrated that blockade of PD-L1 causes significant increase in lymphoctyte mediated toxicity in DDRD positive tumours.

In further support of this approach is the recent report for activity of PD-L1 inhibitors in mismatch repair deficient colorectal cancer (REF ASCO). Mismatch repair proteins have been reported to have a role in the response to S phase replication fork stalling[19] that our study suggests should activate the STING/TBK/IRF3 pathway and upregulate PD-L1 expression. Importantly we have demonstrated that the DDRD assay is sensitive in detecting colorectal MSI tumours.

The S phase specific nature of the immune signal also raises a potentially important issue around combination therapies with immune-checkpoint inhibitors. Interestingly direct activation of the STING pathway using synthetic cyclic dinucleotide molecules has been reported to enhance responses to PD1 antibodies, which is in keeping with our data[20]. Another logical combination may be an S phase specific DNA damaging agents such as cisplatin along with a PD-L1 inhibitor. Anti-microtubule agents, however, may antagonise PD-L1 inhibitors by causing cell cycle arrest in the mitotic phase thereby preventing the STING-mediated immune response. Additionally we also expect that these effects are not specific to PD-L1 as we have demonstrated activation of a number of additional immune checkpoint targets in DDRD positive tumours.

In summary, we have identified the mechanism of immune response in breast tumours deficient in DNA repair. Activation of the innate immune STING mediated pathway is responsible for chemokine production in response to DNA damage in vitro, resulting in an inflammatory microenvironment in DNA damage repair deficient breast tumors. Expression of PD-L1 is associated with tumors deficient in DNA damage repair, and we provide a rationale for investigating the role of immune treatments in the context of endogenous or exogenous S-phase DNA damage.

REFERENCES

1. Mulligan A M, Raitman I, Feeley L, et al. Tumoral lymphocytic infiltration and expression of the chemokine CXCL10 in breast cancers from the ontario familial breast cancer registry. Clin Cancer Res. 2013; 19(2):336-346. doi: 10.1158/1078-0432.CCR-11-3314 [doi].
2. Groom J R, Luster A D. CXCR3 in T cell function. Exp Cell Res. 2011; 317(5):620-631. doi: 10.1016/j.yexcr.2010.12.017 [doi].
3. Kunz M, Toksoy A, Goebeler M, Engelhardt E, Brocker E, Gillitzer R. Strong expression of the lymphoattractant C-X-C chemokine mig is associated with heavy infiltration of T cells in human malignant melanoma. J Pathol. 1999; 189(4):552-558. doi: 10.1002/(SICI)1096-9896(199912)189:4<552::AID-PATH469>3.0.CO; 2-1[pii].
4. Ohtani H, Jin Z, Takegawa S, Nakayama T, Yoshie O. Abundant expression of CXCL9 (MIG) by stromal cells that include dendritic cells and accumulation of CXCR3+ T cells in lymphocyte-rich gastric carcinoma. J Pathol. 2009; 217(1):21-31. doi: 10.1002/path.2448 [doi].
5. Muthuswamy R, Berk E, Junecko B F, et al. N F-kappaB hyperactivation in tumor tissues allows tumor-selective reprogramming of the chemokine microenvironment to enhance the recruitment of cytolytic T effector cells. Cancer Res. 2012; 72(15):3735-3743. doi: 10.1158/0008-5472.CAN-11-4136 [doi].
6. Brzostek-Racine S, Gordon C, Van Scoy S, Reich N C. The DNA damage response induces IFN. J Immunol. 2011; 187(10):5336-5345. doi: 10.4049/jimmunol.1100040 [doi].
7. Motani K, Ito S, Nagata S. DNA-mediated cyclic GMP-AMP synthase-dependent and -independent regulation of innate immune responses. J Immunol. 2015; 194(10): 4914-4923. doi: 10.4049/jimmunol.1402705 [doi].
8. Kim T, Kim T Y, Song Y H, Min I M, Yim J, Kim T K. Activation of interferon regulatory factor 3 in response to DNA-damaging agents. J Biol Chem. 1999; 274(43): 30686-30689.
9. Ablasser A, Goldeck M, Caviar T, et al. cGAS produces a 2'-5'-linked cyclic dinucleotide second messenger that activates STING. Nature. 2013; 498(7454):380-384. doi: 10.1038/nature12306 [doi].
10. Soria J, Gettinger S, Gordon M S, et al. Biomarkers associated wtih clinical activity of PD-L1 blockade in non-small cell lung carcinoma (NSCLC) patients (pts) in a phase I study of MPDL3280A. Annals of Oncology. 2014; 25(Suppl 4):iv426-Abstract 1322 P.
11. Mulligan J M, Hill L A, Deharo S, et al. Identification and validation of an anthracycline/cyclophosphamide-based chemotherapy response assay in breast cancer. J Natl Cancer Inst. 2014; 106(1):djt335. doi: 10.1093/jnci/djt335 [doi].
12. Gene Expression Classification of Colon Cancer into Molecular Subtypes: Characterization, Validation, and Prognostic Value. Laetitia Marisa, Aurélien de Reyniès, Alex Duval, Janick Selves, Marie Pierre Gaub, Laure Vescovo, Marie-Christine Etienne-Grimaldi, Renaud Schiappa, Dominique Guenot, Mira Ayadi, Sylvain Kirzin, Maurice Chazal, Jean-François Fléjou, Daniel Benchimol, Anne Berger, Arnaud Lagarde, Erwan Pencreach, Francoise Piard, Dominique Elias, Yann Parc, Sylviane Olschwang, Gerard Milano, Pierre Laurent-Puig, Valérie Boige PLoS Med. 2013; 10(5):e1001453. doi: 10.1371/journal.pmed.1001453. Epub 2013 May 21.
13. Gene expression signatures as a guide to treatment strategies for in-transit metastatic melanoma. Augustine C K, Jung S H, Sohn I, Yoo J S et al, Mol Cancer Ther 2010 April; 9(4):779-90. PMID: 20371714
14. Dung T. Le, Jennifer N. Uram, Hao Wang, Bjarne Bartlett, Holly Kemberling, Aleksandra Eyring, Andrew Skora, Nilofer Saba Azad, Daniel A. Laheru, Ross C. Donehower, Brandon Luber, Todd S. Crocenzi, George A. Fisher, Steve M Duffy, James J. Lee, Minori Koshiji, James R. Eshleman, Robert A Anders, Bert Vogelstein, Luis A. Diaz PD-1 blockade in tumors with mismatch repair deficiency. J Clin Oncol 33, 2015 (suppl; abstr LBA100).
15. Development and independent validation of a prognostic assay for stage II colon cancer using formalin-fixed paraffin-embedded tissue. Kennedy R D, Bylesjo M, Kerr P, Davison T, Black J M, Kay E W, Holt R J, Proutski V, Ahdesmaki M, Farztdinov V, Goffard N, Hey P, McDyer F, Mulligan K, Mussen J, O'Brien E, Oliver G, Walker S M, Mulligan J M, Wilson C, Winter A, O'Donoghue D, Mulcahy H, O'Sullivan J, Sheahan K, Hyland J, Dhir R, Bathe O F, Winqvist O, Manne U, Shanmugam C, Ramaswamy S, Leon E J, Smith W I Jr, McDermott U, Wilson R H, Longley D, Marshall J, Cummins R, Sargent D J, Johnston P G, Harkin D P. J Clin Oncol. 2011 Dec. 10; 29(35):4620-6. doi: 10.1200/JC0.2011.35.4498. Epub 2011 Nov. 7.
16 Dnase2a deficiency uncovers lysosomal clearance of damaged nuclear DNA via autophagy. Lan Y Y, Londoño D, Bouley R, Rooney M S, Hacohen N. Cell Rep. 2014 Oct. 9; 9(1):180-92.
17 STING manifests self DNA-dependent inflammatory disease. Ahn J1, Gutman D, Saijo S, Barber G N. Proc Natl Acad Sci USA. 2012 Nov. 20; 109(47):19386-91.
18 Safety and activity of anti-PD-L1 antibody in patients with advanced cancer. Brahmer J R, Tykodi S S, Chow L Q, Hwu W J, Topalian S L, Hwu P, Drake C G, Camacho L H, Kauh J, Odunsi K, Pitot H C, Hamid O, Bhatia S, Martins R, Eaton K, Chen S, Salay T M, Alaparthy S, Grosso J F, Korman A J, Parker S M, Agrawal S, Goldberg S M, Pardoll D M, Gupta A, Wigginton J M. N Engl J Med. 2012 Jun. 28; 366(26):2455-65.
19 Mammalian BTBD12/SLX4 assembles a Holliday junction resolvase and is required for DNA repair. Svendsen JM1, Smogorzewska A, Sowa M E, O'Connell B C, Gygi S P, Elledge S J, Harper J W. Cell. 2009 Jul. 10; 138(1): 63-77.
20 STING agonist formulated cancer vaccines can cure established tumors resistant to PD-1 blockade. Fu J, Kanne D B, Leong M, Glickman L H, McWhirter S M, Lemmens E, Mechette K, Leong J J, Lauer P, Liu W, Sivick K E, Zeng Q, Soares K C, Zheng L, Portnoy D A, Woodward J J, Pardoll D M, Dubensky T W Jr, Kim Y. Sci Transl Med. 2015 Apr. 15; 7(283):283ra52.

Example 5

Recursive feature elimination was performed on the 44 gene signature to define subsets of signatures comprising a single gene up to 43 genes.

Samples

The DDRD training set comprising 107 samples with known DDRD status were used for this analysis.

Methods

The DDRD signature of length 44 was used as a starting point for this analysis, where the absolute weight of the 44 genes was considered as a means for ranking the individual genes. The lowest ranked gene, i.e. the gene with the lowest absolute weight, was removed from the signature and the model parameters were re-trained using partial least squares (PLS) regression with the 43 gene expression data against the DDRD class labels. The weighting parameters of the 43 gene signature were used to reduce the signature by one gene as previously described, and this process was repeated until only one gene remained. Leave one out cross validation was used to enable performance estimates to be calculated for each signature length evaluated. The performance of the signature was measured using area under the receiver operating characteristic curve (AUC), which assess the ability of the signature to discriminate between the DDRD positive and DDRD negative samples at each feature length considered. Details of each of the sub-signatures are provided in Table 3-45.

Results

Table 50 shows the AUC performance for predicting the subtype using a minimum of one gene up to 43 genes (see Tables 3-45 for details of the sub signatures). At a minimum of one gene, the AUC performance is significantly greater than 0.5, therefore it is possible to predict the DDRD molecular subgroup significantly better than by chance with a minimum of one gene.

TABLE 50

AUC performance for predicting the subtype using sub signatures of 1 to 43 genes

| Sub signature size | AUC (leave-one-out CV) |
|---|---|
| 1 | 0.7694 |
| 2 | 0.7925 |
| 3 | 0.7847 |
| 4 | 0.7866 |
| 5 | 0.7910 |
| 6 | 0.7899 |
| 7 | 0.7746 |
| 8 | 0.7873 |
| 9 | 0.8000 |
| 10 | 0.8026 |
| 11 | 0.8190 |
| 12 | 0.8172 |
| 13 | 0.8276 |
| 14 | 0.8265 |
| 15 | 0.8265 |
| 16 | 0.8377 |
| 17 | 0.8459 |
| 19 | 0.8496 |
| 20 | 0.8642 |
| 21 | 0.8612 |
| 22 | 0.8679 |
| 23 | 0.8813 |
| 24 | 0.8847 |
| 25 | 0.8899 |
| 26 | 0.8948 |
| 27 | 0.8937 |
| 28 | 0.8996 |
| 28 | 0.8526 |
| 29 | 0.9000 |
| 30 | 0.9049 |
| 31 | 0.9101 |
| 32 | 0.9108 |
| 33 | 0.9157 |
| 34 | 0.9149 |

TABLE 50-continued

AUC performance for predicting the subtype using sub signatures of 1 to 43 genes

| Sub signature size | AUC (leave-one-out CV) |
|---|---|
| 35 | 0.9231 |
| 36 | 0.9231 |
| 37 | 0.9216 |
| 38 | 0.9228 |
| 39 | 0.9257 |
| 40 | 0.9269 |
| 41 | 0.9310 |
| 42 | 0.9306 |
| 43 | 0.9317 |

Example 6

In Silico Validation of the DDRD Assay in a Cohort of Melanoma Patients Treated with Immune Checkpoint Modulators and/or DNA-Damaging Agents Methods This study analysed RNAseq gene expression data from a TCGA cohort of 474 patients with skin cutaneous melanoma. Level 3 normalised gene expression data was downloaded from the TCGA data portal and the data matrix reduced to include only the DDRD genes. To remove zero counts in the data matrix, a constant value of 0.01 was added to all gene expression values and the resulting data matrix log transformed (using natural log).

DDRD assay scores were generated (as described in Mulligan et al. 2014) and dichotomized such that 75% of samples (with highest DDRD scores) were classified as DDRD-positive and 25% of samples (with lowest DDRD scores) were classified as DDRD-negative.

Patients who had received an immune based therapy (immune checkpoint modulator such as Ipilimumab or pembrolizumab) and/or a DNA damaging agent were subsequently analysed for differences in survival outcome based on their DDRD classification. Kaplan Meier plots were used to visualise differences in survival probability for DDRD positive vs DDRD negative and the Logrank test used to assess if the survival curves differ significantly. A hazard ratio was also calculated for the DDRD assay to estimate the relative risk of an event occurring in the DDRD positive compared to the DDRD negative group. The endpoints used for this analysis were time to local recurrence, time to distant recurrence, time to death (overall survival).

Results

Figure 31:
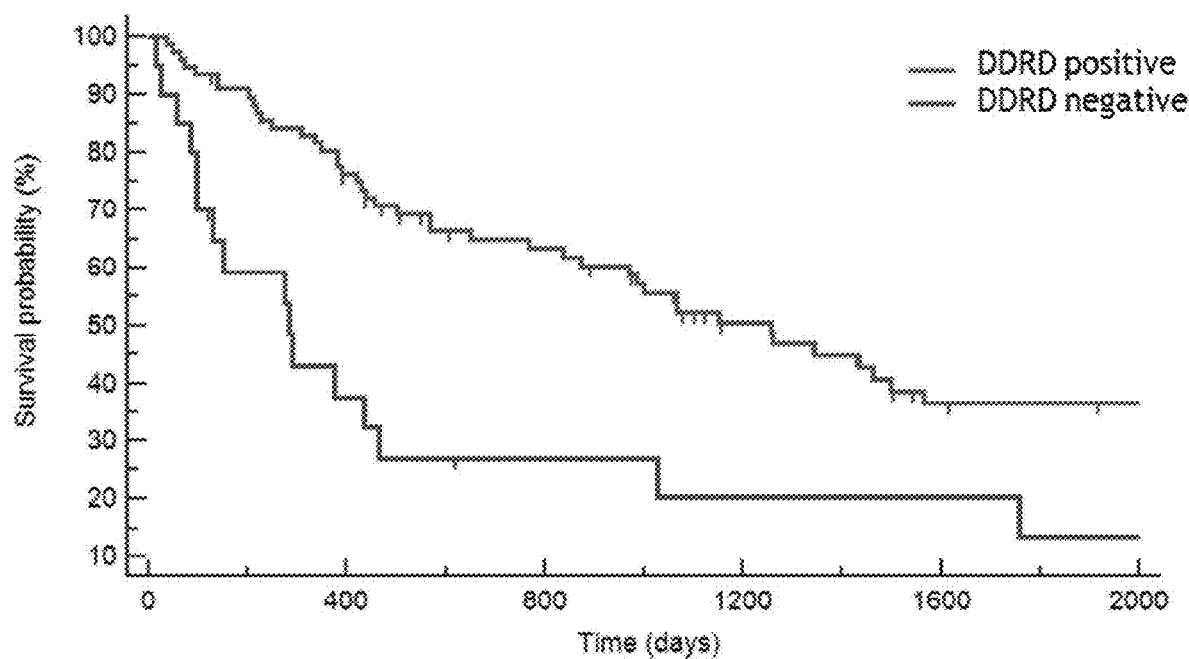
FIG. 31: Kaplan Meier illustrating the difference in local recurrence survival rates for DDRD positive and DDRD negative patients that were treated with an immune based therapy (immune checkpoint modulator such as Ipilimumab or pembrolizumab) and/or a DNA damaging agent. HR=0.39 [95% CI: 0.18-0.84], p=0.0008.
Figure 32:
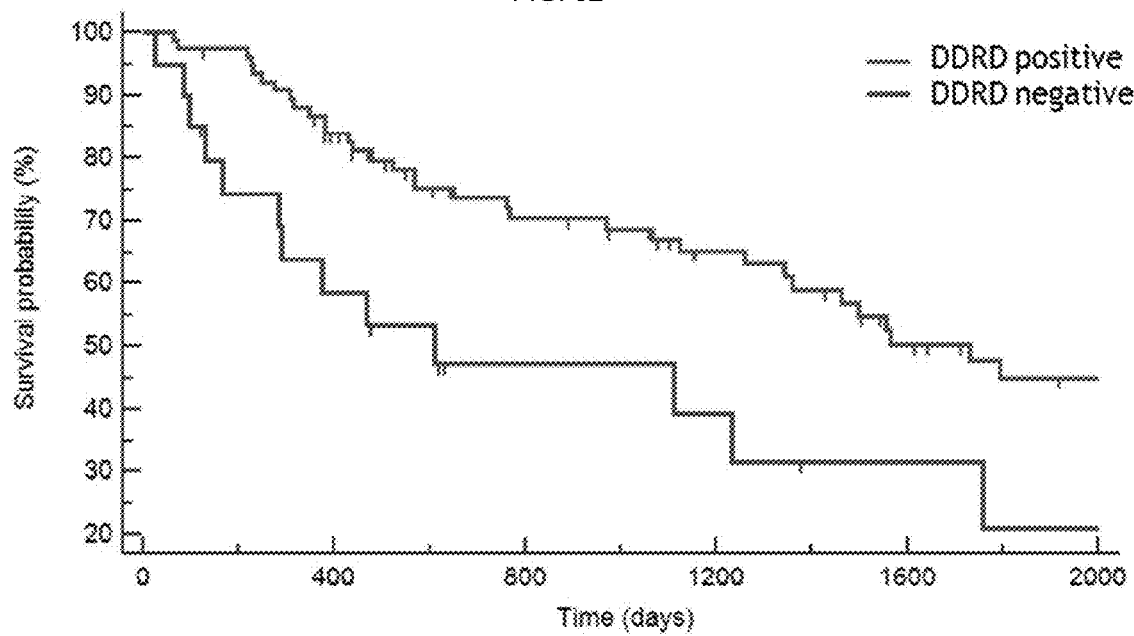
FIG. 32: Kaplan Meier illustrating the difference in distant recurrence survival rates for DDRD positive and DDRD negative patients that were treated with an immune based therapy (immune checkpoint modulator such as Ipilimumab or pembrolizumab) and/or a DNA damaging agent. HR=0.44 [95% CI: 0.19-0.99], p=0.0095.
Figure 33:
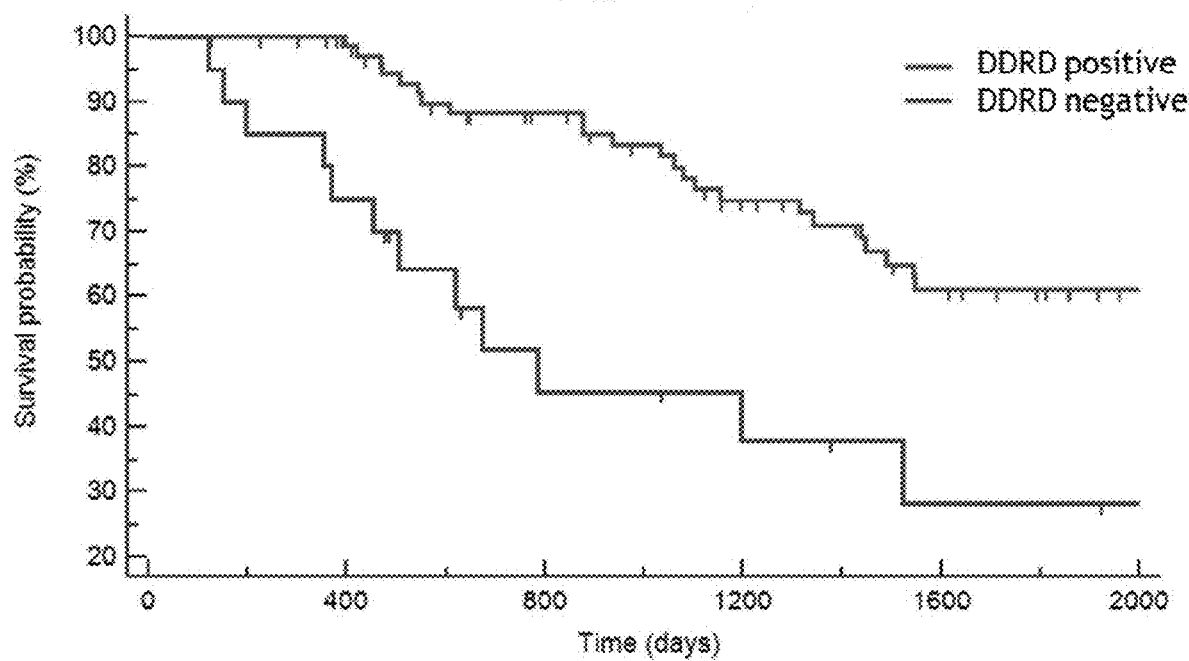
FIG. 33: Kaplan Meier illustrating the difference in overall survival rates for DDRD positive and DDRD negative patients that were treated with an immune based therapy (immune checkpoint modulator such as Ipilimumab or pembrolizumab) and/or a DNA damaging agent. HR=0.31 [95% CI: 0.12-0.81], p=0.0006.

FIGS. 31, 32 and 33 respectively are the Kaplan Meier survival graphs illustrating the difference in survival probability by DDRD status, for time to local recurrence (FIG. 31), time to distant recurrence (FIG. 32) and overall survival time (FIG. 33). The resulting analyses of each endpoint demonstrated that, in a cohort treated with an immune based therapy (immune checkpoint modulator such as Ipilimumab or pembrolizumab) and/or a DNA damaging agent, patients in the DDRD positive group have a significantly lower risk of an event occurring after treatment compared to patients in the DDRD negative group:

Time to local recurrence: HR=0.39 [95% CI: 0.18-0.84], p=0.0008

Time to distant recurrence: HR=0.44 [95% CI: 0.19-0.99], p=0.0095

Time to overall survival: HR=0.31 [95% CI: 0.12-0.81], p=0.0006

Summary

This data demonstrates that the DDRD assay identifies a group of Melanoma patients that have significantly improved survival following treatment with an immune based therapy (immune checkpoint modulator such as Ipilimumab or pembrolizumab) and/or a DNA damaging agent which have been licensed for use in Melanoma.

REFERENCES

Mulligan J M, Hill L A, Deharo S, et al. Identification and validation of an anthracycline/cyclophosphamide-based chemotherapy response assay in breast cancer. J Natl Cancer Inst. 2014; 106(1):djt335. doi: 10.1093/jnci/djt335 [doi].

```
SEQUENCE LISTING
Hs127799.0C7n9_at
                                                      (SEQ ID NO: 1)
GGGACCAAGGTGGAGATCAAACGTAAGTGCACTTTCCTAATGCTTTTTCTTATAAGGTTTTAAATTTG

GAGCCTTTTTGTGTTTGAGATATTAGCTCAGGTCAATTCCAAAGAGTACCAGATTCTTTCAAAAAGTC

AGATGAGTAAGGGATAGAAAAGTAGTTCATCTTAAGGAACAGCCAAGCGCTAGCCAGTTAAGTGAG

GCATCTCAATTGCAAGATTTTCTCTGCATCGGTCAGGTTAGTGATATTAACAGCGAAAAGAGATTTTT

GTTTAGGGGAAAGTAATTAAGTTAACACTGTGGATCACCTTCGGCCAAGGGACACGACTGGAGATTA

AACGTAAGTAATTTTTCACTATTGTCTTCTGAAATTTGGGTCTGATGGCCAGTATTGACTTTTAGAGG

CTTAAATAGGAGTTTGGTAAAGATTGGTAAATGAGGGCATTTAAGATTTGCCATGGGTTGCAAAAGTT

AAACTCAGCTTCAAAAATGGATTTGGAGAAAAAAAGATTAAATTGCTCTAAACTGAATGACACAAAGT

BRMX.5143C1n2_at
                                                      (SEQ ID NO: 2)
TTTATTGGTCTTCAGATGTGGCTGCAAACACTTGAGACTGAACTAAGCTTAAAACACGGTACTTAGCA

ATCGGGTTGCCAGCAAAGCACTGGATGCAAGCCTTGCCTTCCAGAAGCTTACCAGTCGGGTTGCCA

GCAAAGCAGTGGATGCAAGACTTGCCCTCCAGGAGCTTACCATCACAACGAAGAAGACAAATAAAT

GCATAATATATAGACGACATAAATCCATACTGTACACATTTAAGAATAAACAGTCCAGTAGTAAGAGG

CAGTACATATTCAATCTGCTGAGAAATGTAGACAATAACTACTATAAGAATCCTAATGCTACAGAAGT

CACTGGCTGCTGGGAAACCGGGGAAAACTTGGCTATGGACGTGGGGGCTTGTGTCGGACTCTGAA

TAAAGAGCAGAATGATTGGCGTCCTACTGAGATACATAGTAAAGGGGCGAGGGCAGGGAGGAAG

TGGCAAGAATAACATTTGTGAAGATGTCCAGGTGAGAAATAGAGGTTTTAATGCTCAAGATGTTTCCT

TTTCCCTTTTAAATCTGACCTGTGATTTCCAGCATTGCTATTTCGAATATCACTGATTGTTTTTAA

BRSA.1606C1n4_at
                                                      (SEQ ID NO: 3)
TGTGGCACATATACACCATGGAATACTATGCAGCCATAAAAAAGAATGGGATCATGTCCTGTGCAGC

AACGTGGATGGAGCTGGAAGCCATTATCCTAAATGAACTCACTCAGAAACAGAAAACCAAATACCAC

ATGTTCTCACTTATAAGTAGAAGCTAAACATTGAGTACACATGGATACAAAGAAGGGAACCGCAGAC

ACTGGGGCCTACCTGAGGTCGGAGCATGGAAGGAGGGTGAGGATCAAAAAACTACCTATCTGGTAC

TATGCTTTTTATCTGGATGATGAAATAATCTGTACAACAAACCCTGGTGACATGCAATTTACCTATATA

GCAAGCCTACACATGTGCCCCTGAACCTAAAAAAAAAGTTAAAAGAAAAACGTTTGGATTATTTTCCC

TCTTTCGAACAAAGACATTGGTTTGCCCAAGGACTACAAATAAACCAACGGGAAAAAAGAAAGGTTC

CAGTTTTGTCTGAAAATTCTGATTAAGCCTCTGGGCCCTACAGCCTGGAGAACCTGGAGAATCCTAC

ACCCACAGAACCCGGCTTTGTCCCCAAAGAATAAAAACACCTCTCTAAAAAAAAAAAAAAAA

BRIH.1231C2n2_at
                                                      (SEQ ID NO: 4)
TCCTTATGGGGCCCGGTATGTGGGCTCCATGGTGGCTGATGTTCATCGCACTCTGGTCTACGGAGG

GATATTTCTGTACCCCGCTAACAAGAAGAGCCCCAATGGAAAGCTGAGACTGCTGTACGAATGCAA

CCCCATGGCCTACGTCATGGAGAAGGCTGGGGGAATGGCCACCACTGGGAAGGAGGCCGTGTTAG
```

-continued

ACGTCATTCCCACAGACATTCACCAGAGGGCGCCGGTGATCTTGGGATCCCCGACGACGTGCTC

GAGTTCCTGAAGGTGTATGAGAAGCACTCTGCCCAGTGAGCACCTGCCCTGCCTGCATCCGGAGAA

TTGCCTCTACCTGGACCTTTTGTCTCACACAGCAGTACCCTGACCTGCTGTGCACCTTACATTCCTA

GAGAGCAGAAATAAAAAGCATGACTATTTCCACCATCAAATGCTGTAGAATGCTTGGCACTCCCTAA

CCAAATGCTGTCTCCATAATGCCACTGGTGTTAAGATATATTTTGAGTGGATGGAGGAGAAATAAAC

TTATTCCTCCTTAAAAAAAAAAAAAAAAAAAAAAAAAAAAAAAAAAAAAAAAAAAAAAAAAAAAAA

A

BRAD.30779_s_at (SEQ ID NO: 5)

CGGGCGTGGTAGCGGGCGCCTGTAGTCCCAGCTACTCGGGAGGCTGAGGCAGGAGAATGGCGTG

AACCCGGGAGGCGGAGCTTGCAGTGAGCCGAGATCGCGCCACTGCACTCCAGCCTGGGCGACAG

AGCGAGACTCCGTCTCAAAAAAAAAAAAAAAAAAAAAAATACAAAAATTAGCCGGGCGTGGTGGCCC

ACGCCTGTAATCCCAGCTACTCGGGAGGCTAAGGCAGGAAAATTGTTTGAACCCAGGAGGTGGAG

GCTGCAGTGAGCTGAGATTGTGCCACTTCACTCCAGCCTGGGTGACAAAGTGAGACTCCGTCACAA

CAACAACAACAAAAAGCTTCCCCAACTAAAGCCTAGAAGAGCTTCTGAGGCGCTGCTTTGTCAAAAG

GAAGTCTCTAGGTTCTGAGCTCTGGCTTTGCCTTGGCTTTGCCAGGGCTCTGTGACCAGGAAGGAA

GTCAGCATGCCTCTAGAGGCAAGGAGGGGAGGAACACTGCACTCTTAAGCTTCCGCCGTCTCAACC

CCTCACAGGAGCTTACTGGCAAACATGAAAAATCGGCTTACCATTAAAGTTCTCAATGCAACCATAA

AAAAAAAA

BRSA.396C1n2_at (SEQ ID NO: 6)

TACAGATACTCAGAAGCCAATAACATGACAGGAGCTGGGACTGGTTTGAACACAGGGTGTGCAGAT

GGGGAGGGGGTACTGGCCTTGGGCCTCCTATGATGCAGACATGGTGAATTTAATTCAAGGAGGAG

GAGAATGTTTTAGGCAGGTGGTTATATGTGGGAAGATAATTTTATTCATGGATCCAAATGTTTGTTGA

GTCCTTTCTTTGTGCTAAGGTTCTTGCGGTGAACCAGAATTATAACAGTGAGCTCATCTGACTGTTTT

AGGATGTACAGCCTAGTGTTAACATTCTTGGTATCTTTTTGTGCCTTATCTAAAACATTTCTCGATCAC

TGGTTTCAGATGTTCATTTATTATATTCTTTTCAAAGATTCAGAGATTGGCTTTTGTCATCCACTATTG

TATGTTTTGTTTCATTGACCTCTAGTGATACCTTGATCTTTCCCACTTTCTGTTTTCGGATTGGAGAAG

ATGTACCTTTTTGTCAACTCTTACTTTTATCAGATGATCAACTCACGTATTTGGATCTTTATTTGTTTT

CTCAAATAAATATTTAAGGTTATACATTTAAAAAAAAAAAAAAAAAAAAAAAAAA

BRMX.2948C3n7_at (SEQ ID NO: 7)

TGAGAAGTAGTTACTGTGCACATGTGTAGATTTGCAGTTCTGTGGCTCCTGATGGATCTGAGAAGAT

GGACGTGGAGGATGAAAATCTGTCTGATTATTTTGAACTGATGTTTGTTGCTATGGAGATGCTGCCT

ATATGTTGATGTTGCAGACGTTAAGTCACTAGCCCACAGCCTTGTATTCCATACTCAGAGACCCTGC

TACTTACTTGACATCTCAACTTGAAAGTCCAATTAATATGCACTTCAAACTTTAATAGGCTTCAAACAG

AATTTCTTTCATTATCTCTGCAAAACAGCTTCTCTCATCATCTTGAAATTAGTGAATGGCATTTTACTG

TTTTAGTTGGAGTCATTTCTGTGGTTTTCTTTCACATCCTACATAACAATCCATCAGTAAGTTCTATGA

GCTCTTCTTTGAAAACAAACAGAATCCAACTGTTTCATTCCCACTTCTGCTCTGGTCAAGCCACTGCC

AACACTCACCTTTATTATTGTAGCACCCTCATTGCCTAGTTCTGTCCCACAGATTTCCAATAAAAGGT

GAATAAAATCAGGTCACTCTTCTGCTAAAAAAAAAAAAAAAAAAAAAAAAAAAA

Hs539969.0C4n3_at (SEQ ID NO: 8)

NNNNNTTTGCTACAGCCAGGGTTAGCTCAGCAGGTGAAAACCCCGAGGGTGGGTGAAACCCCTCT

GGGGCTCAGACATGCAAACCTTGGGCATCTCTCTGTCCCAGCTGGCCCCGCCAGCCGGTAGGAAG

TTTCCCCTGAGTTCTCAGTTTTTTCTTCTGAAAAATGAGGGGTTGTATGCAAGGTTCTCCTCCTGGCC

TGTGGTCCCCAGAGAAGGGCAGGAAGGAACCTTAGATAATTCTCATATGCATTTAACAGACGAGGA

AACTGAGACCCAGAGCCGTCACATCAATACCTCATTTGATCTTCATAAGAGCACCTGGAGGAGGGG

GGTGGGGTGTTTGTGTTTGTTTAAANNNNNNNNNGTGAAAAAAATGAAGATAGGCATTTTGTAGACA

ATCTGGAAGTTCTGGACCGGAATCCATGATGTAGTCAGGGAAGAAATGACCCGTGTCCAGTAACCC

CAGGCCTCGAGTGTGTGGTGTATTTTTCTACATAATTGTAATCATTCTATACATACAAATTCATGTCTT

GACCATCATATTAATATTTGGTAAGTTTCTCTCTCTTTAGAGACTCCACAATAAAGTTTTCAACATGG

Hs396783.3C1n4_at
(SEQ ID NO: 9)
TNTTNTNTTTTTTTTTTTTTTTTTTTTTTNCATAGTTGTTATCTTAAGGTGATTTC-
CAATTTTTTTTCC

ATTTACATTTTTCCACAAGCATTGTCCACTTTATTCTGTAACCTTTTCAACTACCATTTTGAAATTTGCT

TTTATCCATGTGGTTGTTTGTGATGAACTACAGGTTGCTGACTTTCTTCCCCTTCTGTNNNNNNNNNN

NNNNNNNNNNNNNGTNNTNNNNCTCAAGAGGATCTCATCAGTGGAATCATTAGATCAAAGGATATG

ACTGTTGCTCAGCTCTCTGTGTGTATGTAAATTAATAGGCTGTTTATTTGAGCAGTTGTAGGCTTACA

AAAATATTGAGTCAAAAGTATAGAATTCCCATATATTCTCCTCTTCTCCC

BRMX.13670C1n2_at
(SEQ ID NO: 10)
ATCTTCCCACCTCGATGGGGGGTTGCTGATAAGACCTTCAGGCCTCCTTATTACCATAGGAACTGCA

TGAGTGAGTTCATGGGACTCATCCGAGGTCACTATGAGGCAAAGCAAGGTGGGTTCCTGCCAGGG

GGAGGGAGTCTACACAGCACAATGACCCCCCATGGACCTGATGCTGACTGCTTTGAGAAGGCCAG

CAAGGTCAAGCTGGCACCTGAGAGGATTGCCGATGGCACCATGGCATTTATGTTTGAATCATCTTTA

AGTCTGGCGGTCACAAAGTGGGGACTCAAGGCCTCCAGGTGTTTGGATGAGAACTACCACAAGTGC

TGGGAGCCACTCAAGAGCCACTTCACTCCCAACTCCAGGAACCCAGCAGAACCTAATTGAGACTGG

AACATTGCTACCATAATTAAGAGTAGATTTGTGAAGATTCTTCTTCAGAATCTCATGCTTTCTGGTAGT

ATTGGAGGAGGGGTTGGTTAAAATGAAAATTCACTTTTCATAGTCAAGTAACTCAGAACTTTTATGG

AAACGCATTTGCAAAGTTCTATGGCTGTCACCTTAATTACTCAATAAACTTGCTGGTGTTCTGTGGA

BRAD.30243_at
(SEQ ID NO: 11)
GGGAGCTAAGTATCCAGCCTCTCCCAAACCTCTTTGAACAAAGCTTCTGTCCCTCCCACACCTCTCA

CCTCACAGGCACATCAGGCTGCAGAATGCGCTTTAGAAAGCATTGTTTTAGTCCAGGCACAGTGGC

TCACGCCTGTAATCCCAGCACTTTGGGAGGCCGAGGTGGGTGGATCACAAGGTTGGGAGATTGAG

ACCATCCTGGCTAACACAGTGAAACCCTGTCTCTACTAAAAAATACAAAAAATTAGCTTGGCGTGG

TGGTGGGCGCCTGTAGTCCCAGCAGCTTGGGAGGCTGAGGCTGGAGAATGGTGTGAACCCAGGAG

GCGGAGCTTGCAGTGAGCCAAGATCGCGCCACTGCACTCCAGCCCGGGTGACAGAGCAAGACTCC

GTCTCAAAAAAAGAAAAGAAAAAAGAAAGCATTGTTTTAATTGAGAGGGGCAGGGCTGGAGAAGG

AGCAAGTTGTGGGGAGCCAGGCTTCCCTCACGCAGCCTGTGGTGGATGTGGGAAGGAGATCAACT

TCTCCTCACTCTGGGACAGACGATGTATGGAAACTAAAAAGAACATGCGGCACCTTAAAAAAAAAA

AAAAAAA

BRMX.941C2n2_at
(SEQ ID NO: 12)
TTTATTGGTCTTCAGATGTGGCTGCAAACACTTGAGACTGAACTAAGCTTAAAACACGGTACTTAGCA

ATCGGGTTGCCAGCAAAGCACTGGATGCAAGCCTTGCCTTCCAGAAGCTTACCAGTCGGGTTGCCA

GCAAAGCAGTGGATGCAAGACTTGCCCTCCAGGAGCTTACCATCACAACGAAGAAGACAAATAAAT

GCATAATATATAGACGACATAAATCCATACTGTACACATTTAAGAATAAACAGTCCAGTAGTAAGAGG

CAGTACATATTCAATCTGCTGAGAAATGTAGACAATAACTACTATAAGAATCCTAATGCTACAGAAGT

CACTGGCTGCTGGGAAACCGGGGAAAACTTGGCTATGGACGTGGGGGCTTGTGTCGGACTCTGAA

TAAAGAGCAGAATGATTGGCGTCCTACTGAGATACATAGTAAAGGGGGCGAGGGCAGGGAGGAAG

TGGCAAGAATAACATTTGTGAAGATGTCCAGGTGAGAAATAGAGGTTTTAATGCTCAAGATGTTTCCT

TTTCCCTTTTAAATCTGACCTGTGATTTCCAGCATTGCTATTTCGAATATCACTGATTGTTTTAA

BRMX.4154C1n3_s_at
(SEQ ID NO: 13)
ATCCCAAAGGCCCTTTTTAGGGCCGACCACTTGCTCATCTGAGGAGTTGGACACTTGACTGCGTAAA

GTGCAACAGTAACGATGTTGGAAGGCTTATGATTTTACTGTGTATGTATTTGGGAGAAGAAATTCTGT

CAGCTCCCAAAGGATAAACCAGCAGTTGCTTTATTGGTCTTCAGATGTGGCTGCAAACACTTGAGAC

TGAACTAAGCTTAAAACACGGTACTTAGCAATCGGGTTGCCAGCAAAGCACTGGATGCAAGCCTTG

CCTTCCAGAAGCTTACCAGTCGGGTTGCCAGCAAAGCAGTGGATGCAAGACTTGCCCTCCAGGAGC

TTACCATCACAACGAAGAAGACAAATAAATGCATAATATATAGACGACATAAATCCATACTGTACACA

TTTAAGAATAAACAGTCCAGTAGTAAGAGGCAGTACATATTCAATCTGCTGAGAAATGTAGACAATAA

CTACTATAAGAATCCTAATGCTACAGAAGTCACTGGCTGCTGGGAAACCGGGGAAAACTTGGCTATG

GACGTGGGGGCTTGTGTCGGACTCTGAATAAAGAGCAGAATGATTGGCAAAAAAAAAAAAAAA

BRAD.39498_at
(SEQ ID NO: 14)
CGTCTTCTAAATTTCCCCATCTTCTAAACCCAATCCAAATGGCGTCTGGAAGTCCAATGTGGCAAGG

AAAAACAGGTCTTCATCGAATCTACTAATTCCACACCTTTTATTGACACAGAAAATGTTGAGAATCCC

AAATTTGATTGATTTGAAGAACATGTGAGAGGTTTGACTAGATGATGGATGCCAATATTAAATCTGCT

GGAGTTTCATGTACAAGATGAAGGAGAGGCAACATCCAAAATAGTTAAGACATGATTTCCTTGAATG

TGGCTTGAGAAATATGGACACTTAATACTACCTTGAAAATAAGAATAGAAATAAAGGATGGGATTGTG

GAATGGAGATTCAGTTTTCATTTGGTTCATTAATTCTATAAGCCATAAAACAGGTAATATAAAAAGCTT

CCATGATTCTATTTATATGTACATGAGAAGGAACTTCCAGGTGTTACTGTAATTCCTCAACGTATTGT

TTCGACAGCACTAATTTAATGCCGATATACTCTAGATGAAGTTTTACATTGTTGAGCTATTGCTGTTCT

CTTGGGAACTGAACTCACTTTCCTCCTGAGGCTTTGGATTTGACATTGCATTTGAC

BRAD.34868_s_at
(SEQ ID NO: 15)
ACTCAAATGCTCAGACCAGCTCTTCCGAAAACCAGGCCTTATCTCCAAGACCAGAGATAGTGGGGA

GACTTCTTGGCTTGGTGAGGAAAAGCGGACATCAGCTGGTCAAACAAACTCTCTGAACCCCTCCCT

CCATCGTTTTCTTCACTGTCCTCCAAGCCAGCGGGAATGGCAGCTGCCACGCCGCCCTAAAAGCAC

ACTCATCCCCTCACTTGCCGCGTCGCCCTCCCAGGCTCTCAACAGGGGAGAGTGTGGTGTTTCCTG

CAGGCCAGGCCAGCTGCCTCCGCGTGATCAAAGCCACACTCTGGGCTCCAGAGTGGGGATGACAT

GCACTCAGCTCTTGGCTCCACTGGGATGGGAGGAGAGGACAAGGGAAATGTCAGGGGCGGGGAG

GGTGACAGTGGCCGCCCAAGGCCCACGAGCTTGTTCTTTGTTCTTTGTCACAGGGACTGAAAACCT

CTCCTCATGTTCTGCTTTCGATTCGTTAAGAGAGCAACATTTTACCCACACACAGATAAAGTTTTCCC

TTGAGGAAACAACAGCTTTAAAAGAAAAAGAAAAAAAAAGTCTTTGGTAAATGGCAAAAAAAAAAAA

AAAAA

Hs505575.0C1n42_at
(SEQ ID NO: 16)
GGGATTTGTTAAAATGGAGGTCTTTGGTGACCTTAACAGAAAGGGTTTTTGAGGAGTAGTGGAGTGG

GGAGGGGCAGCAGGAAGGGGAGATTGTACACACCCCAGGAGACAAGTCTTCTAGCAGTTCTGCCA

GAATGGGCAGGAGAGAAGTGCCATAGAGCTGGAAGGCTACATTGAATAGAGAAATTTCTTTAACTTG

```
TTTTTTAAGAAGGGTGATAAAAAGGCATGTTCTGATGGTGATAGGGATGTTTCCATAACTGGAAAGA

AATTGATGTGCAAGAGAAAGAATATAATTGCAGGAGGACTTGAAGAAGTTGGAGAGAAAAAGCCTTT

AGGGACCCTGAACCAATGAATCTGAAATTCCCCAACTGCCAGATGTATCTTCATTTTTCATTTTCCGG

GAGATGTAATATGTCCTAAAAATCACAGTCGCTAGATTGAAATCAACCTTAAAAATCATCTAGTCCAA

TGTCTACTCCCAGTCCACTACTTGAATCCCCTGTGTCCCCTCCCAGTAGTCGTCTTGACAACCTCCA

CTGAAAGGCAATTTCTACACTCCATCCACCCCACCACCAACCCATGGTTCATGATCTCTTCGGA

BREM.1442_at
                                                           (SEQ ID NO: 17)
TTACTATATCAACAACTGATAGGAGAAACAATAAACTCATTTTCAAAGTGAATTTGTTAGAAATGGATG

ATAAAATATTGGTTGACTTCCGGCTTTCTAAGGGTGATGGATTGGAGTTCAAGAGACACTTCCTGAA

GATTAAAGGGAAGCTGATTGATATTGTGAGCAGCCAGAAGGTTTGGCTTCCTGCCACATGATCGGA

CCATCGGCTCTGGGGAATCCTGATGGAGTTTCACTCTTGTCTCCCAGGCTGGAGTACAATGGCATG

ATCTCAGCTTACTGCAACCTCCGTCTCCTGGGTTCAAGCGATTCTCCTGCCTCAGCCTTCCAAGTAG

CTGGGATTACAGGTGCCCACCACCACACCTGGCTAGGTTTTGTATTTTTAGTAGAGATGGGGTTTTT

TTCATGTTGGCCAGGCTGATCTGGAACTCCTGACCTCAAGTGATCCACCTGCCTTGGCCTCCCAAA

GTGCTGGGATTTTAGGTGTGAGCCACCTCGCCTGGCAAGGGATTCTGTTCTTAGTCCTTGAAAAAAT

AAAGTTCTGAATCTTCAAAAAAAAAAAAAAAAAAAAAAAAAAAAAAAAAAAAAAAAAAAAAA

BRHP.827_s_at
                                                           (SEQ ID NO: 18)
GTGTATCATGAGCCAACCCTCAAAGGACCCGTATTACAGTGCCACGTTGGAAAACGCTACAGGAAG

CATGACCTATCCACATCTTTCCAAGATAGACACTAACATGTCATGTCCCAAACATTAGCACGTGGGG

GTTGAGCTCTGTGCAGTAATCGAGATTGGGAGAATTTGGGCAGCGCGTGAGAAGTGCTAAGCTACT

TGTTTTCTCACTTGAGCCCGGGTAGGCTGTGTTGGCCCTCACTTGGGATTCTCAGCAGTTACATGAA

AGTTGTGCTGATAATCTCTTCTCTTGTACCAATTTTAGTCAGGCAGAAAATGGTAAACATGAGGGTGC

TCTTGTGACTTAATTTTTGTTCAAGGGACTAAATTGCTTATGTTTATTCCCTGTCAGCGGAGTGGAGA

ATGTCATTCATCAATAAACCAAAGCCAATAGCTGGAGAATTGAGATCTGGTTGAAAGTGGTTTATGGT

TTACATGCTGTACTATCCTGAGGAATTGCGAGATATTGCTGAGGGGAAAAAAAATGACCTTTTCTTG

AAATGTAACTTGAAAACAAAATAAATGTGGAACATAAAAAAAAAAAAAAAAAAAAAAAAA

BRRS.18322_s_at
                                                           (SEQ ID NO: 19)
CCAGAGGCAGAAGGATTGGGACTAGGCCAACATAGAGATTGGCGATGGTTGTGAGATTCTAAGAGT

GTGTGTGCATCTTGACAATATTAGAGGAGGCTGAGCCCAAGCAGGCACATTCTCTTCGACCCCTCC

CTCATTCAGTCTGCTTTGGAGTCTACTGAACATCAAGCTTGCTATGAGCAGGATCTTAGAGCTGAGG

AATTGGCCTCCCAATCCGAACAGGTGTTATAATCCTTTCTTAATAGGTTGTGCTGTGGACCCAATGT

GAGGGCTGTGCTGGTGTAAATGGTGACATATTGAGCTGGGGGATGCTTTCGGGGTGGGGGACT

GGTTCCATTCCATCAAAGGCCCTCTTGAGAGTCTATCCAGGGACCCATTGTTTTACTTTAACAGACC

AGAAAAGATGTTTGTTTTCCATGTCATTACCCCCAGGGGATACCGAATGTGTGGGTAGAAATTTCTC

TGTAGATTAAAAATCAGATTTTTACATGGATTCAACAAAGGAGCGTCACTTGGATTTTTGTTTTCATCC

ATGAATGTAGCTGCTTCTGTGTAAAATGCCATTTTGCTATTAAAAATCAATTCACGCTGGAAAAAA

BRRS.18792_s_at
                                                           (SEQ ID NO: 20)
GCACGTCTACGGGGCTGGACAGAGTGTGGTTAACCGGGGAACTGGGCAAGCCGGCGCCGAGCCT

GCGTCAGCCGTGCAAGCCGCTCCTTCAGGAACTTCCGCTTGTCGCTGGTGTCGCTCCGCTCCTTCA

GGAGCCAGCTGTAGGTGTCCTTGTCCTGCAGGAGCTGCAGCATGCCTTCTGAAGCTGCTGGCCG

TACGTCTGGAGCATGAAGAACTGGATGATCAAAGGGATGTGGCTGGAGATGCGCTTGCTGGCCTCC
```

TGGTGATAGGCCATCAGGTGCTGAAAGATCTCCTCCATGGAAGAGTCTGTTGCCGAGCTGGACTGG

AAAGCCCCAAAATCCCAGGATTTCTTCTTCTTTTCTTCTTCCAGCTCCTTCTCTCTGACCTTCTGCAA

TGCACCCCTGTATACCTGGTCCTGGCAGTAGACAATCTGTTCCATCTGGAAGTGGAGGCGGATCAG

CTTCTCACCTTCTCTCTCTTGTTCTGCTCTAATGTCTTCAATTTTGGACTTGGCGGTTCTGTGGAGGT

TAAAAAACTCTTCAAAATTTTTTATCGCCAACTTTTTTGTACAAAGTTGGCCTTATAAAGAAAGCATTG

CT

Hs632609.0C1n37_at
(SEQ ID NO: 21)
NNNNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNCCAAATGAGTGATGCATTGACC

GTTCGTAATTCTTGGATGCAAAAGTAGAACTCAAGCTACTTAATAACAATCATGGTGGCATGGGCAC

CAGCAAGTCAGGGTGGACAACAGCCATAGTTCTGGAGCATGGTCCTCAAGACTACCTTTTGTATGC

AGAGTATTAACACTTTAACTCTTAGATCCTTGGAACATAAGGAAGAGAGGCTGGAACAAAAAGGGGT

TGGCATTTGGAGGTGGAGAGGTAGTGTAAGGCACAACTGTTTATCAACTGGTATCTAAGTATTTCAG

GCCAGACACGTGGCTCACACCTCTAATCCCAGCACTTTGGGAGCTGAGCCAGGAGGATTGCTTGAG

TCTAGGAGTTCAAGACCGGTCTGGGCAACATGGTGAAACCCTGTCTCTACAAAAAAATACAAAAATT

AGCCAGGTGTGGTGGGGCACGCCTATGGTCCCAGCTACTGGGGAGGCTGAGATGGGAGGATCCA

CCTGAGC

Hs449575.0C1n22_at
(SEQ ID NO: 22)
TTTTTTTTAATTAACTTGACTTTATTGATAGTTACAGCACAATTTATTAATTAACTTGACTTTATTGATA

GTTACAGCACAATCTGTCCAAAACCACCAGAATATACATTCTTTTCAAGAGCTCAAATGGAACATTTA

CCACAAAAGACCATATTCTGGGCTTCAAAATAAGCCTAAATAAATACAAAAGCATTTAGGACCTATGA

ATCAGAAGACTGAATATGCACATATACAAAATGAGAATCATTCTCTCACATACAAAACTTATATAGGT

AGTAAAGATACAGTTGATTAGGTAGATTTGAATGTTGAATCACTGACATTTCCTGAAGGTAGAGCTAC

AAATTACTTTTTTAAAACCACTAACCCACCCCCACCTTACCTCACTTACTCTTTTTGGCCTTACCACCT

ACTTTAGTCATACCCTATACATGTTACTCAGACCAAATGGCTCTCATAAACAATCTCAGTATATGT

BRAD.18827_s_at
(SEQ ID NO: 23)
TTAAGAAGGTATGGAAAGAGTCTGGGAGTGACTAAACTATCCAATGTCATTGAAATAAAGCAATGAA

GAATAAGAGTAATTTTTGTTGCTTTATTAAATTTTTTCTCACAGAATTCTTTATAAAAACACCATGTCCC

TAAAATGTCATTCAACATATATGCACACCTTCGATGTATAGGACACTGATCAAAAAGACAGAGAAAT

GTGTCCCTGGTGTTTTGTTTTTGNNNNNNNNNNNNNNNNNNNNNNNNNNNNNNNNNNNNNNNNN

NNNNNNNNNNNNNNNNNNNNNNNNNNNNNNNNNNNNNNNNNNNNNNNGGGACTACAGGCACATAC

CACCACACCTGGCTTCATGTTCCCGGTATTAGTACAATGCCAAAATATTTAAAATTCTTAAAGGTTAA

CTCAAATATCTTAAGTTTTACTTCACTTACAATTTCAATAATGCTGAAATTTTGATTGAATATTGTGTTT

GTAGTGCTACCTCTTTTTCGTTCATAAGAACAAAAGCCTATCATTCTCTTAGTTTCTAAAAAATATATG

TTCATATGGTTTAGATACATATATAAATATNTACACAAAACAATGTTTTTTGAGTTGTA

BREM.2466_s_at
(SEQ ID NO: 24)
GCCCGTGCCGCCCCAGCCGCTGCCGCCTGCACCGGACCCGGAGCCGCCATGCCCAAGTGTCCCA

AGTGCAACAAGGAGGTGTACTTCGCCGAGAGGGTGACCTCTCTGGGCAAGGACTGGCATCGGCCC

TGCCTGAAGTGCGAGAAATGTGGGAAGACGCTGACCTCTGGGGGCCACGCTGAGCACGAAGGCAA

ACCCTACTGCAACCACCCCTGCTACGCAGCCATGTTTGGGCCTAAAGGCTTTGGGCGGGGCGGAG

```
CCGAGAGCCACACTTTCAAGTAAACCAGGTGGTGGAGACCCCATCCTTGGCTGCTTGCAGGGCCAC

TGTCCAGGCAAATGCCAGGCCTTGTCCCCAGATGCCCAGGGCTCCCTTGTTGCCCCTAATGCTCTC

AGTAAACCTGAACACTTGGAAAAAAAAAAAAAAAAAA

BRAD.2605_at
                                                            (SEQ ID NO: 25)
CAACCAGGAAGAACCGTACCAGAACCACTCCGGCCGATTCGTCTGCACTGTACCCGGCTACTACTA

CTTCACCTTCCAGGTGCTGTCCCAGTGGGAAATCTGCCTGTCCATCGTCTCCTCCTCAAGGGGCCA

GGTCCGACGCTCCCTGGGCTTCTGTGACACCACCAACAAGGGGCTCTTCCAGGTGGTGTCAGGGG

GCATGGTGCTTCAGCTGCAGCAGGGTGACCAGGTCTGGGTTGAAAAAGACCCCAAAAAGGGTCAC

ATTTACCAGGGCTCTGAGGCCGACAGCGTCTTCAGCGGCTTCCTCATCTTCCCATCTGCCTGAGCC

AGGGAAGGACCCCCTCCCCCACCCACCTCTCTGGCTTCCATGCTCCGCCTGTAAAATGGGGCGC

TATTGCTTCAGCTGCTGAAGGGAGGGGGCTGGCTCTGAGAGCCCCAGGACTGGCTGCCCCGTGAC

ACATGCTCTAAGAAGCTCGTTTCTTAGACCTCTTCCTGGAATAAACATCTGTGTCTGTGTCTGCTGAA

CATGAGCTTCAGTTGCTACTCGGAGCATTGAGAGGGAGGCCTAAGAATAATAACAATCCAGTGCTTA

AGAGTCA

BRAD.33618_at
                                                            (SEQ ID NO: 26)
GGGTCGACCCTTGCCACTACACTTCTTAAGGCGAGCATCAAAAGCCGGGGAGGTTGATGTTGAACA

GCACACTTTAGCCAAGTATTTGATGGAGCTGACTCTCATCGACTATGATATGGTGCATTATCATCCTT

CTAAGGTAGCAGCAGCTGCTTCCTGCTTGTCTCAGAAGGTTCTAGGACAAGGAAAATGGAACTTAAA

GCAGCAGTATTACACAGGATACACAGAGAATGAAGTATTGGAAGTCATGCAGCACATGGCCAAGAA

TGTGGTGAAAGTAAATGAAAACTTAACTAAATTCATCGCCATCAAGAATAAGTATGCAAGCAGCAAAC

TCCTGAAGATCAGCATGATCCCTCAGCTGAACTCAAAAGCCGTCAAAGACCTTGCCTCCCCACTGAT

AGGAAGGTCCTAGGCTGCCGTGGGCCCTGGGGATGTGTGCTTCATTGTGCCCTTTTTCTTATTGGT

TTAGAACTCTTGATTTTGTACATAGTCCTCTGGTCTATCTCATGAAACCTCTTCTCAGACCAGTTTTCT

AAACATATATTGAGGAAAAATAAAGCGATTGGTTTTTCTTAAGGTAAAAAAAAAAAAAAAAAA

BRAD.36579_s_at
                                                            (SEQ ID NO: 27)
CAGAAAGGCCCGCCCCTCCCCAGACCTCGAGTTCAGCCAAAACCTCCCCATGGGCAGCAGAAAA

CTCATTGTCCCCTTCCTCTAATTAAAAAAGATAGAAACTGTCTTTTTCAATAAAAAGCACTGTGGATTT

CTGCCCTCCTGATGTGCATATCCGTACTTCCATGAGGTGTTTTCTGTGTGCAGAACATTGTCACCTC

CTGAGGCTGTGGGCCACAGCCACCTCTGCATCTTCGAACTCAGCCATGTGGTCAACATCTGGAGTT

TTTGGTCTCCTCAGAGAGCTCCATCACACCAGTAAGGAGAAGCAATATAAGTGTGATTGCAAGAATG

GTAGAGGACCGAGCACAGAAATCTTAGAGATTTCTTGTCCCCTCTCAGGTCATGTGTAGATGCGATA

AATCAAGTGATTGGTGTGCCTGGGTCTCACTACAAGCAGCCTATCTGCTTAAGAGACTCTGGAGTTT

CTTATGTGCCCTGGTGGACACTTGCCCACCATCCTGTGAGTAAAAGTGAAATAAAAGCTTTGACTAG

AAAAAAAAAAAAAAAAAAAAAAAAAAAAAAAAAAAAAAAAAAAAAAAAAAAAA

BRAD1_5440961_s_at
                                                            (SEQ ID NO: 28)
TCAGCACTGAGTGTTCAAAGACAGTAGGACGTCGGTTGCTGACCTGCCTCTTAGAAGCTAGTTTAAC

TCAGCGGGTAAGGATCTAGGACTTCTACATTAGTTACCACTGTAATGATAACACCACCAGAAAAGTC

TGTAGTTTAATATTTCCCACCTTATGCCTGTTTCTTCATTCACGCAAAGAAAATAAAAATATAATACCT

AAGCCTCTTTGTATTACATAAAGCAAAATGCAAAGCACTGTATCTTCCAAATACTTCCTCTTGATATG

GTGGAATTATAGAGTAGTATCATTTGTAACNTGAAATGTCTTCTAGGGTTGCTATGCGAAAGCAAGA

CTGTGGTTTCATTCCAATTTCCTGTATATCGGAATCATCACCATCTGTGTATGTGTGATTGAGGTGTT
```

```
GGGGATGTCCTTTGCACTGACCCTGAACTGCCAGATTGACAAAACCAGCCAGACCATAGGGCTATG

ATCTGCAGTAGTCCTGTGGTGAAGAGACTTGTTTCATCTCCGGGAAATGCAAAACCATTTATAGGCA

TGAAGCCCTACATGATCACTTGCAGGGTGANCCTCCTCCCATCCTTTTCCCTTTTAGGGTC

BRAD1_66786229_s_at
                                                            (SEQ ID NO: 29)
GCCTGGGACGCTGCTGCTGTTCAGGAAACGATGGCAGAACGAGAAGCTCGGGTTGGATGCCGGGG

ATGAATATGAAGATGAAAACCTTTATGAAGGCCTGAACCTGGACGACTGCTCCATGTATGAGGACAT

CTCCCGGGGCCTCCAGGGCACCTACCAGGATGTGGGCAGCCTCAACATAGGAGATGTCCAGCTGG

AGAAGCCGTGACACCCCTACTCCTGCCAGGCTGCCCCCGCCTGCTGTGCACCCAGCTCCAGTGTC

TCAGCTCACTTCCCTGGGACATTCTCCTTTCAGCCCTTCTGGGGCTTCCTTAGTCATATTCCCCCA

GTGGGGGTGGGAGGGTAACCTCACTCTTCTCCAGGCCAGGCCTCCTTGGACTCCCCTGGGGGTG

TCCCACTCTTCTTCCCTCTAAACTGCCCCACCTCCTAACCTAATCCCCCGCCCCGCTGCCTTTCCC

AGGCTCCCCTCACCCCAGCGGGTAATGAGCCCTTAATCGCTGCCTCTAGGGGAGCTGATTGTAGCA

GCCTCGTTAGTGTCACCCCCTCCTCCCTGATCTGTCAGGGCCACTTAGTGATAATAAATTCTTCCCA

ACTGCA

BREM.2104_at
                                                            (SEQ ID NO: 30)
GGATTCAGCCAGTGCGGATTTTCCATATAATCCAGGACAAGGCCAAGCTATAAGAAATGGAGTCAAC

AGAAACTCGGCTATCATTGGAGGCGTCATTGCTGTGGTGATTTTCACCATCCTGTGCACCCTGGTCT

TCCTGATCCGGTACATGTTCCGCCACAAGGGCACCTACCATACCAACGAAGCAAAGGGGGCGGAG

TCGGCAGAGAGCGCGGACGCCGCCATCATGAACAACGACCCCAACTTCACAGAGACCATTGATGAA

AGCAAAAAGGAATGGCTCATTTGAGGGGTGGCTACTTGGCTATGGGATAGGGAGGAGGGAATTACT

AGGGAGGAGAGAAAGGGACAAAAGCACCCTGCTTCATACTCTTGAGCACATCCTTAAAATATCAGCA

CAAGTTGGGGGAGGCAGGCAATGGAATATAATGGAATATTCTTGAGACTGATCACAAAAAAAAAAA

CCTTTTTAATATTTCTTTATAGCTGAGTTTTCCCTTCTGTATCAAAACAAAATAATACAAAAAATGCTTT

TAGAGTTTAAGCAATGGTTGAAATTTGTAGGTAATATCTGTCTTATTTTGTGTGTGTTTAGAGGT

BRAG_AK097020.1_at
                                                            (SEQ ID NO: 31)
ATGTCCAAAAAGATACAGAAGAACTAAAGAGCTGTGGTATACAAGACATATTTGTTTTCTGCACCAGA

GGGGAACTGTCAAAATATAGAGTCCCAAACCTTCTGGATCTCTACCAGCAATGTGGAATTATCACCC

ATCATCATCCAATCGCAGATGGAGGGACTCCTGACATAGCCAGCTGCTGTGAAATAATGGAAGAGC

TTACAACCTGCCTTAAAAATTACCGAAAAACCTTAATACACTGCTATGGAGGACTTGGGAGATCTTGT

CTTGTAGCTGCTTGTCTCCTACTATACCTGTCTGACACAATATCACCAGAGCAAGCCATAGACAGCC

TGCGAGACCTAAGAGGATCCGGGGCAATACAGACCATCAAGCAATACAATTATCTTCATGAGTTTCG

GGACAAATTAGCTGCACATCTATCATCAAGAGATTCACAATCAAGATCTGTATCAAGATAAAGGAATT

CAAATAGCATATATATGACCATGTCTGAAATGTCAGTTCTCTAGCATAATTTGTATTGAAATGAAACCA

CCAGTGTTATCAACTTGAATGTAAATGTACATGTGCAGATATTCCTAAAGTTTTATTGAC

BRAD.20415_at
                                                            (SEQ ID NO: 32)
GGTTTCCTTCCCAGGACAGCTGCAGGGTAGAGATCATTTTAAGTGCTTGTGGAGTTGACATCCCTAT

TGACTCTTTCCCAGCTGATATCAGAGACTTAGACCCAGCACTCCTTGGATTAGCTCTGCAGAGTGTC

TTGGTTGAGAGAATAACCTCATAGTACCAACATGACATGTGACTTGGAAAGAGACTAGAGGCCACAC

TTGATAAATCATGGGGCACAGATATGTTCCCACCCAACAAATGTGATAAGTGATTGTGCAGCCAGAG

CCAGCCTTCCTTCAATCAAGGTTTCCAGGCAGAGCAAATACCCTAGAGATTCTCTGTGATATAGGAA
```

-continued

```
ATTTGGATCAAGGAAGCTAAAAGAATTACAGGGATGTTTTTAATCCCACTATGGACTCAGTCTCCTG

GAAATAGGTCTGTCCACTCCTGGTCATTGGTGGATGTTAAACCCATATTCCTTTCAACTGCTGCCTG

CTAGGGAAAACTGCTCCTCATTATCATCACTATTATTGCTCACCACTGTATCCCCTCTACTTGGCAAG

TGGTTGTCAAGTTCTAGTTGTTCAATAAATGTGTTAATAATGCTTAAAAAAAAAAAAAAAAA

BRAD.29668_at
                                                        (SEQ ID NO: 33)
ATTCCAGGAAGCATGGGATTTTATTTTGCTTGATTTTGGGCACATGAAATAATAGCTCTAGGAAAATG

CGCATCTTAATGACTCTTTGTAAAGAGAGGCATTTCTTACAACTGTGATGTTTGCTTACATAAAAGTT

ACCTCATAAGTTAATTCTAACTTTTATTCTTGAATTTTATTTCATTTCAATAGCTTGTTTCATTTGCACG

CCTTTGTATTTTGATTGACCTGTAGAATGGATGTTAGGAAACTCAAAATTGAACACAGTGAAACAAAT

GGTATTTGAAGAAATGTAATATCTTTTATATTCTATTTATGATATCCATAATCAAATGAGATTATTTTAC

CACATAAATGTTTTAAATATCAGATTTTTAGTTTGCAGTTTTAGGAAAATGCTTTAGATAGAAAAGGTT

CTTATGCATTGAATTTGGAGTACTACCAACAATGAATTTATTTTTTATATTCTTACACATTTTATT

GGTCATTGTCACAGATAGTAAATACTAAAAATTTCAGGTCAGTTTGTTTTGAAACTGAAATTGGAAAT

AAATCTGGAAATGTTTTGTTGCACTAAAATAATAAAATGAATTGTACTG

BRAD.30228_at
                                                        (SEQ ID NO: 34)
TAGGCCAGCCCTGTCACCACCTCCACTGCCATGACCAGGCCGAAGGCAGGGAACGCCCTCCCCAG

TCCCGCTGTCCAGCAAGGCCCCGAGACTTTTCTTCTGTGATTTCCAAAAGCAAGGCAGCCGTGCTG

TTCTAGTTCCTCTCCATCCGCCACCTCCCCTCCCGCTGCCCCAGAAGTTTCTATCATTCCATGGAGA

AAGCTGTGTTCCAATGAATCCTACCTCTTGCCCAGTCCCAGGCAGAGTAAGCAGGGCCCACCTAGG

GACCAAGAAAGAGTAGGAAGAAGGGGACGAGCCGGGAGCAAAACCACCTCAGACACCCGGGCCTT

CTCAGCCTTCTCCCCGCGGCCAGCTGGGTCTCCGGGGACCCTGGGCCCTGGGCCGCCCATTCCTG

GCCCTCCCGCTGCATCTCAGACCTGACACCCAACGGGGGATGTGGTGGCCTGTGCCCACCTTCT

CTCCCTCCTCCCGACCCGCCCCTCGCCCCCACCCCTGTGTGTTTCGCCAGTTAAGCACCTGTGAC

TCCAGTACCTACTACTGGTTTTGGGTTGGTTGTTCTGTCTTTTTTTAATTAAATAAAAACATTTTTAAA

ATGTT

BRAD.34830_at
                                                        (SEQ ID NO: 35)
TGCTCAGACCAGCTCTTCCGAAAACCAGGCCTTATCTCCAAGACCAGAGATAGTGGGGAGACTTCT

TGGCTTGGTGAGGAAAAGCGGACATCAGCTGGTCAAACAAACTCTCTGAACCCCTCCCTCCATCGT

TTTCTTCACTGTCCTCCAAGCCAGCGGGAATGGCAGCTGCCACGCCGCCCTAAAAGCACACTCATC

CCCTCACTTGCCGCGTCGCCCTCCCAGGCTCTCAACAGGGGAGAGTGTGGTGTTTCCTGCAGGCC

AGGCCAGCTGCCTCCGCGTGATCAAAGCCACACTCTGGGCTCCAGAGTGGGGATGACATGCACTC

AGCTCTTGGCTCCACTGGGATGGGAGGAGAGGACAAGGGAAATGTCAGGGGCGGGGAGGGTGAC

AGTGGCCGCCCAAGGCCCACGAGCTTGTTCTTTGTTCTTTGTCACAGGGACTGAAAACCTCTCCTCA

TGTTCTGCTTTCGATTCGTTAAGAGAGCAACATTTTACCCACACACAGATAAAGTTTTCCCTTGAGGA

AACAACAGCTTTAAAAGAAAAAGAAAAAAAAAGTCTTTGGTAAATGGCAAAAAAAAAAAAAAAAAAA

AAAAA

BRAD.37011_s_at
                                                        (SEQ ID NO: 36)
TCCCCAGACACCGCCACATGGCTTCCTCCTGCGTGCATGTGCGCACACACACACACACGCACAC

ACACACACACACTCACTGCGGAGAACCTTGTGCCTGGCTCAGAGCCAGTCTTTTTGGTGAGGGT

AACCCCAAACCTCCAAAACTCCTGCCCCTGTTCTCTTCCACTCTCCTTGCTACCCAGAAATCATCTAA

ATACCTGCCCTGACATGCACACCTCCCCTGCCCCACCAGCCCACTGGCCATCTCCACCCGGAGCTG
```

-continued

CTGTGTCCTCTGGATCTGCTCGTCATTTTCCTTCCCTTCTCCATCTCTCTGGCCCTCTACCCCTGATC

TGACATCCCCACTCACGAATATTATGCCCAGTTTCTGCCTCTGAGGGAAAGCCCAGAAAAGGACAG

AAACGAAGTAGAAAGGGGCCCAGTCCTGGCCTGGCTTCTCCTTTGGAAGTGAGGCATTGCACGGG

GAGACGTACGTATCAGCGGCCCCTTGACTCTGGGGACTCCGGGTTTGAGATGGACACACTGGTGT

GGATTAACCTGCCAGGGAGACAGAGCTCACAATAAAAATGGCTCAGATGCCACTTCAAAGAAAAAAA

AAA

BRAD.37762_at (SEQ ID NO: 37)
GGGCGGTTCTCCAAGCACCCAGCATCCTGCTAGACGCGCCGCGCACCGACGGAGGGGACATGGG

CAGAGCAATGGTGGCCAGGCTCGGGCTGGGGCTGCTGCTGCTGGCACTGCTCCTACCCACGCAGA

TTTATTCCAGTGAAACAACAACTGGAACTTCAAGTAACTCCTCCCAGAGTACTTCCAACTCTGGGTTG

GCCCCAAATCCAACTAATGCCACCACCAAGGTGGCTGGTGGTGCCCTGCAGTCAACAGCCAGTCTC

TTCGTGGTCTCACTCTCTCTTCTGCATCTCTACTCTTAAGAGACTCAGGCCAAGAAACGTCTTCTAAA

TTTCCCCATCTTCTAAACCCAATCCAAATGGCGTCTGGAAGTCCAATGTGGCAAGGAAAAACAGGTC

TTCATCGAATCTACTAATTCCA

BRAD.40217_at (SEQ ID NO: 38)
ACCCTGTGCCAGAAAAGCCTCATTCGTTGTGCTTGAACCCTTGAATGCCACCAGCTGTCATCACTAC

ACAGCCCTCCTAAGAGGCTTCCTGGAGGTTTCGAGATTCAGATGCCCTGGGAGATCCCAGAGTTTC

CTTTCCCTCTTGGCCATATTCTGGTGTCAATGACAAGGAGTACCTTGGCTTTGNCACATGTCAAGGC

TGAAGAAACAGTGTCTCCAACAGAGCTCCTTGTGTTATCTGTTTGTACATGTGCATTTGTACAGTAAT

TGGTGTGACAGTGTTCTTTGTGTGAATTACAGGCAAGAATTGTGGCTGAGCAAGGCACATAGTCTAC

TCAGTCTATTCCTAAGTCCTAACTCCTCCTTGTGGTGTTGGATTTGTAAGGCACTTTATCCCTTTTGT

CTCATGTTTCATCGTAAATGGCATAGGCAGAGATGATACCTAATTCTGCATTTGATTGTCACTTTTTG

TACCTGCATTAATTTAATAAAATATTCTTATTTATTTTGTTANNTNGTANANNANNATGTCCATTTTCTT

GTTTATTTTGTGTTTAATAAAATGTTCAGTTTAACATCCCANNNGAGAAAGTTAAAAAA

BRAD1_4307876_at (SEQ ID NO: 39)
CTCCTGGTTCAAAAGCAGCTAAACCAAAAGAAGCCTCCAGACAGCCCTGAGATCACCTAAAAAGCT

GCTACCAAGACAGCCACGAAGATCCTACCAAAATGAAGCGCTTCCTCTTCCTCCTACTCACCATCAG

CCTCCTGGTTATGGTACAGATACAAACTGGACTCTCAGGACAAAACGACACCAGCCAAACCAGCAG

CCCCTCAGCATCCAGCAACATAAGCGGAGGCATTTTCCTTTTCTTCGTGGCCAATGCCATAATCCAC

CTCTTCTGCTTCAGTTGAGGTGACACGTCTCAGCCTTAGCCCTGTGCCCCCTGAAACAGCTGCCAC

CATCACTCGCAAGAGAATCCCCTCCATCTTTGGGAGGGGTTGATGCCAGACATCACCAGGTTGTAG

AAGTTGACAGGCAGTGCCATGGGGGCAACAGCCAAAATAGGGGGGTAATGATGTAGGGGCCAAGC

AGTGCCCAGCTGGGGGTCAATAAAGTTACCCTTGTACTTGCAAAAAAAAAAAAAAAAAAA

BREM.2505_at (SEQ ID NO: 40)
GCCATCAAGAATTTACTGAAAGCAGTTAGCAAGGAAAGGTCTAAAAGATCTCCTTAAAACCAGAGGG

GAGCAAAATCGATGCAGTGCTTCCAAGGATGGACCACACAGAGGCTGCCTCTCCCATCACTTCCCT

ACATGGAGTATATGTCAAGCCATAATTGTTCTTAGTTTGCAGTTACACTAAAAGGTGACCAATCATGG

TCACCAAATCAGCTGCTACTACTCCTGTAGGAAGGTTAATGTTCATCATCCTAAGCTATTCAGTAATA

ACTCTACCCTGGCACTATAATGTAAGCTCTACTGAGGTGCTATGTTCTTAGTGGATGTTCTGACCCT

GCTTCAAATATTTCCCTCACCTTTCCCATCTTCCAAGGGTATAAGGAATCTTTCTGCTTTGGGGTTTA

-continued

TCAGAATTCTCAGAATCTCAAATAACTAAAAGGTATGCAATCAAATCTGCTTTTTAAAGAATGCTCTTT

ACTTCATGGACTTCCACTGCCATCCTCCCAAGGGGCCCAAATTCTTTCAGTGGCTACCTACATACAA

TTCCAAACACATACAGGAAGGTAGAAATATCTGAAAATGTATGTGTAAGTATTCTTATTT

Hs149363.0CB4n5_s_at (SEQ ID NO: 41)

GGGAAATCAGTGAATGAAGCCTCCTATGATGGCAAATACAGCTCCTATTGATAGGACATAGTGGAAG

TGGGCTACAACGTAGTACGTGTCGTGTAGTACGATGTCTAGTGATGAGTTTGCTAATACAATGCCAG

TCAGGCCACCTACGGTGAAAAGAAAGATGAATCCTAGGGCTCAGAGCACTGCAGCAGATCATTTCA

TATTGCTTCCGTGGAGTGTGGCGAGTCAGCTAAATGGCAGGGGCAGCAAGATGGTGTTGCAGACC

CAGGTCTTCATTTCTCTGTTGCTCTGGATCTCTGGTGCCTACGGGGACATCGTGATGACCCAGTCTC

CAGACTCCCTGGCTGTGTCTCTGGGCGAGAGGGCCACCATCAAGTGCAAGTCCAGCCAGAGTATTT

TATATAGGTCCAACAACAAGAACTACTTAGCTTGGTACCAGCAGAAAGCAGGACAGCCTCCTAAATT

GTTCATTTACTGGGCATCTACCCGGGAATCCGGGGTCCCTGACCGATT

Hs172587.9C1n9_at (SEQ ID NO: 42)

AACGAAAGTCTAGCCTTTCGTACCCGTATATATAAAGACACCCCTGTTCTGATTGGACAAGGCAGCC

TTTCCCCTGCAGCTCGATTGGTGGAGACGCCCACTCCCTGACAGAACATCTCCTGCATGTAGACCA

AATATTAAAACTTTCCTCCGTCCATCTTTAACTGCTGGTGTTTTCAACCCTTTCCCCTCTGTGCCATG

TTTCTAGCTTTTATTTAAAACGTACTTTGGTTTTCCTTGGCAAATTGTGTCTAGCTACTAGGATGACG

TGTCTTAATTTTTTTTAAATGTTGGCGCTGAAACTGGCTTTGATCAACGTTTTAAAAAGACGCGCGC

TAGTTGTGATTGGCCAAGTGATTTCTTCTTACCCTCTTAAGTTTAGAAAGGTTAATTTCATATCTTGAT

TTGTCTATTTAAACTTGGAGATATTTTCAATAATTTGTTCCAAATGCACCATGACTATTAACTCATAAG

TAACAATATGAAACCTGATGTTAAGCTACATGAACACATTTAATTTCACCACAATATGACATCCTCATA

TGAAAGCACTCTCTTATCTTTTACAAGTTCAACTGGTATTTGTGTAATCTGCTGT

Hs271955.16C1n9_at (SEQ ID NO: 43)

TGCTACCATGCCTGACTAGTTTTTGTATTTTTAGTAGAGACAGGGTTTGACCATATTGGCCAGGTTG

GTCTTGGACTCCTGACAAGTGATCCGCCCTCCTCNNNCNCNCGAAGTGCTAGGGTTACNAGGTGTG

AACCACCATGCCTAACTATCGTTGCTACTTTCTATTGGAAGAGAAGGCAGCCCTGATTTAGTCTGTTT

ACAGTCTGCATTATGTGGAGAATAGAGAGCCATCATAGTCCCTAAAACTTTCCTTGCCAGTTAACCC

AGCAGGACAACCTGTCTTTGTCTCTTGACAACTGTTAACTGAGAACAGGGCCCTTGCTCCTCTAGGT

GTGCACATTAAGGACTTTGCACAGTGTGGATGTAGCTCATGCTGCTCTGCCNTNNAGTACATGCTGC

TTGAATTTTCATCATNANCCTCCACNCCTTNCACCTNCNNGNNAAAAAAAAAGCGTGCAGGAAGTAG

CATTTCAGATCCTTCTCCACCACCTCTGCTTCCCTTCTCCCTTCTTTTCCTCCTTGCAGCATTCCCTT

TAGTACNAGGGAGGGATGGTGGTTGAAAATGGGGGGAATGATGTTGCTCAGAAAAAAAAAAAA

Hs368433.18C1n6_at (SEQ ID NO: 44)

ATAATGCTGGAAACAGAAGCACCAAACTGATTGTGCAATTACTCCTTTTGTAGAAGAGGCCAAAATC

CTCCTCCTCCTTCCTTTCTCCTATATTCACTCCTCCAGGATCATAAAGCCTCCCTCTTGTTTATCTGT

GTCTGTCTGTCTGATTGGTTAGATTTGGCTNCCCTTCCAAGCTAATGGTGTCAGGTGGAGAACAGAG

CAACCTTCCCTCGGAAGGAGACAATTCGAGGTGCTGGTACATTTCCCTTGTTTTCTATGTTCTTCTTT

CTAGTGGGTCTCATGTAGAGATAGAGATATTTTTTGTTTTAGAGATTCCAAAGTATATATTTTTAGTG

TAAGAAATGTACCCTCTCCACACTCCATGATGTAAATAGAACCAGGAATAAATGTGTCATTGTGATAA

-continued

TCCCATAGCAATTTATGGTAAGAACAAGACCCCTTTCCCTCACCACCGAGTCTCGTGGTCTGTGTCT

GTGAACCAGGGCAGGTAATTGTGACACTGCATCTCATAGAACTCTGCCTGCCCAGATTTTTGTGTGC

TCACCTCAATGGGTGAAAAATAAAGTCTGTGTAAACTGTTAAAAAAAAAAAAAAAAAAA

Hs435736.0C1n27_s_at (SEQ ID NO: 45)

TCCTCAGACCCAGTAATTCCACCCCTAGGAATCCAGCTTACACACACAAGAAAGAAAAGATAAATGT

ACAAGGTTAGTCACTGCACAGTGAGACAGCAAAAGATTAGAAAGAACCCAAGTGATTATTGATCTGG

GTTTTATTCCTTTATAGCCCAACCATATGATGGAATACTATAATGTTGTAAAAATGGGTTAAGAGTTCT

TTATGAATTGGTGTGGAAACATCGCCAAGATATGAAAGCCAAATGCAGAAAAATATATGTGGTATGC

TATTATCTATGTGAAAAGACATTACTATTCTCTGGAAGGATAAACACAAATTTGAGAATGGTGGATA

TCTGGGGTGAGAGGTATCCTTTTCACTGTTCTTTAAAAGTTTTGNNATTTTGGTGTTTGCCTATTCAA

AAAAATGGTTAAAATCAGTTGCCACCAATTAAAAATTAGGAGAATGCATATAAAGAANNNAANTTCCT

GTTAAAAAAAAAAAAAAAAAAA

Hs493096.15C1n6_at (SEQ ID NO: 46)

GCCCATAGTCCCATCTTTTTACAGGCATTTTTTACACCTGGAGCAGCCAGAGGACGCATGCATGGCT

CTTCGGAAGGTAATTTAGGGATCACCCATGTAAGTTTCCTAAGGATTTCTTTAACATGGTTCTTCTGA

TTCAGTCCGGCCAATTAAATCTAAATCCACCCCTGAAAGCCATCTGGTGTGGATAACAAGCCCACAA

ATGAGCAGTCAGCTTTTTGTGCCCTTTAGGGCCTGGGACAACCACGGGATCTAAAAGGGGCTGGAA

CTAGAGGTCTTGAGCTCCTGTTCCTAAAATCATCTTCATCCTATATCTGCAGCCTTCTCCTGCCACG

GCATGCACCCACACATGCGAGCCTCCCGGGTACTGTCATCCTGAATTCTGAGACCATCCAGCACTT

CCTTTAGTTTTGCCCTGGTGCTGTTGACTTTTGTTTACTGAAGAGTGTGCTGGAGGCAGGACAAGGG

ACATGGAAGGCTGCAATTTAAGAGTCTAAAAGGTTTTAGAATCCTGAAGGAGGTTTAACAAGCTGAA

TTGAAGAATAATACCTTTCTCAACTGGAGAGAATTTACATGATTGCATTATTGTTAAAATTAACA

Hs493096.2C1n15_s_at (SEQ ID NO: 47)

ATCATTTAGTTGAATCATTATAAGTCTAGGACTGTCTGTAGATGTAAATTTGTTAAGAATTAGGACTCA

AGAGTAGAATTCCTTTAATCCACATAGACTTACAATGGTGCTGTGCACATGAGCCCCTAAATCATT

GCTGACTGAGTAGATTTCCCAGGGTAAGCCCAAGAAGTTACTCCTAGAAGGGGCTGGTAGGGGAAA

GAGCCAACATCCCACATGCCTGCCCACTTTGGGTCTGGTCCCAAGAAACAAACTCCAGTGGCCTCG

AAAATTTAATATTGCTGTCAGAAGGGCCTCCCCTTCAAAGGAACAGGTCCTGATAGCTCTTGTTATAT

GCAAAGTGGAAAGGTAACGTGACTGTTCTCTGCATTTCCTGCCTTTCAATTGAGTGAAGACAGACAG

ATGATTTATTGGGCATTTCCTAGCCTCCCCTTCACCATAGGAAACCAGACTGAAAAAAAGGTGCAAA

TTTTAAAAAGATGTGTGAGTATCTTGAGGGGGCTGGGGAGAATTCCTGTGTACCACTAAAGCAAAA

AAAGAAAACTCTCTAACAGCAGGACCTCTGATCTGGAGGCATATTGACCATAAATTTACGCCA

Hs592929.0CB2n8_at (SEQ ID NO: 48)

TTTTTCTGAGCAACATCATTCCCCCCATTTTCAACCACCATCCCTCCCTGGTACTAAAGGGAATGCTG

CAAGGAGGAAAAGAAGGGAGAAGGGAAGCAGAGGTGGTGGAGAAGGATCTGAAATGCTACTTCCT

GCACGCTTTTTTTCTTCTTGGAGGTGGAAGGAGTGGAGGATGATGATGAAAATTCAAGCAGCATGTA

CTAGACGGCAGAGCAGCATGAGCTACATCCACACTGTGCAAAGTCCTTAATGTGCACACCTAGAGG

AGCAAGGGCCCTGTTCTCAGTTAACAGTTGTCAAGAGACAAAGACAGGTTGTCCTGCTGGGTTAACT

```
Hs79953.0C1n23_at
                                                              (SEQ ID NO: 49)
ATCAGAACAATTTCATGTTATACAAATAACATCAGAAAAATATCTTAAATTATATGGCATATTCTATTGA

TTCATCCACAAATTTATAAGTCCTTACCACCTTTCATTATATTGGTACTAGGCATTATAGTAGTGCTAG

GCACTATAGTAATGCTGGGGTATAAACAAGAATAAAACAAAATAAGTTCCTTATTTCAGGTAACTTAC

AGTATAGGTCAGTGGTTCTTAGCTTGCTTTTTAATTATGAATTCCTTTGAAAGTCTAGTAAAATAATCC

AACACCATTATTCCCCATTGCACATACCCCCAGATGTTTTAGACATATTTTCAATTGCTCCATGGACC

TTAAGAAAACTTGGTTGGTGTGCAGTTTGGTGTATTATGGGTAAGACTGGACCTGGTGTTAGAAAAT

CTGCATTTGAGGCTTTGTTCTGACAGTGTCTAGTGTAAACATGGGCAGACCACTTAAACCTCTCTTTA

GTCTTCTCTGTAGAATGATGATAATACCATCTAATTAGCAGGATTGTTGTTTTATTCAGTGAGACAGC

ATATGTAAATAACTTAGTAAAATAAAAAGCAACGTGTTTATAATGGTAAAAAA

BRMX.2377C1n3_at
                                                              (SEQ ID NO: 50)
TGGGAATCATGAACTCCTTCGTCAACGACATCTTCGAACGCATCGCGGGTGAGGCTTCCCGCCTGG

CGCATTACAACAAGCGCTCGACCATCACCTCCAGGGAGATCCAGACGGCCGTGCGCCTGCTGCTG

CCCGGGGAGTTGGCCAAGCACGCCGTGTCCGAGGGCACCAAGGCCGTCACCAAGTACACCAGCG

CTAAGTAAACTTGCCAAGGAGGGACTTTCTCTGGAATTTCCTGATATGACCAAGAAAGCTTCTTATCA

AAAGAAGCACAATTGCCTTCGGTTACCTCATTATCTACTGCAGAAAAGAAGACGAGAATGCAACCAT

ACCTAGATGGACTTTTCCACAAGCTAAAGCTGGCCTCTTGATCTCATTCAGATTCCAAAGAGAATCAT

TTACAAGTTAATTTCTGTCTCCTTGGTCCATTCCTTCTCTAATAATCATTTACTGTTCCTCAAAGAA

TTGTCTACATTACCCATCTCCTCTTTTGCCTCTGAGAAAGAGTATATAAGCTTCTGTACCCCACTGGG

GGGTTGGGGTAATATTCTGTGGTCCTCAGCCCTGTACCTTAATAAATTTGTATGCCTTTTCTCTT

BRAD.33405_at
                                                              (SEQ ID NO: 51)
GAAAGTGATAATACAGAAAGGTGGGGCTGGTGTAGGGNTNAAGNCAGGATGCTTTGGNANAGCATG

NAAGGTCNCCGANTCCAGTGNTNAGGAACTAATGANGGGTTTNTNAAGANCGTNATGAGATCAATG

CNGATGAGNCACTTAGAAGNAGCAATTAGTTAGGCAAAGGGAAGTGAATGTGNAGGAGGAACAAGC

ATTCCAGGCAAGAAGAACACCCTATCGAAAAGCCTGGAAGCAAAACATTAGTGAGGCTACCTTTCAT

AAAATTGCTTTCTGTAAGTCATGCCATTGTGTAGTCTTAATTGCTTTCTCTCACCAGGGAAGGTGTGGG

AAGGACTTGTGAAATACATATTCGAGGAAAAACTATGCACAAGGCCGTGCATTTAAAAATAAACTCC

CTAAGGCTGGGGTGAAACCTGCTACGGTCTGCGCAAGTTGACTGTTAATGAATTTGATTCTCAGGTG

TGAGTGATTAAAAGAACACTGATCATGTCATTTTCTTTTTGGTCACTAATTCCCTCCCTCCCTTCTCTT

TCTTTTCTTTTTCTTTTCTTTTCTTTTCTTTCTTTCTTCCCGACAGAGAAAGACTCCATCTC

Hs584242.2C1n64_at
                                                              (SEQ ID NO: 52)
TAAGATGTTTAAGTATATCCAACCGTCCCAGACCACATTGGCCTATTTCCTCCTCTTGGCAACACTGC

TCGGGTTTTCCCCTCGCATCATCCTTATGCTATGACACTGGACTAAATTGTAATAATACATTTTCTTGT

TAATCTCCTCATTATACTATGAGCTCCTTGAGGACAGGTACTTTGTCTTGCTCACATCTGTAGATTCA

ATGCCTGGCACAGCGATTGATATTGCAAGGGCACTTAATAAATGGTTTTTGAATAAAAGAATTGCTTA

AAGTAAAATATAGCTGTAAATTGTATTATAAAAGGACAGTGGGTGGCAGTCTGAGGTCTGCTATTTAC

TGGTTTGGGCAAGTTACTTAATCTGTTTGCTTCCTCAGCTGTACGATGGGTAAAATAATAGTGGTTAT
```

-continued

CACAACAGGGTGGTTACAGCGATGAAATGAGATTATGTGTGTAGGCTACCACATAATTGTAAAGCTG

ATATTTAAATGGAACAGATACTGCACAGACACTTGAGGTCTGAGAATAAGATTAGGTCAACCAGAGT

ATTAATGGGTTAAATAAAGGTGACATCCTATGCAACCAACGGTTTGATCTTTATGCT

BRRS1RC_NM_004065_at (SEQ ID NO: 53)

GTCTTCCAGTCAGTCAGTGTCTTCCAGAAAAATCTACGTCTTCCACCAAATCCAGGTCTTCCAGTCA

ATCCACATCTTCCGGAAAAAATCCAGGTCTTCCAGCCAATATATGTCTTCCTGAAGATCCACGTCTTC

CAGAAAATCCATGTCTTCCAGAAAATCCATGTCTTCCAGTAACCTCCCAGTCTTCCAGAAAATCCAC

GTCTTCCCAACAATCCAAGTCTTCCGGATAATTTGGGTCTTCCTGAAAATCTACGTCTTCCAAAAAG

CCATGTCTTCCAGAAAATCCACATCTTCCAATGGCCTCCAGGTCTTCCAGACTATCCATGTCTTCCA

GAAAATCCTTGTCTTCCCTTAAATCTATAGCTTCCAAAAAATCCGGGTCTTCCAGGAAATCCGTGTCT

TCCAGCAAGTCCACGTCTTCCAACAAAGCCATGTCTTCCAGACTATCCATGTCTTCCAGAAAATCCTT

GTCTTCCCTCAAATCCATAGCTTCCGAAAAATCCAGGTCTTCCAGGAAATCCGTGTCTTCCAGCAAA

TCCACGTCTTCCAACAAAGCCATGTCTTCCATCAAATTAATGTCTTCCAGCCTACTTGTG

BRRS.8182_at (SEQ ID NO: 54)

AGCATCGTTTATGAAAACAACTAAATATTCACTAATGGTGCCAGTGGAATAAATCAGAGAACATCCCC

TGCTACGTAACTCTCTGCATACATCAAAGAGAATGGTGTGGCTTTGCTTTTTCAACAATCTACTGAGT

GGCCATGGGCATGTGGATATGGCCATGAATGAGCAAGATCCTCTCTGATCCTGTAGAAGTTAAGTTC

TACCAGATAACTTGCTGCTTCAACAAAAAGATTTACCTTTTTAAATAAATGTTGTAGAATACTTAAAAA

AAACAAACTAGAATTTGCCTGTGTGCAGCCAGTAACATGTCTATTTAACCTGGACACCTTTTGAGGAA

TATTCTCAGATTGCCCCCATGCTGTTTATAAGACATTGTTCCTTATACACCTGTTTATGAATGAAAAGA

AACATAAGGAGTGGGTACAAAGACTTCTATCTATGAATGATTAAAAAGGCTAGAGTACGAATACTTCT

TGAACCTTTGGTACTAAATGCTTTTCATGTTCTATATAAATGTAGAAAACATTTTACAAATCCTGTAAA

TAAACTGTTTATTTTTTATAGAAAGCCAAAAAAAAAAAAAAAAAAAAAAAAAA

BRMX.13815C1n5_at (SEQ ID NO: 55)

TCTTTCAACATTTAGATAGTCTTTCTTAATATTTCCAGGAGAGTACCTCATTTTTATTTTGAAAACCATT

CAGCACATTTATCTTATGTAACATGCAGAGCATATATCTATCTGTATTTTTAAAATTTTCCTGTTACTC

ATTGATACATAGTACTTAATTACATGTTATTCCATGTACACTGAAAACAATATAGGAAATATATACATC

TAAGACTTCTACTTTGTACAGTCTTTCATTAAATAAGAATACTTACACATACATTTTCAGATATTTCTAC

CTTCCTGTATGTGTTTGGAATTGTATGTAGGTAGCCACTGAAAGAATTTGGGCCCCTTGGGAGGATG

GCAGTGGAAGTCCATGAAGTAAAGAGCATTCTTTAAAAAGCAGATTTGATTGCATACCTTTTAGTTAT

TTGAGATTCTGAGAATTCTGATAAACCCCAAAGCAGAAAGATTCCTTAGTACCCTTGGAAGATGGGA

AAGGTGAGGGAAATATTTGAAGCAGGGTCAGAACATCCACTAAGAACATAGCACCTCAGTAGAGCTT

ACATTATAGTGCCAGGGTAGAGTTATTACTGAACCAACTTTTTTGTACAAAGT

BRMX.2637C1n26_at (SEQ ID NO: 56)

TCCATCAGGGCACGGTAGAAGTTGGAGTCTGTAGGACTTGGCAAATGCATTCTTTCATCCCCCTGAA

TGACAAGGTAGCGCTGGGGGTCTCGGGCCATTTTGGAGAATTCGATGATCAACTCACGGAACTTTG

GGCGACTATCTGCGTCTATCATCCAGCACTTGACCATGATCATGTAGACATCGATGGTACATATGGG

TGGCTGAGGGAGGCGTTCTCCTTTCTCCAGGATGGAGGAGATCTCGCTGGCAGGGATTCCGTCATA

TGGCTTGGATCCAAAGGTCATCAACTCCCAAACGGTCACCCCGTAGCTCCAGACATCACTCTGGTG

GGTATAGATTCTGTGTAAAATTGATTCCAATGCCATCCACTTGATAGGCACTTTGCCTCCTTCTGCAT

GGTATTCTTTCTCTTCCGCACCCAGCAGTTTGGCCAGCCCAAAATCTGTGATCTTGACATGCTGCGG

TGTTTTCACCAGTACGTTCCTGGCTGCCAGGTCGCGGTGCACCAAGCGACGGTCCTCCAAGTAGTT

CATGCCCTTTGCGATCTGCACACACCAGTTGAGCAGGTACTGGGAGCCAATATTGTCTTTGTGCCAA

BRAD.36737_at (SEQ ID NO: 57)

CTGTCCAGAATGTAGAGGACAGACCCATGGGAACTTCAAAATTCCCCTCTCAATNCCCATTTTATGT

TAGAAAATCAAGTACCGAGAATGTTAANGTTAAATTATGTGACCAAAACAAGGAAAGAGGCTGGTAA

AACTGCATTTTGCACAAAAGTGTTGATTCAACATGAAGTCAAATAATATGTTCTAATGAAACCACACC

TCTCACACACATATCCTTTCTCTCAAACCTCGGTGTTACTCTGGCCAAAAGTCTTAGGTTTCTTGAAG

TGTTTGTGGAAGAGTAGATGGAGTTTTATTTAACATTATCAAGAAATCCAAGCTGCAGACCCCACACA

TA

BRAD.3853_at (SEQ ID NO: 58)

AGACTTTTTAGTAGCTTCCAACTACAAAAAAGAGAAATAATCAATTATGTACTAATCAGACACTTTTA

AAAATTACAACAGTTTATTCAGAGAAACAAGCTTTGTGTGACATTCTAAGCGGATTTTATTCTGCAGG

TCCTTTTAACATAATGAGTAATATTTGTGTTGGGAATGACTGAGAAGAAATTTCATAATGATGTGAAG

ATCTACCTGTAAATAGTTCCTCTGTCGTATGCTGGTATTTATATTCTAGCATCTCAACAGTGCTGATG

GTCACTCATCTTGGAGTTCCCTGAATTTTTTTTTTTTTCAAAACTCCTGTAATGTTACATTACCCATA

CTTTTGTTGTTGCTGCTGTTGTTGTTGTTTTGAGACGGAGTGTCGCTCTGTCGCCCAGGCTGGAGTG

CANGTNGNNCCGCGCCCGGCACATGACTGCATACTTTCAAGGAGAGGACTCAGAGCTTTTATTTATT

TAAAGAAACTTGAAAGGAGGAAAGTGGATTAAGAAAAAAAAAA

BRAD1_19760734_at (SEQ ID NO: 59)

TTTTTTTTTTTTTTACATAAAGGCATGAATATACAAGGTAATGTCAGCAGCTGTACTCCACTCTTTATT

CGTTGCAAATCTACCTATTTGTTTCCAAAGGATGTCTGCAAATAAATAGGTAACATTGTACAGCTTTC

AACAGTGGATCAGAACATAGATGTCTCTTCTAATTCACAAGTACCAATGGCTCAATTAATTTAAGGGA

CATTTTCTGAGTTGTGTGATTTCACATGTATTTATCGTGTCTAGAAGTGTGCAAACTTTTGTTTCATTT

CTCTCTTAGATTTCTGTAGGAAGAGTTAAAGGATGTGAAGTAGTCATTTTACTTATTCATAACACATTT

TAGGGAAAATTGTGCTGTTGCTGTTGGGGAGAAAGTTAAAGCTATCAACTATAACCTGGACTCCAGT

CCAATTTTTCACATCTGGTTGCTACTTTTAAAAAGGATCATTTTAATTTTTAAATGCAGAATGTGTTGC

ACTTTACCTTTGACATTCCAGGTTTCCTCATGGTCATTTAGAAAAATAAAGCAGGAAATTCTAATGCC

TTAGCATCTACTTTAATAAGATGTTTGCATTTATAAAAATAACAAGAAACTGA

BRMX.2797C4n2_at (SEQ ID NO: 60)

TTTAATTTTTTGGAAGGATATACACCACATATCCCATGGGCAATAAAGCGCATTCAATGTGTTTATAA

GCCAAACAGTCACTTTGTTTAAGCAAACACAAGTACAAAGTAAAATAGAACCACAAAATAATGAACTG

CATGTTCATAACATACAAAAATCGCCGCCTACTCAGTAGGTAACTACAACATTCCAACTCCTGAATAT

ATTTATAAATTTACATTTTCAGTTAAAAAAATAGACTTTTGAGAGTTCAGATTTTGTTTTAGATTTTGTT

TTCTTACATTCTGGAGAACCCGAAGCTNCAGCTCAGCCCCTCTTCCCTTATTTTGCTCCCCAAAGCC

TTCCCCCCAAATCATCACTCNCCTGCCCCCCTTAAGGGCTAGAGGGTGAGGCATGTCCCTCACAAT

TGGCACATGGTNCAAGGCCATCAGGCAAGGGNGCATTCACACAAAAGGGCACCAGG

BRMX.10399C1n5_at (SEQ ID NO: 61)

GAAACAACTGGTAAACACAGTAAGCCCATTTCTGGGCTTTTAGAAAAACATTGCTCTCTTTTCTTTCC

CCACCCAGTGTATTCCCAAGGACTTAATGCTGCACTCTGACCTAGCCCTCAATGATGGTTAAAACTG

ATTCTGAACCAAAGGTAAACAGGGTTCCTCCCCATGCCTTGGAGAGCTCCAGTCTGCAGAAAGCTA

-continued

ATGAAGCCCTTGAAGCAGTATCTTGTCTTCCATCCACACTTTATTGAAATGCTTTTGAATCTTATTGTG

TTGTAATTACATACTATAGAAAACTCCGCCAACCTCTATTTCAAGGTTTGGGCCCATGACTCTCGCTA

AAACATTTCAGTTCCATTTTCCAGAACATACCATTTCTAAATGCATCTGTGAGGGCCCTCCACAAGTA

TTTTCAGTCCACATTTCAGAAAACTTGAAAGTGACGCAGGTTCCTGACTTAGTTGATGGTGGGTAAA

GGGAATGCCATTATGAGTGGTGGAGGTTGTTTTCTTTTTTCTTGCCATATTCTCAGCATAATATTTGA

AACCTACAAAAGAAGTTTGATAATATAACTGTATATTTTATGCCTGCACTAGTGGAGGA

BRMX.8912C1n3_at
(SEQ ID NO: 62)
GAGGTAGGAACTGATATTCCCATTGTACAGATGAGAAGACAGATGCTCAGAGAGCTTATTTGTCTGT

TGAAGCCAAAACCTGTGCCCTTGACCACAATGGACACTATATCTTCTGAGCTCCACTTAATTAGAGA

ATTTGGATCAAGTGACTAAATAAATCACACACCACACACATTAAGATACGCCAGAGTGACAGGGACA

TTAAATAAATCAAGTATCCATGAAGTTTGCTGCCTTCCAAATCAGCCCCCTATTCTTTTGCCCTAAGA

TATCCCATCATAGTCTGTTTCCTTCCCTTCTCTCTTTGCCCTCAACCTTTCCTTCCCTCTTATCCATGG

GAATGACTCTAGGAATCCTGTTGAGTGTATGTGTGTGCGTGTTCTTTTCTTTTTCTCTCATGAATATTA

CACTTTTATTAGCCAGCTATACTTGTGTTGATGAAAAAGACAAAATGGAATTTTGTTTTCCTTTAACAA

TCAAGTATGAATGGTCTGCTTACAGGATGTCCCTTCTTGGGGTCCTTGGAGGTAACAAAAGCTCATC

ATTAAACAGGTAGCTATCATTTCTACATGCTTAGTATCACTTCCGATTATCTTATTC

BRMX.13731C1n18_at
(SEQ ID NO: 63)
GGGCTGAGGGTCCTGAGGAGAGAGAGAGAGGCCACGTGGATGGAGGACTGTCACCCCCTTCTCG

GTTCTGTCACCCCCTTGAGTCTAACTCACTGTTGAGGGGAGGAAGAAGGGGGATGGACGGAAGGG

AGACCGAGGAAAGGCTTTCGGGAGTGGGGACATTATCCCCCCAGAGGTGTGCTGCCCCACCCAGC

TGCACCCCACAATCTGGCCAACTCATTTCACAGTATAAATCACTCCAGCAGGACGGCATCACAGCAG

CCCCTGCTGCCTGAAATCAGAGCGGCCCAACGAGGAAGGCCAGGAGGGTCGGCTGGCAGGGGGC

AGGGTCTTGGGATAACACTGTCATCAGAAACAAGGCTGGGGCTGATTTCGGGGTGGGGAGCCTT

AGGAGGCCAGAAATTCCAATCAGAGCCAGTTTTTCTGGGAGGGAGTGGCTAGACAGTCAAGGAAGG

ACGTTCACATTTCAAAAGAAGTCGGGTGGGGGATGAGATTATTCTAGGGGGGCATCGAATTCCCT

TTAAGGGGGGGGCTCACTTCTGCCCAGAGTAAAGAGGATCTCACACCATGGAAATGTGCCAACTTT

TTTGTACAAAGT

BRAD.25947_at
(SEQ ID N: 64)
CTTCCATTCCTCATGATTTTAGGGTTATCCTCATTCAGATCTACTCTAGTTATAATAGTACTTTAAACA

GAGCACAGAATTAAACCATTAGTATGTGAATCTGCAAAAAGAGAACTTGTTTTAGACTCTTCTACAGT

TTAGACTTCAATGTGCATACTAAATGCATAACATTCGTATCAAATAATTAACATTTATATACAATTAACA

AATAAGGACAAATTTTATACAAAACTTCTACTACTGCTATAATTTTTGAAAACATTTAACCCACTAGCA

AGAGGTAAGACAGCACTGCCTTTTTAAAAGACAGGTCACTTGAATAGAGAATATAAGATATAACCATA

AGTAGGAGTATAAACAATAATTTTTCTTCTTGTGGAATGTTTTTAAATTTCCTTTCTTATATTATTATTC

TTCCTTAGGTTTTTTTAGACAGGTCATTTCTTCCTGAATGATTTTCCTTTTTCTTTTAT-
TTTTATTTTTTG

AAGGAGGATTATTTACTGGTGGTCTAAAAGAAGTACCTTCAACTTCTTCATAATTGTAGCCAAAGCGG

AAATGGAATATTTAATAATTCTTACATCTCACTAATGTAGTCTTCTG

BRMX.5143C1n2(2)_at
(SEQ ID NO: 65)
AATAATTATAAAGTTTATTTAAATGTTGATTGTCCCAAGGTCTACAGTTTCTTTTCTGTTGTGTCATCA

GTGACAAAGAGTAAAAAAAAGGAAACTCCCATATTTAGCACTTTAGAGTAAAACACATGGATCATCGT

-continued

TATTAACAGTCCTCTGGGCGTGCTGGAGCTCACTGAGAAGGCTTCTATTTTGAGCTTGGAATGTTGT

GCTGAGCTGTGCAGCCTGTTCCTGCATCTGTTGTTCCTGCATTTTCTGTTGCTCTGCCAGCCAATTT

TGTTTGGCTATCTCCATTTAACTCACTTGTTCCTGATGGAGTCTCTCCCTCTCCTGCATCATTTGCTC

GTTCTGCCTTTGAATCGCCGCCAACCTTTGCGCTTCAGCCTTTTCAGCTTCTGCTTTCACTTGTGCCT

CTGAGGAGAAAAAGATAATC

Hs633116.0C1n30_at
(SEQ ID NO: 66)
GTGTCAACATTTATGCTCCTAAAGGATGTTGGGTCAAATGAAATGTTCCTCATTGTTTCTCTCTCTTG

ATCTCTCCTTCACTCCTTCTCTTCCTTGCAGGATCTCCAACTCCTTCATAAGGGCACTCTGTGTTACC

CCTTTAAACAAAATAAAGAAGTCCTACATTCTGCCCAGATTTTTTTCAGGCTCCACCAAAGGGTTGGG

TGAATTATGGCCCAAAAGTTGGTGAGGATGATGGTGAACCTTCAATCACCTTCAGTCTCCCAACCAA

CAATGGTCATGGCTTGTTTTCTCCCTGGATTACATGGAGAAAATCATGCCCTACTTTTTGGACCTGTT

GCTTCTACATTTGTATGGTAACTGTGAAACCATCCTAATGAACAGCAAACATTAACCACTACATAAAA

TGTAGACTTTGAATAAAAACACAGCTAAGTACTAACCAGCTTGCCCTTTAAGCCAATTCCCTGTAGCT

ACTTACAGCACGACTGTTAGCTCCTTTCCTTATAGTTTCTTACTGCCTTAAAGTCACATAGATGTGGT

CACAAGGCACTAACTTCCCTTAGTTATTTCTATAAGATAATATATGTAACGTTGGCA

BRSA.1606C1n4(2)_at
(SEQ ID NO: 67)
AGTGCAGAGAGGATGAGAATATCCTTCATGGGGTCCAGTTCCAAATCTGAAGCATAATTTCCAACCA

TCAAAATATTGGAAATAGGAATGCCTAGCATTTTATGGACATTCATGACCCGGCTTTGAGAAGTCATA

GATCTACTCATGTTTAAAAAGTTGTCTTGAAGAACCTCACTGCAATCATCCACTTTAGTAAGCAAGGC

CACATATGCTATACCACAGTTTAATACTTCTTTGTGAACTTGCTTCACTTTTGCCAACATTTTAGAGTA

GAGATTGTCAATAGAGTTGATGTCTAAGACATAAGCCACACAGTGAATCCTGTCCTTCAGAGATGGA

GAGGTGATAAAAGTAGAATGCTCAGGTGTAATTGGTTTACGGGAATTAAACTGTTATAAAAACATAAG

GTAACATTCAGAAATCAGAGAGCCTCTGTTTAACCCTTAAAGACACAATTAATGCTTCTAATACTGTA

ACTACTGATCTCCCTCTTTCTCCTCAGCTACTCTTTCCCCAAACAGTAGCACCTCCTCTTTACTTCCT

TTCTCACTGGGGGGCATAATGCCACCAACTTTTTTGTACAAAGTTCCCTTTTTAATG

BRAD.41047_at
(SEQ ID NO: 68)
TTATCTTATACTAAATTCCAACATGTATCTGAGTTTGCTTCTAGATTTTCTGTTCTGTCCCAGTGGTTG

GATATTTCTTCATACACGTCTATCATACTGTTTTGACTATAGAGGCTTTTCAGTGTCATTTAATATCTG

TGATGGCAATCCCTACTCAAAGCTCTTTGTTTTCAGTGTTCCTGTATTGCTCTTTTGTTAATCCCTTAA

TATAAAAGTAAATAATAACCCAGTTGGCATATTATTTTGATGACATTAAATTGGGGAGAATAGATACT

GTGATTTTTGAAGCTTCCTACAAATATGATATGCTTTTCATTTGTGCAAGTACTTTAGTATAATGTTAA

CTGGTGGTGGTAATGGAGGAAATTCTGTCATGTTCCTTACTTTTAGTTTCCTCTAGCGCTTTCTATTT

TTTTATTTTTTTTCAGATGGAGTCTTGCTCTGTCTTCTATCCAGGCTGAGGCAGGAGGATCACTTGAA

CCCAGTAGTTCAAGGCTGCAGTGAGCTATGGTTACACCACTGCACTCCAGCCTGGGTGACAGAGCA

AGATGCCATCTCTTAAAAAAAAAAAAAAAAA

BRAD.4420_at
(SEQ ID NO: 69)
GTTAATATCTTTTTCGTTTATTGTCTGTCTCTGAAGGTAGGGACTTTGCCTCATTTACTGCTTTTCAGT

TCTTGGAACAATGCTCGGCACATAGGCAATCAACGAATGTTTGTTGAATAAATGATTTTTTTCTCTGG

AAATTGTCAAAATCTGCATGAGGTGTATCAGGCCAGCCATTGTCAGCCTCAGTTTAGAGGCAAGGAA

ATAGGTTCAGAAAGGTTCAAGGACGTGCTGAAGTCACAGGGCGAGGCAGCAGCAGAGAGCCTGCT

TGTTGAGAGCCAAGTCTTATGGGACTTGCCTCCTTCTCTCCCACTGAGGCTGGGGACACCAGGTGG

```
CCCAGAGGCATGTGGATACCTCCAGTGGGAGGTTAGGAGAGTGCTACACAGAAACTCTGAGTTCTA

ACACTCTTGGGACCATAAAAAATGGAACAAGTCTGGGCATGGTAACTCACGCCTGTAATCACAGTAT

TTTGAGAGGCTGAGGTGGGAGGATCACTTGTGGCCAGGAGTTCGAGGCTGCAGTGAGCTATGATC

CTGCCACTGTACTCCAGCCTGGGCAACACAGAGAGACCTCACTTCTTTAAAAAAAAAAAAAAAAAAA

Hs137007.0C1n9_at
                                                      (SEQ ID NO: 70)
AGGAGAAAGGGAAGTCAAATGTCTCGTCCAAGTCTACACAGCTAAAAAGGGGCAGAACTAGGGTGA

CGCTCAGGCCTCATTTAGAGATCGGGGGTTGGCGAGAAGTGGGGTGGGCTTCTGGAGGGGCTGG

GAGAGCCCCACAAGGCTGCAGAGGGTGGTGAGCCCGGAGTGGGCCTGGCCTGGTGTGGGCTGGG

GGTATGGGCAGGAGCTGCAGACAGCAGGGCTGCACCAGCGGACCAGTTTCAGAGGCAAGGGTTCT

AGGCCCTTGAGAATCCACAGTGCCAAACAGACCCAGATAGCTACGGGGTTGGTACCTGGGGAGGC

CTTAGGACAGGCAGAAAGTCCCAGAGGCGAGGGCGTTGCCTGGGGACGTTTTTGCTCCCTGTCCT

GCTGACAGAGCATAGGAAGTGTGAATGTTTTCTACCCCTCCTCTCTCGGCTCAGCAGAGCTCCAG

CGAGCCAAGTCCTTGTCTGTGGAGACGCATCAGTCCCTGGCTCTAGGGAATAGGGAGTCCCACAGA

CAGGGGGTGTCAGCAAGCTGAGAGGGTCTGTAAGTAGGTACGGAATTGAGTCAGGAAACAGTCT

GGGTGTGGAGTGAG

BRSA.18050C1n3_at
                                                      (SEQ ID NO: 71)
TGCAAAAAGCCAAAAAAAGCAGCTTTTAACATTATATCATTATATCACAATTTTGAAACATGGGNNNN

NNNNNNNNNNNNNNNCCATTGTGTGGATAAAATGGTCTCCGTGACATTGAGCAGAGTGTTATCNNN

NNNNNNNNNACATTATTGCACAGAGATTTCTCATCAATGTTCTTCAGTTTTTATGTCTTTTCCTAAAT

GTGAATAAGTGCTATGGATAAAATACAAATGTAGAAAATAACAGCAGCATGATTTGTCAAAGTTAATC

CCTATAATTTAGTAAGAAAAAATGGATATAAACAAAATAAGTGCTCTTTCTAAACTGTACTAAATTTTC

AAAAATATTGTTTTAATGCAGTGAAGGTCCTGAAAAGCCTATTGAAAGCGATGCTGAGTCCTGTTTTC

AAAAGTGTCCTGTTTGGGTTTTCTTGGTGAAGAGCAGAATTTCAAGTGAAGTAATCGACGGACTAAT

TTAAAACAAAACAGCCCTCGGCTTCCCTATTGGCCTGTGAGGGCACCGGCTCCGGGACCCTGACCT

GGGAGGCAGCGAGTGGTGGGGGTGCCTGGCCCCCATCTACACGTACACAGGCTGGCCAA

BRMX.2948C3n7(2)_at
                                                      (SEQ ID NO: 72)
GCACGTCTACGGGGCTGGACAGAGTGTGGTTAACCGGGGAACTGGGCAAGCCGGCGCCGAGCCT

GCGTCAGCCGTGCAAGCCGCTCCTTCAGGAACTTCCGCTTGTCGCTGGTGTCGCTCCGCTCCTTCA

GGAGCCAGCTGTAGGTGTCCTTGTCCTGCAGGAGCTGCAGCATGGCCTTCTGAAGCTGCTGGCCG

TACGTCTGGAGCATGAAGAACTGGATGATCAAAGGGATGTGGCTGGAGATGCGCTTGCTGGCCTCC

TGGTGATAGGCCATCAGGTGCTGAAAGATCTCCTCCATGGAAGAGTCTGTTGCCGAGCTGGACTGG

AAAGCCCCAAAATCCCAGGATTTCTTCTTCTTTTCTTCTTCCAGCTCCTTCTCTCTGACCTTCTGCAA

TGCACCCCTGTATACCTGGTCCTGGCAGTAGACAATCTGTTCCATCTGGAAGTGGAGGCGGATCAG

CTTCTCACCTTCTCTCTCTTGTTCTGCTCTAATGTCTTCAATTTTGGACTTGGCGGTTCTGTGGAGGT

TAAAAAACTCTTCAAAATTTTTTATCGCCAACTTTTTTGTACAAAGTTGGCCTTATAAAGAAAGCATTG

CT

Hs43047.0C4n40_at
                                                      (SEQ ID NO: 73)
NNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNNN
```

```
NNNNNNNNNNNNNNNNNNNNNNNNNNNNNNNNNNNNNNNNNNNNNNNNNNNNNNNNNNNNN

NNNNNCTAAAAAAATATGTACTGCTTATTTTGTTAGCATACTTTTAATTATATTCTTATTCTTTCTACCC

CTCTCAAAATGTATTTTTCCAGCTTGCCATTTAATTGGTAAACAGCTGTAAAGTTCAAACGTGAAATTC

TTAAAGCTCCCTAGAGACATACACAATAACTTCTGTGGCATGGACTTTTCTCGGCATTAAAAAAATCT

AGTACCTCTCTTGGCCAGAACCCCTAATTTTACACTTTATGGTGTTGCGTCGTTTTTCNNNNNNNNN

NNNNNNNNNNNNNNNNNNNNNTTACTGGCAAGTTTTTCCTCCAAACAGTTTTCTAATCAAGTCTAATAA

GTT

Hs926.1C10n7_at
                                                               (SEQ ID NO: 74)
NNNNNNNNNNNNNNNNNNNNNNNNNNNNNNNNNNNNNNNNNNNNNNGATGAGCCAGGCATGGTGGT

ATGTGCCTTTAGTCCCAGCTATCTGGGAATNNNNNNNNNNNNNNNNNNNNNNNNNNNNNNTGACGGCAA

GAGCCTGTCTCTGNNNNNNNNNNNNNNNNNNNNNNNNNNNNNTCTGATCAGTTAAATGAATATGGA

AACTTAATCTTGTACCCCTTACCTCCCAAGCATACAGCCACAGTTTACCGTTGGAGGGATCTTTCCA

CGGAGGTAAACAGTGCTGTTTTCTCCAAGTGCCAGAACAAAAACACAACAGCACACACACAATGAGA

TGGTTTGGCTCTGTGTCCCCAACCAAATCTCATCTCAAATTGTGTTTGGCTCTGTGTCCCCAACCAA

ATCTCATCTCAAATTGTGTTTGGCTCTGTGTCCCCATCCAAATCTCATCTCAAATTGTAATCCCCATG

TGTCAAGAGAGCAACCTGGTGGGAGGTGACTAGGTCATGGGGGTGGTTTTTCTCATGCTGCTCTCA

TGATGGTAAGTGAGTTCTCACAGGATCTGATAGTTTAAAAGTGTTTAGGGGCTGGGAGCAGTGGCT

CAT

Hs528836.0CB6n98_s_at
                                                               (SEQ ID NO: 75)
GGGTGAGGACCCACAGCTCTGATGTGGGCGCTTCAGGCCATGGTGGAGCTGAGATTCAGGTTGGC

TTTTCCCCTCAGCTCCCAGCTGGCTGGTGAACCCATCATCATAGCCAAAAGTACTCAGCAGCAGCA

CCTCCAGGTCCAGAGGCACCTCCAGCTGCATGCACACACAATGAATGAAAGACTGCCAGGTGTCCG

AACCCTGGACATGCAGCTTGTTGAGTTGCAGGATGACTCTCTGTTCAGGGTCCAAGGTCTCGTTCCT

GGAATCCAGGTCCGTGTTGGGGAGGAAGAACTTCATCTTGGCGTTCAGCCATTCTGGGTCTTTGGT

GAGCAGCCTCACAAGACAGCTCCACAGGTTCTTGTTGCCGAGCTGGAGGCCAACGGGGTCCATGA

GGAGCCAGCCTTGGTCTCCTCGTTCATGATAGGTGCTCTAGGGTCCCCACGGAGAGGGTCTCATG

GGTGTCTGGGCTATGTGTGCCTTGAGCTGGATTGACAGGTTGTTTCCATAGTGCAGACTCCCTCAG

CGCTCGCGGCTCCTCCGCGCTCTGCACGAAACTGAAAGTAGAAGCCGCCGCCTAGAGCTGCTCCG

CCAGTGCAT

BRMX.7284C1n6_at
                                                               (SEQ ID NO: 76)
TGGCAAGGACATTGTTTTTGTCTAGTGTCTCAAGCTTCTCTACCAAGAGAGTCATATTTCTTATCTCC

ACCTCCAGCTGGTCAACAATTTCTGAGCTTCCACCAAAACTCTCCTTCAGCTGTATGACCAGTTTTTC

CATCTCCTTCACTTCTACCTTGATCAGCTCGAAGTCCAGTTCAGTGTAAGAAATGGTATCCTTCTCCA

TGATGTCAATTCGGACAGTTAGGTTTAACAGTTTCTTTTCATACACACTAATTAATTGGACATATTCCC

TCACTTTAGAAAGTTCTTTCTCAAACTTCTGAGAAAGAACATGAGCTGTGAATTCCAAGCGTTCCACT

CTGTCCACGGGAAAGGTGGTGTCTGGCAGGGAAACAGAGCACTGGCAGGTCCCACGGTCATCCAC

GGAGCCGGTGAAATTGGAAAACAACTGGGACACAGAACCTCCGCTGCCTAAGCTGCGGCTGGAGC

TGGAGCCCGACCTGGAGCTGGAGCTGAAGCTGGAGCTGGAGTCAACACCTGGGAAAGAGCTGAAG

CCGGGGCTGGGAATTGGAGGTCCCACATCCCCCAAATCCCCTGCAGCTTGGCCAAGGAAGCCAA
```

BRAD1_19751014_at
(SEQ ID NO: 77)
TCTTTTATTGAAAGAAAAAACAATACAATGGACTTTAAAAAGCTACATTTGTTATGGTTCATAAGGACA

GAGGTTTACACAGGTTTTATATATGTACACACTGACAATACTATATCACAACATCAGAGGCACCATTT

TTGCCACAGAATTAGGTAATGAATAAAACTTCTCCAAATTAATCTGTTTAAAAAATATCTAAATGGTA

CAGTATATTTGAGGATTATATAAATATGTGAGACATATTTAGATATTTTTAAAAATAGTGTTTATATAT

ATGCATCACAATCTTCTCTAATTCTCAAAATATTATGGCACCAAAATTCTGTTTGTCAAATAAAACACA

AGATGCTGTAATATGTATCCAAGCACCAGCTTAGCACAGTATTTAATTCTCCCCCAAACTGAAAGACT

GCTAACAGGTACAAACTGAACTGAATATTTCACACAACCATTGAAATAATTTAGGCCCTCAAATTTTTT

TTTTATTAGCTGATTGTTTTTAGAGAAAAAAGAGGGAGCTAAACCATTTACATTAATGTTGCTCTGTGT

GATAGAATCAATCCTAGGGCTCAGAGAAGATATTCCTAGGCACTGGAGA

BRMX.13502C1n6_at
(SEQ ID NO: 78)
TCAAACTTGAATCNTTTAAATTTATTTTCTGCTTAAGCAGGTTTGAGTTGGGTTTTCTATTTGCAATAG

CAAAAGTCCTGACTGGCAAGGTTTAAAAGTTTGAAGACTCTCACAGGTAAGTGCAGCTCAGGATCCT

GTGAGTGCAGCAGAAAGTCTTAAGAAATGGCAGGGGCTGGTTGAACCCAGATTTTCCATTGGCTGA

GCAGATATCCCCAGAGGCGTAGAAAATTAAATTTGTTTTATGTTGTTCCAAAAGAGGAGAACTGAGG

CCAGAGGAGCACACTTCTGAGACACTCATTTTTGCTGGGTAGAGGAACTCTCTGGGCAAGCAGGAC

CATCGATATTAGAGCAGCTGGCCTCAGGAGGGGAGTAAGAGCCCCATCCCTGAAGGTACACAAGTT

GTGGCAGCAACCATCTGGCCTGCAGTTTCCAGAGGGGAGTCAGGCGTGGGGTGGGACTGGAGTGA

ACGGGTACC

BRMX.1111C4n3_at
(SEQ ID NO: 79)
TTTTTTCTTCTTTTCCTCTTGGGTTTTCCCAAAGTAGAGTTGTTTGCAATATCCACAGTATCCATTTTG

CCACATGCTTGGTCACTTTCCTTCCTTGCTTCCGGGCTTTCTGGCACTTCTCCTTGTTTAAGACTTAG

TTTGATGTCAGGCCTCTCTTCCCTTTCTTTTCGATCACTTTCTTGGAAAGACAATTTGTCTTGGATTG

CATTTTTGAAGCTTTTATAAATGTGAATTAAATCGGGGTATTCCTGCATGTTGACCTCGCTGAACAGT

GCTTCCAAAACTGACAGGTTAAATGTCTTCTCCAGTTCACTGAGAACATTGTACACCACTCTTTGTAC

AGGGACCAGGTTTCTACAAGAATCTTCAGAATCTTCAAACATTTTATTTGTGATGAGTTCCCGATCGC

GGAGGCCCTCAAGGAATGGAAATGTCTTTTTTATTGCATTTGATATCTCCAGCTTATGTCTTTTGAAG

TGCTTGAATACAGTGTCATAGACAAGTCCCTCATCTACATCCTGGTCTTCCGTGAACAGCCTGGCTC

GGAAGGTCCTACGCCCACGGACTCTCACTGATTGCTAGCACAGCAGTCTGAGCCAA

Hs369056.9C26n3_at
(SEQ ID NO: 80)
CCTTCCCCATTTCTCACTTTCCACAGGTGGGATGTGGCAGTCCTCATGGAAGACTCTTGAACAAGTG

TCGCAACAGAACAGCTCCCCTCCGTCCCGGCACACCTCACACTCATCCAAGTTTCTCATCTAGAAG

GTAAAACAGTGTCCACGTCACTGGGAATCACAAGATTCAGGAAGGCCACCCCTCTGGGCATCTAGA

ACACACTGCTTATGTGTGAGCCTGTATAGACAGGCATATGCTTCTCCCTGGGATATGAAGGAAAAAT

ATGGCATGGAGATTTCAGAACAAATCCTGGTCTGCAGTGAAGTTCAGGAGGAAGGGGTATATGTCA

GAATAAAAACGTTTTCCTTATAAAACCAGAGATTATGACACAGAAAGCCTAGCAACAAAGCAAGAGG

ATGATCTTATAGGAATCTGAATAATTGTATTATGCTGCAGATAAAACCAGGTTTTGAAGTAAAAGTGT

TAAATCCATTTGTCTATACTACAAATCAACTCATGAAAGGGAGACCCAGAGAATTACATATGATGGAA

TAACCTTCTAAGATATCATCACATCCCATATTCTTGGCCATAAGTTCCCCATGAGTTGAAGACAG

```
BRMX.24432C1n2_at
                                                  (SEQ ID NO: 81)
GTGGCTGTTGCTGGCCCCACCTCCGCTTATGTCCTTAACATGCCTCAGGTGGTTCATCCCTTTTGGC

ACTCATGGTGCCCCCTGTGGGCTGATACAGGAGTGAGTCTACTGTGAAGGCACTCAGTATAGTGGA

AAAAACAAATATCAACCTCCTGCTTTTTTTCAGTGTAAAAACTATAAGCTCTATGGGAGTTTCTGCAG

ATGGTACCATAATGGCCTGAGGGAGGAGTATCACAGTCACAGAGTATTGGTTCTCTCACTGCATAAG

CCATGGTTTTACCCACCTTCACAGGCTAAAGGTGCTTCATAACCTTGTTCATGTATTGAGGTTCTGTT

GGCTCTTGTAATGGTAATTTCACATGTGGGCAGTTGTTCATATTGATGTTTCTATAGGGGTATGATAG

CTGGAGAGGTCTGCGCCACTGTCTTGCTCTGCCTTGATCANNNNNNNNNNNNNAACAAGAATTTGTC

TCCTCCTAGTTTTTCTTTTTCTCTTAACCGACCTAGGTTTAGCCTTTTAATCCTTCTCCCTCCTCTGCT

TCTAATGTCATTGTTTCTTTGTATGCCTATCATATCTACATGCTACATGACCTTCAGCTGG

BRRS.17773_at
                                                  (SEQ ID NO: 82)
AGTTTTAAGGAAAAATTGTATGATTTAAAAGATTATAAAACTTTATTACTGGGCTATTTACACATTTTAA

TTGTTTCTCATAAAATATATAACATTACAATATTTATGGAAGTAGGATATTTTTGTATCATATGTACGAT

GATAATTTATAGGGTATTTTAAATGATGTTTTTTAGCCTCCTTAAGTTTTAAGTGGATCTTGCAAATGA

AAACAAGTATTATTGAGTTTGACATACTCAAATTGCCCAAATATCAGCTGTTTAAACAACCAAGTCAT

CATTGATACTTTAGTAAAGGTTAGTAAATGTCATCAAAGGCTTATTTGCAGTTTACAGTTTTTATTACT

TAGGAGACTTAAGGAGTACCTGCCAGGTTTGTCCATGCTAATGCTACGATTTTGTTTTTGTAGTTCAA

CCATATTTTGTATGGAGATACTTTGAGGCTCTGTAAATTTCTGGTTACTCCTCAGAACCCACTAGATT

TAGCATTTCATGGATGACTTGTGTTTGAACAATTATTACTATAATGGTTGCCAGATGATTATTTTCTTA

TTCTCTTCTTTGTTCTACATGGAGAAATAAAACCAATAAATAAGGGAGA

BRAD.10849_at
                                                  (SEQ ID NO: 83)
GTGCCAATGTGAAGTCTGGATTTTAATTGGCATGTTATTGGGTATCAAGAAAATTAATGCACAAACC

ACTTATTATCATTTGTTATGAAATCCCAATTATCTTTACAAAGTGTTTAAAGTTTGAACATAGAAAATAA

TCTCTCTGCTTAATTGTTATCTCAGAAGACTACATTAGTGAGATGTAAGAATTATTAAATATTCCATTT

CCGCTTTGGCTACAATTATGAAGAAGTTGAAGGTACTTCTTTTAGACCACCAGTAAATAATCCTCCTT

C

BRAD.10890_at
                                                  (SEQ ID NO: 84)
AATGCTTATGTCTAAAAGAGCTCGCTGGCAAGCTGCCTCTTGAGTTTGTTATAAAAGCGAACTGTTC

ACAAAATGATCCCATCAAGGCCCTCCCATAATTAACACTCAAAACTATTTTTAAAATATGCATTTGAAG

CATCTGTTGATTGTATGGATGTAAGTGTTCTTACATAGTTAGTTATAT

BRAD.11026_at
                                                  (SEQ ID NO: 85)
CTGGGCACCTCTGGGACAGCAAAAAAAACTGCAGAATGCATCCCTAAAACTCACGAGAGAGGCAGT

AAGGAACCCAGCACAAAAGAACCCTCAACCCATATACCACCACTGGATTCCAAGGGAGCCAACTCG

GTCTGAGAGAGGAGGAGGTATCTTGGGATCAAGACTGCAGTTTGGGAATGCATGGACACCGGATTT

GTTTCTTA

BRAD.12809_at
                                                  (SEQ ID NO: 86)
ACCATGTTCATCTTGTCCTCCAAGTTATGGGGATCTTGTACTGACAATCTGTGTTTTCCAGGAGTTA

CGTCAAACTACCTGTACTGGTTTAAATAAGTTTACCTTTTCCTCCAGGAAATATAATGATTTCTGGGA

ACATGGGCATGTATATATATATGGAGAGAGAATTTTGCACATATTTATACATATTTTGTGCTAATCTT

GTTTTCCTCTTAGTATTCCTTTGTATAAATTAGTGTTTGTCTAGCATGTTTGTTTAATCCTTT
```

-continued

BRAD.14326_s_at
(SEQ ID NO: 87)
GATGGCTGGTCTGCCCCCTAGGAGACTCCGTCGCTCCAATTACTTCCGACTTCCTCCCTGTGAAAAT

GTGGATTTGCAGAGACCCAATGGTCTGTGATCATTGAAAAAGAGGAAAGAAGAAAAAATGTATGGGT

GAGAGGAAGGAGGATCTCCTTCTTCTCCAACCATTGACAGCTAACCCTTAGACAGTATTTCTTAAAC

CAATCCTTTTGCAATGTCCAGCTTTTACCCCTA

BRAD.15436_s_at
(SEQ ID NO: 88)
GGCATGGAGCATCTGTACAGCATGAAGTGCAAGAACGTGGTGCCCCTCTATGACCTGCTGCTGGAG

ATGCTGGACGCCCACCGCCTACATGCGCCCACTAGCCGTGGAGGGGCATCCGTGGAGGAGACGG

ACCAAAGCCACTTGGCCACTGCGGGCTCTACTTCATCGCATTCCTTGCAAAAGTATTACATCACGGG

GGAGGCAGAGGGTTTCCCTGCCACAGTCTGAGAG

BRAD.15833_s_at
(SEQ ID NO: 89)
GAAATTAGAGTCCTATATTCAACTAAAGTTACAACTTCCATAACTTCTAAAAAGTGGGGAACCAGAGA

TCTACAGGTAAAACCTGGTGAATCTCTAGAAGTTATACAAACCACAGATGACACAAAAGTTCTCTGCA

GAAATGAAGAAGGGAAATATGGTTATGTCCTTCGGAGTTACCTAGCGGACAATGATGGAGAGATCTA

TGATGATATTGCTGATGGCTGCATCTATGACAATGACT

BRAD.19080_s_at
(SEQ ID NO: 90)
TTAGATTTCCAGCTTGTCACCTTCAAGGTTACCTTGTGAATAGGACTTTTTTGAGCTATTTCTATCCA

GTTGACTATGGATTTTGCCTGTTGCTTTGTTTCCACCAACTCTCCCTGAAGATGAGGCGCACAGACA

GACAACTCACAGGCAAGAACAGCCTGGTCCATCTTGAAAGATTCTCAAGACTATTCTCCACAAG

BRAD.2707_at
(SEQ ID NO: 91)
TGTTTAAAAATGTTGTGGGTACATAGTATGTGTTGTGGGTACATCGTATGTGTTGTGGGTACATAGTA

TNGTGGGGTCCATGAGATGTTTTGATACAGGCATGCAATGTGAAATAAGCACATCATGGGGAATGG

GGTATCCCTCCCCTCAAGCGTTTATCCTTCAAGTTATAAAAAATTCAATTACAGTCTTAGTTATGTCAA

AATGTAC

BRAD.27716_s_at
(SEQ ID NO: 92)
ACCAGAATTTATGGATGAACTGATTGCTTATATTTTAGTCAGGGTTTATAAATGTAGATGGTCAAATTT

ACATTGCCTAGTGATGGAAAATTCAACTTTTTTTGATTTTTTTTCCAATATTAAAAAAGGCTCTGTAT

GCATGGTGGG

BRAD.28628_s_at
(SEQ ID NO: 93)
AAGATTCCTGTGTACTGGTTTACATTTGTGTGAGTGGCATACTCAAGTCTGCTGTGCCTGTCGTCGT

GACTGTCAGTATTCTCGCTATTTTATAGTCGTGCCATGTTGTTACTCACAGCGCTCTGACATACTTTC

ATGTGGTAGGTTCTTTCTCAGGAACTCAGTTTAACTATTATTTATTGATATATCATTACCTTTGAAAAG

CTTCTACTGGCACAATTTATTAT

BRAD.28643_at
(SEQ ID NO: 94)
TCTCCTCTCATCTGCATTTCTCAGAAATGCCCTCCCTGCCCAGTGGTGACTTTCCCTCGTCACTCCT

ATGGAGTTCTACCTGGAGCCCAGCCATGTGTGGAACTGTGAAGTTTACTCCTCTGTAAAGATGGTTT

AAAGAAAGTCAGCTTCTGAAATGTAACAATGCTAACCCTTGCTGGAACCCTGTAAGAAATAGCCCTG

CTGATAGTTTTCTAGGTTTATCATGTTTGATTTTTACACTGAAA

BRAD.28663_s_at
(SEQ ID NO: 95)
GAATTTTCTCTATTTCCAGCACGCTGATTTGATTTAAAAATGTAATAAGACCAAGAGTTGGAGTAAA

GGGATATTCATTCCATGTTAAAAGTGGCTTCATAGCTACTGACAAATGTCTGAACTATTGTCGTGCCC

-continued

TTCAAAACTGGAGTTTTCTAAAATAATCTTATTTTTATACTTGTATGTTCCAGCAATTTAAGATATATAC

CATTGAAAGGGAAAT

BRAD.29038_at
(SEQ ID NO: 96)
GGCTGAGCAAGGCACATAGTCTACTCAGTCTATTCCTAAGTCCTAACTCCTCCTTGTGGTGTTGGAT

TTGTAAGGCACTTTATCCCTTTTGTCTCATGTTTCATCGTAAATGGCATAGGCAGAGATGATACCTAA

TTCTGCATTTGATTGTCACTTTTTGTACCTGCATTAATTTA

BRAD.30917_at
(SEQ ID NO: 97)
AACGCAGGCCGCTTTATTCCTCTGTACTTAGATCAACTTGACCGTACTAAAATCCCTTTCTGTTTTAA

CCAGTTAAACATGCCTCTTCTACAGCTCCATTTTTGATAGTTGGATAATCCAGTATCTGCCAAGAGCA

TGTTGGGTCTCCCGTGACTGCTGCCTCATCGATACCCCATTTAGCTCCAGAAAGCAAAGAAAACTCG

AGTAACACTTGTTTGA

BRAD.31470_at
(SEQ ID NO: 98)
TCATCTCCGTATTCTTCAGCTTCATCCAAAACTGACTTAGAAGCCTCCCTTGACCCTCACCTGACTAT

TCACAGGTTATAGCACTTTATGTTTTTCAGTTCTGTTATTTTAATTGGTGCCTCTGTTTGTGATCTTTA

AGAACATAAAATTCTGGCAAGTAACTATTTGCTA

BRAD.32716_at
(SEQ ID NO: 99)
CACTTTGCAGCCTTGAGAGGTGCAGAAGAGACACCGAGGGGTTCACCACCAGAGCCACCATTGTCA

GAGAGGCGTCCAGCTGTGTCCACCTGGGACTCTGCCTTCAGGGCTTCTTGCCTGGCTGGGAGCTG

CACAGGCAGACTCCTGGGACGGTGTGCCGACAGCTCTGGGCACCCCCTTCTAGGATCTGATTCCT

GAGGAATCACAATGTGGATTTCACAATCACTTCCAGTGTCTTTTGCCAACCTCTGTGAACAGATGT

BRAD.33042_at
(SEQ ID NO: 100)
AAGTTTGCACAGTTCTAGACACGATAAATACATGTGAAATCACACAACTCAGAAAATGTCCCTTAAAT

TAATTGAGCCATTGGTACTTGTGAATTAGAAGAGACATCTATGTTCTGATCCACTGTTGAAAGCTGTA

CAATGTTACCTATTTATTTGCAGACATCCTTTGGAAACAAATAGGTAGATTTGCAACAAATAAAGAGT

GGAGTACAGCTGCTGACATTACCTTGTATATTCATGCCTTTATG

BRAD.33341_at
(SEQ ID NO: 101)
GACTGCACAGCAGCAAGACAGATTGCCATGGAGCATGTTGTGCCCAACTAGGGACAGCGCAGATA

GATTCTGTAATTTGCCTAACAATGTCTATAGGATGATCCCATTTGTCAAAAAAAAAANNGAACTGGGC

TTTATTGATGTCACCTAAATGCACCTAAACTTCTTTTTTGCCCCATGCTCTTCTGTACTCTTGATCTTT

CCCCAAATTTTTAAAAACATGACACTCATTCCCTTATTTTTCCTACTTAG

BRAD.33405_at
(SEQ ID NO: 102)
TTAATTGCTTTCTCTCACCAGGGAAGGTGTGGGAAGGACTTGTGAAATACATATTCGAGGAAAAACT

ATGCACAAGGCCGTGCATTTAAAAATAAACTCCCTAAGGCTGGGGTGAAACCTGCTACGGTCTGCG

CAAGTTGACTGTTAATGAATTTGATTCTCAGGTGTGAGTGATTAAAAGAACACTGATCATGTCATTTT

CTTTTTGGTCACTAATTCCCTCC

BRAD.33431_at
(SEQ ID NO: 103)
GTCATCCAGAGTTATAATGGCCCATTATCTAATGGTCAGAGTTTACTTAGGCTTTCACTACTTCCACT

GCCCACTTGAAACAGGGAAAAATATTTTCCCCCCGCGCTGTGAGTGTGCTATTTAGAGCTGACCACA

AGCGGGGGGAAGAGAGGATGGCTCGGATGCTGCATTTCCACTGAGAACACAAGGCTGGCAAAGCT

TGTCTGCTGCCCAGCAAGCACTTCAGGCTCACACCATTTTAGGTTCACTTTAAGTAGTTTCTCAAT

BRAD.35695_at
(SEQ ID NO: 104)
TGGACAGTGGACGTCTGTCACCCAAGAGAGTTGTGGGAGACAAGATCACAGCTATGAGCACCTCGC

ACGGTGTCCAGGATGCACAGCACAATCCATGATGCGTTTTCTCCCCTTACGCACTTTGAAACCCATG

CTAGAAAAGTGAATACATCTGACTGTGCTCCACTCCAACCTCCAGCCTGGATGTCCCTGTCTGGGC

CCTTTTTCTGTTTTTTATTCTATGTTCAGCACCACTGGCACCAAATACATTT

BRAD.35710_at
(SEQ ID NO: 105)
TCCATGGCAACAGTCCCAACATGTTTGAGACTTCAGCTAAAGGAATGGATGTATNNNGGNGTGTAGT

CTTCAGTATATCACTGTATTTCCGTAATACTAGACTCNAAGNTATGCNAGATNGNTTATTCCCTTNGT

GAANNNGGAGTTGCTCATTACGTTCTTGAAATATCGCACATCCTGTTGGTTCTTCAAAGGAAGCCTT

TCCACCAGATTAGTGTTCAAGTCTTTGCAGAGGAGACCAACTTTT

BRAD.37907_at
(SEQ ID NO: 106)
AAGGCTATGCTTTCAATCTCCTACACAAATTTTACATCTGGAATGATCTGAAGGTTCTTCAAAGACAT

TCAAAATTAGGCTTTTTTATGTCCTGTTTTAAGTGAAAATATTTATTCTTCTAAGGGTCCATTTTATTTG

TATTCATTCTTTTGTAAACCTCTTTACATTTCTCTTTACATTTTATTCTTTGCCCAAATCAAAAGTGATT

CCT

BRAD.40353_at
(SEQ ID NO: 107)
CTTAGCATTAGAACACTCAGTAATCATATGAATTGTGCATTTGTTTGTTTTGCTTAACTCTTTCTGTTT

GTTTATGTTTGGGGTTTTATTGTTGTTGTTTCACTTTTCTCCCATCTCTTCCTGACTTGGTCAAATCCA

AAGGAATNTTCCAAATTGTGGGGAGCAAGGCATCTGAAATGGCTAAAAC

BRAD.40654_s_at
(SEQ ID NO: 108)
ATGCTATATGCTGTATCCCACCTTTCTCTGAATGTTACATTTTCTCCCCTATCCCAGGCTGCATCTAA

GAAAACTCAAAGGGAATATGCTATCTATCTTTTCCGAGCAATGAAAGCTCTNGGGTTTTTTCCTTGCT

TTTCAGGGCACNATACTTCTCTTTCTTCCTGGTTAGACAGGATAAGTTCTGAGTCCCNTGGTATCATC

AGCTTACTTCTTCTCTGTTAAATATTCACA

BRAD.4701_at
(SEQ ID NO: 109)
GTGGTCTTCCTCTGAATATTAGCAGAAGTTTCTTATTCAAAGGCCTCCTCCCAGAAGAAGTCAGTGG

GAAGAGATGGCCAGGGGAGGAAGTGGGTTTATTTTCTGTTGCTATTGATAGTCATTGTATTACTAGA

AATGAACTGTTGATGAATAGAATATATTCAGGACAATTTGGTCAATTCCAATGCAAGTACGGAAACTG

AGTTGTCCCAAATTGATGTGACAGTCAGGCTGTTTCATCTTTTTTG

BRAD.5967_at
(SEQ ID NO: 110)
TATCCTATTACTGTACTTAGTTGGCTATGCTGGCATGTCATTATGGGTAAAAGTTTGATGGATTTATTT

GTGAGTTATTTGGTTATGAAAATCTAGAGATTGAAGTTTTTCATTAGAAAATAACACACATAACAAGTC

TATGATCATTTTGCATTTCTGTAATCACAGAATAGTTCTGCAATATTTCATGTATATTGGAATTGAAGT

TCAATTGAATTTTATCTGTATTTAGTAAAAATTAACTTTAGCTTTGATACTAATGAATAAAGCTGGGTTT

BRAD.7701_at
(SEQ ID NO: 111)
GGGATTTTGAGCTATCATCTCTGCACATGCTTAGTGAGAAGACTACACAACATTTCTAAGAATCTGAG

ATTTTATATTGTCAGTTAACCACTTTCATTATTCATTCACCTCAGGACATGCAGAAATATTTCAGTCAG

AACTGGGAAACAGAAGGACCTACATTCTGCTGTCACTTATGTGTCAAGAAGCAGATGATCGATGAGG

CAGGTCAGTTGTAAGTGAGTCACATTGTAGCATTAAATTCT

-continued

BREM.1048_at
(SEQ ID NO: 112)
TTGAATAGATCATCAGTGGCCACTGATGTAATTAATCATGTCTATGTAATGAAGCTGCCATAAAAAAC

CCAGGAGGACAGTGTTGAGAGAGCTTCTAGGTTGGTGAACACTTGGGGGTGTCTGGAAGACAGCC

CACCTGGAGAGGACACGGAGGCTCTTCGCACCTTCCCCCATACCTGGCTCTCTCCATCTCTTCATTT

GTCCATCTGTATCTTTTTCATTATATTATCCTTGATAATAAACTGGTAAATATAAGTGTTTCCCTAAGTT

CTATGAGCCACCAT

BREM.1129_at
(SEQ ID NO: 113)
AGGCCTCTGATTGCACTTGTGTAGGATGAAGCTGGTGGGTGATGGGAACTCAGCACCTCCCCTCAG

GCAGAAAAGAATCATCTGTGGAGCTTCAAAAGAAGGGGCCTGGAGTCTCTGCAGACCAATTCAACC

CAAATCTCGGGGGCTCTTTCATGATTCTAATGGGCAACCAGGGTTGAAACCCTTATTTCTAGGGTCT

TCAGTTGTACAAGACTGTGGGTCTGTACCAGAGCCCCCGTCAGAGTAGAATAAAAGGCTGGGTAGG

GTAGAGATTCCCATGTGCAGTGGAG

BREM.1226_at
(SEQ ID NO: 114)
ATACGTTTTTCACTTTCTGACCAGGACCATGCCTGTGGAGTAGATGTTGACAAGAAACACTGACCAG

ATCAAAATGTGTCTCAAGGAGAATGGCACAATTTTGTGCAAATGAATCAAGGAAGTCTTATTGCACAA

GAGTATCCTGGAACCCAGTGCAATTGATTTTTTAGAAAAATATATCACATAGGGGAAAAAAACTGGAA

TATGTTGAAGGAGACGTATATAATATTTAGCATCCAGATTGATGACTTCTGCCCTAACTATGCAATG

BREM.1262_at
(SEQ ID NO: 115)
CGCTTGAACCTGGAAAGTGGACATTGCAGTGAGCTGAGATTGTGCCACTGCACTCCAGCCTGGGCA

ACACAGCGAGACTCTGTCTCAAAAAAAAAAAAAAAGAAAGAAAAAAAAGAGAAAACTCAGAGATTC

GTGGAGACTGGAACCACGGGTGTGGAGAGAGGGGTTAGTAGAGACCAGATTCTGCAGGTACTATA

ATGACATTCCCAGGCTAAGGAGTTTAGATCTT

BREM.130_at
(SEQ ID NO: 116)
ATCTACACCCTCAGGAATAAGAAAGTGAAGGGGGCAGCGAGGAGGCTGCTGCGGAGTCTGGGGAG

AGGCCAGGCTGGGCAGTGAGTAGTTGGGGAGGGGAGAAAGTATTAAGCCAGAACCCAAGGATGGA

AATACCCCTTAGTGAGTCAGTTTAGACTTCAGGCTGTTCATTTTTGTATGATAATCTGCAAGATTTGT

CCTAAGGAGTCCAATGGGGGATATGTTTTCCTCCCGTGAGGAAATGTTTAGTTCTTGAGGGAAAAT

CCCTAAATCCTCTATATA

BREM.1689_s_at
(SEQ ID NO: 117)
GGGTAGCAAGTTCACCACAGTGTTAATGGGGGTCCCAAGGTATTCTTCCCCCAGGCCTAGGTATAG

GGCTATTACTCCTCTCTGCTCCAGGTGTAGACATACATTTACATT

BREM.2334_at
(SEQ ID NO: 118)
TGGAGGGTGAAATTCTGATAGACTTGAGGCTTTGAGATGTGGTCCTGGGGTGGAGCAAGACAAGAA

AAGTACTGGAGATTGGGGTTTGAGGAGTCTATGCAATTATTTTTATTTTTAAAAATCTTTGTGGCTAC

ATAGCAGGTGTATATATTTATGTGGTAAGTGAGATATTTCGATACAGACATACAATGTATAATCACAG

GCATACAATGTAGACAGGCATAAAGTGTATAGTCAC

BREM.2382_at
(SEQ ID NO: 119)
AATGTGAAACTGCTCCATGAACCCCAAAGAATTATGCACATAGATGCGATCATTAAGATGCGAAGCC

ATCGAGTTACCACCTGGCATGCTTAAACTGTAAAGAGTGGGTCAAAGTAAACTGAATTGGAAAATCC

AAAGTTATGCAGAAAAACAATAAAGGAGATAGTAAAAAGGGTTAACGAGCCAGTCCAGGGGAAGCG

-continued

AAGAAGACAAAAAGAGTCCTTTTCTGGGCCAAGTTTGATAAATTAGGCCTCCCGACCCTTTGCTCTG

TTGCTTTATCAACTCTACTCGGCAATAACAAT

BREM.532_at (SEQ ID NO: 120)
GATTAAGAACAGTTTTTTCAACAAATAGTGTTGGGACAATGGGTGTCCACATGCAAAAGAATAAAGTT

GTCCCCTTACCTTACACCATCTCCAAAAATTAACTCAAAATATGTCAAAGACATAAACGTAAGAGCTA

AAACTGTAAAACTCCTAGAATAAAACATAGGAGTAAATCTTCATGACCTTGGATTAGGCCATTGTGTC

TTAAATATAACACCAAAAGAATAAGTAATAAAAAAATAGATAAATTGAACTCCATCAAAATTAAAAGCC

TTTGTGCTTCATAGGACACCA

BRHP.106_s_at (SEQ ID NO: 121)
TCTCAAGCTATGATCAGAAGACTTTAATTATATATTTTCATCCTATAAGCTTAAATAGGAAAGTTTCTT

CAACAGGATTACAGTGTAGCTACCTACATGCTGAAAAATATAGCCTTTAAATCATTTTTATATTATAAC

TCTGTATAATAGAGATAAGTCCATTTTTTAAAAATGTTTTCCCCAAACCATAAAACCCTATACAAGTTG

TTCTAGTAACAATACATGAGAAAGATGTCTATGTAGCTGAAAATAAAATGACGTCACAAGAC

BRIH.10647C1n2_at (SEQ ID NO: 122)
TCTTTCTTTTCCAGACAACTTTGAATGGAGAGGAGCAAATTAGTCTTTTGGTTTAATTCTGTCTCAGTT

TGCTTATCTAAAGAAAGGAAAACAGAGTGGCTACACTTGTTTAGAACCATATGCATACTCCAGAGAA

AGATGCTCTATTAATCCAAAAAAATACAGCCACTTGAAACCAGCCAAAGCGAAAGTGTAAGGGACTT

CATGGAAAGGAGGCAGTTCACCAAAGTATTGAGGGGTTTTATATTTTAAACTCCGCCAGTGAATTGA

CGTGTTATGTCACTTAC

BRIH.1453C1n2_at (SEQ ID NO: 123)
GAATTTATTGGAGCATGACCACGGAGGATAGTATGAGCCCTAAAAATCCAGACTCTTTCGATACCCA

GGACCAAGCCACAGCAGGTCCTCCATCCCAACAGCCATGCCCGCATTAGCTCTTAGACCCACAGAC

TGGTTTTGCAACGTTTACACCGACTAGCCAGGAAGTACTTCCACCTCGGGCACATTTTGGGAAGTTG

CATTCCTTTGTCTTCAAACTGTGAAGCATTTACAGAAACGCATCCAGCAAGAATATTGTCCCTTTGAG

CAGAAAT

BRIH.1518C1n4_at (SEQ ID NO: 124)
TCCCCGGTTACTACCTCTTATCCATCCCCGGCCACCACCTCATACCCATCCCCTGTGCCCACCTCCT

TCTCCTCTCCCGGCTCCTCGACCTACCCATCCCCTGTGCACAGTGGCTTCCCCTCCCCGTCGGTGG

CCACCACGTACTCCTCTGTTCCCCCTGCTTTCCCGGCCCAGGTCAGCAGCTTCCCTTCCTCAGCTG

TCACCAACTCCTTCAGCGCCTCCACAGGGCTTTCGGACATGACAGCAACCTTTTCTCCCAGGACAAT

TGAAATTTGC

BRIH.2770C3n31_at (SEQ ID NO: 125)
ATGAAGACTTGGCTGATTCAGATGCCAGGGCCTTGTATGAAGCAGGAGAAAGGAGAAAGGGGACA

GACGTAAACGTGTTCAATACCATCCTTACCACCAGAAGCTATCCACAACTTCGCAGAGTGTTTCAGA

AATACACCAAGTACAGTAAGCATGACATGAACAAAGTTCTGGACCTGGAGTTGAAAGGTGACATTGA

GAAATGCCTCACAGCTATCGTGAAGTGCGCCACAAGCAAACCAGCTTTCTTTGCAGAGAAGCTTCAT

CAAGCCATGAAAGTATGTACCATTCT

BRIH.365C1n2_at (SEQ ID NO: 126)

TGCCTTGTGTCTTCCGTTTGACGGAAGAGAATGGATTCTGGTATCTAGACCAAATCAGAAGGGAACA

GTACATTCCAAATGAAGAATTTCTTCATTCTGATCTCCTAGAAGACAGCAAATACCGAAAAATCTACT

CCTTTACTCTTAAGCCTCGAACAATTGAAGATTTTGAGTCTATGAATACATACCTGCAGACATCTCCA

TCATCTGTGTTTACTAGTAATCATTTTGTTCCTT

BRIH.5410C1n7_at (SEQ ID NO: 127)

GGTATAGCATATGTGGCCTTGCTTACTAAAGTGGATGATTGCAGTGAGGTTCTTCAAGACAACTTTTT

AAACATGAGTAGATCTATGACTTCTCAAAGCCGGGTCATGAATGTCCATAAAATGCTAGGCATTCCT

ATTTCCAATATTTTGATGGTTGGAAATTATGCTTCAGATTTGGAACTGGACCCCATGAAGGATATTCT

CATCCTCTCTGCACTGAGGCAGATGCTGCGGGCTGCAGATGATTTTTTAGAAGATTTGCCTCTTGAG

GAAACTGGTGCATTT

BRIH.5478C1n2_s_at (SEQ ID NO: 128)

TGCTTATCCGTTAGCCGTGGTGATTTAGCAGGAAGCTGTGAGAGCAGTTTGGTTTCTAGCATGAAGA

CAGAGCCCCACCCTCAGATGCACATGAGCTGGCGGGATTGAAAGATGCTGTCTTCGTACTGGGAAA

GGGATTTTCAGCCCTCAGAATCGCTCCACCTTGCAGCTCTCCCCTTCTCTGTATTCCTAGAAACTGA

CACATGCTGAACATCACAGCTTATTTCCTCATT

BRIH.5650C1n2_at (SEQ ID NO: 129)

TAGGCACCACATGGGATCCTTGTTCTTCCTCCTTGTAAGCAGTAATTGAAATCAGTTTGGCAGCCTG

GTTTACAGTGACCATGGTGGCTTGTCTCCCGTGCTCTTACCTCACTCTGTTGATGTTGTAAAACCTC

CAGCTAACTTCATGGGGTGGCTGACCCACGTTGCTCATTTATTCATTCAACACATATTCATTGACCAT

CTACTCTATGCCAGGTATTGTTATCAGCACTGGGAATAGATCAGTGAACTATTGATCTATTTGTCTAA

BRIH.5952C1n2_s_at (SEQ ID NO: 130)

CTCAGTTCTGGTCCTTCAAGCCTGTATGGTTTGGATTTTCAGTAGGGGACAGTTGATGTGGAGTCAA

TCTCTTTGGTAC

BRIH.7359C1n3_s_at (SEQ ID NO: 131)

CTGAGGTGCTATGTTCTTAGTGGATGTTCTGACCCTGCTTCAAATATTTCCCTCACCTTTCCCATCTT

CCAAGGGTATAAGGAATCTTTCTGCTTTGGGGTTTATCAGAATTCTCAGAATCTCAAATAACTAAAAG

GTATGCAATCAAATCTGCTTTTTAAAGAATGCTCTTTACTTCATGGACTTCCACTGCCATCCTCCCAA

GGGGCCCAAATTCTTTCAGTGGCTACCTACATACAATTCCAAACACATACAG

BRIHRC.10930C1n2_s_at (SEQ ID NO: 132)

TAACAAATCATCAACTTCCACTGGTCAATATATAGATTTTGGGTGTCTGAGGCCCCAAGATTAGATGC

CACTAATCTCCAAAGATTCCCTCCAA

BRMX.13731C1n18_at (SEQ ID NO: 133)

GCAGGGTCTTGGGATAACACTGTCATCAGAAACAAGGCTGGGGGCTGATTTCGGGGTGGGGAGCC

TTAGGAGGCCAGAAATTCCAATCAGAGCCAGTTTTTCTGGGAGGGAGTGGCTAGACAGTCAAGGAA

GGACGTTCACATTTCAAAAGAAGTCGGGTGGGGGGATGAGATTATTCTAGGGGGGCATCGAATTCC

CTTTAAGGGGGGGGCTCACTTCTGCCCAGAGTAAAGAGGATCTCACACCATGGAAAT

BRMX.25436C1n2_at (SEQ ID NO: 134)

TAGTTATACTTACACACTCCTCTCATGTTGTCTATGGAGTGGTGGATGCTGCAGGGAGGGTGACATC

CTAGTTAGTCCTAAGAGCCAGACTGCCTGAAGCTCACTATAACAAGTCCTGCCTTGGGGAAGAAGG

-continued

AAGTGTGTCTCTGTGAACCTCCCACCTGGGCCGAAAGGGAGGCCACTCTCTCTGCTGCCTCTCCCC

AACCTTGGCCTTCTGTGCTCCTAGTGAACCTCTCACCCCCTGCCTACAGCCTCGAATCTCAGACCAT

GATGACCTCTGGTCACCCTGAATCAGAGCTTT

BRMX.25712C1n2_at
(SEQ ID NO: 135)
GTAAAATTCCTATGTCAGCACCCTAATGAGACAAATGACATCCTAATTCTTCCCCTTGGCTTGCCAGT

TTGTAGGTACTAGTTTTTCAGAAGTTACTCTAAAATATTTCTGATTGCAGCTCCTTCCTAAAGAGCAG

TATGAGCAGCATGTGGTTATTTATGTATTCACTCTTTTCTCCTACTTCTGTGGTGACCTGGAACAAAT

TCTCTTATGTATGTAAAGATTGGACAGCCCACCTGATTCCGATGTCACTTAGATACACTGTTTTTGTA

TCAGCCTCTTCTCTTAGAAA

BRMX.3079C1n3_at
(SEQ ID NO: 136)
GATTGTTGGCCAATAGACCTTCCACTCCAGTAGAGAGGGAGGACTTGGCTCTGAGAACCTCCATCT

GACCTAAGAGGAAACCTCCTCTCCTATGGCCATCTCCTCCTCCTGTCCTTTAAGTCCTCTGTGGTTA

CTATATCTCCTTTTCCCTTTCTTACCCTTTCGCTTAGCAATTTCAAT

BRMX.3079C2n3_at
(SEQ ID NO: 137)
AAGTTCTTTGGGATAGAGGGTGAAGAACTTGGGACATGGGCTGTTTCAGGGCAGCTGAAGTTCAAA

GGGGAATAGGTAATTGGGGGGAAGGGGGGAAGTTGGGGCAGAAAGGGATTGTTGGGCCAATAGG

ACCTTTCCACT

BRPD.10690C1n5_at
(SEQ ID NO: 138)
AGGATTATACTTCAGTCCCTGCTTTACATTTATTTCTTAAAGAAGCTTCTGGTAAATTAGAGCAATAGC

ATCGGCTTAGTTTAGTGTTGTTCTGTTGGACTAAGGATATCAGTTCTATCCGTATGGTCGGGCCTAA

AGCCTGGGAAATATTTAATGAAGGNNNNNNNNNNNNNNNNNNNNNNNNNNNNNNNNNNNNNNNA

TAACAAATAACAAAACAAAAACCAAGCCATTTCCCTTTATAGTAAGA

BRPD.4019C1n3_s_at
(SEQ ID NO: 139)
ACAGAAGCCATTGCCTCCCTTGTTTACCTTGGGTCCACCTCCACCAAAACCCAACAGACCACCAAAT

GTTGACCTGACGAAATTCCACAAAACCTCTTCTGGAAACAGTACTAGCAAAGGCCAGACGTCTTACT

CAACAACTTCCCTGCCACCACCTCCACCATCCCATCCGGCCAGCCAACCACCATTGCCAGCATCTC

ACCCATCACAACCACCAGTCCCAAGCCTACCTCCCAGAAACATTAAACCTCCGTTTGAC

BRPD.5301C1n2_s_at
(SEQ ID NO: 140)
GCACAGCTCAGCACAACATTCCAAGCTCAAAATAGAAGCCTTCTCAGTGAGCTCCAGCACGCCCAG

AGGACTGTTAATAACGATGATCCATGTGTTTACTCTAAAGTGCTAAATATGGGAGTTTCCTTTTTTTT

ACTCTTTGTCACTGATGACACAACAGAAAAGAAACTGTAGACCTTGGGACAATCAACATTTAAA

BRRS.12588_at
(SEQ ID NO: 141)
CCTGCCCTGGAAGTAATCTTGCTGTCCTGGAATCTCCTCGGGGATGAGGCAGCTGCCGAGCTGGC

CCAGGTGCTGCCGAAGATGGGCCGGCTGAAGAGAGTGGACCTGGAGAAGAATCAGATCACAGCTT

TGGGGGCCTGGCTCCTGGCTGAAGGACTGGCCCAGGGGTCTAGCATCCAAGTCATCCGCCTCTGG

AATAACCCCATTCCCTGCGACATGGCCCAGCACCTGAAGAGCCAGGAGCCCAGGCTGGACTTTGC

CTTCTTTGACAACCAGCCC

BRRS.13369_s_at
(SEQ ID NO: 142)
GCACAGCTCAGCACAACATTCCAAGCTCAAAATAGAAGCCTTCTCAGTGAGCTCCAGCACGCCCAG

AGGACTGTTAATAACGATGATCCATGTGTTTACTCTAAAGTGCTAAATATGGGAGTTTCCTTTTTTA

CTCTTTGTCACTGATGACACAACAGAAAAGAAACTGTAGACCTTGGGACAATCAACATTTAAA

-continued

BRRS.13576_at (SEQ ID NO: 143)
GAGAGTTCAACTAAGAAAGGTCACATATGTGAAAGCCCAAGGACACTGTTTGATATACAGCAGGTAT

TCAATCAGTGTTATTTGAAACCAAATCTGAATTTGAAGTTTGAATCTTCTGAGTTGGAATGAATTTTTT

TCTAGCTGAGGGAAACTGTATTTTTCTTTCCCCAAAGAGGAATGTAA

BRRS.13647_at (SEQ ID NO: 144)
CTCGATTATTCCCTGTACAATATTTAAAATTTATTGCTTGATACTTTTGACAACAAATTAGGTTTTGTAC

AATTGAACTTAAATAAATGTCATTAAAATAAATAAATGCAATATGTATTAATATTCATTGTATAAAATA

GAAGAATACAAACATATTTGTTAAATATTTACATATGAAATTTAATATAGCTATTTTTATGGAATTTTTC

ATTGATATGAAAAATATGATATTGCATATGCATAGTTCCCATGTTAAATCCCATTCATAACTTTCATTA

AAGCATTTACTTTGA

BRRS.13648_s_at (SEQ ID NO: 145)
GCAAATAAATTCATACATAGTACATACAAAATAAGAGAAAAAATTAAATTGCAGATGGTTAAATATCAC

ATCACTTAACTGATGTTACTGAAAATGTATTTTCCTGCATAATCATATGGTTGACAGTATGCATTAAGA

AGGTAAGTAAAACAATGAAGACAATTTTGATTTAATATGGTAATGCACAATTCCAACTAACGTACATT

CAACAGATCATGAAATTGGGTTATT

BRRS.13767_at (SEQ ID NO: 146)
TTGCCTTCTAAATATACTGAAATGATTTAGATATGTGTCAACAATTAATGATCTTTTATTCAATCTAAGA

AATGGTTTAGTTTTTCTCTTTAGCTCTATGGCATTTCACTCAAGTGGACAGGGGAAAAAGTAATTGCC

ATGGGCTCCAAAGAATTTGCTTTATGTTTTTAGCTAT

BRRS.13859_at (SEQ ID NO: 147)
CCTGGCCACTCGCAAGACCTTTTATCTGAAAACCAGCCAAGCTTTATTCACGACACACTTCTTCCCTT

CACTCTCCCACTTCTGTGGTCAACTCCCTGCAGAACTCCCAAACTGCCGTTCTTTTCGATAGCTCAC

GATGGTGTATGAGTGTCAATCATCTGACCCTTCTTGGAGTCTCATATTTCGTGGAAC

BRRS.13881_at (SEQ ID NO: 148)
CTGAGGACCGGCTGCAGACCTCACTCTGAGTGGCAGGCAGAGAACCAAAGCTGCTTCGCTGCTCT

CCAGGGAGACCCTCCTGGGATGGGCCTGAGAGGCCGGGGCTCAGGGAAGGGGCTGGGATCGGAA

CTTCCTGCTCTTGTTTCTGGACAACTTTCCCCTTCTGCTTTAAAGGTTGTCGATTATT

BRRS.14465_s_at (SEQ ID NO: 149)
AGTGTGATGGATCCCCTTTAGGTTATTTAGGGGTATATGTCCCCTGCTTGAACCCTGAAGGCCAGGT

AATGAGCCATGGCCATTGTCCCCAGCTGAGGACCAGGTGTCTCTAAAAACCCAAACATCCTGGAGA

GTATGCGAGAACCTACCAAGAAAAACAGTCTCATTACTCATATACAGCAGGCAAAGAGACAGAAAAT

TAACTGAAAAGCAGTTTAGAGACTGGGGGAGGCCGGATCTCTAGAGCCATCCTG

BRRS.15053_at (SEQ ID NO: 150)
GCGTTACAGATGGACGTAGCTGCCTTGGTTTTCCAGTCCTCAAGGGAATACTGAAGATGCTGACTG

AAGGGGATTGGATGTTGATTTTAGAAGATGGAGAACTCCAGCCACCTTTGTAAAGCACTAGTGTTTG

TCATTTATGTAAGTCAGGTCGGCTCAGGTCTTGATAGTCCGTCTTGGTGTGAGGCATGC

BRRS.16228_s_at (SEQ ID NO: 151)
CACAGTAATGTCGAAACTAGGCCTTTGAACCAAGGCAGTCTAGGGTAAAATATAGTTTCAAAGTATG

AATAAGAATTGGTATTTGTGTTATCTTTGAGTAAGAAACTGTCCGATATGAATCACAACGTGGGTGAA

TGTAGTATTTTCCTGAAGTGTG

BRRS.16746_s_at (SEQ ID NO: 152)
GGCCATGAACATCACCTGCACAGGACGGGACCAGACAACTGTATCCAGTGTGCCCACTACATTGA

CGGCCCCCACTGCGTCAAGACCTGCCCGGCAGGAGTCATGGGAGAAAACAACACCCTGGTCTGGA

AGTACGCAGACGCCGGCCATGTGTGCCACCTGTGCCATCCAAACTGCACCTACGGG

BRRS.16747_at (SEQ ID NO: 153)
ATCACAGGTTTGAGCTGAATTATCACATGAATATAAATGGGAAATCAGTGTTTTAGAGAGAACTTT

TCGACATATTTCCTGTTCCCTTGGAATAAAAACA

BRRS.16948_s_at (SEQ ID NO: 154)
AGTTTCAGACAAATGTTCAGTGTGAGTGAGGAAAACATGTTCAGTGAGGAAAAAACATTCAGACAAA

TGTTCAGTGAGGAAAAAAAGGGGAAGTTGGGGATAGGCAGATGTTGACTTGAGGAGTTAATGTGAT

CTTTGGGGAGATACATCTTATAGAGTTAGAAATAGAATCTGAATTTCTAAAGGGAGATTCTGGCTTGG

GA

BRRS.17863_s_at (SEQ ID NO: 155)
AACTTAAGCTGAATGTGTAATGGATTTGTCTATAGTTTTACATATTTGGAAGCATTTTAAAATAGGTTT

TAATCTTACATAAAATTACTTTTATACTTGTGTTAACATTTTCTTCTGTGCCTTTTGGGTAATTTAATTT

CTGTTATGAATTTCTGGTGCCTATGAGCTAGCTATCACCTACCTGAAAGGTGCTTAGAGGTGAAGGT

ACTGTTTCTAAAAACACATCACTGTGACACCTTTCTATCCTCACATTTTCAAGCTTGCCTCTTTTCT

BRRS.17909_s_at (SEQ ID NO: 156)
GTGACTGCTTATGAAGGGTTATTGCTCAGCTAAGTATTTCTGAATGAGTCTTAGGTCTGTTGGCCTTC

AATCTCTACCGAAACCCTGAGAACTTGATGATGCTTTTGTTTTCTGAGAATCGTTTCAGTGTGCTGG

BRRS.18137_at (SEQ ID NO: 157)
CATTTGCTGCAACTCTCAGTGGTAAGAATGATTAAGTGCAGCTATAGGAGAATACTTCCATTGGCAT

GCCACCTGCGTAAAACACACAATTTTGTTAAGATATACAATAAAATTATTATGCTAATAGCAAATATTT

TATGTAGCTCACTATGTTCCATGTAGTCTTCTAAGTGCTTCATGTTAGTCCCCAGTTAAACACCTGGT

TTTGGAAGGCTGAG

BRRS.18652_s_at (SEQ ID NO: 158)
GTGAGCCTGCCAGCGTTTGCGACGTCCCCGCACGACAGGCTCATACTTTCTGAGGATCGTGCATAG

CATAGGACGTCTGAACCTTTGTACAAATGTGTAGATGACATCTTGCTACAGCTTTTATTTGTGAAT

BRRS.2573_s_at (SEQ ID NO: 159)
GTAAATTCAATACAATGTCAGTTTTTAAAAGTCAAAGTTAGATCAAGAGAATATTTCAGAGTTTTGGTT

TACACATCAAGAAACAGACACACATACCTAGGAAAGATTTACACAATAGATAATCATCTT

BRRS.2644_at (SEQ ID NO: 160)
ACTGTACAAAGTATAAGTCTTAGATGTATATATTTCCTATATTGTTTTCAGTGTACATGGAATAACATG

TAATTAAGTACTATGTATCAATGAGTAACAGGAAAATTTTAAAAATACAGATAGATATATGCTCTGCAT

GTTACATAAGATAAATGTGCTGAATGGTTTTCAAATAAAAATGAGGTACTCTCCTGGAAATATTAAGA

AAGACTATCTAAATGTTGAAAGA

BRRS.2783_s_at (SEQ ID NO: 161)
GAGGACCGAGCACAGAAATCTTAGAGATTTCTTGTCCCCTCTCAGGTCATGTGTAGATGCGATAAAT

CAAGTGATTGGTGTGCCTGGGTCTCACTACAAGCAGCCTATCTGCTTAAGAGACTCTGGAGTTTCTT

ATGTGCCCTGGTGGACACTTGCCCACCATCCTGTGAGTAAAAGTGAA

-continued

BRRS.2935_at (SEQ ID NO: 162)
TCTGAACTCTCAAAAGTCTATTTTTTTAACTGAAAATGTAAATTTATAAATATATTCAGGAGTTGGAAT

GTTGTAGTTACCTACTGAGTAGGCGGCGATTTTTGTATGTTATGAACATGCAGTTCATTATTTTGTGG

TTCTATTTTACTTTGTACTTGTGTTTGCTTAAACAAAGTGACTGTTTGGCTTATAAACACATTGAATGC

GCTTTATTGCCCATGGGATATGTGGTGTATATCCTTCCAAAAAATTAAAACGAAAATAAAGTAGCTGC

GATTGG

BRRS.3099_at (SEQ ID NO: 163)
ATTCCTGTCATTACCCATTGTAACAGAGCCACAAACTAATACTATGCAATGTTTTACCAATAATGCAAT

ACAAAAGACCTCAAAATACCTGTGCATTTCTTGTAGGAAAACAACAAAAGGTAATTATGTGTAATTAT

ACTAGAAGTTTTGTAATCTGTATCTTATC

BRRS.3131_at (SEQ ID NO: 164)
CAGGACCCATCACGCCTGTGCAGTGGCCCCCACAGAAAGACTGAGCTCAAGGTGGGAACCACGTC

TGCTAACTTGGAGCCCCAGTGCCAAGCACAGTGCCTGCATGTATTTATCCAATAAATGTGAAATTCT

GTCC

BRRS.3220_at (SEQ ID NO: 165)
AAAGTGGCATTTTCTTGATTGGAAAGGGGGAAGGATCTTATTGCACTTGGGCTGTTCAGAATGTAGA

AAGGACATATTTGAGGAAGTATCTATTTGAGCACTGATTTACTCTGTAAAAAGCAAAATCTCTCTGTC

CTAAACTAATGGAAGCGATTCTCCCATGCTCATGTGTAATGGTTTTAACGTTACTCACTGGAGAGATT

GGACTTTCTGGAGTTATTTAACCACTATGTTCAG

BRRS.3319_at (SEQ ID NO: 166)
TTTATAATGTCCCTTCACAAACCCAGTGTTTTAGGAGCATGAGTGCCGTGTGTGTGCGTCCTGTCGG

AGCCCTGTCTCCTCTCTCT

BRRS.3319_s_at (SEQ ID NO: 167)
CACCCTCAGATGCACATGAGCTGGCGGGATTGAAGGATGCTGTCTTCGTACTGGGAAAGGGATTTT

CAGCCCTCAGAATCGCTCCACCTTGCAGCTCTCCCCTTCTCTGTATTCCTAGAAACTGACACATGCT

GAACATCACAGCTTATTTCCTCATTT

BRRS.3645_s_at (SEQ ID NO: 168)
AAATTTAATTTTCTACGCCTCTGGGGATATCTGCTCAGCCAATGGAAAATCTGGGTTCAACCAGCCC

CTGCCATTTCTTAAGACTTTCTGCTGCACTCACAGGATCCTGAGCTGCACTTACCTGTGAGAGTCTT

CAAACTTTTAAACCTTGCCAGTCAGGACTTTTGCTATTGCA

BRRS.4126_s_at (SEQ ID NO: 169)
CTACTCCTTACAGTCTCTAGAATTAAATGTACTCATTTAGACAACATATTAAATGCATATTTTAGCCAC

TTTAGAGAAACCTCATAGGCACAGAGTTTCCAAGATTAATTTTAAGAATATCTTCACGAACTTGACCC

TCCTACTCCACATTGCAACATTTCCATCAGACAGCATTTCAATTCCAGTATTAT

BRRS.455_at (SEQ ID NO: 170)
GTCATCATATATAATTAAACAGCTTTTTAAAGAAACATAACCACAAACCTTTTCAAATAATAATAATAAT

AATAATAAAAAATGTATTTTAAAGATGGCCTGTGGTTATCTTGGAAATTGGTGATTTATGCTAGAAAG

CTTTTAATGTTGGTTTATTGTTGAATTCCTAGAA

-continued

BRRS.4562_at (SEQ ID NO: 171)
CATGGATTAGCTGGAAGATCTGTATTTGATGGAAGACCTTGAAATTATTGGAAGACATGGATTTCCT

GGAAGACGTGGATTTTCCTGGAAGATCTGGATTTGGTGGAAGACCAGTAATTGCTGGAAGACTGGA

TTTGCTGGAAGACTTGATTTACTGGAAGACTTGGAGCTTCTTGGAAGACATGGATTGTCCGGAAGAC

ATGGATTGTCTGGAAGATGTGGATTTTCTGGAAGCTCAG

BRRS.487_s_at (SEQ ID NO: 172)
GTGGAGGAAACTAAACATTCCCTTGATGGTCTCAAGCTATGATCAGAAGACTTTAATTATATATTTTC

ATCCTATAAGCTTAAATAGGAAAGTTTCTTCAACAGGATTACAGTGTAGCTACCTACATGCTGAAAAA

TATAGCCTTTAAATCATTTTTATATTATAACTCTGTATAATAGAGATAAGTCCATTTTTTAAAAATGTTT

TCCCCAAACCATAAAACCCTATACAAGTTGTTCTAGTAACAATACATGA

BRRS.4891_s_at (SEQ ID NO: 173)
TCAATAAGGGCGTTCTTCCTTGCAAGTTGAAACATTATTGTGCTAGGATTGCTCTCTAGACAAGCCA

GAAGTGACTTATTAAACTATTGAAGGAAAAGGACTCAAGAAAAATAATAAAAGACCATAAATAAGGGC

GAAAACATTACCATGTGAAAAGAATGTATTTCACCTGCAAGTTACAAAAAAATAGTTTGTGCATTGCA

AATAAGCAAAGACTTGGATTGACTTTACATTCATC

BRRS.4996_at (SEQ ID NO: 174)
AAGCTGTGTTGTTGCTTCTTGTGAAGGCCATGATATTTTGTTTTTCCCCAATTAATTGCTATTGTGTTA

TTTTACTACTTCTCTCTGTATTTTTTCTTGCATTGACATTATAGACATTGAGGACCTCATCCAAACAAT

TTAAAAATGAGTGTGAAGGGGGAACAAGTCAAAATATTTTTAAAAGATCTTCAAAAATAATGCCTCTG

TCTAGCATGCCAACAAGAATGCAT

BRRS.524_s_at (SEQ ID NO: 175)
TGCCTGTTGTAGACCACAGTCACACACTGCTGTAGTCTTCCCCAGTCCTCATTCCCAGCTGCCTCTT

CCTACTGCTTCCGTCTATCAAAAAGCCCCCTTGGCCCAGGTTCCCTGAGCTGTGGGATTCTGCACT

GGTGCTTTGGATTCCCTGATATGTTCCTTCAAA

BRRS.5356_at (SEQ ID NO: 176)
GTCAGACAGATGTGGTTGCATCCTAACTCCATGTCTCTGAGCATTAGATTTCTCATTTGCCAATAATA

ATACCTCCCTTAGAAGTTTGTTGTGAGGATTAAATAATGTAAATAAAGAACTAGCATAACACTCAAAA

A

BRRS.5451_at (SEQ ID NO: 177)
TCTGTGTGTGCCCTGTAACCTGACTGGTTAACAGCAGTCCTTTGTAAACAGTGTTTTAAACTCTCCTA

GTCAATATCCACCCCATCCAATTTATCAAGGAAGAAATGGTTCAGAAAATATTTTCAGCCTACAGTTA

TGTTCAGTCACACACACATACAAAATGTTCCTTTTGCTTTTAAAGTAATTTTTGACTCCCAGATCAGTC

AGAGCCCCTACAGCATTGTTAA

BRRS.6371_at (SEQ ID NO: 178)
GTTTAAGCCTGGAACTTGTAAGAAAATGAAAATTTAATTTTTTTTCTAGGACGAGCTATAGAAAAGCT

ATTGAGAGTATCTAGTTAATCAGTGCAGTAGTTGGAAACCTTGCTGGTGTATGTGATGTGCTTCTGT

GCTTTTGAATGACTTTATCATCTAGTCTTTGTCTATTTTTCCTTTGATGTTCAAGTCCTAGTCTATAGG

ATTGGCAGTTTAA

-continued

BRRS.6611_at (SEQ ID NO: 179)
GACTGAGGGATCGTAGATTTTTACAATCTGTATCTTTGACAATTCTGGGTGCGAGTGTGAGAGTGTG

AGCAGGGCTTGCTCCTGCCAACCACAATTCAATGAATCCCCGACCCCCCTACCCCATGCTGTACTT

GTGGTTCTCTTTTTGTATTTTGCATCTGACCCCGGGGGGCTGGGACAGATTGGCAATGGGCCGTCC

CCTCTCCCCTTGGTTCTGCACTGTTGCCAATAAAAAGCTCTTAA

BRRS.6619_at (SEQ ID NO: 180)
GGAGGGAAGGCAAGATTCTTTCCCCCTCCCTGCTGAAGCATGTGGTACAGAGGCAAGAGCAGAGC

CTGAGAAGCGTCAGGTCCCACTTCTGCCATGCAGCTACTATGAGCCCTCGGGGCCTCCTCCTGGG

CCTCAGCTTGCCCAGATACATACCTAAATATATATATATATATATGAGGGAGAACGCCTCACCCAGAT

TTTATCATGCTGGAAAGAGTGTATGTATGTGAAGATGCTTGGTCAACTTGTACCCAGTGAACACACA

AA

BRRS.6619-22_at (SEQ ID NO: 181)
GGAGGGAAGGCAAGATTCTTTCCCCCTCCCTGCTGAAGCATGTGGTACAGAGGCAAGAGCAGAGC

CTGAGAAGCGTCAGGTCCCACTTCTGCCATGCAGCTACTATGAGCCCTCGGGGCCTCCTCCTGGG

CCTCAGCTTGCCCAGATACATACCTAAATATATATATATATATATGAGGGAGAACGCCTCACCCAGAT

TTTATCATGCTGGAAAGAGTGTATGTATGTGAAGATGCTTGGTCAACTTGTACCCAGTGAACACACA

AA

BRRS.6684_at (SEQ ID NO: 182)
TATTCTTCTATAACACTCTATATAGAGCTATGTGAGTACTAATCACATTGAATAATAGTTATAAAATTAT

TGTATAGACATCTGCTTCTTAAACAGATTGTGAGTTCTTTGAGAAACAGCGTGGATTTTACTTATCTG

TGTATTCACAGAGCTTAGCACAGTGCCTGGTAATGAGCAAGCATACTTGCCATTACTTTTCCTTCCCA

BRRS.7616_at (SEQ ID NO: 183)
CCTAATTTGAGGGTCAGTTCCTGCAGAAGTGCCCTTTGCCTCCACTCAATGCCTCAATTTGTTTTCTG

CATGACTGAGAGTCTCAGTGTTGGAACGGGACAGTATTTATGTATGAGTTTTTCCTATTTATTTTGAG

TCTGTGAGGTCTTCTTGTCATGTGAGTGTGGTTGTGAATGATTTCTTTTGAAGATATATTGTAGTAGA

TGTTACAATTTTGTCGCCAAACTAAACTTGCTGCTTAATGATTTGCTCACATCTAGTAAA

BRRS.7901_at (SEQ ID NO: 184)
GGACACTTTTGAAAACAGGACTCAGCATCGCTTTCAATAGGCTTTTCAGGACCTTCACTGCATTAAAA

CAATATTTTAAAAATTTAGTACAGTTTAGAAAGAGCACTTATTTTGTTTATATCCATTTTTTCTTACTA

AATTATAGGGATTAACTTTGACAAATCATGCTGCTGTTATTTTCTACATTTGTATTTTATCCATAGCAC

TTATTCACATTTAGGAAAA

BRRS.81_at (SEQ ID NO: 185)
CAGTTTCTGTTCTCTCACAGGTGATAAACAATGCTTTTTGTGCACTACATACTCTTCAGTGTAGAGCT

CTTGTTTTATGGGAAAAGGCTCAAATGCCAAATTGTGTTTGATGGATTAATATGCCCTTTTGCCGATG

CATACTATTACTGATGTGACTCGGTTTTGTCGCAGCTTTGCTTTGTTTAATGAAACACACTTGTAAAC

CTCTTTTGCACTTTGAAAAGAATCCAGCGGGATGCTCGAGCACCTGTAAACAATTTTCTCAACCTAT

TTG

BRRS.81-22_at (SEQ ID NO: 186)
CAGTTTCTGTTCTCTCACAGGTGATAAACAATGCTTTTTGTGCACTACATACTCTTCAGTGTAGAGCT

CTTGTTTTATGGGAAAAGGCTCAAATGCCAAATTGTGTTTGATGGATTAATATGCCCTTTTGCCGATG

-continued

CATACTATTACTGATGTGACTCGGTTTTGTCGCAGCTTTGCTTTGTTTAATGAAACACACTTGTAAAC

CTCTTTTGCACTTTGAAAAAGAATCCAGCGGGATGCTCGAGCACCTGTAAACAATTTTCTCAACCTAT

TTG

BRRS.8480_s_at
(SEQ ID NO: 187)
AGCAAGTGTAGACACCTTCGAGGGCAGAGATCGGGAGATTTAAGATGTTACAGCATATTTTTTTTC

TTGTTTTACAGTATTCAATTTTGTGTTGATTCAGCTAAATTATGAAA

BRRS.8711_at
(SEQ ID NO: 188)
GTCTCACATATTTATATAATCCTCAAATATACTGTACCATTTTAGATATTTTTTAAACAGATTAATTTGG

AGAAGTTTTATTCATTACCTAATTCTGTGGCAAAAATGGTGCCTCTGATGTTGTGATATAGTATTGTC

AGTGTGTACATATATAAAACCTGTGTAAACCTCTGTCCTTATGAACCATAACAAATGTAGCTTTTTA

BRRS.8900_s_at
(SEQ ID NO: 189)
CAGCCCCACCCCTGTAAATGGAATTTACCAGATGAAGGGAATGAAGTCCCTCACTGAGCCTCAGATT

TCCTCACCTGTGAAATGGGCTGAGGCAGGAAATGGGAAAAAGTGTTAGTGCTTCCAGGCGGCACTG

ACAGCCTCAGTAACAATAAAAACAA

BRSA.1686C1n5_at
(SEQ ID NO: 190)
TCAGCTGCCCTGAAACAGCCCATGTCCCAAGTTCTTCACCTCTATCCAAAGAACTTGATTTGCATGG

ATTTTGGATAAATCATTTCAGTATCATCTCCATCATATGCCTGACCCCTTGCTCCCTTCAATGCTAGA

AAATCGAGTTGGCAAAATGGGGTTTGGGCCCCTCAGAGCCCTGCCCTGCACCCTTGTACAGTGTCT

GTGCCATGGATTTCGTTTTTCTTGGGGTACTCTTGATGTGAAGATAATTTGCA

BRSA.8072C1n2_s_at
(SEQ ID NO: 191)
GAGTGTCTCAGAAGTGTGCTCCTCTGGCCTCAGTTCTCCTCTTTTGGAACAACATAAAACAAATTTAA

TTTTCTACGCCTCTGGGGATATCTGCTCAGCCAATGGAAAATCTGGGTTCAACCAGCCCCTGCCATT

TCTTAAGACTTTCTGCTCCACTCACAGGATCCTGAGCTGCACTTACCTGTGAGAGTCTTCAAACTTTT

AAACCTTGCCAGTCAGGACTTTTGCTATTGCA

Hs369056.20C1n2_at
(SEQ ID NO: 192)
GAGGGACGTCAGAAAATCAGTGCATTGTGGAGTCACTTTTCTGATAAAGGGCACATCAGACTGCAAA

TGGTCCAGACAGCCAGATTCAGGACACTGATGAGTTTCTGGGGTCACCATAGCATCCCTGGAGTCA

GCTGCTCTGCAGCCTGAAGGAGGGCTGACAGTGTGGAGTCACTGCTATTACTTAATGAAATTATATA

GAAATTCTATAATGATTATGTAATTGCATAATGAAAACTCTCCATATCAGAGTTCAGAATATCTCCCAA

TTTCCAGTACAGAATATTATCCATAAC

Hs488293.0CB1n69_at
(SEQ ID NO: 193)
GACAGCAATAACTTCGTTTTAGAAACATTCAAGCAATAGCTTTATAGCTTCAACATATGGTACGTTTTA

ACCTTGAAAGTTTTGCAATGATGAAAGCAGTATTTGTACAAATGAAAAGCAGAATTCTCTTTTATATG

GTTTATACTGTTGATCAGAAATGTTGATTGTGCATTGAGTATTAAAAAATTAGATGTATATTATTCATT

GTTCTTTACTCATGAGTACCTTATAATAATAATAATGTATTCTTTGTTAACAATGCCATGTTGGTACTA

GTTATTAATCATATC

Hs494173.0CB4n15_at
(SEQ ID NO: 194)
GGCAGGATATTGTAAGCCTTGAAAAAGAATTAGGCAGGATATCGGAAGCCCTGATTAGATTCTATCC

TAAGAGCAACAGAAGATCACTGACAGTGTTTTAAATAGATAGACTAGTTTATTAGATTTGCAGTTTAG

AAGTTCCCTTTTTTTGTAATTATTGGACAGTGTAGAGACCGGATGGTGAGAGATGAGTTAGGAAGTT

GTGACAGCTCTCTATACCTACCGCTAATGTAGAGGATTATTTATTTTCATTTCATTACCATTCGTGT

Hs513726.0C2n39_s_at (SEQ ID NO: 195)

GTAATATGTTTATAATCCTTTAGATCTTATAAATATGTGGTATAAGGAATGCCATATAATGTGCCAAAA

ATCTGAGTGCATTTAATTTAATGCTTGCTTATAGTGCTAAAGTTAAATGATCTTAATTCTTTGCAATTAT

ATATGAAAAATGACTGATTTTTCTTAAAATATGTAACTTATATAAATATATCTGTTTGTACAGATTTTAA

CCATAA

Hs514006.0C1n8_at (SEQ ID NO: 196)

GTATCCTTGAACTGGAAACCATCCACGATCGAGTATCGAGTCATTCAACACTATCAATTCCTGGGTG

ACTTTTTGAAAAAGTAGTATCTCTTGTTGCAAGAAATGCTCCATCTGTGAGTCCATGTCTCTCACTGG

AATTGGATGGAAGTGGTGAATTTCAGCCAAAGTGGCCAAAGAAATCCTGTTCCTGTGATTCTGACGT

CATCAGCCTCTGCACCTCTGTCTTCCCTTCTGCCACATGTTGCCTGTTCTCCGTGACTTTGGTAAGA

Hs522202.0C1n6_at (SEQ ID NO: 197)

GAGAGAGTGATCACGCTGCTGTGCCCACCTATGCGGTAGACCTTGTTCCTGGGTTGGGAGATGTTT

TATGATCAGGGTGCAGTAGAAAGAGCACACTAGTAGCAGTAAAGAGAGGTGACCCTGGCTGCAGTT

CTGCCTCTAACTTCCTGAGTGACCTCAGGCTAGTCACACAGTGACTGCTCCCCACATTTCTTTTTGT

AAGCTGCAAGGATTGAATCAGACAATAGCCTCTAAGTTTCTTCTGAACTCTCATACTCAGGGATGCC

AA

Hs524348.0CB1n97_at (SEQ ID NO: 198)

TTCCCTCCCACTAATTTGTTGGCCTTTAACAGCAATTTTGAAAACTGGGTCTTCTGGTTATGTTTTTGT

TTTAAAATCTTTAAATTAGAGGATGCTGTGCCATTGAGTACTTTAAGTTAATATGAGGTTCTGGTTCAA

GGAAAACTTACGTTGGATCTGAACCAATGAGCAGATATTTTGATATGTGCCACTCTTGCATATACATC

TCAGTCCTAACTAAAGGTTCTAGTGGCATCCAGGACCTTTAGGGAGGCATTT

Hs524348.2C1n5_s_at (SEQ ID NO: 199)

CACTGCGTCTGGCAATAATGTAACTTTGAAGCTTAAAAATTAATCCCAGTTTGTAGCAATAACAGAAG

ACTATCTACAACGGAAGAAAGAAGCAACTGCCTTACAGTTCTGTAAAGAATTGGCAAGAAAATAAAG

CCTATAGTTGCC

Hs528836.0C1n3_s_at (SEQ ID NO: 200)

CCCTTACTTACATACTAGCTTCCAAGGACAGGTGGAGGTAGGGCCAGCCTGGCGGGAGTGGAGAA

GCCCAGTCTGTCCTATGTAAGGGACAAAGCCAGGTCTAATGGTACTGGGTAGGGGGCACTGCCAA

GACAATAAGCTAGGCTACTGGGTCCAGCTACTACTTTGGTGGGATTCAGGTGAGTCTCCATGCACTT

CACATGTTACCCAGTGTTCTTGTTACTTCCAAGGAGAACCAAGAATGGCTCTGTCACACTCGAAGCC

AGGTTTGATC

Hs591893.1C1n4_s_at (SEQ ID NO: 201)

CCTCCTTTCTAAATGCAGCGACCTGTGTTCTTCAGCCCTATCCCTTTCTATTCCTCTGACCCCGCCTC

CTTTCTAAATGCAGCGACCTCTGTTCTTCAGCCCTATCCCTTTCTATTCCTCTGACCCCGCCTCCTTT

CTAAATGCAGCGACCTCTG

Hs7155.0CB1n102_at (SEQ ID NO: 202)

GGCGTCGGCGCCTAGGGCGAAGTGAGCCAGGGTGCAGTCGGGAAGCTCCAGGACGAAGCGGCGC

GGCGGAGCCATGGCCCCAGCGCAGACCCCGCGCCGCCCGAGCAGCGGCCCCGACAGTGGCCCG

-continued

```
CGCAGGAGCCGGCGGGCGAAGGCCATGGGCGCCTCAGCGACGCCGCCCTCGGCCCCGCCTCGG

AAACGAAACCTGGCGGGAGCCAGGCGCCGGCGGGAAACGAAACCCGGAGGGAGCCAGGCGCCA

GCGGGAAACGAAAGCGAAGCGT
```

IDO_F1
(SEQ ID NO: 203)
AGAGACATCTGTATGCATTCCTG

IDO_R1
(SEQ ID NO: 204)
GGTATTTTGAGGTCTTTTGTATTGC

IDO_P1
(SEQ ID NO: 205)
ACCCATTGTAACAGAGCCACAAACT

CD2_F1
(SEQ ID NO: 206)
TCTCAGGTCATGTGTAGATGCG

CD2_R1
(SEQ ID NO: 207)
CTCCAGAGTCTCTTAAGCAGATAGG

CD2_P1
(SEQ ID NO: 208)
AGACCCAGGCACACCAATCACTTGA

GBP5_F1
(SEQ ID NO: 209)
AACAACAGATGCAGGAACAGG

GBP5_R1
(SEQ ID NO: 210)
AGTCCTCTGGGCGTGCTG

GBP5_P1
(SEQ ID NO: 211)
CACAGCTCAGCACAACATTCCAAGC

PRAME_F1
(SEQ ID NO: 212)
CTGCATACTTGGACACTAAAGCC

PRAME_R1
(SEQ ID NO: 213)
ATGTTTTCCTCACTCACACTGAAC

PRAME_P1
(SEQ ID NO: 214)
AGCAACAAAGCAGCCACAGTTTCAG

ITGAL_F1
(SEQ ID NO: 215)
ACAGAAAGACTGAGCTCAAGGTG

ITGAL_R1
(SEQ ID NO: 216)
TGCAGGCACTGTGCTTGG

ITGAL_P1
(SEQ ID NO: 217)
AACCACGTCTGCTAACTTGGAGCCC

LRP4_F1
(SEQ ID NO: 218)
TGTAAAAGCAAAATCTCTCTGTCC

LRP4_R1
(SEQ ID NO: 219)
AGTCCAATCTCTCCAGTGAGTAAC

LRP4_P1
(SEQ ID NO: 220)
AATGGAAGCGATTCTCCCATGCTCA

```
APOL3_F1
                                                  (SEQ ID NO: 221)
GACCAGGTGTCTCTAAAAACCC

APOL3_R1
                                                  (SEQ ID NO: 222)
TTGCCTGCTGTATATGAGTAATGAG

APOL3_P1
                                                  (SEQ ID NO: 223)
CCTGGAGAGTATGCGAGAACCTACC

CDR1_F1
                                                  (SEQ ID NO: 224)
GAAGACGTGGATTTTCCTGGAAG

CDR1_R1
                                                  (SEQ ID NO: 225)
TCCAAGTCTTCCAGTAAATCAAGTC

CDR1_P1
                                                  (SEQ ID NO: 226)
TCCAGCAAATCCAGTCTTCCAGCAA

FYB_F1
                                                  (SEQ ID NO: 227)
AACAAATCATCAACTTCCACTGGTC

FYB_R1
                                                  (SEQ ID NO: 228)
TGGAGGGAATCTTTGGAGATTAGTG

FYB_P1
                                                  (SEQ ID NO: 229)
TCTAATCTTGGGGCCTCAGACACCC

TSPAN7_F1
                                                  (SEQ ID NO: 230)
GACATTGAGGACCTCATCCAAAC

TSPAN7_R1
                                                  (SEQ ID NO: 231)
GACAGAGGCATTACTTTTGAAGATC

TSPAN7_P1
                                                  (SEQ ID NO: 232)
TTGACTTGTTCCCCCTTCACACTCA

RAC2_F1
                                                  (SEQ ID NO: 233)
CTCAGTTCTCCTCTTTTGGAACAAC

RAC2_R1
                                                  (SEQ ID NO: 234)
TTGAACCCAGATTTTCCATTGGC

RAC2_P1
                                                  (SEQ ID NO: 235)
TCTACGCCTCTGGGGATATCTGCTC

KLHDC7B_F1
                                                  (SEQ ID NO: 236)
TGGCACTGTGGATTCTCAAGG

KLHDC7B_R1
                                                  (SEQ ID NO: 237)
CTGGGGGTATGGGCAGGAG

KLHDC7B_P1
                                                  (SEQ ID NO: 238)
CACCAGCGGACCAGTTTCAGAGGCA

GRB14_F1
                                                  (SEQ ID NO: 239)
CTAATACAGCTGGTGGAGTTCTATC

GRB14_R1
                                                  (SEQ ID NO: 240)
AGCAATCCTAGCACAATAATGTTTC
```

```
GRB14_P1
                                             (SEQ ID NO: 241)
ACTCAATAAGGGCGTTCTTCCTTGC

KIF26A_F1
                                             (SEQ ID NO: 242)
AGGAATTTTTACCAAAACCACAAGC

KIF26A_R1
                                             (SEQ ID NO: 243)
AACAGAACCTTTACAAAACCCTACC

KIF26A_P1
                                             (SEQ ID NO: 244)
AACAGACCACCACGACCAACAACA

CD274_F1
                                             (SEQ ID NO: 245)
TTGGTGTGACAGTGTTCTTTGTG

CD274_R1
                                             (SEQ ID NO: 246)
AGGAGGAGTTAGGACTTAGGAATAG

CD274_P1
                                             (SEQ ID NO: 247)
TGCCTTGCTCAGCCACAATTCTTGC

CD109_F1
                                             (SEQ ID NO: 248)
TGTGGATTTGAATGTGTGTACAAGC

CD109_R1
                                             (SEQ ID NO: 249)
GGCACCATAAAGCCACTTAATAGG

CD109_P1
                                             (SEQ ID NO: 250)
AAGAGCCATGCCACTCCTACCCGG

ETV7_F1
                                             (SEQ ID NO: 251)
CCCTCACTGAGCCTCAGATTTC

ETV7_R1
                                             (SEQ ID NO: 252)
GCCGCCTGGAAGCACTAAC

ETV7_P1
                                             (SEQ ID NO: 253)
TCCCATTTCCTGCCTCAGCCCATTT

MFAP5_F1
                                             (SEQ ID NO: 254)
GGCTGGTCTGCCCCCTAG

MFAP5_R1
                                             (SEQ ID NO: 255)
ACCATTGGGTCTCTGCAAATCC

MFAP5_P1
                                             (SEQ ID NO: 256)
ACTCCGTCGCTCCAATTACTTCCGA

OLFM4_F1
                                             (SEQ ID NO: 257)
AGGACGAGCTATAGAAAAGCTATTG

OLFM4_R1
                                              SEQ ID NO: 258)
CATTCAAAAGCACAGAAGCACATC

OLFM4_P1
                                             (SEQ ID NO: 259)
CACCAGCAAGGTTTCCAACTACTGC

PI15_F1
                                             (SEQ ID NO: 260)
TTTTCCAGGCTAAAGCAAATGAAAG
```

```
PI15_R1
                                                    (SEQ ID NO: 261)
CTATCCTAGCACCATTGTTGCATG

PI15_P1
                                                    (SEQ ID NO: 262)
TTGCTGGTATCAACACAGCCTGCCA

FOSB_F1
                                                    (SEQ ID NO: 263)
TGAGTGAGACTGAGGGATCGTAG

FOSB_R1
                                                    (SEQ ID NO: 264)
GTGGTTGGCAGGAGCAAGC

FOSB_P1
                                                    (SEQ ID NO: 265)
CACACTCTCACACTCGCACCCAGAA

CXCL10_F1
                                                    (SEQ ID NO: 266)
ACCAGAGGGGAGCAAAATCGA

CXCL10_R1
                                                    (SEQ ID NO: 267)
TGCCTCTCCCATCACTTCCC

CXCL10_P1
                                                    (SEQ ID NO: 268)
CCTCTGTGTGGTCCATCCTTGGAAGCA

MX1_F1
                                                    (SEQ ID NO: 269)
CAGCACCTGATGGCCTATCAC

MX1_R1
                                                    (SEQ ID NO: 270)
CAGTTCTTCATGCTCCAGACGTAC

MX1_P1
                                                    (SEQ ID NO: 271)
CGCATCTCCAGCCACATCCCTTTGA

IFI44L_F1
                                                    (SEQ ID NO: 272)
CCTCTTGAGGAAACTGGTGCAATTG

IFI44L_R1
                                                    (SEQ ID NO: 273)
TGATTCTGACATTTGGCCCAGC

IFI44L_P1
                                                    (SEQ ID NO: 274)
TCTCAAATGCAGGGCTGTAACGCTCTC

AC138128.1_F1
                                                    (SEQ ID NO: 275)
GCTAGAGCAGGACTTCGTCTCC

AC138128.1_R1
                                                    (SEQ ID NO: 276)
GAGAAGATCTGGCCTTATGCCCA

AC138128.1_P1
                                                    (SEQ ID NO: 277)
TCTCTGGAACAGCTCATCGCCGCAT

FAM19A5_F1
                                                    (SEQ ID NO: 278)
GGAAGGCTGCGACTTGTTAATCAA

FAM19A5_R1
                                                    (SEQ ID NO: 279)
CTCCTGACAAACACAGCCCC

FAM19A5_P1
                                                    (SEQ ID NO: 280)
CCGTGGTGGTCTTTATCCTCCCGCC
```

```
NLRC5_F1
                                               (SEQ ID NO: 281)
GAGAGTGGACCTGGAGAAGAATCAG

NLRC5_R1
                                               (SEQ ID NO: 282)
TAGCATCCAAGTCATCCGCCT

NLRC5_P1
                                               (SEQ ID NO: 283)
AGTCCTTCAGCCAGGAGCCAGGC

PRICKLE1_F1
                                               (SEQ ID NO: 284)
GTTCGGGATTCGATGGATTCTTTGG

PRICKLE1_R1
                                               (SEQ ID NO: 285)
CCAAGGCCATCATTGTATTCTCTGC

PRICKLE1_P1
                                               (SEQ ID NO: 286)
TCTCCATCCACCGAAGCCCCTGT

EGR1_F1
                                               (SEQ ID NO: 287)
GCAGCACCTTCAACCCTCAG

EGR1_R1
                                               (SEQ ID NO: 288)
TCTCTGAACAACGAGAAGGTGCT

EGR1_P1
                                               (SEQ ID NO: 289)
CCTACGAGCACCTGACCGCAGAGT

CLDN10_F1
                                               (SEQ ID NO: 290)
AGCCGCTCTGTTTATTGGATGG

CLDN10_R1
                                               (SEQ ID NO: 291)
TCTGACAACAACAAAACACCCAGA

CLDN10_P1
                                               (SEQ ID NO: 292)
ACACCACCAATTATGCACAGTGAGGCT

ADAMTS4_F1
                                               (SEQ ID NO: 293)
TGGCTCCAAGAAGAAGTTTGACAAG

ADAMTS4_R1
                                               (SEQ ID NO: 294)
TCCTTCAGGAAATTCAGGTACGGAT

ADAMTS4_P1
                                               (SEQ ID NO: 295)
CCTGACTGCTTGCTGCAACCAGAACC

SP140L_F1
                                               (SEQ ID NO: 296)
AGTGGAGGGGTTTGTACAAGACA

SP140L_R1
                                               (SEQ ID NO: 297)
CAAATGGGACTTAGACTGGAGGCT

SP140L_P1
                                               (SEQ ID NO: 298)
CGCCTCATCTTCCAGAACCACAGGG

ANXA_F1
                                               (SEQ ID NO: 299)
CCACAAGCAAACCAGCTTTCTTTG

ANXA_R1
                                               (SEQ ID NO: 300)
TGATCAGGATTATGGTTTCCCGTTC
```

```
ANXA_P1
                                                        (SEQ ID NO: 301)
TGGCGAGTTCCAACACCTTTCATGGC

RSAD2_F1
                                                        (SEQ ID NO: 302)
GGAAGAGGACATGACGGAACAGA

RSAD2_R1
                                                        (SEQ ID NO: 303)
GTGTTCCAGTGCCTCTTAATTGAGG

RSAD2_P1
                                                        (SEQ ID NO: 304)
CAAAGCACTAAACCCTGTCCGCTGGAA

ESR1_F1
                                                        (SEQ ID NO: 305)
CTGCAGCAGCAGCACCAG

ESR1_R1
                                                        (SEQ ID NO: 306)
CATCAGGCACATGAGTAACAAAGGC

ESR1_P1
                                                        (SEQ ID NO: 307)
CCCAGCTCCTCCTCATCCTCTCCC

IKZF3_F1
                                                        (SEQ ID NO: 308)
GCAGAGATGGGAAGTGAAAGAGC

IKZF3_R1
                                                        (SEQ ID NO: 309)
TCAATGCCTCAGAAATTCATTGGTG

IKZF3_P1
                                                        (SEQ ID NO: 310)
TGCCACATTGCTTGCTAATCTGTCCAG

EGFR_F1
                                                        (SEQ ID NO: 311)
GACAGCTTCTTGCAGCGATACAG

EGFR_R1
                                                        (SEQ ID NO: 312)
CCTTCCTCCCAGTGCCTGA

EGFR_P1
                                                        (SEQ ID NO: 313)
TCGTCTATGCTGTCCTCAGTCAAGGCG

NAT1_F1
                                                        (SEQ ID NO: 314)
AGAGCACTTCCTCATAGACCTTGG

NAT1_R1
                                                        (SEQ ID NO: 315)
TTCAAGCCAGGAAGAAGCAGC

NAT1_P1
                                                        (SEQ ID NO: 316)
TGCATTCAGTCTAGTTCCTGGTTGCCG

LATS2_F1
                                                        (SEQ ID NO: 317)
GCAAGATGGGCTACCTGGAC

LATS2_R1
                                                        (SEQ ID NO: 318)
TTAAGCAGACCTCCCCAGGA

LATS2_P1
                                                        (SEQ ID NO: 319)
ACCCGCACAATCTGCTCATTCCTCG

CYP2B6_F1
                                                        (SEQ ID NO: 320)
TCTCCTTAGGGAAGCGGATTTGTC
```

```
CYP2B6_R1
                                            (SEQ ID NO: 321)
TTCTTCACCACCATCCTCCAGA

CYB2B6_P1
                                            (SEQ ID NO: 322)
CATCGCCCGTGCGGAATTGTTCCT

PTPRC_F1
                                            (SEQ ID NO: 323)
CTGGCCATCTGCAAGCTGAG

PTPRC_R1
                                            (SEQ ID NO: 324)
CAGTTCAGCCTTCAGTTGGTGG

PTPRC_P1
                                            (SEQ ID NO: 325)
AGCAAGGAAGCCAATCCAAGTCACCAA

PPP1R1A_F1
                                            (SEQ ID NO: 326)
ACCCATATACCACCACTGGATTCC

PPP1R1A_R1
                                            (SEQ ID NO: 327)
CAGTTTGGGAATGCATGGACACC

PPP1R1A_P1
                                            (SEQ ID NO: 328)
ACCTCCTCCTCTCTCAGACCGAGTTGG

STING_a
                                            (SEQ ID: 329)
CAGCGGCUGUAUAUUCUCCUCCCUU

STING_b
                                            (SEQ ID: 330)
GGUCAUAUUACAUCGGAUAUU

TBK1_a
                                            (SEQ ID: 331)
GGAAAUAUCAUGCGUGUUAUU

TBK1_b
                                            (SEQ ID: 332)
UGGUGCAGCUAGAGAAUUAUU

IRF3_a
                                            (SEQ ID: 333)
CCUCUGAGAACCCACUGAAUU

IRF3_b
                                            (SEQ ID: 334)
GGACAAUCCCACUCCCUUCUU cGAS_a
                                            (SEQ ID: 335)
AGAGAAAUGUUGCAGGAAAUU cGAS_b
                                            (SEQ ID: 336)
CAGCUUCUAAGAUGCUGUCAAAGUU

BRCA1_a
                                            (SEQ ID: 337)
CCUAUCGGAAGAAGGCAAGUU

BRCA1_b
                                            (SEQ ID: 338)
CAUACAGCUUCAUAAAUAAUU

BRCA2_a
                                            (SEQ ID: 339)
GGACACAAUUACAACUAAAUU

BRCA2_b
                                            (SEQ ID: 340)
GGAGGAAUAUCGUAGGUAAUU
```

-continued

FancD2_a
(SEQ ID: 341)
GCAGAUUCAUGAAGAGAAAUU

FancD2_b
(SEQ ID: 342)
GGUUAAAGCACAUUGUAGAUU

CXCL10 Forward
(SEQ ID NO: 343)
GGCCATCAAGAATTTACTGAAAGCA

CXCL10 Reverse
(SEQ ID NO: 344)
TCTGTGTGGTCCATCCTTGGAA

CCL5 Forward
(SEQ ID NO: 345)
TGCCCACATCAAGGAGTATTT

CCL5 Reverse
(SEQ ID NO: 346)
CTTTCGGGTGACAAAGACG

IDO1 Forward
(SEQ ID NO: 347)
CATCTGCAAATCGTGACTAAG

IDO1 Reverse
(SEQ ID NO: 348)
CAGTCGACACATTAACCTTCCTTC

PDL1 Forward
(SEQ ID NO: 349)
GGCATCCAAGATACAAACTCAAAGA

PDL1 Reverse
(SEQ ID NO: 350)
AGTTCCAATGCTGGATTACGTCT

PUM1(Housekeeping gene) Forward
(SEQ ID NO: 351)
CCAGAAAGCTCTTGAGTTTATTCC

PUM1 (Housekeeping gene) Reverse
(SEQ ID NO: 352)
CATCTAGTTCCCGAACCATCTC

OR2I1P F1
(SEQ ID NO: 353)
CTCAACCCGCTCATCTACAC

OR2I1P R1
(SEQ ID NO: 354)
TCCTTGGGTTCTGGCTTAATAC

OR2I1P P1
(SEQ ID NO: 355)
TCGCTGCCCCCTTCACTTTCTTATT

AL137218.1 F1

TGCTTCATGTTAGTCCCCAG                                            (SEQ ID NO: 356)

AL137218.1 R1

GGGTCTCACTATATTGCTCTGG                                          (SEQ ID NO: 357)

AL137218.1 P1

CCTCAGCCTTCCAAAACCAGGTGT                                        (SEQ ID NO: 358)

The invention claimed is:

1. A method of treating breast cancer in a human subject comprising:
    (a) obtaining or having obtained a biological sample of the breast cancer from the human subject;
    (b) measuring an expression level of CXCL10 in the biological sample;
    (c) calculating a test score by multiplying the expression level of CXCL10 by a weight value of 0.023;
    (d) comparing the test score to a pre-determined threshold score, wherein the pre-determined threshold score is 0.3681;
    (e) determining that the test score is equal to or greater than the pre-determined threshold score; and
    (f) treating the human subject with (i) at least one antagonist of an inhibitory immune check point and/or (ii) at least one agonist of a stimulatory immune check point if the test score is greater than the pre-determined threshold score.

2. The method of claim 1, further comprising: treating the human subject with a DNA damage therapeutic agent in combination with step (f).

3. The method of claim 1, wherein the human subject is treated with at least one antagonist of an inhibitory immune check point.

4. The method of claim 3, further comprising: treating the human subject with a DNA damage therapeutic agent in combination with the at least one antagonist of the inhibitory immune check point.

5. The method of claim 4, wherein the DNA damage therapeutic agent is chosen from the group consisting of a DNA damaging agent, a DNA repair targeted therapy, an inhibitor of DNA damaging signaling, an inhibitor of DNA damage induced cell cycle arrest, and an inhibitor of a process indirectly leading to DNA damage.

6. The method of claim 3, wherein the at least one antagonist is chosen from the group consisting of an antibody, an inhibitory nucleic acid molecule, MGA271, ipilimumab, indoximod, NLG919, lirilumab, IMP321, BMS-986016, CT-011, nivolumab/BMS-936558, BMS-936559, MGB453, LAG525, PDR001, and pembrolizumab.

7. The method of claim 3, wherein the inhibitory immune checkpoint is selected from the group consisting of A2AR, B7-H3 (CD276), B7-H4 (VTCN1), BTLA (CD272), CTLA-4 (CD152), IDO, KIR, LAG3, PD-1/PD-L1, TIM-3, and VISTA.

8. The method of claim 1, wherein the human subject is treated with at least one agonist of a stimulatory immune check point.

9. The method of claim 8, further comprising: treating the human subject with a DNA damage therapeutic agent in combination with the agonist of the inhibitory immune check point.

10. The method of claim 9, wherein the DNA damage therapeutic agent is chosen from the group consisting of a DNA damaging agent, a DNA repair targeted therapy, an inhibitor of DNA damaging signaling, an inhibitor of DNA damage induced cell cycle arrest, and an inhibitor of a process indirectly leading to DNA damage.

11. The method of claim 8, wherein the at least one agonist is selected from the group consisting of an antibody, a lipocalin, a cytokine, CDX-1127, NKTR-214, BMS-663513, TRX518, CP-870893, MEDI0562, MEDI6469, and MEDI6383.

12. The method of claim 8, wherein the stimulatory immune checkpoint is selected from the group consisting of CD27, CD28, CD40, CD122, CD137, OX40, GITR, and ICOS.

13. The method of claim 1, wherein the at least one antagonist is chosen from the group consisting of an antibody, an inhibitory nucleic acid molecule, MGA271, ipilimumab, indoximod, NLG919, lirilumab, IMP321, BMS-986016, CT-011, nivolumab/BMS-936558, BMS-936559, MGB453, LAG525, PDR001, and pembrolizumab.

14. The method of claim 1, wherein the inhibitory immune checkpoint is selected from the group consisting of A2AR, B7-H3 (CD276), B7-H4 (VTCN1), BTLA (CD272), CTLA-4 (CD152), IDO, KIR, LAG3, PD-1/PD-L1, TIM-3, and VISTA.

15. The method of claim 1, wherein the at least one agonist is selected from the group consisting of an antibody, a lipocalin, a cytokine, CDX-1127, NKTR-214, BMS-663513, TRX518, CP-870893, MEDI0562, MEDI6469, and MEDI6383.

16. The method of claim 1, wherein the stimulatory immune checkpoint is selected from the group consisting of CD27, CD28, CD40, CD122, CD137, OX40, GITR, and ICOS.

17. The method of claim 2, wherein the DNA damage therapeutic agent is chosen from the group consisting of a DNA damaging agent, a DNA repair targeted therapy, an inhibitor of DNA damaging signaling, an inhibitor of DNA damage induced cell cycle arrest, and an inhibitor of a process indirectly leading to DNA damage.

* * * * *

SEQUENCE LISTING

<160> NUMBER OF SEQ ID NOS: 358

<210> SEQ ID NO 1
<211> LENGTH: 541
<212> TYPE: DNA
<213> ORGANISM: Homo sapiens

<400> SEQUENCE: 1

```
gggaccaagg tggagatcaa acgtaagtgc actttcctaa tgcttttct tataaggttt      60
taaatttgga gcctttttgt gtttgagata ttagctcagg tcaattccaa agagtaccag    120
attctttcaa aaagtcagat gagtaaggga tagaaaagta gttcatctta aggaacagcc    180
aagcgctagc cagttaagtg aggcatctca attgcaagat tttctctgca tcggtcaggt    240
tagtgatatt aacagcgaaa agagattttt gtttagggga aagtaattaa gttaacactg    300
tggatcacct tcggccaagg gacacgactg gagattaaac gtaagtaatt tttcactatt    360
gtcttctgaa atttgggtct gatggccagt attgactttt agaggcttaa ataggagttt    420
ggtaaagatt ggtaaatgag ggcatttaag atttgccatg ggttgcaaaa gttaaactca    480
gcttcaaaaa tggatttgga gaaaaaaga ttaaattgct ctaaactgaa tgacacaaag    540
t                                                                   541
```

<210> SEQ ID NO 2
<211> LENGTH: 600
<212> TYPE: DNA
<213> ORGANISM: Homo sapiens

<400> SEQUENCE: 2

```
tttattggtc ttcagatgtg gctgcaaaca cttgagactg aactaagctt aaaacacggt     60
acttagcaat cgggttgcca gcaaagcact ggatgcaagc cttgccttcc agaagcttac    120
cagtcgggtt gccagcaaag cagtggatgc aagacttgcc ctccaggagc ttaccatcac    180
aacgaagaag acaaataaat gcataatata tagacgacat aaatccatac tgtacacatt    240
taagaataaa cagtccagta gtaagaggca gtacatattc aatctgctga gaaatgtaga    300
caataactac tataagaatc ctaatgctac agaagtcact ggctgctggg aaaccgggga    360
aaacttggct atggacgtgg gggcttgtgt cggactctga ataaagagca gaatgattgg    420
cgtcctactg agatacatag taaggggggc gagggcaggg aggaagtggc aagaataaca    480
tttgtgaaga tgtccaggtg agaaatagag gttttaatgc tcaagatgtt tccttttccc    540
```

```
ttttaaatct gacctgtgat ttccagcatt gctatttcga atatcactga ttgtttttaa      600
```

<210> SEQ ID NO 3
<211> LENGTH: 600
<212> TYPE: DNA
<213> ORGANISM: Homo sapiens

<400> SEQUENCE: 3

```
tgtggcacat atacaccatg gaatactatg cagccataaa aaagaatggg atcatgtcct       60
gtgcagcaac gtggatggag ctggaagcca ttatcctaaa tgaactcact cagaaacaga      120
aaaccaaata ccacatgttc tcacttataa gtagaagcta acattgagt acacatggat      180
acaaagaagg gaaccgcaga cactggggcc tacctgaggt cggagcatgg aaggagggtg      240
aggatcaaaa aactacctat ctggtactat gcttttatc tggatgatga ataatctgt      300
acaacaaacc ctggtgacat gcaatttacc tatatagcaa gcctacacat gtgccctga      360
acctaaaaaa aaagttaaaa gaaaacgtt tggattattt tccctctttc gaacaaagac      420
attggtttgc ccaaggacta caaataaacc aacgggaaaa agaaaggtt ccagttttgt      480
ctgaaaattc tgattaagcc tctgggccct acagcctgga gaacctggag aatcctacac      540
ccacagaacc cggctttgtc cccaaagaat aaaaacacct ctctaaaaaa aaaaaaaaaa      600
```

<210> SEQ ID NO 4
<211> LENGTH: 600
<212> TYPE: DNA
<213> ORGANISM: Homo sapiens

<400> SEQUENCE: 4

```
tccttatggg gcccggtatg tgggctccat ggtggctgat gttcatcgca ctctggtcta       60
cggagggata tttctgtacc ccgctaacaa gaagagcccc aatggaaagc tgagactgct      120
gtacgaatgc aaccccatgg cctacgtcat ggagaaggct gggggaatgg ccaccactgg      180
gaaggaggcc gtgttagacg tcattcccac agacattcac cagagggcgc cggtgatctt      240
gggatccccc gacgacgtgc tcgagttcct gaaggtgtat gagaagcact ctgcccagtg      300
agcacctgcc ctgcctgcat ccggagaatt gcctctacct ggacctttg tctcacacag      360
cagtaccctg acctgctgtg caccttacat tcctagagag cagaaataaa aagcatgact      420
atttccacca tcaaatgctg tagaatgctt ggcactccct aaccaaatgc tgtctccata      480
atgccactgg tgttaagata tattttgagt ggatggagga gaaataaact tattcctcct      540
taaaaaaaaa aaaaaaaaaa aaaaaaaaaa aaaaaaaaaa aaaaaaaaaa aaaaaaaaaa      600
```

<210> SEQ ID NO 5
<211> LENGTH: 600
<212> TYPE: DNA
<213> ORGANISM: Homo sapiens

<400> SEQUENCE: 5

```
cgggcgtggt agcgggcgcc tgtagtccca gctactcggg aggctgaggc aggagaatgg       60
cgtgaacccg ggaggcggag cttgcagtga gccgagatcg cgccactgca ctccagcctg      120
ggcgacagag cgagactccg tctcaaaaaa aaaaaaaaaa aaaaaatac aaaaattagc      180
cgggcgtggt ggcccacgcc tgtaatccca gctactcggg aggctaaggc aggaaaattg      240
tttgaaccca ggaggtggag gctgcagtga gctgagattg tgccacttca ctccagcctg      300
ggtgacaaag tgagactccg tcacaacaac aacaacaaaa agcttcccca actaaagcct      360
agaagagctt ctgaggcgct gctttgtcaa aaggaagtct ctaggttctg agctctggct      420
```

```
ttgccttggc tttgccaggg ctctgtgacc aggaaggaag tcagcatgcc tctagaggca    480
aggaggggag gaacactgca ctcttaagct tccgccgtct caaccectca caggagctta    540 ctggcaaaca tgaaaaatcg gcttaccatt aaagttctca atgcaaccat aaaaaaaaaa    600
```

<210> SEQ ID NO 6
<211> LENGTH: 600
<212> TYPE: DNA
<213> ORGANISM: Homo sapiens

<400> SEQUENCE: 6

```
tacagatact cagaagccaa taacatgaca ggagctggga ctggtttgaa cacagggtgt     60
gcagatgggg agggggtact ggccttgggc ctcctatgat gcagacatgg tgaatttaat    120
tcaaggagga ggagaatgtt ttaggcaggt ggttatatgt gggaagataa ttttattcat    180
ggatccaaat gtttgttgag tcctttcttt gtgctaaggt tcttgcggtg aaccagaatt    240
ataacagtga gctcatctga ctgttttagg atgtacagcc tagtgttaac attcttggta    300 tcttttgtg ccttatctaa acatttctc gatcactggt ttcagatgtt catttattat      360
attcttttca aagattcaga gattggcttt tgtcatccac tattgtatgt tttgtttcat    420
tgacctctag tgataccttg atctttccca ctttctgttt tcggattgga gaagatgtac    480
cttttttgtc aactcttact tttatcagat gatcaactca cgtatttgga tctttatttg    540
ttttctcaaa taaatattta aggttataca tttaaaaaaa aaaaaaaaaa aaaaaaaaa    600
```

<210> SEQ ID NO 7
<211> LENGTH: 600
<212> TYPE: DNA
<213> ORGANISM: Homo sapiens

<400> SEQUENCE: 7

```
tgagaagtag ttactgtgca catgtgtaga tttgcagttc tgtggctcct gatggatctg     60
agaagatgga cgtggaggat gaaaatctgt ctgattattt tgaactgatg tttgttgcta    120
tggagatgct gcctatatgt tgatgttgca gacgttaagt cactagccca cagccttgta    180
ttccatactc agagaccctg ctacttactt gacatctcaa cttgaaagtc caattaatat    240
gcacttcaaa ctttaatagg cttcaaacag aatttctttc attatctctg caaacagct     300 tctctcatca tcttgaaatt agtgaatggc attttactgt tttagttgga gtcatttctg    360
tggttttctt tcacatccta cataacaatc catcagtaag ttctatgagc tcttctttga    420
aaacaaacag aatccaactg tttcattccc acttctgctc tggtcaagcc actgccaaca    480 ctcacccttta ttattgtagc accctcattg cctagttctg tcccacagat ttccaataaa    540
aggtgaataa aatcaggtca ctcttctgct aaaaaaaaaa aaaaaaaaaa aaaaaaaaa    600
```

<210> SEQ ID NO 8
<211> LENGTH: 600
<212> TYPE: DNA
<213> ORGANISM: Homo sapiens
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (356)..(364)
<223> OTHER INFORMATION: n is a, c, g, or t

<400> SEQUENCE: 8

```
nnnnntttgc tacagccagg gttagctcag caggtgaaaa ccccgagggt gggtgaaacc    60 cctctgggc tcagacatgc aaaccttggg catctctctg tcccagctgg ccccgccagc   120
cggtaggaag tttcccctga gttctcagtt ttttcttctg aaaaatgagg ggttgtatgc   180
aaggttctcc tcctggcctg tggtccccag agaagggcag gaaggaacct tagataattc   240
tcatatgcat ttaacagacg aggaaactga gacccagagc cgtcacatca atacctcatt   300
tgatcttcat aagagcacct ggaggagggg ggtggggtgt ttgtgttttgt ttaaannnnn   360 nnnngtgaaa aaatgaaga taggcatttt gtagacaatc tggaagttct ggaccggaat    420
ccatgatgta gtcagggaag aaatgacccg tgtccagtaa ccccaggcct cgagtgtgtg   480
gtgtattttt ctacataatt gtaatcattc tatacataca aattcatgtc ttgaccatca   540
tattaatatt tggtaagttt ctctctcttt agagactcca caataaagtt ttcaacatgg   600
```

<210> SEQ ID NO 9
<211> LENGTH: 394
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (201)..(223)
<223> OTHER INFORMATION: n is a, c, g, or t
<220> FEATURE:
<221> NAME/KEY: misc_feature
<222> LOCATION: (226)..(227)
<223> OTHER INFORMATION: n is a, c, g, or t
<220> FEATURE:
<221> NAME/KEY: misc_feature
<222> LOCATION: (229)..(232)
<223> OTHER INFORMATION: n is a, c, g, or t

<400> SEQUENCE: 9

```
tnttntnttt tttttttttt tttttttttt tncatagttg ttatcttaag gtgatttcca    60 atttttttt ccatttacat ttttccacaa gcattgtcca ctttattctg taacctttc    120 aactaccatt ttgaaatttg cttttatcca tgtggttgtt tgtgatgaac tacaggttgc   180
tgactttctt ccccttctgt nnnnnnnnnn nnnnnnnnnn nngtnntnn nnctcaagag   240 gatctcatca gtggaatcat tagatcaaag gatatgactg ttgctcagct ctctgtgtgt   300
atgtaaatta ataggctgtt tatttgagca gttgtaggct tacaaaaata ttgagtcaaa   360
agtatagaat tcccatatat tctcctcttc tccc                               394
```

<210> SEQ ID NO 10
<211> LENGTH: 600
<212> TYPE: DNA
<213> ORGANISM: Homo sapiens

<400> SEQUENCE: 10

```
atcttcccac ctcgatgggg ggttgctgat aagaccttca ggcctcctta ttaccatagg    60
```

```
aactgcatga gtgagttcat gggactcatc cgaggtcact atgaggcaaa gcaaggtggg      120
ttcctgccag ggggagggag tctacacagc acaatgaccc cccatggacc tgatgctgac      180
tgctttgaga aggccagcaa ggtcaagctg gcacctgaga ggattgccga tggcaccatg      240
gcatttatgt ttgaatcatc tttaagtctg gcggtcacaa agtggggact caaggcctcc      300
aggtgtttgg atgagaacta ccacaagtgc tgggagccac tcaagagcca cttcactccc      360
aactccagga acccagcaga acctaattga gactggaaca ttgctaccat aattaagagt      420
agatttgtga agattcttct tcagaatctc atgctttctg gtagtattgg aggagggggt      480
tggttaaaat gaaaattcac ttttcatagt caagtaactc agaacttta tggaaacgca      540 tttgcaaagt tctatggctg tcaccttaat tactcaataa acttgctggt gttctgtgga      600

<210> SEQ ID NO 11
<211> LENGTH: 600
<212> TYPE: DNA
<213> ORGANISM: Homo sapiens

<400> SEQUENCE: 11
gggagctaag tatccagcct ctcccaaacc tctttgaaca aagcttctgt ccctcccaca       60
cctctcacct cacaggcaca tcaggctgca gaatgcgctt tagaaagcat tgttttagtc      120
caggcacagt ggctcacgcc tgtaatccca gcactttggg aggccgaggt gggtggatca      180
caaggttggg agattgagac catcctggct aacacagtga accctgtctc tactaaaaaa      240
aatacaaaaa attagcttgg cgtggtggtg ggcgcctgta gtcccagcag cttgggaggc      300
tgaggctgga gaatggtgtg aacccaggag gcggagcttg cagtgagcca agatcgcgcc      360
actgcactcc agcccgggtg acagagcaag actccgtctc aaaaaaaaga aagaaaaaa      420 gaaagcattg ttttaattga gagggcaggg gctggagaag gagcaagttg tggggagcca      480
ggcttccctc acgcagcctg tggtggatgt gggaaggaga tcaacttctc ctcactctgg      540
gacagacgat gtatggaaac taaaaagaac atgcggcacc ttaaaaaaaa aaaaaaaaaa      600

<210> SEQ ID NO 12
<211> LENGTH: 600
<212> TYPE: DNA
<213> ORGANISM: Homo sapiens

<400> SEQUENCE: 12
tttattggtc ttcagatgtg gctgcaaaca cttgagactg aactaagctt aaaacacggt       60
acttagcaat cgggttgcca gcaaagcact ggatgcaagc cttgccttcc agaagcttac      120
cagtcgggtt gccagcaaag cagtggatgc aagacttgcc ctccaggagc ttaccatcac      180
aacgaagaag acaaataaat gcataatata tagacgacat aaatccatac tgtacacatt      240
taagaataaa cagtccagta gtaagaggca gtacatattc aatctgctga gaaatgtaga      300
caataactac tataagaatc ctaatgctac agaagtcact ggctgctggg aaaccgggga      360
aaacttggct atggacgtgg gggcttgtgt cggactctga ataaagagca gaatgattgg      420
cgtcctactg agatacatag taagggggc gagggcaggg aggaagtggc aagaataaca      480
tttgtgaaga tgtccaggtg agaaatagag gttttaatgc tcaagatgtt cctttccc      540 ttttaaatct gacctgtgat ttccagcatt gctatttcga atatcactga ttgttttaa      600

<210> SEQ ID NO 13
<211> LENGTH: 600
<212> TYPE: DNA
```

<213> ORGANISM: Homo sapiens

<400> SEQUENCE: 13

| | | | | | |
|---|---|---|---|---|---|
| atcccaaagg | cccttttag | ggccgaccac | ttgctcatct | gaggagttgg | acacttgact | 60
| gcgtaaagtg | caacagtaac | gatgttggaa | ggcttatgat | tttactgtgt | atgtatttgg | 120
| gagaagaaat | tctgtcagct | cccaaaggat | aaaccagcag | ttgctttatt | ggtcttcaga | 180
| tgtggctgca | aacacttgag | actgaactaa | gcttaaaaca | cggtacttag | caatcgggtt | 240
| gccagcaaag | cactggatgc | aagccttgcc | ttccagaagc | ttaccagtcg | ggttgccagc | 300
| aaagcagtgg | atgcaagact | tgccctccag | gagcttacca | tcacaacgaa | gaagacaaat | 360
| aaatgcataa | tatatagacg | acataaatcc | atactgtaca | catttaagaa | taaacagtcc | 420
| agtagtaaga | ggcagtacat | attcaatctg | ctgagaaatg | tagacaataa | ctactataag | 480
| aatcctaatg | ctacagaagt | cactggctgc | tgggaaaccg | gggaaaactt | ggctatggac | 540
| gtgggggctt | gtgtcggact | ctgaataaag | agcagaatga | ttggcaaaaa | aaaaaaaaaa | 600

<210> SEQ ID NO 14
<211> LENGTH: 600
<212> TYPE: DNA
<213> ORGANISM: Homo sapiens

<400> SEQUENCE: 14

| | | | | | |
|---|---|---|---|---|---|
| cgtcttctaa | atttccccat | cttctaaacc | caatccaaat | ggcgtctgga | agtccaatgt | 60
| ggcaaggaaa | aacaggtctt | catcgaatct | actaattcca | caccttttat | tgacacagaa | 120
| aatgttgaga | atcccaaatt | tgattgattt | gaagaacatg | tgagaggttt | gactagatga | 180
| tggatgccaa | tattaaatct | gctggagttt | catgtacaag | atgaaggaga | ggcaacatcc | 240
| aaaatagtta | agacatgatt | tccttgaatg | tggcttgaga | aatatggaca | cttaatacta | 300
| ccttgaaaat | aagaatagaa | ataaaggatg | ggattgtgga | atggagattc | agttttcatt | 360
| tggttcatta | attctataag | ccataaaaca | ggtaatataa | aaagcttcca | tgattctatt | 420
| tatatgtaca | tgagaaggaa | cttccaggtg | ttactgtaat | tcctcaacgt | attgtttcga | 480
| cagcactaat | ttaatgccga | tatactctag | atgaagtttt | acattgttga | gctattgctg | 540
| ttctcttggg | aactgaactc | actttcctcc | tgaggctttg | gatttgacat | tgcatttgac | 600

<210> SEQ ID NO 15
<211> LENGTH: 600
<212> TYPE: DNA
<213> ORGANISM: Homo sapiens

<400> SEQUENCE: 15

| | | | | | |
|---|---|---|---|---|---|
| actcaaatgc | tcagaccagc | tcttccgaaa | accaggcctt | atctccaaga | ccagagatag | 60
| tggggagact | tcttggcttg | gtgaggaaaa | gcggacatca | gctggtcaaa | caaactctct | 120
| gaacccctcc | ctccatcgtt | ttcttcactg | tcctccaagc | cagcgggaat | ggcagctgcc | 180
| acgccgccct | aaaagcacac | tcatccctc | acttgccgcg | tcgccctccc | aggctctcaa | 240
| caggggagag | tgtggtgttt | cctgcaggcc | aggccagctg | cctccgcgtg | atcaaagcca | 300
| cactctgggc | tccagagtgg | ggatgacatg | cactcagctc | ttggctccac | tgggatggga | 360
| ggagaggaca | agggaaatgt | caggggcggg | gagggtgaca | gtggccgccc | aaggcccacg | 420
| agcttgttct | tgttctttg | tcacagggac | tgaaaacctc | tcctcatgtt | ctgctttcga | 480
| ttcgttaaga | gagcaacatt | ttacccacac | acagataaag | ttttcccttg | aggaaacaac | 540
| agctttaaaa | gaaaagaaa | aaaaagtct | ttggtaaatg | gcaaaaaaaa | aaaaaaaaaa | 600

<210> SEQ ID NO 16
<211> LENGTH: 600
<212> TYPE: DNA
<213> ORGANISM: Homo sapiens

<400> SEQUENCE: 16

```
gggatttgtt aaaatggagg tctttggtga ccttaacaga aagggttttt gaggagtagt      60
ggagtgggga gggcagcag gaaggggaga ttgtacacac cccaggagac aagtcttcta     120
gcagttctgc cagaatgggc aggagagaag tgccatagag ctggaaggct acattgaata     180
gagaaatttc tttaacttgt tttttaagaa gggtgataaa aaggcatgtt ctgatggtga     240
tagggatgtt tccataactg aaagaaatt gatgtgcaag agaaagaata taattgcagg     300
aggacttgaa gaagttggag agaaaaagcc tttagggacc ctgaaccaat gaatctgaaa     360
ttccccaact gccagatgta tcttcatttt tcattttccg ggagatgtaa tatgtcctaa     420
aaatcacagt cgctagattg aaatcaacct taaaaatcat ctagtccaat gtctactccc     480
agtccactac ttgaatcccc tgtgtcccct cccagtagtc gtcttgacaa cctccactga     540
aaggcaattt ctacactcca tccaccccac caccaaccca tggttcatga tctcttcgga     600
```

<210> SEQ ID NO 17
<211> LENGTH: 600
<212> TYPE: DNA
<213> ORGANISM: Homo sapiens

<400> SEQUENCE: 17

```
ttactatatc aacaactgat aggagaaaca ataaactcat tttcaaagtg aatttgttag      60
aaatggatga taaatattg gttgacttcc ggctttctaa gggtgatgga ttggagttca     120
agagacactt cctgaagatt aaagggaagc tgattgatat tgtgagcagc cagaaggttt     180
ggcttcctgc cacatgatcg gaccatcggc tctggggaat cctgatggag tttcactctt     240
gtctcccagg ctggagtaca atggcatgat ctcagcttac tgcaacctcc gtctcctggg     300
ttcaagcgat tctcctgcct cagccttcca agtagctggg attacaggtg cccaccacca     360
cacctggcta ggttttgtat ttttagtaga gatggggttt ttttcatgtt ggccaggctg     420
atctggaact cctgacctca gtgatccac ctgccttggc ctcccaaagt gctgggattt     480
taggtgtgag ccacctcgcc tggcaaggga ttctgttctt agtccttgaa aaaataaagt     540
tctgaatctt caaaaaaaaa aaaaaaaaaa aaaaaaaaaa aaaaaaaaaa aaaaaaaaaa     600
```

<210> SEQ ID NO 18
<211> LENGTH: 600
<212> TYPE: DNA
<213> ORGANISM: Homo sapiens

<400> SEQUENCE: 18

```
gtgtatcatg agccaaccct caaaggaccc gtattacagt gccacgttgg aaaacgctac      60
aggaagcatg acctatccac atctttccaa gatagacact aacatgtcat gtcccaaaca     120
ttagcacgtg ggggttgagc tctgtgcagt aatcgagatt gggagaattt gggcagcgcg     180
tgagaagtgc taagctactt gttttctcac ttgagcccgg gtaggctgtg ttggccctca     240
cttgggattc tcagcagtta catgaaagtt gtgctgataa tctcttctct tgtaccaatt     300
ttagtcaggc agaaaatggt aaacatgagg gtgctcttgt gacttaattt ttgttcaagg     360
gactaaattg cttatgttta ttccctgtca gcggagtgga gaatgtcatt catcaataaa     420
```

```
ccaaagccaa tagctggaga attgagatct ggttgaaagt ggtttatggt ttacatgctg      480
tactatcctg aggaattgcg agatattgct gaggggaaaa aaaaatgacc ttttcttgaa      540
atgtaacttg aaaacaaaat aaaatgtgga acataaaaaa aaaaaaaaaa aaaaaaaaaa      600

<210> SEQ ID NO 19
<211> LENGTH: 600
<212> TYPE: DNA
<213> ORGANISM: Homo sapiens

<400> SEQUENCE: 19
ccagaggcag aaggattggg actaggccaa catagagatt ggcgatggtt gtgagattct       60
aagagtgtgt gtgcatcttg acaatattag aggaggctga gcccaagcag gcacattctc      120
ttcgacccct ccctcattca gtctgctttg gagtctactg aacatcaagc ttgctatgag      180
caggatctta gagctgagga attggcctcc caatccgaac aggtgttata atcctttctt      240
aataggttgt gctgtggacc caatgtgagg gctgtgctgg tgtaaatggt gacatattga      300
gctgggggga tgctttcggg gtgggggac tggttccatt ccatcaaagg ccctcttgag      360
agtctatcca gggacccatt gttttacttt aacagaccag aaaagatgtt tgttttccat      420
gtcattaccc cagggata ccgaatgtgt gggtagaaat ttctctgtag attaaaaatc      480
agatttttac atggattcaa caaggagcg tcacttggat ttttgttttc atccatgaat      540
gtagctgctt ctgtgtaaaa tgccattttg ctattaaaaa tcaattcacg ctggaaaaaa      600

<210> SEQ ID NO 20
<211> LENGTH: 600
<212> TYPE: DNA
<213> ORGANISM: Homo sapiens

<400> SEQUENCE: 20
gcacgtctac ggggctggac agagtgtggt taaccgggga actgggcaag ccggcgccga       60
gcctgcgtca gccgtgcaag ccgctccttc aggaacttcc gcttgtcgct ggtgtcgctc      120
cgctccttca ggagccagct gtaggtgtcc ttgtcctgca ggagctgcag catggccttc      180
tgaagctgct ggccgtacgt ctggagcatg aagaactgga tgatcaaagg gatgtggctg      240
gagatgcgct tgctggcctc ctggtgatag gccatcaggt gctgaaagat ctcctccatg      300
gaagagtctg ttgccgagct ggactggaaa gccccaaaat cccaggattt cttcttcttt      360
tcttcttcca gctccttctc tctgaccttc tgcaatgcac ccctgtatac ctggtcctgg      420
cagtagacaa tctgttccat ctggaagtgg aggcggatca gcttctcacc ttctctctct      480
tgttctgctc taatgtcttc aattttggac ttggcggttc tgtggaggtt aaaaaactct      540
tcaaaatttt ttatcgccaa cttttttgta caaagttggc cttataaaga aagcattgct      600

<210> SEQ ID NO 21
<211> LENGTH: 600
<212> TYPE: DNA
<213> ORGANISM: Homo sapiens
<220> FEATURE:
<221> NAME/KEY: misc_feature
<222> LOCATION: (1)..(107)
<223> OTHER INFORMATION: n is a, c, g, or t

<400> SEQUENCE: 21
nnnnnnnnnn nnnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnncca atgagtgat      120 gcattgaccg ttcgtaattc ttggatgcaa agtagaact caagctactt aataacaatc      180
```

```
atggtggcat gggcaccagc aagtcagggt ggacaacagc catagttctg gagcatggtc        240
ctcaagacta cctttgtat gcagagtatt aacactttaa ctcttagatc cttggaacat         300
aaggaagaga ggctggaaca aaagggggtt ggcatttgga ggtggagagg tagtgtaagg        360
cacaactgtt tatcaactgg tatctaagta tttcaggcca gacacgtggc tcacacctct        420
aatcccagca ctttgggagc tgagccagga ggattgcttg agtctaggag ttcaagaccg        480
gtctgggcaa catggtgaaa ccctgtctct acaaaaaat acaaaatta gccaggtgtg          540 gtggggcacg cctatggtcc cagctactgg ggaggctgag atgggaggat ccacctgagc        600
```

<210> SEQ ID NO 22
<211> LENGTH: 477
<212> TYPE: DNA
<213> ORGANISM: Homo sapiens

<400> SEQUENCE: 22

```
tttttttaa ttaacttgac tttattgata gttacagcac aatttattaa ttaacttgac          60
tttattgata gttacagcac aatctgtcca aaaccaccag aatatacatt cttttcaaga        120
gctcaaatgg aacatttacc acaaaagacc atattctggg cttcaaaata agcctaaata       180
aatacaaaag catttaggac ctatgaatca gaagactgaa tatgcacata tacaaaatga      240
gaatcattct ctcacataca aaacttatat aggtagtaaa gatacagttg attaggtaga     300
tttgaatgtt gaatcactga catttcctga aggtagagct acaaattact tttttaaaac     360
cactaaccca ccccaccctt acctcactta ctcttttttgg ccttaccacc tactttagtc    420
ataccctata catgttactc agaccaaatg gctctcataa acaatctcag tatatgt         477
```

<210> SEQ ID NO 23
<211> LENGTH: 600
<212> TYPE: DNA
<213> ORGANISM: Homo sapiens
<220> FEATURE:
<221> NAME/KEY: misc_feature
<222> LOCATION: (229)..(316)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t

<400> SEQUENCE: 23

```
ttaagaaggt atggaaagag tctgggagtg actaaactat ccaatgtcat tgaaataaag        60
caatgaagaa taagagtaat ttttgttgct ttattaaatt ttttctcaca gaattcttta      120
taaaaacacc atgtccctaa aatgtcattc aacatatatg cacaccttcg atgtatagga     180
cactgatcaa aaaagacaga gaaatgtgtc cctggtgttt tgttttgnn nnnnnnnnnn      240 nnnnnnnnnn nnnnnnnnnn nnnnnnnnnn nnnnnnnnnn nnnnnnnnnn nnnnnnnnnn     300
nnnnnnnnnn nnnnnggga ctacaggcac ataccaccac acctggcttc atgttcccgg      360
tattagtaca atgccaaaat atttaaaatt cttaaaggtt aactcaaata tcttaagttt     420
tacttcactt acaatttcaa taatgctgaa attttgattg aatattgtgt ttgtagtgct     480
acctcttttt cgttcataag aacaaaagcc tatcattctc ttagtttcta aaaatatat     540 gttcatatgg tttagataca tatataaata tntacacaaa acaatgtttt ttgagttgta    600
```

<210> SEQ ID NO 24
<211> LENGTH: 429
<212> TYPE: DNA

<213> ORGANISM: Homo sapiens

<400> SEQUENCE: 24

| | | | | | | |
|---|---|---|---|---|---|---|
| gcccgtgccg | ccccagccgc | tgccgcctgc | accggacccg | gagccgccat | gcccaagtgt | 60 |
| cccaagtgca | acaaggaggt | gtacttcgcc | gagagggtga | cctctctggg | caaggactgg | 120 |
| catcggccct | gcctgaagtg | cgagaaatgt | gggaagacgc | tgacctctgg | gggccacgct | 180 |
| gagcacgaag | gcaaacccta | ctgcaaccac | ccctgctacg | cagccatgtt | tgggcctaaa | 240 |
| ggctttgggc | ggggcggagc | cgagagccac | actttcaagt | aaaccaggtg | gtggagaccc | 300 |
| catccttggc | tgcttgcagg | gccactgtcc | aggcaaatgc | caggccttgt | ccccagatgc | 360 |
| ccagggctcc | cttgttgccc | ctaatgctct | cagtaaacct | gaacacttgg | aaaaaaaaaa | 420 |
| aaaaaaaaa | | | | | | 429 |

<210> SEQ ID NO 25
<211> LENGTH: 600
<212> TYPE: DNA
<213> ORGANISM: Homo sapiens

<400> SEQUENCE: 25

| | | | | | | |
|---|---|---|---|---|---|---|
| caaccaggaa | gaaccgtacc | agaaccactc | cggccgattc | gtctgcactg | tacccggcta | 60 |
| ctactacttc | accttccagg | tgctgtccca | gtgggaaatc | tgcctgtcca | tcgtctcctc | 120 |
| ctcaaggggc | caggtccgac | gctccctggg | cttctgtgac | accaccaaca | ggggctctt | 180 |
| ccaggtggtg | tcaggggca | tggtgcttca | gctgcagcag | ggtgaccagg | tctgggttga | 240 |
| aaaagacccc | aaaagggtc | acatttacca | gggctctgag | gccgacagcg | tcttcagcgg | 300 |
| cttcctcatc | ttcccatctg | cctgagccag | ggaaggaccc | cctcccccac | ccacctctct | 360 |
| ggcttccatg | ctccgcctgt | aaaatggggg | cgctattgct | tcagctgctg | aagggagggg | 420 |
| gctggctctg | agagcccag | gactggctgc | cccgtgacac | atgctctaag | aagctcgttt | 480 |
| cttagaccct | ttcctggaat | aaacatctgt | gtctgtgtct | gctgaacatg | agcttcagtt | 540 |
| gctactcgga | gcattgagag | ggaggcctaa | gaataataac | aatccagtgc | ttaagagtca | 600 |

<210> SEQ ID NO 26
<211> LENGTH: 600
<212> TYPE: DNA
<213> ORGANISM: Homo sapiens

<400> SEQUENCE: 26

| | | | | | | |
|---|---|---|---|---|---|---|
| gggtcgaccc | ttgccactac | acttcttaag | gcgagcatca | aaagccgggg | aggttgatgt | 60 |
| tgaacagcac | actttagcca | agtatttgat | ggagctgact | ctcatcgact | atgatatggt | 120 |
| gcattatcat | ccttctaagg | tagcagcagc | tgcttcctgc | ttgtctcaga | aggttctagg | 180 |
| acaaggaaaa | tggaacttaa | agcagcagta | ttacacagga | tacacagaga | atgaagtatt | 240 |
| ggaagtcatg | cagcacatgg | ccaagaatgt | ggtgaaagta | aatgaaaact | taactaaatt | 300 |
| catcgccatc | aagaataagt | atgcaagcag | caaactcctg | aagatcagca | tgatccctca | 360 |
| gctgaactca | aaagccgtca | agaccttgc | ctccccactg | ataggaaggt | cctaggctgc | 420 |
| cgtgggccct | gggatgtgt | gcttcattgt | gcccttttc | ttattggttt | agaactcttg | 480 |
| attttgtaca | tagtcctctg | gtctatctca | tgaaacctct | tctcagacca | gttttctaaa | 540 |
| catatattga | ggaaaaataa | agcgattggt | ttttcttaag | gtaaaaaaaa | aaaaaaaaa | 600 |

<210> SEQ ID NO 27
<211> LENGTH: 600

```
<212> TYPE: DNA
<213> ORGANISM: Homo sapiens

<400> SEQUENCE: 27
cagaaaggcc cgcccctccc cagacctcga gttcagccaa aacctcccca tggggcagca      60
gaaaactcat tgtccccttc ctctaattaa aaaagataga aactgtcttt ttcaataaaa     120
agcactgtgg atttctgccc tcctgatgtg catatccgta cttccatgag gtgttttctg     180
tgtgcagaac attgtcacct cctgaggctg tgggccacag ccacctctgc atcttcgaac     240
tcagccatgt ggtcaacatc tggagttttt ggtctcctca gagagctcca tcacaccagt     300
aaggagaagc aatataagtg tgattgcaag aatggtagag gaccgagcac agaaatctta     360
gagatttctt gtcccctctc aggtcatgtg tagatgcgat aaatcaagtg attggtgtgc     420
ctgggtctca ctacaagcag cctatctgct taagagactc tggagtttct tatgtgccct     480
ggtggacact tgcccaccat cctgtgagta aaagtgaaat aaaagctttg actagaaaaa     540
aaaaaaaaaa aaaaaaaaaa aaaaaaaaaa aaaaaaaaaa aaaaaaaaaa aaaaaaaaaa     600

<210> SEQ ID NO 28
<211> LENGTH: 600
<212> TYPE: DNA
<213> ORGANISM: Homo sapiens
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t

<400> SEQUENCE: 28
tcagcactga gtgttcaaag acagtaggac gtcggttgct gacctgcctc ttagaagcta      60
gtttaactca gcgggtaagg atctaggact tctacattag ttaccactgt aatgataaca     120
ccaccagaaa agtctgtagt ttaatatttc ccaccttatg cctgtttctt cattcacgca     180
aagaaaataa aaatataata cctaagcctc tttgtattac ataaagcaaa atgcaaagca     240
ctgtatcttc caaatacttc ctcttgatat ggtggaatta tagagtagta tcatttgtaa     300
cntgaaatgt cttctagggt tgctatgcga aagcaagact gtggtttcat tccaatttcc     360
tgtatatcgg aatcatcacc atctgtgtat gtgtgattga ggtgttgggg atgtcctttg     420 cactgacccct gaactgccag attgacaaaa ccagccagac catagggcta tgatctgcag     480
tagtcctgtg gtgaagagac ttgtttcatc tccgggaaat gcaaaaccat ttataggcat     540
gaagccctac atgatcactt gcagggtgan cctcctccca tccttttccc ttttagggtc     600

<210> SEQ ID NO 29
<211> LENGTH: 600
<212> TYPE: DNA
<213> ORGANISM: Homo sapiens

<400> SEQUENCE: 29
gcctgggacg ctgctgctgt tcaggaaacg atggcagaac gagaagctcg ggttggatgc      60
cggggatgaa tatgaagatg aaaacccttta tgaaggcctg aacctggacg actgctccat     120
gtatgaggac atctcccggg gcctccaggg cacctaccag gatgtgggca gcctcaacat     180
aggagatgtc cagctggaga agccgtgaca ccctactcc tgccaggctg ccccgcctg     240 ctgtgcaccc agctccagtg tctcagctca cttccctggg acattctcct ttcagccctt     300
```

```
ctgggggctt ccttagtcat attcccccag tgggggtgg gagggtaacc tcactcttct    360
ccaggccagg cctccttgga ctcccctggg ggtgtcccac tcttcttccc tctaaactgc    420
cccacctcct aacctaatcc cccgccccg ctgcctttcc caggctcccc tcaccccagc    480
gggtaatgag cccttaatcg ctgcctctag gggagctgat tgtagcagcc tcgttagtgt    540
caccccctcc tccctgatct gtcagggcca cttagtgata ataaattctt cccaactgca    600
```

<210> SEQ ID NO 30
<211> LENGTH: 600
<212> TYPE: DNA
<213> ORGANISM: Homo sapiens

<400> SEQUENCE: 30

```
ggattcagcc agtgcggatt ttccatataa tccaggacaa ggccaagcta taagaaatgg     60
agtcaacaga aactcggcta tcattggagg cgtcattgct gtggtgattt tcaccatcct    120
gtgcaccctg gtcttcctga tccggtacat gttccgccac aagggcacct accataccaa    180
cgaagcaaag gggcggagt cggcagagag cgcgacgcc gccatcatga caacgaccc    240
caacttcaca gagaccattg atgaaagcaa aaaggaatgg ctcatttgag gggtggctac    300
ttggctatgg gataggagg agggaattac tagggaggag agaaagggac aaaagcaccc    360
tgcttcatac tcttgagcac atccttaaaa tatcagcaca gttgggga ggcaggcaat    420
ggaatataat ggaatattct tgagactgat cacaaaaaaa aaaaccttt ttaatatttc    480
tttatagctg agttttccct tctgtatcaa aacaaataa tacaaaaaat gcttttagag    540
tttaagcaat ggttgaaatt tgtaggtaat atctgtctta ttttgtgtgt gtttagaggt    600
```

<210> SEQ ID NO 31
<211> LENGTH: 600
<212> TYPE: DNA
<213> ORGANISM: Homo sapiens

<400> SEQUENCE: 31

```
atgtccaaaa agatacagaa gaactaaaga gctgtggtat acaagacata tttgttttct     60
gcaccagagg ggaactgtca aaatatagag tcccaaacct tctggatctc taccagcaat    120
gtggaattat cacccatcat catccaatcg cagatggagg gactcctgac atagccagct    180
gctgtgaaat aatggaagag cttacaacct gccttaaaaa ttaccgaaaa accttaatac    240
actgctatgg aggacttggg agatcttgtc ttgtagctgc ttgtctccta ctatacctgt    300
ctgacacaat atcaccagag caagcctag acagcctgcg agacctaaga ggatccgggg    360
caatacagac catcaagcaa tacaattatc ttcatgagtt tcgggacaaa ttagctgcac    420
atctatcatc aagagattca caatcaagat ctgtatcaag ataaaggaat tcaaatagca    480
tatatatgac catgtctgaa atgtcagttc tctagcataa tttgtattga aatgaaacca    540
ccagtgttat caacttgaat gtaaatgtac atgtgcagat attcctaaag ttttattgac    600
```

<210> SEQ ID NO 32
<211> LENGTH: 600
<212> TYPE: DNA
<213> ORGANISM: Homo sapiens

<400> SEQUENCE: 32

```
ggtttccttc ccaggacagc tgcagggtag agatcatttt aagtgcttgt ggagttgaca     60
tccctattga ctctttccca gctgatatca gagacttaga cccagcactc cttggattag    120
ctctgcagag tgtcttggtt gagagaataa cctcatagta ccaacatgac atgtgacttg    180
```

```
gaaagagact agaggccaca cttgataaat catggggcac agatatgttc ccacccaaca    240
aatgtgataa gtgattgtgc agccagagcc agccttcctt caatcaaggt ttccaggcag    300
agcaaatacc ctagagattc tctgtgatat aggaaatttg gatcaaggaa gctaaaagaa    360
ttacagggat gttttttaatc ccactatgga ctcagtctcc tggaaatagg tctgtccact    420
cctggtcatt ggtggatgtt aaacccatat tcctttcaac tgctgcctgc tagggaaaac    480
tgctcctcat tatcatcact attattgctc accactgtat cccctctact ggcaagtgg     540 ttgtcaagtt ctagttgttc aataaatgtg ttaataatgc ttaaaaaaaa aaaaaaaaaa    600
```

<210> SEQ ID NO 33
<211> LENGTH: 600
<212> TYPE: DNA
<213> ORGANISM: Homo sapiens

<400> SEQUENCE: 33

```
attccaggaa gcatgggatt ttattttgct tgattttggg cacatgaaat aatagctcta     60
ggaaaatgcg catcttaatg actctttgta aagagaggca tttcttacaa ctgtgatgtt    120
tgcttacata aaagttacct cataagttaa ttctaacttt tattcttgaa ttttatttca    180
tttcaatagc ttgtttcatt tgcacgcctt tgtatttga ttgacctgta gaatggatgt     240
taggaaactc aaaattgaac acagtgaaac aaatggtatt tgaagaaatg taatatcttt    300
tatattctat ttatgatatc cataatcaaa tgagattatt ttaccacata aatgttttaa    360
atatcagatt tttagtttgc agttttagga aaatgcttta gatagaaaag gttcttatgc    420
attgaatttg gagtactacc aacaatgaat gaatttattt tttatattct tacacatttt    480
attggtcatt gtcacagata gtaaatacta aaaatttcag gtcagttgt tttgaaactg     540 aaattggaaa taaatctgga aatgttttgt tgcactaaaa taataaatg aattgtactg     600
```

<210> SEQ ID NO 34
<211> LENGTH: 600
<212> TYPE: DNA
<213> ORGANISM: Homo sapiens

<400> SEQUENCE: 34

```
taggccagcc ctgtcaccac ctccactgcc atgaccaggc cgaaggcagg gaacgccctc     60
cccagtcccg ctgtccagca aggccccgag acttttcttc tgtgatttcc aaaagcaagg    120
cagccgtgct gttctagttc ctctccatcc gccacctccc ctcccgctgc cccagaagtt    180
tctatcattc catggagaaa gctgtgttcc aatgaatcct acctcttgcc cagtcccagg    240
cagagtaagc agggcccacc tagggaccaa gaaagagtag gaagaagggg acgagccggg    300
agcaaaacca cctcagacac ccgggccttc tcagccttct ccccgcggcc agctgggtct    360
ccggggaccc tgggccctgg gccgcccatt cctggccctc ccgctgcatc tcagacctga    420
cacccaacgg ggggatgtgg tggcctgtgc ccacttctc tccctcctcc cgaccgcccc     480
cctcgccccc accctgtgt gtttcgccag ttaagcacct gtgactccag tacctactac    540
tggttttggg ttggttgttc tgtctttttt ttaattaaat aaaaacattt ttaaaatgtt    600
```

<210> SEQ ID NO 35
<211> LENGTH: 600
<212> TYPE: DNA
<213> ORGANISM: Homo sapiens

<400> SEQUENCE: 35

```
tgctcagacc agctcttccg aaaaccaggc cttatctcca agaccagaga tagtggggag    60
acttcttggc ttggtgagga aaagcggaca tcagctggtc aaacaaactc tctgaacccc   120
tccctccatc gttttcttca ctgtcctcca agccagcggg aatggcagct gccacgccgc   180
cctaaaagca cactcatccc ctcacttgcc gcgtcgccct cccaggctct caacagggga   240
gagtgtggtg tttcctgcag gccaggccag ctgcctccgc gtgatcaaag ccacactctg   300
ggctccagag tggggatgac atgcactcag ctcttggctc cactgggatg ggaggagagg   360
acaagggaaa tgtcaggggc ggggagggtg acagtggccg cccaaggccc acgagcttgt   420
tctttgttct ttgtcacagg gactgaaaac ctctcctcat gttctgcttt cgattcgtta   480
agagagcaac attttaccca cacacagata aagttttccc ttgaggaaac aacagcttta   540
aaagaaaaag aaaaaaaaag tctttggtaa atggcaaaaa aaaaaaaaaa aaaaaaaaa    600
```

<210> SEQ ID NO 36
<211> LENGTH: 600
<212> TYPE: DNA
<213> ORGANISM: Homo sapiens
<400> SEQUENCE: 36

```
tccccagaca ccgccacatg gcttcctcct gcgtgcatgt gcgcacacac acacacacac    60
gcacacacac acacacacac tcactgcgga gaaccttgtg cctggctcag agccagtctt   120
tttggtgagg gtaaccccaa acctccaaaa ctcctgcccc tgttctcttc cactctcctt   180
gctacccaga aatcatctaa atacctgccc tgacatgcac acctcccctg ccccaccagc   240
ccactggcca tctccacccg gagctgctgt gtcctctgga tctgctcgtc attttccttc   300
ccttctccat ctctctggcc ctctacccct gatctgacat ccccactcac gaatattatg   360
cccagtttct gcctctgagg gaaagcccag aaaaggacag aaacgaagta gaaggggcc    420 cagtcctggc ctggcttctc ctttggaagt gaggcattgc acgggagac gtacgtatca    480 gcggcccctt gactctgggg actccgggtt tgagatggac acactggtgt ggattaacct   540
gccagggaga cagagctcac aataaaaatg gctcagatgc cacttcaaag aaaaaaaaaa   600
```

<210> SEQ ID NO 37
<211> LENGTH: 420
<212> TYPE: DNA
<213> ORGANISM: Homo sapiens
<400> SEQUENCE: 37

```
gggcggttct ccaagcaccc agcatcctgc tagacgcgcc gcgcaccgac ggaggggaca    60
tgggcagagc aatggtggcc aggctcgggc tggggctgct gctgctggca ctgctcctac   120
ccacgcagat ttattccagt gaaacaacaa ctggaacttc aagtaactcc tcccagagta   180
cttccaactc tggggttggcc ccaaatccaa ctaatgccac caccaaggtg gctggtggtg   240
ccctgcagtc aacagccagt ctcttcgtgg tctcactctc tcttctgcat ctctactctt   300
aagagactca ggccaagaaa cgtcttctaa atttccccat cttctaaacc caatccaaat   360
ggcgtctgga agtccaatgt ggcaaggaaa acaggtctt catcgaatct actaattcca   420
```

<210> SEQ ID NO 38
<211> LENGTH: 600
<212> TYPE: DNA
<213> ORGANISM: Homo sapiens
<220> FEATURE:
<221> NAME/KEY: misc_feature
<222> LOCATION: (187)..(187)
<223> OTHER INFORMATION: n is a, c, g, or t

```
<220> FEATURE:
<221> NAME/KEY: misc_feature
<222> LOCATION: (514)..(515)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (523)..(524)
<223> OTHER INFORMATION: n is a, c, g, or t
<220> FEATURE:
<221> NAME/KEY: misc_feature
<222> LOCATION: (526)..(527)
<223> OTHER INFORMATION: n is a, c, g, or t
<220> FEATURE:
<221> NAME/KEY: misc_feature
<222> LOCATION: (583)..(585)
<223> OTHER INFORMATION: n is a, c, g, or t

<400> SEQUENCE: 38
accctgtgcc agaaaagcct cattcgttgt gcttgaaccc ttgaatgcca ccagctgtca     60
tcactacaca gccctcctaa gaggcttcct ggaggtttcg agattcagat gccctgggag    120
atcccagagt ttcctttccc tcttggccat attctggtgt caatgacaag gagtaccttg    180
gctttgncac atgtcaaggc tgaagaaaca gtgtctccaa cagagctcct tgtgttatct    240
gtttgtacat gtgcatttgt acagtaattg gtgtgacagt gttctttgtg tgaattacag    300
gcaagaattg tggctgagca aggcacatag tctactcagt ctattcctaa gtcctaactc    360
ctccttgtgg tgttggattt gtaaggcact ttatcccttt tgtctcatgt ttcatcgtaa    420
atggcatagg cagagatgat acctaattct gcatttgatt gtcactttt gtacctgcat     480 taatttaata aaatattctt atttattttg ttanntngta nannannatg tccattttct    540
tgtttatttt gtgtttaata aaatgttcag tttaacatcc cannngagaa agttaaaaaa    600

<210> SEQ ID NO 39
<211> LENGTH: 523
<212> TYPE: DNA
<213> ORGANISM: Homo sapiens

<400> SEQUENCE: 39
ctcctggttc aaaagcagct aaaccaaaag aagcctccag acagccctga gatcacctaa     60
aaagctgcta ccaagacagc cacgaagatc ctaccaaaat gaagcgcttc ctcttcctcc    120
tactcaccat cagcctcctg gttatggtac agatacaaac tggactctca ggacaaaacg    180
acaccagcca aaccagcagc ccctcagcat ccagcaacat aagcggaggc attttccttt    240
tcttcgtggc caatgccata atccacctct tctgcttcag ttgaggtgac acgtctcagc    300
cttagccctg tgccccctga acagctgcc accatcactc gcaagagaat ccctccatc     360 tttgggaggg gttgatgcca gacatcacca ggttgtagaa gttgacaggc agtgccatgg    420
gggcaacagc caaataggg gggtaatgat gtagggggcca agcagtgccc agctgggggt   480
caataaagtt accctgtac ttgcaaaaaa aaaaaaaaa aaa                        523

<210> SEQ ID NO 40
<211> LENGTH: 600
<212> TYPE: DNA
<213> ORGANISM: Homo sapiens
```

```
<400> SEQUENCE: 40
gccatcaaga atttactgaa agcagttagc aaggaaaggt ctaaaagatc tccttaaaac    60
cagaggggag caaatcgat gcagtgcttc caaggatgga ccacacagag gctgcctctc   120
ccatcacttc cctacatgga gtatatgtca agccataatt gttcttagtt tgcagttaca   180
ctaaaaggtg accaatcatg gtcaccaaat cagctgctac tactcctgta ggaaggttaa   240
tgttcatcat cctaagctat tcagtaataa ctctaccctg cactataat gtaagctcta    300 ctgaggtgct atgttcttag tggatgttct gaccctgctt caaatatttc cctcaccttt   360
cccatcttcc aagggtataa ggaatctttc tgctttgggg tttatcagaa ttctcagaat   420
ctcaaataac taaaaggtat gcaatcaaat ctgcttttta aagaatgctc tttacttcat   480
ggacttccac tgccatcctc caagggggcc caaattcttt cagtggctac ctacatacaa   540
ttccaaacac atacaggaag gtagaaatat ctgaaaatgt atgtgtaagt attcttattt   600

<210> SEQ ID NO 41
<211> LENGTH: 513
<212> TYPE: DNA
<213> ORGANISM: Homo sapiens

<400> SEQUENCE: 41
gggaaatcag tgaatgaagc ctcctatgat ggcaaataca gctcctattg ataggacata    60
gtggaagtgg gctacaacgt agtacgtgtc gtgtagtacg atgtctagtg atgagtttgc   120
taatacaatg ccagtcaggc cacctacggt gaaagaaag atgaatccta gggctcagag    180
cactgcagca gatcatttca tattgcttcc gtggagtgtg gcgagtcagc taatgcag    240 gggcagcaag atggtgttgc agacccaggt cttcatttct ctgttgctct ggatctctgg   300
tgcctacggg gacatcgtga tgacccagtc tccagactcc ctggctgtgt ctctgggcga   360
gagggccacc atcaagtgca gtccagcca gagtatttta tataggtcca acaacaagaa   420
ctacttagct tggtaccagc agaaagcagg acagcctcct aaattgttca tttactgggc   480
atctacccgg gaatccgggg tccctgaccg att                                513

<210> SEQ ID NO 42
<211> LENGTH: 600
<212> TYPE: DNA
<213> ORGANISM: Homo sapiens

<400> SEQUENCE: 42
aacgaaagtc tagcctttcg tacccgtata tataaagaca cccctgttct gattggacaa    60
ggcagccttt cccctgcagc tcgattggtg gagacgccca ctccctgaca gaacatctcc   120
tgcatgtaga ccaaatatta aaactttcct ccgtccatct ttaactgctg gtgttttcaa   180 cccttttcccc tctgtgccat gtttctagct tttatttaaa acgtactttg gttttccttg   240
gcaaaattgt gtctagctac taggatgacg tgtcttaatt ttttttttaaa tgttggcgct   300 gaaactggct ttgatcaacg ttttaaaaag acgcgcgcta gttgtgattg ccaagtgat    360 ttcttcttac cctcttaagt ttagaaaggt taatttcata tcttgatttg tctatttaaa   420
cttggagata ttttcaataa tttgttccaa atgcaccatg actattaact cataagtaac   480
aatatgaaac ctgatgttaa gctacatgaa cacatttaat ttcaccacaa tatgacatcc   540
tcatatgaaa gcactctctt atcttttaca agttcaactg gtatttgtgt aatctgctgt   600

<210> SEQ ID NO 43
<211> LENGTH: 600
```

```
<212> TYPE: DNA
<213> ORGANISM: Homo sapiens
<220> FEATURE:
<221> NAME/KEY: misc_feature
<222> LOCATION: (102)..(104)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (389)..(390)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t

<400> SEQUENCE: 43
tgctaccatg cctgactagt ttttgtattt ttagtagaga cagggtttga ccatattggc     60
caggttggtc ttggactcct gacaagtgat ccgccctcct cnnncncncg aagtgctagg    120
gttacnaggt gtgaaccacc atgcctaact atcgttgcta ctttctattg gaagagaagg    180
cagccctgat ttagtctgtt tacagtctgc attatgtgga gaatagagag ccatcatagt    240
ccctaaaact ttccttgcca gttaacccag caggacaacc tgtctttgtc tcttgacaac    300
tgttaactga gaacagggcc cttgctcctc taggtgtgca cattaaggac tttgcacagt    360
gtggatgtag ctcatgctgc tctgccntnn agtacatgct gcttgaattt tcatcatnan    420
cctccacncc ttncacctnc nngnnaaaaa aaaagcgtgc aggaagtagc atttcagatc    480
cttctccacc acctctgctt cccttctccc ttcttttcct ccttgcagca ttcccttag    540
```

```
tacnagggag ggatggtggt tgaaaatggg gggaatgatg ttgctcagaa aaaaaaaaa      600
```

<210> SEQ ID NO 44
<211> LENGTH: 600
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 44

```
ataatgctgg aaacagaagc accaaactga ttgtgcaatt actccttttg tagaagaggc      60
caaaatcctc ctcctccttc ctttctccta tattcactcc tccaggatca taaagcctcc     120
ctcttgttta tctgtgtctg tctgtctgat tggttagatt tggctncect tccaagctaa     180
tggtgtcagg tggagaacag agcaaccttc cctcggaagg agacaattcg aggtgctggt     240
acatttccct tgttttctat gttcttcttt ctagtgggtc tcatgtagag atagagatat     300
tttttttgttt tagagattcc aaagtatata ttttttagtgt aagaaatgta ccctctccac    360
actccatgat gtaaatagaa ccaggaataa atgtgtcatt gtgataatcc catagcaatt    420
tatggtaaga acaagacccc tttccctcac caccgagtct cgtggtctgt gtctgtgaac    480
cagggcaggt aattgtgaca ctgcatctca tagaactctg cctgcccaga ttttttgtgtg    540
ctcacctcaa tgggtgaaaa ataaagtctg tgtaaactgt taaaaaaaaa aaaaaaaaa     600
```

<210> SEQ ID NO 45
<211> LENGTH: 497
<212> TYPE: DNA
<213> ORGANISM: Homo sapiens
<220> FEATURE:
<221> NAME/KEY: misc_feature
<222> LOCATION: (383)..(384)
<223> OTHER INFORMATION: n is a, c, g, or t
<220> FEATURE:
<221> NAME/KEY: misc_feature
<222> LOCATION: (464)..(466)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t

<400> SEQUENCE: 45

```
tcctcagacc cagtaattcc acccctagga atccagctta cacacacaag aaagaaaaga      60
taaatgtaca aggttagtca ctgcacagtg agacagcaaa agattagaaa gaacccaagt    120
gattattgat ctgggtttta ttcctttata gcccaaccat atgatggaat actataatgt    180
tgtaaaaatg ggttaagagt tctttatgaa ttggtgtgga aacatcgcca agatatgaaa    240
gccaaatgca gaaaaatata tgtggtatgc tattatctat gtgaaaaaga cattactatt    300
ctctggaagg ataaacacaa atttgagaat ggtggatatc tggggtgaga ggtatccttt    360
tcactgttct ttaaaagttt tgnnatttg gtgtttgcct attcaaaaaa atggttaaaa    420
tcagttgcca ccaattaaaa attaggagaa tgcatataaa gaannnaant tcctgttaaa    480
aaaaaaaaa aaaaaaa                                                    497
```

<210> SEQ ID NO 46
<211> LENGTH: 600
<212> TYPE: DNA
<213> ORGANISM: Homo sapiens

<400> SEQUENCE: 46

```
gcccatagtc ccatctttt  acaggcattt tttacacctg gagcagccag aggacgcatg   60
catggctctt cggaaggtaa tttagggatc acccatgtaa gtttcctaag gatttcttta  120
acatggttct tctgattcag tccggccaat taaatctaaa tccacccctg aaagccatct  180 ggtgtgata  acaagcccac aaatgagcag tcagctttt  gtgccctta  gggcctggga  240 caaccacggg atctaaaagg ggctggaact agaggtcttg agctcctgtt cctaaaatca  300
tcttcatcct atatctgcag ccttctcctg ccacggcatg cacccacaca tgcgagcctc  360
ccgggtactg tcatcctgaa ttctgagacc atccagcact cctttagtt  ttgccctggt  420 gctgttgact tttgtttact gaagagtgtg ctggaggcag acaagggac  atggaaggct  480 gcaatttaag agtctaaaag gttttagaat cctgaaggag gtttaacaag ctgaattgaa  540
gaataatacc tttctcaact ggagagaatt tacatgattg cattattgtt aaaattaaca  600

<210> SEQ ID NO 47
<211> LENGTH: 600
<212> TYPE: DNA
<213> ORGANISM: Homo sapiens

<400> SEQUENCE: 47
atcatttagt tgaatcatta taagtctagg actgtctgta gatgtaaatt tgttaagaat   60
taggactcaa gagtagaatt cctttaatcc acatagactt acaatggtgc tgtgcacatg  120
gagcccctaa atcattgctg actgagtaga tttcccaggg taagcccaag aagttactcc  180
tagaaggggc tggtagggga aagagccaac atcccacatg cctgcccact ttgggtctgg  240
tcccaagaaa caaactccag tggcctcgaa aatttaatat tgctgtcaga agggcctccc  300
cttcaaagga acaggtcctg atagctcttg ttatatgcaa agtggaaagg taacgtgact  360
gttctctgca tttcctgcct ttcaattgag tgaagacaga cagatgattt attgggcatt  420
tcctagcctc cccttcacca taggaaacca gactgaaaaa aaggtgcaaa ttttaaaaag  480
atgtgtgagt atcttgaggg ggctggggga gaattcctgt gtaccactaa agcaaaaaaa  540
gaaaactctc taacagcagg acctctgatc tggaggcata ttgaccataa atttacgcca  600

<210> SEQ ID NO 48
<211> LENGTH: 491
<212> TYPE: DNA
<213> ORGANISM: Homo sapiens

<400> SEQUENCE: 48
tttttctgag caacatcatt ccccccattt tcaaccacca tccctccctg gtactaaagg   60
gaatgctgca aggaggaaaa gaagggagaa gggaagcaga ggtggtggag aaggatctga  120
aatgctactt cctgcacgct ttttttcttc ttggaggtgg aaggagtgga ggatgatgat  180
gaaaattcaa gcagcatgta ctagacggca gagcagcatg agctacatcc acactgtgca  240
aagtccttaa tgtgcacacc tagaggagca agggccctgt tctcagttaa cagttgtcaa  300
gagacaaaga caggttgtcc tgctgggtta actggcaagg aaagttttag ggactatgat  360
ggctctctat tctccacata atgcagactg taaacagact aaatcagggc tgccttctct  420
tccaatagaa agtagcaacg atagttaggc atggtggttc acaccttgta accctagcac  480
ttcgtgggca g                                                      491

<210> SEQ ID NO 49
<211> LENGTH: 600
<212> TYPE: DNA
```

<213> ORGANISM: Homo sapiens

<400> SEQUENCE: 49

| | | | | | |
|---|---|---|---|---|---|
| atcagaacaa | tttcatgtta | tacaaataac | atcagaaaaa | tatcttaaat | tatatggcat | 60 |
| attctattga | ttcatccaca | aatttataag | tccttaccac | ctttcattat | attggtacta | 120 |
| ggcattatag | tagtgctagg | cactatagta | atgctggggt | ataaacaaga | ataaaacaaa | 180 |
| ataagttcct | tatttcaggt | aacttacagt | ataggtcagt | ggttcttagc | ttgcttttta | 240 |
| attatgaatt | cctttgaaag | tctagtaaaa | taatccaaca | ccattattcc | ccattgcaca | 300 |
| tacccccaga | tgttttagac | atattttcaa | ttgctccatg | gaccttaaga | aaacttggtt | 360 |
| ggtgtgcagt | ttggtgtatt | atgggtaaga | ctggacctgg | tgttagaaaa | tctgcatttg | 420 |
| aggctttgtt | ctgacagtgt | ctagtgtaaa | catgggcaga | ccacttaaac | ctctctttag | 480 |
| tcttctctgt | agaatgatga | taataccatc | taattagcag | gattgttgtt | ttattcagtg | 540 |
| agacagcata | tgtaaataac | ttagtaaaat | aaaaagcaac | gtgtttataa | tggtaaaaaa | 600 |

<210> SEQ ID NO 50
<211> LENGTH: 600
<212> TYPE: DNA
<213> ORGANISM: Homo sapiens

<400> SEQUENCE: 50

| | | | | | |
|---|---|---|---|---|---|
| tgggaatcat | gaactccttc | gtcaacgaca | tcttcgaacg | catcgcgggt | gaggcttccc | 60 |
| gcctggcgca | ttacaacaag | cgctcgacca | tcacctccag | ggagatccag | acggccgtgc | 120 |
| gcctgctgct | gcccggggag | ttggccaagc | acgccgtgtc | cgagggcacc | aaggccgtca | 180 |
| ccaagtacac | cagcgctaag | taaacttgcc | aaggagggac | tttctctgga | atttcctgat | 240 |
| atgaccaaga | aagcttctta | tcaaaagaag | cacaattgcc | ttcggttacc | tcattatcta | 300 |
| ctgcagaaaa | gaagacgaga | atgcaaccat | acctagatgg | acttttccac | aagctaaagc | 360 |
| tggcctcttg | atctcattca | gattccaaag | agaatcattt | acaagttaat | ttctgtctcc | 420 |
| ttggtccatt | ccttctctct | aataatcatt | tactgttcct | caaagaattg | tctacattac | 480 |
| ccatctcctc | ttttgcctct | gagaaagagt | atataagctt | ctgtacccca | ctgggggggtt | 540 |
| ggggtaatat | tctgtggtcc | tcagccctgt | accttaataa | atttgtatgc | cttttctctt | 600 |

<210> SEQ ID NO 51
<211> LENGTH: 600
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature

```
<222> LOCATION: (67)..(67)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 51
gaaagtgata atacagaaag gtggggctgg tgtagggntn aagncaggat gctttggnan      60
agcatgnaag gtcnccgant ccagtgntna ggaactaatg angggtttnt naagancgtn     120
atgagatcaa tgcngatgag ncacttagaa gnagcaatta gttaggcaaa gggaagtgaa     180
tgtgnaggag gaacaagcat tccaggcaag aagaacaccc tatcgaaaag cctggaagca     240
aaacattagt gaggctacct ttcataaatt gctttctgta agtcatgcca ttgtgtagtc     300
ttaattgctt tctctcacca gggaaggtgt gggaaggact tgtgaaatac atattcgagg     360
aaaaactatg cacaaggccg tgcatttaaa aataaactcc ctaaggctgg ggtgaaacct     420
gctacggtct gcgcaagttg actgttaatg aatttgattc tcaggtgtga gtgattaaaa     480
gaacactgat catgtcattt tcttttggt cactaattcc ctccctccct tctctttctt      540
ttcttttttc ttttctttc ttttctttc tttcttcccg acagagaaag actccatctc       600

<210> SEQ ID NO 52
```

<211> LENGTH: 600
<212> TYPE: DNA
<213> ORGANISM: Homo sapiens

<400> SEQUENCE: 52

```
taagatgttt aagtatatcc aaccgtccca gaccacattg gcctatttcc tcctcttggc    60
aacactgctc gggttttccc ctcgcatcat ccttatgcta tgacactgga ctaaattgta   120
ataatacatt ttcttgttaa tctcctcatt atactatgag ctccttgagg acaggtactt   180
tgtcttgctc acatctgtag attcaatgcc tggcacagcg attgatattg caagggcact   240
taataaatgg tttttgaata aaagaattgc ttaaagtaaa atatagctgt aaattgtatt   300
ataaaaggac agtgggtggc agtctgaggt ctgctattta ctggtttggg caagttactt   360
aatctgtttg cttcctcagc tgtacgatgg gtaaaataat agtggttatc acaacagggt   420
ggttacagcg atgaaatgag attatgtgtg taggctacca cataattgta aagctgatat   480
ttaaatggaa cagatactgc acagacactt gaggtctgag aataagatta ggtcaaccag   540
agtattaatg ggttaaataa aggtgacatc ctatgcaacc aacggtttga tctttatgct   600
```

<210> SEQ ID NO 53
<211> LENGTH: 600
<212> TYPE: DNA
<213> ORGANISM: Homo sapiens

<400> SEQUENCE: 53

```
gtcttccagt cagtcagtgt cttccagaaa atctacgtc ttccaccaaa tccaggtctt     60
ccagtcaatc cacatcttcc ggaaaaaatc caggtcttcc agccaatata tgtcttcctg   120
aagatccacg tcttccagaa atccatgtc ttccagaaaa tccatgtctt ccagtaacct   180
cccagtcttc cagaaaatcc acgtcttccc aacaatccaa gtcttccgga taatttgggt   240
cttcctgaaa atctacgtct tccaaaaaag ccatgtcttc cagaaaatcc acatcttcca   300
atggcctcca ggtcttccag actatccatg tcttccagaa atccttgtc ttcccttaaa   360
tctatagctt ccaaaaaatc cgggtcttcc aggaaatccg tgtcttccag caagtccacg   420
tcttccaaca aagccatgtc ttccagacta ccatgtctt ccagaaaatc cttgtcttcc   480
ctcaaatcca tagcttccga aaaatccagg tcttccagga atccgtgtc ttccagcaaa   540
tccacgtctt ccaacaaagc catgtcttcc atcaaattaa tgtcttccag cctacttgtg   600
```

<210> SEQ ID NO 54
<211> LENGTH: 600
<212> TYPE: DNA
<213> ORGANISM: Homo sapiens

<400> SEQUENCE: 54

```
agcatcgttt atgaaaacaa ctaaatattc actaatggtg ccagtggaat aaatcagaga    60
acatccctg ctacgtaact ctctgcatac atcaaagaga atggtgtggc tttgcttttt   120
caacaatcta ctgagtggcc atgggcatgt ggatatggcc atgaatgagc aagatcctct   180
ctgatcctgt agaagttaag ttctaccaga taacttgctg cttcaacaaa agatttacc   240
tttttaaata aatgttgtag aatacttaaa aaaacaaac tagaatttgc ctgtgtgcag   300
ccagtaacat gtctatttaa cctggacacc ttttgaggaa tattctcaga ttgccccat   360
gctgttttata agacattgtt ccttatacac ctgtttatga atgaaaagaa acataaggag   420
tgggtacaaa gacttctatc tatgaatgat taaaaaggct agagtacgaa tacttcttga   480
acctttggta ctaaatgctt ttcatgttct atataaatgt agaaaacatt ttacaaatcc   540
```

```
tgtaaataaa ctgtttattt tttatagaaa gccaaaaaaa aaaaaaaaaa aaaaaaaaaa      600

<210> SEQ ID NO 55
<211> LENGTH: 600
<212> TYPE: DNA
<213> ORGANISM: Homo sapiens

<400> SEQUENCE: 55
tctttcaaca tttagatagt ctttcttaat atttccagga gagtacctca ttttattt         60 gaaaaccatt cagcacattt atcttatgta acatgcagag catatatcta tctgtatttt     120
taaaattttc ctgttactca ttgatacata gtacttaatt acatgttatt ccatgtacac     180
tgaaaacaat ataggaaata tatacatcta agacttctac tttgtacagt ctttcattaa     240
ataagaatac ttacacatac attttcagat atttctacct tcctgtatgt gtttggaatt     300
gtatgtaggt agccactgaa agaatttggg ccccttggga ggatggcagt ggaagtccat     360
gaagtaaaga gcattcttta aaaagcagat ttgattgcat acctttagt tatttgagat      420 tctgagaatt ctgataaacc ccaaagcaga aagattcctt agtacccttg aagatggga     480 aaggtgaggg aaatatttga agcagggtca gaacatccac taagaacata gcacctcagt    540
agagcttaca ttatagtgcc agggtagagt tattactgaa ccaacttttt tgtacaaagt    600

<210> SEQ ID NO 56
<211> LENGTH: 600
<212> TYPE: DNA
<213> ORGANISM: Homo sapiens

<400> SEQUENCE: 56
tccatcaggg cacggtagaa gttggagtct gtaggacttg gcaaatgcat tctttcatcc      60
ccctgaatga caaggtagcg ctgggggtct cgggccattt tggagaattc gatgatcaac    120
tcacggaact ttgggcgact atctgcgtct atcatccagc acttgaccat gatcatgtag    180
acatcgatgg tacatatggg tggctgaggg aggcgttctc ctttctccag gatggaggag    240
atctcgctgg cagggattcc gtcatatggc ttggatccaa aggtcatcaa ctcccaaacg    300
gtcaccccgt agctccagac atcactctgg tgggtataga ttctgtgtaa aattgattcc    360
aatgccatcc acttgatagg cactttgcct ccttctgcat ggtattcttt ctcttccgca    420
cccagcagtt tggccagccc aaaatctgtg atcttgacat gctgcggtgt tttaccagt     480 acgttcctgg ctgccaggtc gcggtgcacc aagcgacggt cctccaagta gttcatgccc    540
tttgcgatct gcacacacca gttgagcagg tactgggagc aatattgtc tttgtgccaa     600

<210> SEQ ID NO 57
<211> LENGTH: 340
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 57
ctgtccagaa tgtagaggac agacccatgg gaacttcaaa attcccctct caatncccat      60
tttatgttag aaaatcaagt accgagaatg ttaangttaa attatgtgac caaaacaagg    120
```

| | |
|---|---|
| aaagaggctg gtaaaactgc attttgcaca aaagtgttga ttcaacatga agtcaaataa | 180 |
| tatgttctaa tgaaaccaca cctctcacac acatatcctt tctctcaaac ctcggtgtta | 240 |
| ctctggccaa aagtcttagg tttcttgaag tgtttgtgga agagtagatg gagttttatt | 300 |
| taacattatc aagaaatcca agctgcagac cccacacata | 340 |

<210> SEQ ID NO 58
<211> LENGTH: 520
<212> TYPE: DNA
<213> ORGANISM: Homo sapiens
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (418)..(419)
<223> OTHER INFORMATION: n is a, c, g, or t

<400> SEQUENCE: 58

| | |
|---|---|
| agactttta gtagcttcca actacaaaaa aagagaaata atcaattatg tactaatcag | 60 |
| acacttttaa aaattacaac agtttattca gagaaacaag ctttgtgtga cattctaagc | 120 |
| ggattttatt ctgcaggtcc ttttaacata atgagtaata tttgtgttgg gaatgactga | 180 |
| gaagaaattt cataatgatg tgaagatcta cctgtaaata gttcctctgt cgtatgctgg | 240 |
| tatttatatt ctagcatctc aacagtgctg atggtcactc atcttggagt tccctgaatt | 300 |
| tttttttttt tttcaaaact cctgtaatgt tacattaccc atactttgt tgttgctgct | 360 |
| gttgttgttg ttttgagacg gagtgtcgct ctgtcgccca ggctggagtg cangtngnnc | 420 |
| cgcgcccggc acatgactgc atactttcaa ggagaggact cagagctttt atttatttaa | 480 |
| agaaacttga aaggaggaaa gtggattaag aaaaaaaaaa | 520 |

<210> SEQ ID NO 59
<211> LENGTH: 600
<212> TYPE: DNA
<213> ORGANISM: Homo sapiens

<400> SEQUENCE: 59

| | |
|---|---|
| tttttttttt ttttacataa aggcatgaat atacaaggta atgtcagcag ctgtactcca | 60 |
| ctctttattc gttgcaaatc tacctatttg tttccaaagg atgtctgcaa ataaataggt | 120 |
| aacattgtac agctttcaac agtggatcag aacatagatg tctcttctaa ttcacaagta | 180 |
| ccaatggctc aattaattta agggacattt tctgagttgt gtgatttcac atgtatttat | 240 |
| cgtgtctaga agtgtgcaaa cttttgtttc atttctctct tagatttctg taggaagagt | 300 |
| taaaggatgt gaagtagtca ttttacttat tcataacaca ttttagggaa aattgtgctg | 360 |
| ttgctgttgg ggagaaagtt aaagctatca actataacct ggactccagt ccaattttc | 420 |
| acatctggtt gctactttta aaaggatca ttttaatttt taaatgcaga atgtgttgca | 480 |
| ctttacctt gacattccag gtttcctcat ggtcatttag aaaaataaag caggaaattc | 540 |
| taatgcctta gcatctactt taataagatg tttgcattta taaaaataac aagaaactga | 600 |

<210> SEQ ID NO 60
<211> LENGTH: 463
<212> TYPE: DNA
<213> ORGANISM: Homo sapiens

```
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t

<400> SEQUENCE: 60
tttaattttt tggaaggata tacaccacat atcccatggg caataaagcg cattcaatgt    60
gtttataagc caaacagtca ctttgtttaa gcaaacacaa gtacaaagta aaatagaacc   120
acaaaataat gaactgcatg ttcataacat acaaaaatcg ccgcctactc agtaggtaac   180
tacaacattc caactcctga atatatttat aaatttacat tttcagttaa aaaaatagac   240
ttttgagagt tcagattttg ttttagattt tgttttctta cattctggag aacccgaagc   300
tncagctcag cccctcttcc cttattttgc tccccaaagc cttcccccca aatcatcact   360
cncctgcccc ccttaagggc tagagggtga ggcatgtccc tcacaattgg cacatggtnc   420
aaggccatca ggcaagggng cattcacaca aaagggcacc agg                     463

<210> SEQ ID NO 61
<211> LENGTH: 600
<212> TYPE: DNA
<213> ORGANISM: Homo sapiens

<400> SEQUENCE: 61
gaaacaactg gtaaacacag taagcccatt tctgggcttt tagaaaaaca ttgctctctt    60
ttctttcccc acccagtgta ttcccaagga cttaatgctg cactctgacc tagccctcaa   120
tgatggttaa aactgattct gaaccaaagg taaacagggt tcctcccccat gccttggaga  180 gctccagtct gcagaaagct aatgaagccc ttgaagcagt atcttgtctt ccatccacac   240
tttattgaaa tgcttttgaa tcttattgtg ttgtaattac atactataga aaactccgcc   300
aacctctatt tcaaggtttg ggcccatgac tctcgctaaa acatttcagt tccatttttcc  360 agaacatacc atttctaaat gcatctgtga gggccctcca caagtatttt cagtccacat   420
ttcagaaaac ttgaaagtga cgcaggttcc tgacttagtt gatggtgggt aaagggaatg   480
ccattatgag tggtggaggt tgttttcttt tttcttgcca tattctcagc ataatatttg   540
aaacctacaa aagaagtttg ataatataac tgtatatttt atgcctgcac tagtggagga   600

<210> SEQ ID NO 62
<211> LENGTH: 600
<212> TYPE: DNA
<213> ORGANISM: Homo sapiens

<400> SEQUENCE: 62
gaggtaggaa ctgatattcc cattgtacag atgagaagac agatgctcag agagcttatt    60
tgtctgttga agccaaaacc tgtgcccttg accacaatgg acactatatc ttctgagctc   120
cacttaatta gagaatttgg atcaagtgac taaataaatc acacaccaca cacattaaga   180
tacgccagag tgacagggac attaaataaa tcaagtatcc atgaagtttg ctgccttcca   240
```

```
aatcagcccc ctattctttt gccctaagat atcccatcat agtctgtttc cttcccttct    300
ctctttgccc tcaacctttc cttccctctt atccatggga atgactctag gaatcctgtt    360
gagtgtatgt gtgtgcgtgt tcttttcttt ttctctcatg aatattacac ttttattagc    420
cagctatact tgtgttgatg aaaaagacaa aatggaattt tgttttcctt taacaatcaa    480
gtatgaatgg tctgcttaca ggatgtccct tcttggggtc cttggaggta acaaaagctc    540
atcattaaac aggtagctat catttctaca tgcttagtat cacttccgat tatcttattc    600
```

<210> SEQ ID NO 63
<211> LENGTH: 600
<212> TYPE: DNA
<213> ORGANISM: Homo sapiens

<400> SEQUENCE: 63

```
gggctgaggg tcctgaggag agagagagag gccacgtgga tggaggactg tcaccccctt     60
ctcggttctg tcaccccctt gagtctaact cactgttgag gggaggaaga agggggatgg    120
acggaaggga gaccgaggaa aggctttcgg gagtggggac attatccccc cagaggtgtg    180
ctgccccacc cagctgcacc ccacaatctg gccaactcat ttcacagtat aaatcactcc    240
agcaggacga catcacagca gcccctgctg cctgaaatca gagcggccca acgaggaagg    300
ccaggagggt cggctggcag ggggcagggt cttgggataa cactgtcatc agaaacaagg    360
ctgggggctg atttcggggt ggggagcctt aggaggccag aaattccaat cagagccagt    420
ttttctggga gggagtggct agacagtcaa ggaaggacgt tcacatttca aaagaagtcg    480
ggtgggggga tgagattatt ctaggggggc atcgaattcc ctttaagggg ggggctcact    540
tctgcccaga gtaaagagga tctcacacca tggaaatgtg ccaactttt tgtacaaagt     600
```

<210> SEQ ID NO 64
<211> LENGTH: 600
<212> TYPE: DNA
<213> ORGANISM: Homo sapiens

<400> SEQUENCE: 64

```
cttccattcc tcatgatttt agggttatcc tcattcagat ctactctagt tataatagta     60
ctttaaacag agcacagaat taaaccatta gtatgtgaat ctgcaaaaag agaacttgtt    120
ttagactctt ctacagttta gacttcaatg tgcatactaa atgcataaca ttcgtatcaa    180
ataattaaca tttatataca attaacaaat aaggacaaat tttatacaaa acttctacta    240
ctgctataat ttttgaaaac atttaaccca ctagcaagag gtaagacagc actgcctttt    300
taaaagacag gtcacttgaa tagagaatat aagatataac cataagtagg agtataaaca    360 ataattttc ttcttgtgga atgtttttaa atttcctttc ttatattatt attcttcctt    420 aggtttttt agacaggtca tttcttcctg aatgattttc cttttctttt tatttttatt    480
ttttgaagga ggattattta ctggtggtct aaaagaagta ccttcaactt cttcataatt    540
gtagccaaag cggaaatgga atatttaata attcttacat ctcactaatg tagtcttctg    600
```

<210> SEQ ID NO 65
<211> LENGTH: 427
<212> TYPE: DNA
<213> ORGANISM: Homo sapiens

<400> SEQUENCE: 65

```
aataattata aagtttattt aaatgttgat tgtcccaagg tctacagttt cttttctgtt     60
gtgtcatcag tgacaaagag taaaaaaaag gaaactccca tatttagcac tttagagtaa    120
```

```
aacacatgga tcatcgttat aacagtcct ctgggcgtgc tggagctcac tgagaaggct        180
tctattttga gcttggaatg ttgtgctgag ctgtgcagcc tgttcctgca tctgttgttc        240
ctgcattttc tgttgctctg ccagccaatt ttgtttggct atctccattt aactcacttg        300
ttcctgatgg agtctctccc tctcctgcat catttgctcg ttctgccttt gaatcgccgc        360
caacctttgc gcttcagcct tttcagcttc tgctttcact tgtgcctctg aggagaaaaa        420
gataatc                                                                  427

<210> SEQ ID NO 66
<211> LENGTH: 600
<212> TYPE: DNA
<213> ORGANISM: Homo sapiens

<400> SEQUENCE: 66
gtgtcaacat ttatgctcct aaaggatgtt gggtcaaatg aaatgttcct cattgtttct        60
ctctcttgat ctctccttca ctccttctct tccttgcagg atctccaact ccttcataag        120
ggcactctgt gttaccccctt taaacaaaat aaagaagtcc tacattctgc ccagattttt       180
ttcaggctcc accaaagggt tgggtgaatt atggcccaaa agttggtgag gatgatggtg        240
aaccttcaat caccttcagt ctcccaacca acaatggtca tggcttgttt ctccctgga        300 ttacatggag aaaatcatgc cctactttt ggacctgttg cttctacatt tgtatggtaa        360
ctgtgaaacc atcctaatga acagcaaaca ttaaccacta cataaaatgt agactttgaa       420
taaaaacaca gctaagtact aaccagcttg ccctttaagc caattccctg tagctactta       480
cagcacgact gttagctcct ttccttatag tttcttactg ccttaaagtc acatagatgt        540
ggtcacaagg cactaacttc ccttagttat ttctataaga taatatatgt aacgttggca        600

<210> SEQ ID NO 67
<211> LENGTH: 600
<212> TYPE: DNA
<213> ORGANISM: Homo sapiens

<400> SEQUENCE: 67
agtgcagaga ggatgagaat atccttcatg gggtccagtt ccaaatctga agcataattt       60
ccaaccatca aaatattgga aataggaatg cctagcattt tatggacatt catgacccgg       120 cttttgagaag tcatagatct actcatgttt aaaaagttgt cttgaagaac ctcactgcaa      180
tcatccactt tagtaagcaa ggccacatat gctataccac agtttaatac ttctttgtga      240
acttgcttca cttttgccaa cattttagag tagagattgt caatagagtt gatgtctaag     300
acataagcca cacagtgaat cctgtccttc agagatggag aggtgataaa agtagaatgc     360
tcaggtgtaa ttggtttacg ggaattaaac tgttataaaa acataaggta acattcagaa     420
atcagagagc ctctgtttaa cccttaaaga cacaattaat gcttctaata ctgtaactac     480
tgatctccct cttctcctc agctactctt tccccaaaca gtagcacctc ctctttactt       540
cctttctcac tgggggcat aatgccacca acttttttgt acaaagttcc cttttaatg        600

<210> SEQ ID NO 68
<211> LENGTH: 577
<212> TYPE: DNA
<213> ORGANISM: Homo sapiens

<400> SEQUENCE: 68
ttatcttata ctaaattcca acatgtatct gagtttgctt ctagattttc tgttctgtcc        60
```

```
cagtggttgg atatttcttc atacacgtct atcatactgt tttgactata gaggcttttc    120
agtgtcattt aatatctgtg atggcaatcc ctactcaaag ctctttgttt tcagtgttcc    180
tgtattgctc ttttgttaat cccttaatat aaaagtaaat aataacccag ttggcatatt    240
attttgatga cattaaattg gggagaatag atactgtgat ttttgaagct tcctacaaat    300
atgatatgct tttcatttgt gcaagtactt tagtataatg ttaactggtg gtggtaatgg    360
aggaaattct gtcatgttcc ttacttttag tttcctctag cgctttctat ttttttattt    420
tttttcagat ggagtcttgc tctgtcttct atccaggctg aggcaggagg atcacttgaa    480
cccagtagtt caaggctgca gtgagctatg gttacaccac tgcactccag cctgggtgac    540
agagcaagat gccatctctt aaaaaaaaaa aaaaaaa                              577

<210> SEQ ID NO 69
<211> LENGTH: 600
<212> TYPE: DNA
<213> ORGANISM: Homo sapiens

<400> SEQUENCE: 69
gttaatatct ttttcgttta ttgtctgtct ctgaaggtag ggactttgcc tcatttactg     60
cttttcagtt cttggaacaa tgctcggcac ataggcaatc aacgaatgtt tgttgaataa    120 atgattttt tctctggaaa ttgtcaaaat ctgcatgagg tgtatcaggc cagccattgt     180
cagcctcagt ttagaggcaa ggaaataggt tcagaaaggt tcaaggacgt gctgaagtca    240
cagggcgagg cagcagcaga gagcctgctt gttgagagcc aagtcttatg ggacttgcct    300
ccttctctcc cactgaggct ggggacacca ggtggcccag aggcatgtgg atacctccag    360
tgggaggtta ggagagtgct acacagaaac tctgagttct aacactcttg ggaccataaa    420
aaatggaaca gtctgggca tggtaactca cgcctgtaat cacagtattt tgagaggctg     480
aggtgggagg atcacttgtg gccaggagtt cgaggctgca gtgagctatg atcctgccac    540
tgtactccag cctgggcaac acagagagac ctcacttctt taaaaaaaaa aaaaaaaaa     600

<210> SEQ ID NO 70
<211> LENGTH: 600
<212> TYPE: DNA
<213> ORGANISM: Homo sapiens

<400> SEQUENCE: 70
aggagaaagg gaagtcaaat gtctcgtcca agtctacaca gctaaaaagg ggcagaacta     60
gggtgacgct caggcctcat ttagagatcg ggggttggcg agaagtgggg tgggcttctg    120
gaggggctgg gagagcccca caaggctgca gagggtggtg agcccggagt gggcctggcc    180
tggtgtgggc tgggggtatg ggcaggagct gcagacagca gggctgcacc agcggaccag    240
tttcagaggc aagggttcta ggcccttgag aatccacagt gccaaacaga cccagatagc    300
tacggggttg gtacctgggg aggccttagg acaggcagaa agtcccagag gcgagggcgt    360
tgcctgggga cgttttgct ccctgtcctg ctgacagagc ataggaagtg tgaatgtttt     420 ctacccctc ctctctcggc tcagcagagc tccagcgagc caagtccttg tctgtggaga     480
cgcatcagtc cctggctcta gggaatagg agtcccacag acaggggggt gtcagcaagc     540
tgagagggtc tgtaagtagg tacggaattg agtcaggaaa cagtctgggt gtggagtgag    600

<210> SEQ ID NO 71
<211> LENGTH: 600
<212> TYPE: DNA
<213> ORGANISM: Homo sapiens
```

```
<220> FEATURE:
<221> NAME/KEY: misc_feature
<222> LOCATION: (65)..(83)
<223> OTHER INFORMATION: n is a, c, g, or t
<220> FEATURE:
<221> NAME/KEY: misc_feature
<222> LOCATION: (132)..(144)
<223> OTHER INFORMATION: n is a, c, g, or t

<400> SEQUENCE: 71
tgcaaaaagc caaaaaagc agcttttaac attatatcat tatatcacaa ttttgaaaca      60
tgggnnnnnn nnnnnnnnnn nnnccattgt gtggataaaa tggtctccgt gacattgagc    120
agagtgttat cnnnnnnnnn nnnnacatta ttgcacagag atttctcatc aatgttcttc    180 agttttatg tcttttccta aatgtgaata agtgctatgg ataaaataca aatgtagaaa    240
ataacagcag catgatttgt caaagttaat ccctataatt tagtaagaaa aaatggatat    300
aaacaaaata agtgctcttt ctaaactgta ctaaattttc aaaaatattg ttttaatgca    360
gtgaaggtcc tgaaaagcct attgaaagcg atgctgagtc ctgttttcaa aagtgtcctg    420
tttgggtttt cttggtgaag agcagaattt caagtgaagt aatcgacgga ctaatttaaa    480
acaaaacagc cctcggcttc cctattggcc tgtgagggca ccggctccgg gaccctgacc    540
tgggaggcag cgagtggtgg gggtgcctgg cccccatcta cacgtacaca ggctggccaa    600

<210> SEQ ID NO 72
<211> LENGTH: 600
<212> TYPE: DNA
<213> ORGANISM: Homo sapiens

<400> SEQUENCE: 72
gcacgtctac ggggctggac agagtgtggt taaccgggga actgggcaag ccggcgccga     60
gcctgcgtca gccgtgcaag ccgctccttc aggaacttcc gcttgtcgct ggtgtcgctc    120
cgctccttca ggagccagct gtaggtgtcc ttgtcctgca ggagctgcag catggccttc    180
tgaagctgct ggccgtacgt ctggagcatg aagaactgga tgatcaaagg gatgtggctg    240
gagatgcgct tgctggcctc ctggtgatag gccatcaggt gctgaaagat ctcctccatg    300
gaagagtctg ttgccgagct ggactggaaa gcccaaaat cccaggattt cttcttcttt     360
tcttcttcca gctccttctc tctgaccttc tgcaatgcac ccctgtatac ctggtcctgg    420
cagtagacaa tctgttccat ctggaagtgg aggcggatca gcttctcacc ttctctctct    480
tgttctgctc taatgtcttc aattttggac ttggcggttc tgtggaggtt aaaaaactct    540
tcaaaatttt ttatcgccaa cttttttgta caaagttggc cttataaaga aagcattgct    600

<210> SEQ ID NO 73
<211> LENGTH: 600
<212> TYPE: DNA
<213> ORGANISM: Homo sapiens
<220> FEATURE:
<221> NAME/KEY: misc_feature
<222> LOCATION: (1)..(261)
<223> OTHER INFORMATION: n is a, c, g, or t
<220> FEATURE:
<221> NAME/KEY: misc_feature
<222> LOCATION: (522)..(549)
<223> OTHER INFORMATION: n is a, c, g, or t

<400> SEQUENCE: 73
nnnnnnnnnn nnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
```

| | |
|---|---|
| nnnnnnnnnn nnnnnnnnnn nnnnnnnnnn nnnnnnnnnn nnnnnnnnnn nnnnnnnnnn | 180 |
| nnnnnnnnnn nnnnnnnnnn nnnnnnnnnn nnnnnnnnnn nnnnnnnnnn nnnnnnnnnn | 240 |
| nnnnnnnnnn nnnnnnnnnn nctaaaaaaa tatgtactgc ttattttgtt agcatacttt | 300 |
| taattatatt cttattctttt ctaccctct caaaatgtat ttttccagct tgccatttaa | 360 |
| ttggtaaaca gctgtaaagt tcaaacgtga aattcttaaa gctccctaga gacatacaca | 420 |
| ataacttctg tggcatggac ttttctcggc attaaaaaaa tctagtacct ctcttggcca | 480 |
| gaaccctaa ttttacactt tatggtgttg cgtcgttttt cnnnnnnnnn nnnnnnnnn | 540 |
| nnnnnnnnnt tactggcaag ttttccctcc aaacagtttt ctaatcaagt ctaataagtt | 600 |

<210> SEQ ID NO 74
<211> LENGTH: 600
<212> TYPE: DNA
<213> ORGANISM: Homo sapiens
<220> FEATURE:
<221> NAME/KEY: misc_feature
<222> LOCATION: (1)..(44)
<223> OTHER INFORMATION: n is a, c, g, or t
<220> FEATURE:
<221> NAME/KEY: misc_feature
<222> LOCATION: (95)..(121)
<223> OTHER INFORMATION: n is a, c, g, or t
<220> FEATURE:
<221> NAME/KEY: misc_feature
<222> LOCATION: (144)..(172)
<223> OTHER INFORMATION: n is a, c, g, or t

<400> SEQUENCE: 74

| | |
|---|---|
| nnnnnnnnnn nnnnnnnnnn nnnnnnnnnn nnnnnnnnnn nnnngatgag ccaggcatgg | 60 |
| tggtatgtgc ctttagtccc agctatctgg gaatnnnnnn nnnnnnnnnn nnnnnnnnnn | 120 |
| ntgacggcaa gagcctgtct ctgnnnnnnn nnnnnnnnnn nnnnnnnnnn nntctgatca | 180 |
| gttaaatgaa tatggaaact taatcttgta ccccttacct cccaagcata cagccacagt | 240 |
| ttaccgttgg agggatcttt ccacggaggt aaacagtgct gttttctcca agtgccagaa | 300 |
| caaaaacaca acagcacaca caatgagaa tggtttggct ctgtgtcccc aaccaaatct | 360 |
| catctcaaat tgtgtttggc tctgtgtccc caaccaaatc tcatctcaaa ttgtgtttgg | 420 |
| ctctgtgtcc ccatccaaat ctcatctcaa attgtaatcc ccatgtgtca agagagcaac | 480 |
| ctggtgggag gtgactaggt catggggtg gttttttctca tgctgctctc atgatggtaa | 540 |
| gtgagttctc acaggatctg atagtttaaa agtgtttagg ggctgggagc agtggctcat | 600 |

<210> SEQ ID NO 75
<211> LENGTH: 600
<212> TYPE: DNA
<213> ORGANISM: Homo sapiens

<400> SEQUENCE: 75

| | |
|---|---|
| gggtgaggac ccacagctct gatgtgggcg cttcaggcca tggtggagct gagattcagg | 60 |
| ttggcttttc ccctcagctc ccagctggct ggtgaaccca tcatcatagc caaaagtact | 120 |
| cagcagcagc acctccaggt ccagaggcac ctccagctgc atgcacacac aatgaatgaa | 180 |
| agactgccag gtgtccgaac cctggacatg cagcttgttg agttcagga tgactctctg | 240 |
| ttcagggtcc aaggtctcgt tcctggaatc caggtccgtg ttggggagga agaacttcat | 300 |
| cttggcgttc agccattctg ggtctttggt gagcagcctc acaagacagc tccacaggtt | 360 |
| cttgttgccg agctggaggc caacgggtc catgaggagc cagccttggt ctcctcgttc | 420 |
| atgataggtg ctctagggtc cccacggaga gggtctcatg ggtgtctggg ctatgtgtgc | 480 |

```
cttgagctgg attgacaggt tgtttccata gtgcagactc cctcagcgct cgcggctcct      540
ccgcgctctg cacgaaactg aaagtagaag ccgccgccta gagctgctcc gccagtgcat      600

<210> SEQ ID NO 76
<211> LENGTH: 600
<212> TYPE: DNA
<213> ORGANISM: Homo sapiens

<400> SEQUENCE: 76
tggcaaggac attgttttttg tctagtgtct caagcttctc taccaagaga gtcatatttc      60
ttatctccac ctccagctgg tcaacaattt ctgagcttcc accaaaactc tccttcagct      120
gtatgaccag ttttccatc tccttcactt ctaccttgat cagctcgaag tccagttcag      180
tgtaagaaat ggtatccttc tccatgatgt caattcggac agttaggttt aacagtttct      240
tttcatacac actaattaat tggacatatt ccctcacttt agaaagttct ttctcaaact      300
tctgagaaaa aacatgagct gtgaattcca agcgttccac tctgtccacg ggaaaggtgg      360
tgtctggcag ggaaacagag cactggcagg tcccacggtc atccacggag ccggtgaaat      420
tggaaaacaa ctgggacaca gaacctccgc tgcctaagct gcggctggag ctggagcccg      480
acctggagct ggagctgaag ctggagctgg agtcaacacc tgggaaagag ctgaagccgg      540
ggctgggaat tggaggtccc acatccccca atcccctgc agcttggcca aggaagccaa      600

<210> SEQ ID NO 77
<211> LENGTH: 600
<212> TYPE: DNA
<213> ORGANISM: Homo sapiens

<400> SEQUENCE: 77
tcttttattg aaagaaaaaa caatacaatg gactttaaaa agctacattt gttatggttc      60
ataaggacag aggtttacac aggttttata tatgtacaca ctgacaatac tatatcacaa      120
catcagaggc accattttttg ccacagaatt aggtaatgaa taaaacttct ccaaattaat      180
ctgtttaaaa aatatctaaa atggtacagt atatttgagg attatataaa tatgtgagac      240
atatttagat attttttaaa aatagtgttt atatatatgc atcacaatct tctctaattc      300
tcaaaatatt atggcaccaa aattctgttt gtcaaataaa acacaagatg ctgtaatatg      360
tatccaagca ccagcttagc acagtattta attctccccc aaactgaaag actgctaaca      420
ggtacaaact gaactgaata tttcacacaa ccattgaaat aatttaggcc ctcaaatttt      480
ttttttatta gctgattgtt tttagagaaa aagaggggag ctaaaccatt tacattaatg      540
ttgctctgtg tgatagaatc aatcctaggg ctcagagaag atattcctag gcactggaga      600

<210> SEQ ID NO 78
<211> LENGTH: 475
<212> TYPE: DNA
<213> ORGANISM: Homo sapiens
<220> FEATURE:
<221> NAME/KEY: misc_feature
<222> LOCATION: (14)..(14)
<223> OTHER INFORMATION: n is a, c, g, or t

<400> SEQUENCE: 78
tcaaacttga atcntttaaa tttatttttct gcttaagcag gtttgagttg ggttttctat      60
ttgcaatagc aaaagtcctg actggcaagg tttaaaagtt tgaagactct cacaggtaag     120
tgcagctcag gatcctgtga gtgcagcaga aagtcttaag aaatggcagg ggctggttga     180
```

| | |
|---|---|
| acccagattt tccattggct gagcagatat ccccagaggc gtagaaaatt aaatttgttt | 240 |
| tatgttgttc caaaagagga gaactgaggc cagaggagca cacttctgag acactcattt | 300 |
| ttgctgggta gaggaactct ctgggcaagc aggaccatcg atattagagc agctggcctc | 360 |
| aggaggggag taagagcccc atccctgaag gtacacaagt tgtggcagca accatctggc | 420 |
| ctgcagtttc cagaggggag tcaggcgtgg ggtgggactg gagtgaacgg gtacc | 475 |

<210> SEQ ID NO 79
<211> LENGTH: 600
<212> TYPE: DNA
<213> ORGANISM: Homo sapiens

<400> SEQUENCE: 79

| | |
|---|---|
| ttttttcttc ttttcctctt gggttttccc aaagtagagt tgtttgcaat atccacagta | 60 |
| tccatttttgc cacatgcttg gtcacttttcc ttccttgctt ccgggctttc tggcacttct | 120 |
| ccttgtttaa gacttagttt gatgtcaggc ctctcttccc tttcttttcg atcactttct | 180 |
| tggaaagaca atttgtcttg gattgcattt ttgaagcttt tataaatgtg aattaaatcg | 240 |
| gggtattcct gcatgttgac ctcgctgaac agtgcttcca aaactgacag gttaaatgtc | 300 |
| ttctccagtt cactgagaac attgtacacc actctttgta cagggaccag gtttctacaa | 360 |
| gaatcttcag aatcttcaaa cattttattt gtgatgagtt cccgatcgcg gaggccctca | 420 |
| aggaatggaa atgtctttttt tattgcattt gatatctcca gcttatgtct tttgaagtgc | 480 |
| ttgaatacag tgtcatagac aagtccctca tctacatcct ggtcttccgt gaacagcctg | 540 |
| gctcggaagg tcctacgccc acggactctc actgattgct agcacagcag tctgagccaa | 600 |

<210> SEQ ID NO 80
<211> LENGTH: 600
<212> TYPE: DNA
<213> ORGANISM: Homo sapiens

<400> SEQUENCE: 80

| | |
|---|---|
| ccttccccat ttctcacttt ccacaggtgg gatgtggcag tcctcatgga agactcttga | 60 |
| acaagtgtcg caacagaaca gctcccctcc gtcccggcac acctcacact catccaagtt | 120 |
| tctcatctag aaggtaaaac agtgtccacg tcactgggaa tcacaagatt caggaaggcc | 180 |
| acccctctgg gcatctagaa cacactgctt atgtgtgagc ctgtatagac aggcatatgc | 240 |
| ttctccctgg gatatgaagg aaaaatatgg catggagatt tcagaacaaa tcctggtctg | 300 |
| cagtgaagtt caggaggaag gggtatatgt cagaataaaa acgttttcct tataaaacca | 360 |
| gagattatga cacagaaagc ctagcaacaa agcaagagga tgatcttata ggaatctgaa | 420 |
| taattgtatt atgctgcaga taaaaccagg ttttgaagta aaagtgttaa atccatttgt | 480 |
| ctatactaca aatcaactca tgaaagggag acccagagaa ttacatatga tggaataacc | 540 |
| ttctaagata tcatcacatc ccatattctt ggccataagt tccccatgag ttgaagacag | 600 |

<210> SEQ ID NO 81
<211> LENGTH: 600
<212> TYPE: DNA
<213> ORGANISM: Homo sapiens
<220> FEATURE:
<221> NAME/KEY: misc_feature
<222> LOCATION: (445)..(456)
<223> OTHER INFORMATION: n is a, c, g, or t

<400> SEQUENCE: 81

| | |
|---|---|
| gtggctgttg ctggccccac ctccgcttat gtccttaaca tgcctcaggt ggttcatccc | 60 |

```
ttttggcact catggtgccc cctgtgggct gatacaggag tgagtctact gtgaaggcac    120
tcagtatagt ggaaaaaaca aatatcaacc tcctgctttt tttcagtgta aaaactataa    180
gctctatggg agtttctgca gatggtacca taatggcctg agggaggagt atcacagtca    240
cagagtattg gttctctcac tgcataagcc atggttttac ccaccttcac aggctaaagg    300
tgcttcataa ccttgttcat gtattgaggt tctgttggct cttgtaatgg taatttcaca    360
tgtgggcagt tgttcatatt gatgtttcta taggggtatg atagctggag aggtctgcgc    420
cactgtcttg ctctgccttg atcannnnnn nnnnnnaaca agaatttgtc tcctcctagt    480
ttttcttttt ctcttaaccg acctaggttt agccttttaa tccttctccc tcctctgctt    540
ctaatgtcat tgtttctttg tatgcctatc atatctacat gctacatgac cttcagctgg    600

<210> SEQ ID NO 82
<211> LENGTH: 600
<212> TYPE: DNA
<213> ORGANISM: Homo sapiens

<400> SEQUENCE: 82
agttttaagg aaaaattgta tgatttaaaa gattataaaa ctttattact gggctattta     60
cacattttaa ttgtttctca taaaatatat aacattacaa tatttatgga agtaggatat    120
ttttgtatca tatgtacgat gataaattat agggtatttt aaatgatgtt ttttagcctc    180
cttaagtttt aagtggatct tgcaaatgaa acaagtatt attgagtttg acatactcaa     240
attgcccaaa tatcagctgt ttaaacaacc aagtcatcat tgatacttta gtaaaggtta    300
gtaaatgtca tcaaaggctt atttgcagtt tacagttttt attacttagg agacttaagg    360
agtacctgcc aggtttgtcc atgctaatgc tacgattttg tttttgtagt tcaaccatat    420
tttgtatgga gatactttga ggctctgtaa atttctggtt actcctcaga acccactaga    480
tttagcattt catggatgac ttgtgtttga acaattatta ctataatggt tgccagatga    540
ttattttctt attctcttct tgttctacac tggagaaata aaaccaataa ataagggaga    600

<210> SEQ ID NO 83
<211> LENGTH: 276
<212> TYPE: DNA
<213> ORGANISM: Homo sapiens

<400> SEQUENCE: 83
gtgccaatgt gaagtctgga ttttaattgg catgttattg ggtatcaaga aaattaatgc     60
acaaaaccac ttattatcat ttgttatgaa atcccaatta tctttacaaa gtgtttaaag    120
tttgaacata gaaaataatc tctctgctta attgttatct cagaagacta cattagtgag    180
atgtaagaat tattaaatat tccatttccg ctttggctac aattatgaag aagttgaagg    240
tacttctttt agaccaccag taaataatcc tccttc                              276

<210> SEQ ID NO 84
<211> LENGTH: 184
<212> TYPE: DNA
<213> ORGANISM: Homo sapiens

<400> SEQUENCE: 84
aatgcttatg tctaaaagag ctcgctggca agctgcctct tgagtttgtt ataaaagcga     60
actgttcaca aaatgatccc atcaaggccc tcccataatt aacactcaaa actatttta    120 aaatatgcat ttgaagcatc tgttgattgt atggatgtaa gtgttcttac atagttagtt    180
```

```
                                                   atat                                                  184

<210> SEQ ID NO 85
<211> LENGTH: 206
<212> TYPE: DNA
<213> ORGANISM: Homo sapiens

<400> SEQUENCE: 85
ctgggcacct ctgggacagc aaaaaaaact gcagaatgca tccctaaaac tcacgagaga      60
ggcagtaagg aacccagcac aaaagaaccc tcaacccata taccaccact ggattccaag     120
ggagccaact cggtctgaga gaggaggagg tatcttggga tcaagactgc agtttgggaa     180
tgcatggaca ccggatttgt ttctta                                          206

<210> SEQ ID NO 86
<211> LENGTH: 268
<212> TYPE: DNA
<213> ORGANISM: Homo sapiens

<400> SEQUENCE: 86
accatgttca tcttgtcctc caagttatgg gggatcttgt actgacaatc tgtgttttcc      60
aggagttacg tcaaactacc tgtactggtt taaataagtt tacctttcc tccaggaaat     120 ataatgattt ctgggaacat ggcatgtat atatatat ggagagagaa ttttgcacat     180
attatacata ttttgtgcta atcttgtttt cctcttagta ttcctttgta taaattagtg     240
tttgtctagc atgtttgttt aatcctttt                                       268

<210> SEQ ID NO 87
<211> LENGTH: 234
<212> TYPE: DNA
<213> ORGANISM: Homo sapiens

<400> SEQUENCE: 87
gatggctggt ctgcccccta ggagactccg tcgctccaat tacttccgac ttcctccctg      60
tgaaaatgtg gatttgcaga gacccaatgg tctgtgatca ttgaaaaaga ggaaagaaga     120
aaaaatgtat gggtgagagg aaggaggatc tccttcttct ccaaccattg acagctaacc     180
cttagacagt atttcttaaa ccaatccttt tgcaatgtcc agcttttacc ccta           234

<210> SEQ ID NO 88
<211> LENGTH: 231
<212> TYPE: DNA
<213> ORGANISM: Homo sapiens

<400> SEQUENCE: 88
ggcatggagc atctgtacag catgaagtgc aagaacgtgg tgcccctcta tgacctgctg      60
ctggagatgc tggacgccca ccgcctacat gcgcccacta gccgtggagg ggcatccgtg     120
gaggagacgg accaaagcca cttggccact gcgggctcta cttcatcgca ttccttgcaa     180
aagtattaca tcacggggga ggcagagggt ttccctgcca cagtctgaga g              231

<210> SEQ ID NO 89
<211> LENGTH: 241
<212> TYPE: DNA
<213> ORGANISM: Homo sapiens

<400> SEQUENCE: 89
gaaattagag tcctatattc aactaaagtt acaacttcca taacttctaa aaagtgggga      60
accagagatc tacaggtaaa acctggtgaa tctctagaag ttatacaaac cacagatgac     120
```

```
acaaaagttc tctgcagaaa tgaagaaggg aaatatggtt atgtccttcg gagttaccta    180
gcggacaatg atggagagat ctatgatgat attgctgatg ctgcatcta tgacaatgac    240 t                                                                    241

<210> SEQ ID NO 90
<211> LENGTH: 199
<212> TYPE: DNA
<213> ORGANISM: Homo sapiens

<400> SEQUENCE: 90
ttagatttcc agcttgtcac cttcaaggtt accttgtgaa taggactttt ttgagctatt     60
tctatccagt tgactatgga ttttgcctgt tgctttgttt ccaccaactc tccctgaaga   120
tgaggcgcac agacagacaa ctcacaggca agaacagcct ggtccatctt gaaagattct   180
caagactatt ctccacaag                                                 199

<210> SEQ ID NO 91
<211> LENGTH: 210
<212> TYPE: DNA
<213> ORGANISM: Homo sapiens
<220> FEATURE:
<221> NAME/KEY: misc_feature
<222> LOCATION: (70)..(70)
<223> OTHER INFORMATION: n is a, c, g, or t

<400> SEQUENCE: 91
tgtttaaaaa tgttgtgggt acatagtatg tgttgtgggt acatcgtatg tgttgtgggt     60
acatagtatn gtggggtcca tgagatgttt tgatacaggc atgcaatgtg aaataagcac   120
atcatgggga atgggtatc cctcccctca agcgtttatc cttcaagtta taaaaaattc    180
aattacagtc ttagttatgt caaaatgtac                                     210

<210> SEQ ID NO 92
<211> LENGTH: 148
<212> TYPE: DNA
<213> ORGANISM: Homo sapiens

<400> SEQUENCE: 92
accagaattt atggatgaac tgattgctta tattttagtc agggtttata aatgtagatg     60
gtcaaattta cattgcctag tgatggaaaa ttcaactttt tttgattttt ttttccaata   120
ttaaaaaagg ctctgtatgc atggtggg                                       148

<210> SEQ ID NO 93
<211> LENGTH: 227
<212> TYPE: DNA
<213> ORGANISM: Homo sapiens

<400> SEQUENCE: 93
aagattcctg tgtactggtt tacatttgtg tgagtggcat actcaagtct gctgtgcctg     60
tcgtcgtgac tgtcagtatt ctcgctattt tatagtcgtg ccatgttgtt actcacagcg   120
ctctgacata ctttcatgtg gtaggttctt tctcaggaac tcagtttaac tattatttat   180
tgatatatca ttacctttga aaagcttcta ctggcacaat ttattat                  227

<210> SEQ ID NO 94
<211> LENGTH: 245
<212> TYPE: DNA
<213> ORGANISM: Homo sapiens
```

<400> SEQUENCE: 94

```
tctcctctca tctgcatttc tcagaaatgc cctccctgcc cagtggtgac tttccctcgt    60
cactcctatg gagttctacc tggagcccag ccatgtgtgg aactgtgaag tttactcctc   120
tgtaaagatg gtttaaagaa agtcagcttc tgaaatgtaa caatgctaac ccttgctgga   180
accctgtaag aaatagccct gctgatagtt ttctaggttt atcatgtttg atttttacac   240
tgaaa                                                               245
```

<210> SEQ ID NO 95
<211> LENGTH: 221
<212> TYPE: DNA
<213> ORGANISM: Homo sapiens

<400> SEQUENCE: 95

```
gaattttttct ctatttccag cacgctgatt tgatttaaaa atgtaataag accaagagtt    60
ggagtaaagg gatattcatt ccatgttaaa agtggcttca tagctactga caaatgtctg   120
aactattgtc gtgcccttca aaactggagt tttctaaaat aatcttattt ttatacttgt   180
atgttccagc aatttaagat atataccatt gaaagggaaa t                        221
```

<210> SEQ ID NO 96
<211> LENGTH: 176
<212> TYPE: DNA
<213> ORGANISM: Homo sapiens

<400> SEQUENCE: 96

```
ggctgagcaa ggcacatagt ctactcagtc tattcctaag tcctaactcc tccttgtggt    60
gttggatttg taaggcactt tatccttttt gtctcatgtt tcatcgtaaa tggcataggc   120
agagatgata cctaattctg catttgattg tcacttttg tacctgcatt aattta        176
```

<210> SEQ ID NO 97
<211> LENGTH: 219
<212> TYPE: DNA
<213> ORGANISM: Homo sapiens

<400> SEQUENCE: 97

```
aacgcaggcc gctttattcc tctgtactta gatcaacttg accgtactaa aatccctttc    60
tgttttaacc agttaaacat gcctcttcta cagctccatt tttgatagtt ggataatcca   120
gtatctgcca agagcatgtt gggtctcccg tgactgctgc ctcatcgata ccccatttag   180
ctccagaaag caaagaaaac tcgagtaaca cttgtttga                           219
```

<210> SEQ ID NO 98
<211> LENGTH: 171
<212> TYPE: DNA
<213> ORGANISM: Homo sapiens

<400> SEQUENCE: 98

```
tcatctccgt attcttcagc ttcatccaaa actgacttag aagcctccct tgaccctcac    60
ctgactattc acaggttata gcactttatg ttttcagtt ctgttatttt aattggtgcc   120
tctgtttgtg atctttaaga acataaaatt ctggcaagta actatttgct a             171
```

<210> SEQ ID NO 99
<211> LENGTH: 262
<212> TYPE: DNA
<213> ORGANISM: Homo sapiens

<400> SEQUENCE: 99

```
cactttgcag ccttgagagg tgcagaagag acaccgaggg gttcaccacc agagccacca       60
ttgtcagaga ggcgtccagc tgtgtccacc tgggactctg ccttcagggc ttcttgcctg      120
gctgggagct gcacaggcag actcctggga cggtgtgccg acagctctgg gcaccccctt      180
ctaggatctg attcctgagg aatcacaatg tggatttcac aatcacttcc agtgtctttt      240
gccaacctct gtgaacagat gt                                                262

<210> SEQ ID NO 100
<211> LENGTH: 248
<212> TYPE: DNA
<213> ORGANISM: Homo sapiens

<400> SEQUENCE: 100
aagtttgcac agttctagac acgataaata catgtgaaat cacacaactc agaaaatgtc       60
ccttaaatta attgagccat tggtacttgt gaattagaag agacatctat gttctgatcc      120
actgttgaaa gctgtacaat gttacctatt tatttgcaga catcctttgg aaacaaatag      180
gtagatttgc aacaaataaa gagtggagta cagctgctga cattaccttg tatattcatg      240
cctttatg                                                                248

<210> SEQ ID NO 101
<211> LENGTH: 252
<212> TYPE: DNA
<213> ORGANISM: Homo sapiens
<220> FEATURE:
<221> NAME/KEY: misc_feature
<222> LOCATION: (123)..(124)
<223> OTHER INFORMATION: n is a, c, g, or t

<400> SEQUENCE: 101
gactgcacag cagcaagaca gattgccatg gagcatgttg tgcccaacta gggacagcgc       60
agatagattc tgtaatttgc ctaacaatgt ctataggatg atcccatttg tcaaaaaaaa      120
aanngaactg ggcttattg atgtcaccta aatgcaccta aacttctttt ttgccccatg       180
ctcttctgta ctcttgatct ttccccaaat ttttaaaaac atgacactca ttcccttatt      240
tttcctactt ag                                                           252

<210> SEQ ID NO 102
<211> LENGTH: 224
<212> TYPE: DNA
<213> ORGANISM: Homo sapiens

<400> SEQUENCE: 102
ttaattgctt tctctcacca gggaaggtgt gggaaggact tgtgaaatac atattcgagg       60
aaaaactatg cacaaggccg tgcatttaaa aataaactcc ctaaggctgg ggtgaaacct      120
gctacggtct gcgcaagttg actgttaatg aatttgattc tcaggtgtga gtgattaaaa      180
gaacactgat catgtcattt tcttttttggt cactaattcc ctcc                      224

<210> SEQ ID NO 103
<211> LENGTH: 266
<212> TYPE: DNA
<213> ORGANISM: Homo sapiens

<400> SEQUENCE: 103
gtcatccaga gttataatgg cccattatct aatggtcaga gtttacttag gctttcacta       60
cttccactgc ccacttgaaa cagggaaaaa tattttcccc ccgcgctgtg agtgtgctat      120
```

```
ttagagctga ccacaagcgg ggggaagaga ggatggctcg gatgctgcat ttccactgag    180
aacacaaggc tggcaaagct tgtctgctgc ccagcaagca cttcaggctc acaccatttt    240
aggttcactt taagtagttt ctcaat                                         266
```

<210> SEQ ID NO 104
<211> LENGTH: 251
<212> TYPE: DNA
<213> ORGANISM: Homo sapiens

<400> SEQUENCE: 104

```
tggacagtgg acgtctgtca cccaagagag ttgtgggaga caagatcaca gctatgagca     60
cctcgcacgg tgtccaggat gcacagcaca atccatgatg cgttttctcc ccttacgcac    120
tttgaaaccc atgctagaaa agtgaataca tctgactgtg ctccactcca acctccagcc    180
tggatgtccc tgtctgggcc ctttttctgt tttttattct atgttcagca ccactggcac    240
caaatacatt t                                                          251
```

<210> SEQ ID NO 105
<211> LENGTH: 247
<212> TYPE: DNA
<213> ORGANISM: Homo sapiens
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (139)..(141)
<223> OTHER INFORMATION: n is a, c, g, or t

<400> SEQUENCE: 105

```
tccatggcaa cagtcccaac atgtttgaga cttcagctaa aggaatggat gtatnnnggn     60
gtgtagtctt cagtatatca ctgtatttcc gtaatactag actcnaagnt atgcnagatn    120
gnttattccc ttngtgaann nggagttgct cattacgttc ttgaaatatc gcacatcctg    180
ttggttcttc aaaggaagcc tttccaccag attagtgttc aagtctttgc agaggagacc    240
aactttt                                                               247
```

```
<210> SEQ ID NO 106
<211> LENGTH: 211
<212> TYPE: DNA
<213> ORGANISM: Homo sapiens

<400> SEQUENCE: 106
aaggctatgc tttcaatctc ctacacaaat tttacatctg gaatgatctg aaggttcttc    60
aaagacattc aaaattaggc ttttttatgt cctgttttaa gtgaaaatat ttattcttct   120
aagggtccat tttatttgta ttcattcttt tgtaaacctc tttacatttc tctttacatt   180
ttattctttg cccaaatcaa aagtgattcc t                                  211

<210> SEQ ID NO 107
<211> LENGTH: 187
<212> TYPE: DNA
<213> ORGANISM: Homo sapiens
<220> FEATURE:
<221> NAME/KEY: misc_feature
<222> LOCATION: (146)..(146)
<223> OTHER INFORMATION: n is a, c, g, or t

<400> SEQUENCE: 107
cttagcatta gaacactcag taatcatatg aattgtgcat ttgtttgttt tgcttaactc    60
tttctgtttg tttatgtttg gggttttatt gttgttgttt cacttttctc ccatctcttc   120
ctgacttggt caaatccaaa ggaatnttcc aaattgtggg gagcaaggca tctgaaatgg   180
ctaaaac                                                            187

<210> SEQ ID NO 108
<211> LENGTH: 234
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 108
atgctatatg ctgtatccca cctttctctg aatgttacat tttctcccct atcccaggct    60
gcatctaaga aaactcaaag ggaatatgct atctatcttt tccgagcaat gaaagctctn   120
gggttttttc cttgcttttc agggcacnat acttctcttt cttcctggtt agacaggata   180
agttctgagt cccntggtat catcagctta cttcttctct gttaaatatt caca         234

<210> SEQ ID NO 109
<211> LENGTH: 248
<212> TYPE: DNA
<213> ORGANISM: Homo sapiens

<400> SEQUENCE: 109
gtggtcttcc tctgaatatt agcagaagtt tcttattcaa aggcctcctc ccagaagaag    60
tcagtgggaa gagatggcca ggggaggaag tgggtttatt ttctgttgct attgatagtc   120
attgtattac tagaaatgaa ctgttgatga atagaatata ttcaggacaa tttggtcaat   180
tccaatgcaa gtacggaaac tgagttgtcc caaattgatg tgacagtcag gctgtttcat   240
```

```
cttttttg                                                              248

<210> SEQ ID NO 110
<211> LENGTH: 277
<212> TYPE: DNA
<213> ORGANISM: Homo sapiens

<400> SEQUENCE: 110
tatcctatta ctgtacttag ttggctatgc tggcatgtca ttatgggtaa aagtttgatg      60
gatttatttg tgagttattt ggttatgaaa atctagagat tgaagttttt cattagaaaa     120
taacacacat aacaagtcta tgatcatttt gcatttctgt aatcacagaa tagttctgca     180
atatttcatg tatattggaa ttgaagttca attgaatttt atctgtattt agtaaaaatt     240
aactttagct ttgatactaa tgaataaagc tgggttt                              277

<210> SEQ ID NO 111
<211> LENGTH: 245
<212> TYPE: DNA
<213> ORGANISM: Homo sapiens

<400> SEQUENCE: 111 gggatttttga gctatcatct ctgcacatgc ttagtgagaa gactacacaa catttctaag    60
aatctgagat tttatattgt cagttaacca ctttcattat tcattaccct caggacatgc    120
agaaatattt cagtcagaac tgggaaacag aaggacctac attctgctgt cacttatgtg   180
tcaagaagca gatgatcgat gaggcaggtc agttgtaagt gagtcacatt gtagcattaa   240
attct                                                                245

<210> SEQ ID NO 112
<211> LENGTH: 284
<212> TYPE: DNA
<213> ORGANISM: Homo sapiens

<400> SEQUENCE: 112
ttgaatagat catcagtggc cactgatgta attaatcatg tctatgtaat gaagctgcca    60 taaaaaccc aggaggacag tgttgagaga gcttctaggt tggtgaacac ttgggggtgt    120
ctggaagaca gcccacctgg agaggacacg gaggctcttc gcaccttccc ccatacctgg   180
ctctctccat ctcttcattt gtccatctgt atctttttca ttatattatc cttgataata   240
aactggtaaa tataagtgtt tccctaagtt ctatgagcca ccat                     284

<210> SEQ ID NO 113
<211> LENGTH: 290
<212> TYPE: DNA
<213> ORGANISM: Homo sapiens

<400> SEQUENCE: 113
aggcctctga ttgcacttgt gtaggatgaa gctggtgggt gatgggaact cagcacctcc    60
cctcaggcag aaaagaatca tctgtggagc ttcaaaagaa ggggcctgga gtctctgcag   120
accaattcaa cccaaatctc gggggctctt tcatgattct aatgggcaac cagggttgaa   180
acccttattt ctagggtctt cagttgtaca agactgtggg tctgtaccag agcccccgtc   240
agagtagaat aaaaggctgg gtagggtaga gattcccatg tgcagtggag                290

<210> SEQ ID NO 114
<211> LENGTH: 270
<212> TYPE: DNA
<213> ORGANISM: Homo sapiens
```

<400> SEQUENCE: 114

```
atacgttttt cactttctga ccaggaccat gcctgtggag tagatgttga caagaaacac      60
tgaccagatc aaaatgtgtc tcaaggagaa tggcacaatt ttgtgcaaat gaatcaagga     120
agtcttattg cacaagagta tcctggaacc cagtgcaatt gatttttag aaaaatatat     180
cacataggg aaaaaaactg gaatatgttg aaggagacgt atataatatt tagcatccag     240
attgatgact tctgccctaa ctatgcaatg                                      270
```

<210> SEQ ID NO 115
<211> LENGTH: 230
<212> TYPE: DNA
<213> ORGANISM: Homo sapiens

<400> SEQUENCE: 115

```
cgcttgaacc tggaaagtgg acattgcagt gagctgagat tgtgccactg cactccagcc      60
tgggcaacac agcgagactc tgtctcaaaa aaaaaaaaa aagaaagaaa aaaagagaa     120
aactcagaga ttcgtggaga ctggaaccac gggtgtggag agaggggtta gtagagacca     180
gattctgcag gtactataat gacattccca ggctaaggag tttagatctt                 230
```

<210> SEQ ID NO 116
<211> LENGTH: 283
<212> TYPE: DNA
<213> ORGANISM: Homo sapiens

<400> SEQUENCE: 116

```
atctacaccc tcaggaataa gaaagtgaag ggggcagcga ggaggctgct gcggagtctg      60
gggagaggcc aggctgggca gtgagtagtt ggggagggga gaaagtatta agccagaacc     120
caaggatgga aatacccctt agtgagtcag tttagacttc aggctgttca ttttgtatg     180
ataatctgca agatttgtcc taaggagtcc aatgggggat atgttttcct cccgtgagga     240
aatgtttagt tcttgaggga aaaatcccta aatcctctat ata                       283
```

<210> SEQ ID NO 117
<211> LENGTH: 111
<212> TYPE: DNA
<213> ORGANISM: Homo sapiens

<400> SEQUENCE: 117

```
gggtagcaag ttcaccacag tgttaatggg ggtcccaagg tattcttccc ccaggcctag      60
gtatagggct attactcctc tctgctccag gtgtagacat acatttacat t              111
```

<210> SEQ ID NO 118
<211> LENGTH: 238
<212> TYPE: DNA
<213> ORGANISM: Homo sapiens

<400> SEQUENCE: 118

```
tggagggtga aattctgata gacttgaggc tttgagatgt ggtcctgggg tggagcaaga      60
caagaaaagt actggagatt ggggtttgag gagtctatgc aattattttt atttttaaaa    120
atctttgtgg ctacatagca ggtgtatata tttatgtggt aagtgagata tttcgataca    180
gacatacaat gtataatcac aggcatacaa tgtagacagg cataaagtgt atagtcac      238
```

<210> SEQ ID NO 119
<211> LENGTH: 299
<212> TYPE: DNA

<213> ORGANISM: Homo sapiens

<400> SEQUENCE: 119

| | |
|---|---|
| aatgtgaaac tgctccatga acccaaaga attatgcaca tagatgcgat cattaagatg | 60 |
| cgaagccatc gagttaccac ctggcatgct taaactgtaa agagtgggtc aaagtaaact | 120 |
| gaattggaaa atccaaagtt atgcagaaaa acaataaagg agatagtaaa aagggttaac | 180 |
| gagccagtcc aggggaagcg aagaagacaa aaagagtcct tttctgggcc aagtttgata | 240 |
| aattaggcct cccgacccttt tgctctgttg ctttatcaac tctactcggc aataacaat | 299 |

<210> SEQ ID NO 120
<211> LENGTH: 294
<212> TYPE: DNA
<213> ORGANISM: Homo sapiens

<400> SEQUENCE: 120

| | |
|---|---|
| gattaagaac agttttttca acaaatagtg ttgggacaat gggtgtccac atgcaaaaga | 60 |
| ataaagttgt cccttacct tacaccatct ccaaaaatta actcaaaata tgtcaaagac | 120 |
| ataaacgtaa gagctaaaac tgtaaaactc ctagaataaa acataggagt aaatcttcat | 180 |
| gaccttggat taggccattg tgtcttaaat ataacaccaa aagaataagt aataaaaaaa | 240 |
| tagataaatt gaactccatc aaaattaaaa gcctttgtgc ttcataggac acca | 294 |

<210> SEQ ID NO 121
<211> LENGTH: 269
<212> TYPE: DNA
<213> ORGANISM: Homo sapiens

<400> SEQUENCE: 121

| | |
|---|---|
| tctcaagcta tgatcagaag actttaatta tatattttca tcctataagc ttaaatagga | 60 |
| aagtttcttc aacaggatta cagtgtagct acctacatgc tgaaaatat agcctttaaa | 120 |
| tcatttttat attataactc tgtataatag agataagtcc atttttaaa aatgttttcc | 180 |
| ccaaaccata aaaccctata caagttgttc tagtaacaat acatgagaaa gatgtctatg | 240 |
| tagctgaaaa taaaatgacg tcacaagac | 269 |

<210> SEQ ID NO 122
<211> LENGTH: 287
<212> TYPE: DNA
<213> ORGANISM: Homo sapiens

<400> SEQUENCE: 122

| | |
|---|---|
| tctttctttt ccagacaact ttgaatggag aggagcaaat tagtcttttg gtttaattct | 60 |
| gtctcagttt gcttatctaa agaaaggaaa acagagtggc tacacttgtt tagaaccata | 120 |
| tgcatactcc agagaaagat gctctattaa tccaaaaaaa tacagccact tgaaaccagc | 180 |
| caaagcgaaa gtgtaaggga cttcatgaa aggaggcagt tcaccaaagt attgaggggt | 240 |
| tttatatttt aaactccgcc agtgaattga cgtgttatgt cacttac | 287 |

<210> SEQ ID NO 123
<211> LENGTH: 275
<212> TYPE: DNA
<213> ORGANISM: Homo sapiens

<400> SEQUENCE: 123

| | |
|---|---|
| gaatttattg gagcatgacc acggaggata gtatgagccc taaaaatcca gactctttcg | 60 |
| atacccagga ccaagccaca gcaggtcctc catcccaaca gccatgcccg cattagctct | 120 |

```
tagacccaca gactggtttt gcaacgttta caccgactag ccaggaagta cttccacctc    180
gggcacattt tgggaagttg cattcctttg tcttcaaact gtgaagcatt tacagaaacg    240
catccagcaa gaatattgtc cctttgagca gaaat                               275
```

<210> SEQ ID NO 124
<211> LENGTH: 276
<212> TYPE: DNA
<213> ORGANISM: Homo sapiens

<400> SEQUENCE: 124

```
tccccggtta ctacctctta tccatccccg gccaccacct catacccatc ccctgtgccc    60
acctccttct cctctcccgg ctcctcgacc tacccatccc ctgtgcacag tggcttcccc    120
tccccgtcgg tggccaccac gtactcctct gttcccctg ctttcccggc ccaggtcagc     180
agcttccctt cctcagctgt caccaactcc ttcagcgcct ccacagggct ttcggacatg    240
acagcaacct tttctcccag gacaattgaa atttgc                              276
```

<210> SEQ ID NO 125
<211> LENGTH: 292
<212> TYPE: DNA
<213> ORGANISM: Homo sapiens

<400> SEQUENCE: 125

```
atgaagactt ggctgattca gatgccaggg ccttgtatga agcaggagaa aggagaaagg    60
ggacagacgt aaacgtgttc aataccatcc ttaccaccag aagctatcca caacttcgca    120
gagtgtttca gaaatacacc aagtacagta agcatgacat gaacaaagtt ctggacctgg    180
agttgaaagg tgacattgag aaatgcctca cagctatcgt gaagtgcgcc acaagcaaac    240
cagctttctt tgcagagaag cttcatcaag ccatgaaagt atgtaccatt ct            292
```

<210> SEQ ID NO 126
<211> LENGTH: 237
<212> TYPE: DNA
<213> ORGANISM: Homo sapiens

<400> SEQUENCE: 126

```
tgccttgtgt cttccgtttg acggaagaga atggattctg gtatctagac caaatcagaa    60
gggaacagta cattccaaat gaagaatttc ttcattctga tctcctagaa gacagcaaat    120
accgaaaaat ctactccttt actcttaagc ctcgaacaat tgaagatttt gagtctatga    180 atacataccct gcagacatct ccatcatctg tgtttactag taatcatttt gttcctt      237
```

<210> SEQ ID NO 127
<211> LENGTH: 285
<212> TYPE: DNA
<213> ORGANISM: Homo sapiens

<400> SEQUENCE: 127

```
ggtatagcat atgtggcctt gcttactaaa gtggatgatt gcagtgaggt tcttcaagac    60
aactttttaa acatgagtag atctatgact tctcaaagcc gggtcatgaa tgtccataaa    120
atgctaggca ttcctatttc caatattttg atggttggaa attatgcttc agatttggaa    180
ctggacccca tgaaggatat tctcatcctc tctgcactga ggcagatgct gcgggctgca    240
gatgattttt tagaagattt gcctcttgag gaaactggtg cattt                    285
```

<210> SEQ ID NO 128

```
<211> LENGTH: 233
<212> TYPE: DNA
<213> ORGANISM: Homo sapiens

<400> SEQUENCE: 128
tgcttatccg ttagccgtgg tgatttagca ggaagctgtg agagcagttt ggtttctagc     60
atgaagacag agccccaccc tcagatgcac atgagctggc gggattgaaa gatgctgtct    120
tcgtactggg aaagggattt tcagccctca gaatcgctcc accttgcagc tctcccttc     180 tctgtattcc tagaaactga cacatgctga acatcacagc ttatttcctc att           233

<210> SEQ ID NO 129
<211> LENGTH: 270
<212> TYPE: DNA
<213> ORGANISM: Homo sapiens

<400> SEQUENCE: 129
taggcaccac atgggatcct tgttcttcct ccttgtaagc agtaattgaa atcagtttgg     60
cagcctggtt tacagtgacc atggtggctt gtctcccgtg ctcttacctc actctgttga   120
tgttgtaaaa cctccagcta acttcatggg gtggctgacc cacgttgctc atttattcat   180
tcaacacata ttcattgacc atctactcta tgccaggtat tgttatcagc actgggaata   240
gatcagtgaa ctattgatct atttgtctaa                                    270

<210> SEQ ID NO 130
<211> LENGTH: 79
<212> TYPE: DNA
<213> ORGANISM: Homo sapiens

<400> SEQUENCE: 130
ctcagttctg gtccttcaag cctgtatggt ttggattttc agtaggggac agttgatgtg     60
gagtcaatct ctttggtac                                                 79

<210> SEQ ID NO 131
<211> LENGTH: 256
<212> TYPE: DNA
<213> ORGANISM: Homo sapiens

<400> SEQUENCE: 131
ctgaggtgct atgttcttag tggatgttct gaccctgctt caaatatttc cctcacccttt    60 cccatcttcc aagggtataa ggaatctttc tgctttgggg tttatcagaa ttctcagaat   120
ctcaaataac taaaaggtat gcaatcaaat ctgcttttta aagaatgctc tttacttcat   180
ggacttccac tgccatcctc ccaaggggcc caaattcttt cagtggctac ctacatacaa   240
ttccaaacac atacag                                                   256

<210> SEQ ID NO 132
<211> LENGTH: 94
<212> TYPE: DNA
<213> ORGANISM: Homo sapiens

<400> SEQUENCE: 132
taacaaatca tcaacttcca ctggtcaata tatagatttt gggtgtctga ggccccaaga     60
ttagatgcca ctaatctcca aagattccct ccaa                                94

<210> SEQ ID NO 133
<211> LENGTH: 254
<212> TYPE: DNA
<213> ORGANISM: Homo sapiens
```

<400> SEQUENCE: 133

```
gcagggtctt gggataacac tgtcatcaga aacaaggctg ggggctgatt tcggggtggg      60
gagccttagg aggccagaaa ttccaatcag agccagtttt tctgggaggg agtggctaga     120
cagtcaagga aggacgttca catttcaaaa gaagtcgggt gggggggatga gattattcta     180
gggggggcatc gaattcccct taaggggggg gctcacttct gcccagagta aagaggatct     240
cacaccatgg aaat                                                       254
```

<210> SEQ ID NO 134
<211> LENGTH: 298
<212> TYPE: DNA
<213> ORGANISM: Homo sapiens

<400> SEQUENCE: 134

```
tagttatact tacacactcc tctcatgttg tctatggagt ggtggatgct gcagggaggg      60
tgacatccta gttagtccta agagccagac tgcctgaagc tcactataac aagtcctgcc     120
ttggggaaga aggaagtgtg tctctgtgaa cctcccacct gggccgaaag ggaggccact     180
ctctctgctg cctctccccca accttggcct tctgtgctcc tagtgaacct ctcaccccct     240
gcctacagcc tcgaatctca gaccatgatg acctctggtc accctgaatc agagcttt      298
```

<210> SEQ ID NO 135
<211> LENGTH: 292
<212> TYPE: DNA
<213> ORGANISM: Homo sapiens

<400> SEQUENCE: 135

```
gtaaaattcc tatgtcagca ccctaatgag acaaatgaca tcctaattct tcccctcggc      60
ttgccagttt gtaggtacta gttttcaga agttactcta aaatatttct gattgcagct     120
ccttcctaaa gagcagtatg agcagcatgt ggttatttat gtattcactc ttttctccta     180
cttctgtggt gacctggaac aaattctctt atgtatgtaa agattggaca gcccacctga     240
ttccgatgtc acttagatac actgttttg tatcagcctc ttctcttaga aa              292
```

<210> SEQ ID NO 136
<211> LENGTH: 180
<212> TYPE: DNA
<213> ORGANISM: Homo sapiens

<400> SEQUENCE: 136

```
gattgttggc caatagacct tccactccag tagagaggga ggacttggct ctgagaacct      60
ccatctgacc taagaggaaa cctcctctcc tatggccatc tcctcctcct gtcctttaag     120
tcctctgtgg ttactatatc tccttttccc tttcttaccc tttcgcttag caatttcaat     180
```

<210> SEQ ID NO 137
<211> LENGTH: 141
<212> TYPE: DNA
<213> ORGANISM: Homo sapiens

<400> SEQUENCE: 137

```
aagttctttg ggatagaggg tgaagaactt gggacatggg ctgtttcagg gcagctgaag      60
ttcaaagggg aataggtaat tgggggggaag ggggaagtt ggggcagaaa gggattgttg     120
ggccaatagg acctttccac t                                               141
```

<210> SEQ ID NO 138

```
<211> LENGTH: 248
<212> TYPE: DNA
<213> ORGANISM: Homo sapiens
<220> FEATURE:
<221> NAME/KEY: misc_feature
<222> LOCATION: (161)..(200)
<223> OTHER INFORMATION: n is a, c, g, or t

<400> SEQUENCE: 138
aggattatac ttcagtccct gctttacatt tatttcttaa agaagcttct ggtaaattag      60
agcaatagca tcggcttagt ttagtgttgt tctgttggac taaggatatc agttctatcc     120
gtatggtcgg gcctaaagcc tgggaaatat ttaatgaagg nnnnnnnnnn nnnnnnnnnn     180
nnnnnnnnnn nnnnnnnnnn ataacaaata acaaaacaaa aaccaagcca tttcccttta     240
tagtaaga                                                              248

<210> SEQ ID NO 139
<211> LENGTH: 259
<212> TYPE: DNA
<213> ORGANISM: Homo sapiens

<400> SEQUENCE: 139
acagaagcca ttgcctccct tgtttacctt gggtccacct ccaccaaaac ccaacagacc      60
accaaatgtt gacctgacga aattccacaa aacctcttct ggaaacagta ctagcaaagg     120
ccagacgtct tactcaacaa cttccctgcc accacctcca ccatcccatc cggccagcca     180
accaccattg ccagcatctc acccatcaca accaccagtc ccaagcctac ctcccagaaa     240
cattaaacct ccgtttgac                                                  259

<210> SEQ ID NO 140
<211> LENGTH: 199
<212> TYPE: DNA
<213> ORGANISM: Homo sapiens

<400> SEQUENCE: 140
gcacagctca gcacaacatt ccaagctcaa aatagaagcc ttctcagtga gctccagcac      60
gcccagagga ctgttaataa cgatgatcca tgtgttttac tctaaagtgc taaatatggg     120
agtttccttt ttttactct ttgtcactga tgacacaaca gaaagaaac tgtagacctt      180 gggacaatca acatttaaa                                                  199

<210> SEQ ID NO 141
<211> LENGTH: 279
<212> TYPE: DNA
<213> ORGANISM: Homo sapiens

<400> SEQUENCE: 141
cctgccctgg aagtaatctt gctgtcctgg aatctcctcg gggatgaggc agctgccgag      60
ctggcccagg tgctgccgaa gatgggccgg ctgaagagag tggacctgga gaagaatcag     120
atcacagctt tggggggcctg gctcctggct gaaggactgg cccaggggtc tagcatccaa     180
gtcatccgcc tctggaataa ccccattccc tgcgacatgg cccagcacct gaagagccag     240
gagcccaggc tggactttgc cttctttgac aaccagccc                             279

<210> SEQ ID NO 142
<211> LENGTH: 198
<212> TYPE: DNA
<213> ORGANISM: Homo sapiens

<400> SEQUENCE: 142
```

```
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt ttttactctt tgtcactgat gacacaacag aaaagaaact gtagaccttg   180
ggacaatcaa catttaaa                                                  198

<210> SEQ ID NO 143
<211> LENGTH: 183
<212> TYPE: DNA
<213> ORGANISM: Homo sapiens

<400> SEQUENCE: 143
gagagttcaa ctaagaaagg tcacatatgt gaaagcccaa ggacactgtt tgatatacag    60
caggtattca atcagtgtta tttgaaacca aatctgaatt tgaagtttga atcttctgag   120
ttggaatgaa ttttttttcta gctgagggaa actgtatttt tctttcccca agaggaatg   180 taa                                                                  183

<210> SEQ ID NO 144
<211> LENGTH: 294
<212> TYPE: DNA
<213> ORGANISM: Homo sapiens

<400> SEQUENCE: 144
ctcgattatt ccctgtacaa tatttaaaat ttattgcttg atacttttga caacaaatta    60
ggttttgtac aattgaactt aaataaatgt cattaaaata aataaatgca atatgtatta   120
atattcattg tataaaaata gaagaataca acatatttg ttaaatattt acatatgaaa   180
tttaatatag ctatttttat ggaattttc attgatatga aaaatatgat attgcatatg   240
catagttccc atgttaaatc ccattcataa ctttcattaa agcatttact ttga          294

<210> SEQ ID NO 145
<211> LENGTH: 231
<212> TYPE: DNA
<213> ORGANISM: Homo sapiens

<400> SEQUENCE: 145
gcaaataaat tcatacatag tacatacaaa ataagagaaa aaattaaatt gcagatggtt    60
aaatatcaca tcacttaact gatgttactg aaaatgtatt ttcctgcata atcatatggt   120
tgacagtatg cattaagaag gtaagtaaaa caatgaagac aattttgatt taatatggta   180
atgcacaatt ccaactaacg tacattcaac agatcatgaa attgggttat t             231

<210> SEQ ID NO 146
<211> LENGTH: 175
<212> TYPE: DNA
<213> ORGANISM: Homo sapiens

<400> SEQUENCE: 146
ttgccttcta aatatactga aatgatttag atatgtgtca acaattaatg atctttatt    60 caatctaaga aatggtttag ttttttctctt tagctctatg gcatttcact caagtggaca   120
ggggaaaaag taattgccat gggctccaaa gaatttgctt tatgttttta gctat        175

<210> SEQ ID NO 147
<211> LENGTH: 192
<212> TYPE: DNA
<213> ORGANISM: Homo sapiens
```

<400> SEQUENCE: 147

```
cctggccact cgcaagacct tttatctgaa aaccagccaa gctttattca cgacacactt    60
cttcccttca ctctcccact tctgtggtca actccctgca gaactcccaa actgccgttc   120
ttttcgatag ctcacgatgg tgtatgagtg tcaatcatct gacccttctt ggagtctcat   180
atttcgtgga ac                                                       192
```

<210> SEQ ID NO 148
<211> LENGTH: 187
<212> TYPE: DNA
<213> ORGANISM: Homo sapiens

<400> SEQUENCE: 148

```
ctgaggaccg gctgcagacc tcactctgag tggcaggcag agaaccaaag ctgcttcgct    60
gctctccagg gagaccctcc tgggatgggc ctgagaggcc ggggctcagg gaaggggctg   120
ggatcggaac ttcctgctct tgtttctgga caactttccc cttctgcttt aaaggttgtc   180
gattatt                                                             187
```

<210> SEQ ID NO 149
<211> LENGTH: 254
<212> TYPE: DNA
<213> ORGANISM: Homo sapiens

<400> SEQUENCE: 149

```
agtgtgatgg atccccttta ggttatttag gggtatatgt ccctgcttg aaccctgaag     60
gccaggtaat gagccatggc cattgtcccc agctgaggac caggtgtctc taaaaaccca   120
aacatcctgg agagtatgcg agaacctacc aagaaaaaca gtctcattac tcatatacag   180
caggcaaaga gacagaaaat taactgaaaa gcagtttaga gactggggga ggccggatct   240
ctagagccat cctg                                                     254
```

<210> SEQ ID NO 150
<211> LENGTH: 192
<212> TYPE: DNA
<213> ORGANISM: Homo sapiens

<400> SEQUENCE: 150

```
gcgttacaga tggacgtagc tgccttggtt ttccagtcct caaggaata ctgaagatgc      60
tgactgaagg ggattggatg ttgattttag aagatggaga actccagcca cctttgtaaa   120
gcactagtgt ttgtcattta tgtaagtcag gtcggctcag gtcttgatag tccgtcttgg   180
tgtgaggcat gc                                                       192
```

<210> SEQ ID NO 151
<211> LENGTH: 157
<212> TYPE: DNA
<213> ORGANISM: Homo sapiens

<400> SEQUENCE: 151

```
cacagtaatg tcgaaactag gcctttgaac caaggcagtc tagggtaaaa tatagtttca    60
aagtatgaat aagaattggt atttgtgtta tctttgagta agaaactgtc cgatatgaat   120
cacaacgtgg gtgaatgtag tattttcctg aagtgtg                            157
```

<210> SEQ ID NO 152
<211> LENGTH: 187
<212> TYPE: DNA
<213> ORGANISM: Homo sapiens

<400> SEQUENCE: 152

```
ggccatgaac atcacctgca caggacgggg accagacaac tgtatccagt gtgcccacta    60
cattgacggc ccccactgcg tcaagacctg cccggcagga gtcatgggag aaaacaacac   120
cctggtctgg aagtacgcag acgccggcca tgtgtgccac ctgtgccatc caaactgcac   180
ctacggg                                                             187
```

<210> SEQ ID NO 153
<211> LENGTH: 102
<212> TYPE: DNA
<213> ORGANISM: Homo sapiens

<400> SEQUENCE: 153

```
atcacaggtt tgagctgaat tatcacatga atataaatgg gaaatcagtg ttttagagag    60
agaactttc gacatatttc ctgttccctt ggaataaaaa ca                       102
```

<210> SEQ ID NO 154
<211> LENGTH: 203
<212> TYPE: DNA
<213> ORGANISM: Homo sapiens

<400> SEQUENCE: 154

```
agtttcagac aaatgttcag tgtgagtgag gaaaacatgt tcagtgagga aaaacattc    60
agacaaatgt tcagtgagga aaaaagggg aagttgggga taggcagatg ttgacttgag   120
gagttaatgt gatcttgggg gagatacatc ttatagagtt agaaatagaa tctgaatttc   180
taaagggaga ttctggcttg gga                                           203
```

<210> SEQ ID NO 155
<211> LENGTH: 273
<212> TYPE: DNA
<213> ORGANISM: Homo sapiens

<400> SEQUENCE: 155

```
aacttaagct gaatgtgtaa tggatttgtc tatagtttta catatttgga agcattttaa    60
aataggtttt aatcttacat aaaattactt ttatacttgt gttaacattt tcttctgtgc   120
cttttgggta atttaatttc tgttatgaat ttctggtgcc tatgagctag ctatcaccta   180
cctgaaaggt gcttagaggt gaaggtactg tttctaaaaa cacatcactg tgacaccttt   240
ctatcctcac attttcaagc ttgcctcttt tct                                273
```

<210> SEQ ID NO 156
<211> LENGTH: 135
<212> TYPE: DNA
<213> ORGANISM: Homo sapiens

<400> SEQUENCE: 156

```
gtgactgctt atgaagggtt attgctcagc taagtatttc tgaatgagtc ttaggtctgt    60
tggccttcaa tctctaccga aaccctgaga acttgatgat gcttttgttt tctgagaatc   120
gtttcagtgt gctgg                                                    135
```

<210> SEQ ID NO 157
<211> LENGTH: 218
<212> TYPE: DNA
<213> ORGANISM: Homo sapiens

<400> SEQUENCE: 157

```
catttgctgc aactctcagt ggtaagaatg attaagtgca gctataggag aatacttcca    60
ttggcatgcc acctgcgtaa aacacacaat tttgttaaga tatacaataa aattattatg   120
ctaatagcaa atattttatg tagctcacta tgttccatgt agtcttctaa gtgcttcatg   180
ttagtcccca gttaaacacc tggttttgga aggctgag                           218

<210> SEQ ID NO 158
<211> LENGTH: 132
<212> TYPE: DNA
<213> ORGANISM: Homo sapiens

<400> SEQUENCE: 158
gtgagcctgc cagcgtttgc gacgtccccg cacgacaggc tcatactttc tgaggatcgt    60
gcatagcata ggacgtctga acctttgtac aaatgtgtag atgacatctt gctacagctt   120
ttatttgtga at                                                        132

<210> SEQ ID NO 159
<211> LENGTH: 129
<212> TYPE: DNA
<213> ORGANISM: Homo sapiens

<400> SEQUENCE: 159
gtaaattcaa tacaatgtca gttttttaaaa gtcaaagtta gatcaagaga atatttcaga    60
gttttggttt acacatcaag aaacagacac acatacctag gaaagattta cacaatagat   120
aatcatctt                                                            129

<210> SEQ ID NO 160
<211> LENGTH: 229
<212> TYPE: DNA
<213> ORGANISM: Homo sapiens

<400> SEQUENCE: 160
actgtacaaa gtataagtct tagatgtata tatttcctat attgttttca gtgtacatgg    60
aataacatgt aattaagtac tatgtatcaa tgagtaacag gaaaatttta aaaatacaga   120
tagatatatg ctctgcatgt tacataagat aaatgtgctg aatggttttc aaataaaaat   180
gaggtactct cctggaaata ttaagaaaga ctatctaaat gttgaaaga                229

<210> SEQ ID NO 161
<211> LENGTH: 181
<212> TYPE: DNA
<213> ORGANISM: Homo sapiens

<400> SEQUENCE: 161
gaggaccgag cacagaaatc ttagagattt cttgtcccct ctcaggtcat gtgtagatgc    60
gataaatcaa gtgattggtg tgcctgggtc tcactacaag cagcctatct gcttaagaga   120
ctctggagtt tcttatgtgc cctggtggac acttgcccac catcctgtga gtaaaagtga   180
a                                                                    181

<210> SEQ ID NO 162
<211> LENGTH: 280
<212> TYPE: DNA
<213> ORGANISM: Homo sapiens

<400> SEQUENCE: 162
tctgaactct caaaagtcta ttttttttaac tgaaaatgta aatttataaa tatattcagg    60
agttggaatg ttgtagttac ctactgagta ggcggcgatt tttgtatgtt atgaacatgc   120
```

```
agttcattat tttgtggttc tattttactt tgtacttgtg tttgcttaaa caaagtgact    180
gtttggctta taaacacatt gaatgcgctt tattgcccat gggatatgtg gtgtatatcc    240
ttccaaaaaa ttaaaacgaa aataaagtag ctgcgattgg                          280

<210> SEQ ID NO 163
<211> LENGTH: 166
<212> TYPE: DNA
<213> ORGANISM: Homo sapiens

<400> SEQUENCE: 163
attcctgtca ttacccattg taacagagcc acaaactaat actatgcaat gttttaccaa    60
taatgcaata caaagacct caaaatacct gtgcatttct tgtaggaaaa caacaaaagg    120
taattatgtg taattatact agaagttttg taatctgtat cttatc                   166

<210> SEQ ID NO 164
<211> LENGTH: 136
<212> TYPE: DNA
<213> ORGANISM: Homo sapiens

<400> SEQUENCE: 164
caggacccat cacgcctgtg cagtggcccc cacagaaaga ctgagctcaa ggtgggaacc    60
acgtctgcta acttggagcc ccagtgccaa gcacagtgcc tgcatgtatt tatccaataa    120
atgtgaaatt ctgtcc                                                    136

<210> SEQ ID NO 165
<211> LENGTH: 237
<212> TYPE: DNA
<213> ORGANISM: Homo sapiens

<400> SEQUENCE: 165
aaagtggcat tttcttgatt ggaaaggggg aaggatctta ttgcacttgg gctgttcaga    60
atgtagaaag gacatatttg aggaagtatc tatttgagca ctgatttact ctgtaaaaag    120
caaaatctct ctgtcctaaa ctaatggaag cgattctccc atgctcatgt gtaatggttt    180
taacgttact cactggagag attggacttt ctggagttat ttaaccacta tgttcag      237

<210> SEQ ID NO 166
<211> LENGTH: 86
<212> TYPE: DNA
<213> ORGANISM: Homo sapiens

<400> SEQUENCE: 166
tttataatgt cccttcacaa acccagtgtt ttaggagcat gagtgccgtg tgtgtgcgtc    60
ctgtcggagc cctgtctcct ctctct                                         86

<210> SEQ ID NO 167
<211> LENGTH: 159
<212> TYPE: DNA
<213> ORGANISM: Homo sapiens

<400> SEQUENCE: 167
caccctcaga tgcacatgag ctggcgggat tgaaggatgc tgtcttcgta ctgggaaagg    60
gattttcagc cctcagaatc gctccacctt gcagctctcc ccttctctgt attcctagaa    120
actgacacat gctgaacatc acagcttatt tcctcattt                           159

<210> SEQ ID NO 168
```

```
<211> LENGTH: 175
<212> TYPE: DNA
<213> ORGANISM: Homo sapiens

<400> SEQUENCE: 168
aaatttaatt ttctacgcct ctggggatat ctgctcagcc aatggaaaat ctgggttcaa      60
ccagcccctg ccatttctta agactttctg ctgcactcac aggatcctga gctgcactta     120
cctgtgagag tcttcaaact tttaaacctt gccagtcagg acttttgcta ttgca          175

<210> SEQ ID NO 169
<211> LENGTH: 191
<212> TYPE: DNA
<213> ORGANISM: Homo sapiens

<400> SEQUENCE: 169
ctactcctta cagtctctag aattaaatgt actcatttag acaacatatt aaatgcatat      60
tttagccact ttagagaaac ctcataggca cagagtttcc aagattaatt ttaagaatat     120
cttcacgaac ttgaccctcc tactccacat tgcaacattt ccatcagaca gcatttcaat     180
tccagtatta t                                                          191

<210> SEQ ID NO 170
<211> LENGTH: 172
<212> TYPE: DNA
<213> ORGANISM: Homo sapiens

<400> SEQUENCE: 170
gtcatcatat ataattaaac agcttttttaa agaaacataa ccacaaacct tttcaaataa     60
taataataat aataataaaa aatgtatttt aaagatggcc tgtggttatc ttggaaattg    120
gtgatttatg ctagaaagct tttaatgttg gtttattgtt gaattcctag aa             172

<210> SEQ ID NO 171
<211> LENGTH: 239
<212> TYPE: DNA
<213> ORGANISM: Homo sapiens

<400> SEQUENCE: 171
catggattag ctggaagatc tgtatttgat ggaagacctt gaaattattg aagacatgg       60 atttcctgga agacgtggat tttcctggaa gatctggatt tggtggaaga ccagtaattg    120
ctggaagact ggatttgctg aagacttga tttactggaa gacttggagc ttcttggaag     180
acatggattg tccggaagac atggattgtc tggaagatgt ggattttctg gaagctcag    239

<210> SEQ ID NO 172
<211> LENGTH: 255
<212> TYPE: DNA
<213> ORGANISM: Homo sapiens

<400> SEQUENCE: 172
gtggaggaaa ctaaacattc ccttgatggt ctcaagctat gatcagaaga ctttaattat     60
atattttcat cctataagct taaataggaa agtttcttca acaggattac agtgtagcta    120
cctacatgct gaaaaatata gcctttaaat cattttttata ttataactct gtataataga    180
gataagtcca tttttttaaaa atgttttccc caaaccataa aaccctatac aagttgttct    240
agtaacaata catga                                                    255

<210> SEQ ID NO 173
<211> LENGTH: 238
```

```
<212> TYPE: DNA
<213> ORGANISM: Homo sapiens

<400> SEQUENCE: 173
tcaataaggg cgttcttcct tgcaagttga acattattg tgctaggatt gctctctaga    60
caagccagaa gtgacttatt aaactattga aggaaaagga ctcaagaaaa ataataaaag   120
accataaata agggcgaaaa cattaccatg tgaaaagaat gtatttcacc tgcaagttac   180
aaaaaaatag tttgtgcatt gcaaataagc aaagacttgg attgacttta cattcatc    238

<210> SEQ ID NO 174
<211> LENGTH: 230
<212> TYPE: DNA
<213> ORGANISM: Homo sapiens

<400> SEQUENCE: 174
aagctgtgtt gttgcttctt gtgaaggcca tgatattttg ttttccccca attaattgct    60
attgtgttat tttactactt ctctctgtat tttttcttgc attgacatta tagacattga   120
ggacctcatc caaacaattt aaaaatgagt gtgaaggggg aacaagtcaa aatatttta   180
aaagatcttc aaaaataatg cctctgtcta gcatgccaac aagaatgcat             230

<210> SEQ ID NO 175
<211> LENGTH: 166
<212> TYPE: DNA
<213> ORGANISM: Homo sapiens

<400> SEQUENCE: 175
tgcctgttgt agaccacagt cacacactgc tgtagtcttc cccagtcctc attcccagct    60
gcctcttcct actgcttccg tctatcaaaa agccccttg gcccaggttc cctgagctgt    120
gggattctgc actggtgctt tggattccct gatatgttcc ttcaaa                 166

<210> SEQ ID NO 176
<211> LENGTH: 137
<212> TYPE: DNA
<213> ORGANISM: Homo sapiens

<400> SEQUENCE: 176
gtcagacaga tgtggttgca tcctaactcc atgtctctga gcattagatt tctcatttgc    60
caataataat acctccctta gaagtttgtt gtgaggatta aataatgtaa ataaagaact   120
agcataacac tcaaaaa                                                  137

<210> SEQ ID NO 177
<211> LENGTH: 227
<212> TYPE: DNA
<213> ORGANISM: Homo sapiens

<400> SEQUENCE: 177
tctgtgtgtg ccctgtaacc tgactggtta acagcagtcc tttgtaaaca gtgttttaaa    60
ctctcctagt caatatccac cccatccaat ttatcaagga agaaatggtt cagaaaatat   120
tttcagccta cagttatgtt cagtcacaca cacatacaaa atgttccttt tgcttttaaa   180
gtaattttg actcccagat cagtcagagc ccctacagca ttgttaa                  227

<210> SEQ ID NO 178
<211> LENGTH: 218
<212> TYPE: DNA
<213> ORGANISM: Homo sapiens
```

<400> SEQUENCE: 178

```
gtttaagcct ggaacttgta agaaaatgaa aatttaattt ttttttctag gacgagctat        60
agaaaagcta ttgagagtat ctagttaatc agtgcagtag ttggaaacct tgctggtgta       120
tgtgatgtgc ttctgtgctt ttgaatgact ttatcatcta gtctttgtct attttttcctt      180
tgatgttcaa gtcctagtct ataggattgg cagtttaa                               218
```

<210> SEQ ID NO 179
<211> LENGTH: 243
<212> TYPE: DNA
<213> ORGANISM: Homo sapiens

<400> SEQUENCE: 179

```
gactgaggga tcgtagattt ttacaatctg tatctttgac aattctgggt gcgagtgtga        60
gagtgtgagc agggcttgct cctgccaacc acaattcaat gaatccccga ccccctacc       120
ccatgctgta cttgtggttc tcttttgta ttttgcatct gaccccgggg ggctgggaca       180
gattggcaat gggccgtccc ctctccctt ggttctgcac tgttgccaat aaaaagctct        240
taa                                                                    243
```

<210> SEQ ID NO 180
<211> LENGTH: 267
<212> TYPE: DNA
<213> ORGANISM: Homo sapiens

<400> SEQUENCE: 180

```
ggagggaagg caagattctt tcccctccc tgctgaagca tgtggtacag aggcaagagc         60
agagcctgag aagcgtcagg tcccacttct gccatgcagc tactatgagc cctcggggcc      120
tcctcctggg cctcagcttg cccagataca tacctaaata tatatatata tatatgaggg      180
agaacgcctc acccagattt tatcatgctg gaaagagtgt atgtatgtga agatgcttgg      240
tcaacttgta cccagtgaac acacaaa                                          267
```

<210> SEQ ID NO 181
<211> LENGTH: 267
<212> TYPE: DNA
<213> ORGANISM: Homo sapiens

<400> SEQUENCE: 181

```
ggagggaagg caagattctt tcccctccc tgctgaagca tgtggtacag aggcaagagc         60
agagcctgag aagcgtcagg tcccacttct gccatgcagc tactatgagc cctcggggcc      120
tcctcctggg cctcagcttg cccagataca tacctaaata tatatatata tatatgaggg      180
agaacgcctc acccagattt tatcatgctg gaaagagtgt atgtatgtga agatgcttgg      240
tcaacttgta cccagtgaac acacaaa                                          267
```

<210> SEQ ID NO 182
<211> LENGTH: 206
<212> TYPE: DNA
<213> ORGANISM: Homo sapiens

<400> SEQUENCE: 182

```
tattcttcta taacactcta tatagagcta tgtgagtact aatcacattg aataatagtt        60
ataaaattat tgtatagaca tctgcttctt aaacagattg tgagttcttt gagaaacagc      120
gtggatttta cttatctgtg tattcacaga gcttagcaca gtgcctggta atgagcaagc      180
atacttgcca ttactttttcc ttccca                                          206
```

<210> SEQ ID NO 183
<211> LENGTH: 264
<212> TYPE: DNA
<213> ORGANISM: Homo sapiens

<400> SEQUENCE: 183
cctaatttga gggtcagttc ctgcagaagt gcccttttgcc tccactcaat gcctcaattt    60
gttttctgca tgactgagag tctcagtgtt ggaacgggac agtatttatg tatgagtttt   120
tcctatttat tttgagtctg tgaggtcttc ttgtcatgtg agtgtggttg tgaatgattt   180
cttttgaaga tatattgtag tagatgttac aattttgtcg ccaaactaaa cttgctgctt   240
aatgatttgc tcacatctag taaa                                          264

<210> SEQ ID NO 184
<211> LENGTH: 226
<212> TYPE: DNA
<213> ORGANISM: Homo sapiens

<400> SEQUENCE: 184
ggacactttt gaaaacagga ctcagcatcg ctttcaatag gcttttcagg accttcactg    60
cattaaaaca atatttttaa aaatttagta cagtttagaa agagcactta ttttgtttat   120
atccattttt tcttactaaa ttatagggat taactttgac aaatcatgct gctgttattt   180
tctacatttg tattttatcc atagcactta ttcacattta ggaaaa                  226

<210> SEQ ID NO 185
<211> LENGTH: 275
<212> TYPE: DNA
<213> ORGANISM: Homo sapiens

<400> SEQUENCE: 185
cagtttctgt tctctcacag gtgataaaca atgcttttg tgcactacat actcttcagt    60
gtagagctct tgttttatgg gaaaaggctc aaatgccaaa ttgtgtttga tggattaata   120 tgccctttg ccgatgcata ctattactga tgtgactcgg ttttgtcgca gctttgcttt   180
gtttaatgaa acacacttgt aaacctcttt tgcactttga aaagaatcc agcgggatgc    240 tcgagcacct gtaaacaatt ttctcaacct atttg                              275

<210> SEQ ID NO 186
<211> LENGTH: 275
<212> TYPE: DNA
<213> ORGANISM: Homo sapiens

<400> SEQUENCE: 186
cagtttctgt tctctcacag gtgataaaca atgcttttg tgcactacat actcttcagt    60
gtagagctct tgttttatgg gaaaaggctc aaatgccaaa ttgtgtttga tggattaata   120 tgccctttg ccgatgcata ctattactga tgtgactcgg ttttgtcgca gctttgcttt   180
gtttaatgaa acacacttgt aaacctcttt tgcactttga aaagaatcc agcgggatgc    240 tcgagcacct gtaaacaatt ttctcaacct atttg                              275

<210> SEQ ID NO 187
<211> LENGTH: 114
<212> TYPE: DNA
<213> ORGANISM: Homo sapiens

<400> SEQUENCE: 187

```
agcaagtgta gacaccttcg agggcagaga tcgggagatt taagatgtta cagcatattt    60 tttttcttg ttttacagta ttcaattttg tgttgattca gctaaattat gaaa           114

<210> SEQ ID NO 188
<211> LENGTH: 205
<212> TYPE: DNA
<213> ORGANISM: Homo sapiens

<400> SEQUENCE: 188
gtctcacata tttatataat cctcaaatat actgtaccat tttagatatt ttttaaacag    60
attaatttgg agaagtttta ttcattacct aattctgtgg caaaaatggt gcctctgatg   120
ttgtgatata gtattgtcag tgtgtacata tataaaacct gtgtaaacct ctgtccttat   180
gaaccataac aaatgtagct tttta                                          205

<210> SEQ ID NO 189
<211> LENGTH: 158
<212> TYPE: DNA
<213> ORGANISM: Homo sapiens

<400> SEQUENCE: 189
cagccccacc cctgtaaatg gaatttacca gatgaaggga atgaagtccc tcactgagcc    60
tcagatttcc tcacctgtga atgggctga ggcaggaaat gggaaaaagt gttagtgctt    120
ccaggcggca ctgacagcct cagtaacaat aaaaacaa                            158

<210> SEQ ID NO 190
<211> LENGTH: 254
<212> TYPE: DNA
<213> ORGANISM: Homo sapiens

<400> SEQUENCE: 190
tcagctgccc tgaaacagcc catgtcccaa gttcttcacc tctatccaaa gaacttgatt    60
tgcatggatt ttggataaat catttcagta tcatctccat catatgcctg acccttgct    120 cccttcaatg ctagaaaatc gagttggcaa atgggggttt gggcccctca gagccctgcc   180
ctgcacccct gtacagtgtc tgtgccatgg atttcgtttt tcttggggta ctcttgatgt   240
gaagataatt tgca                                                      254

<210> SEQ ID NO 191
<211> LENGTH: 235
<212> TYPE: DNA
<213> ORGANISM: Homo sapiens

<400> SEQUENCE: 191
gagtgtctca gaagtgtgct cctctggcct cagttctcct cttttggaac aacataaaac    60
aaatttaatt ttctacgcct ctggggatat ctgctcagcc aatggaaaat ctgggttcaa   120
ccagcccctg ccatttctta agactttctg ctccactcac aggatcctga gctgcactta   180
cctgtgagag tcttcaaact tttaaacctt gccagtcagg acttttgcta ttgca         235

<210> SEQ ID NO 192
<211> LENGTH: 296
<212> TYPE: DNA
<213> ORGANISM: Homo sapiens

<400> SEQUENCE: 192
gagggacgtc agaaaatcag tgcattgtgg agtcactttt ctgataaagg gcacatcaga    60
ctgcaaatgg tccagacagc cagattcagg acactgatga gtttctgggg tcaccatagc   120
```

```
atccctggag tcagctgctc tgcagcctga aggagggctg acagtgtgga gtcactgcta    180
ttacttaatg aaattatata gaaattctat aatgattatg taattgcata atgaaaactc    240
tccatatcag agttcagaat atctcccaat ttccagtaca gaatattatc cataac        296
```

<210> SEQ ID NO 193
<211> LENGTH: 290
<212> TYPE: DNA
<213> ORGANISM: Homo sapiens

<400> SEQUENCE: 193

```
gacagcaata acttcgtttt agaaacattc aagcaatagc tttatagctt caacatatgg    60
tacgttttaa ccttgaaagt tttgcaatga tgaaagcagt atttgtacaa atgaaaagca    120
gaattctctt ttatatggtt tatactgttg atcagaaatg ttgattgtgc attgagtatt    180
aaaaaattag atgtatatta ttcattgttc tttactcatg agtaccttat aataataata    240
atgtattctt tgttaacaat gccatgttgg tactagttat taatcatatc                290
```

<210> SEQ ID NO 194
<211> LENGTH: 269
<212> TYPE: DNA
<213> ORGANISM: Homo sapiens

<400> SEQUENCE: 194

```
ggcaggatat tgtaagcctt gaaaaagaat taggcaggat atcggaagcc ctgattagat    60
tctatcctaa gagcaacaga agatcactga cagtgtttta aatagataga ctagtttatt    120
agatttgcag tttagaagtt ccctttttttt gtaattattg gacagtgtag agaccggatg    180
gtgagagatg agttaggaag ttgtgacagc tctctatacc taccgctaat gtagaggatt    240
atttattttc atttcattac cattcgtgt                                       269
```

<210> SEQ ID NO 195
<211> LENGTH: 215
<212> TYPE: DNA
<213> ORGANISM: Homo sapiens

<400> SEQUENCE: 195

```
gtaaatatgtt tataatcctt tagatcttat aaatatgtgg tataaggaat gccatataat    60
gtgccaaaaa tctgagtgca tttaatttaa tgcttgctta tagtgctaaa gttaaatgat    120
cttaattctt tgcaattata tatgaaaaat gactgatttt tcttaaaata tgtaacttat    180
ataaatatat ctgtttgtac agattttaac cataa                                215
```

<210> SEQ ID NO 196
<211> LENGTH: 269
<212> TYPE: DNA
<213> ORGANISM: Homo sapiens

<400> SEQUENCE: 196

```
gtatccttga actggaaacc atccacgatc gagtatcgag tcattcaaca ctatcaattc    60
ctgggtgact ttttgaaaaa gtagtatctc ttgttgcaag aaatgctcca tctgtgagtc    120
catgtctctc actggaattg gatggaagtg gtgaatttca gccaaagtgg ccaaagaaat    180
cctgttcctg tgattctgac gtcatcagcc tctgcacctc tgtcttccct tctgccacat    240
gttgcctgtt ctccgtgact ttggtaaga                                       269
```

<210> SEQ ID NO 197

<211> LENGTH: 268
<212> TYPE: DNA
<213> ORGANISM: Homo sapiens

<400> SEQUENCE: 197

```
gagagagtga tcacgctgct gtgcccacct atgcggtaga ccttgttcct gggttgggag      60
atgttttatg atcagggtgc agtagaaaga gcacactagt agcagtaaag agaggtgacc     120
ctggctgcag ttctgcctct aacttcctga gtgacctcag gctagtcaca cagtgactgc     180
tccccacatt tcttttttgta agctgcaagg attgaatcag acaatagcct ctaagtttct    240
tctgaactct catactcagg gatgccaa                                        268
```

<210> SEQ ID NO 198
<211> LENGTH: 258
<212> TYPE: DNA
<213> ORGANISM: Homo sapiens

<400> SEQUENCE: 198

```
ttccctccca ctaatttgtt ggcctttaac agcaattttg aaaactgggt cttctggtta      60
tgttttttgtt ttaaaatctt taaattagag gatgctgtgc cattgagtac tttaagttaa    120
tatgaggttc tggttcaagg aaaacttacg ttggatctga accaatgagc agatattttg     180
atatgtgcca ctcttgcata tacatctcag tcctaactaa aggttctagt ggcatccagg     240
acctttaggg aggcattt                                                   258
```

<210> SEQ ID NO 199
<211> LENGTH: 147
<212> TYPE: DNA
<213> ORGANISM: Homo sapiens

<400> SEQUENCE: 199

```
cactgcgtct ggcaataatg taactttgaa gcttaaaaat taatcccagt ttgtagcaat      60
aacagaagac tatctacaac ggaagaaaga agcaactgcc ttacagttct gtaaagaatt     120
ggcaagaaaa taaagcctat agttgcc                                         147
```

<210> SEQ ID NO 200
<211> LENGTH: 274
<212> TYPE: DNA
<213> ORGANISM: Homo sapiens

<400> SEQUENCE: 200

```
cccttactta catactagct tccaaggaca ggtggaggta gggccagcct ggcgggagtg      60
gagaagccca gtctgtccta tgtaagggac aaagccaggt ctaatggtac tgggtagggg    120
gcactgccaa gacaataagc taggctactg ggtccagcta ctactttggt gggattcagg    180
tgagtctcca tgcacttcac atgttaccca gtgttcttgt tacttccaag gagaaccaag    240
aatggctctg tcacactcga agccaggttt gatc                                274
```

<210> SEQ ID NO 201
<211> LENGTH: 155
<212> TYPE: DNA
<213> ORGANISM: Homo sapiens

<400> SEQUENCE: 201

```
cctcctttct aaatgcagcg acctgtgttc ttcagcccta tccctttcta ttcctctgac      60
cccgcctcct ttctaaatgc agcgacctct gttcttcagc ctatcccctt tctattcctc    120
tgaccccgcc tcctttctaa atgcagcgac ctctg                                155
```

<210> SEQ ID NO 202
<211> LENGTH: 275
<212> TYPE: DNA
<213> ORGANISM: Homo sapiens

<400> SEQUENCE: 202
ggcgtcggcg cctagggcga agtgagccag ggtgcagtcg ggaagctcca ggacgaagcg    60
gcgcggcgga gccatggccc cagcgcagac cccgcgccgc ccgagcagcg gccccgacag   120
tggcccgcgc aggagccggc gggcgaaggc catgggcgcc tcagcgacgc cgccctcggc   180
cccgcctcgg aaacgaaacc tggcgggagc caggcgccgg cgggaaacga aacccggagg   240
gagccaggcg ccagcgggaa acgaaagcga agcgt                               275

<210> SEQ ID NO 203
<211> LENGTH: 23
<212> TYPE: DNA
<213> ORGANISM: Homo sapiens

<400> SEQUENCE: 203
agagacatct gtatgcattc ctg                                            23

<210> SEQ ID NO 204
<211> LENGTH: 25
<212> TYPE: DNA
<213> ORGANISM: Homo sapiens

<400> SEQUENCE: 204
ggtattttga ggtcttttgt attgc                                          25

<210> SEQ ID NO 205
<211> LENGTH: 25
<212> TYPE: DNA
<213> ORGANISM: Homo sapiens

<400> SEQUENCE: 205
acccattgta acagagccac aaact                                          25

<210> SEQ ID NO 206
<211> LENGTH: 22
<212> TYPE: DNA
<213> ORGANISM: Homo sapiens

<400> SEQUENCE: 206
tctcaggtca tgtgtagatg cg                                             22

<210> SEQ ID NO 207
<211> LENGTH: 25
<212> TYPE: DNA
<213> ORGANISM: Homo sapiens

<400> SEQUENCE: 207
ctccagagtc tcttaagcag atagg                                          25

<210> SEQ ID NO 208
<211> LENGTH: 25
<212> TYPE: DNA
<213> ORGANISM: Homo sapiens

<400> SEQUENCE: 208
agacccaggc acaccaatca cttga                                          25

<210> SEQ ID NO 209
<211> LENGTH: 21
<212> TYPE: DNA
<213> ORGANISM: Homo sapiens

<400> SEQUENCE: 209
aacaacagat gcaggaacag g                                    21

<210> SEQ ID NO 210
<211> LENGTH: 18
<212> TYPE: DNA
<213> ORGANISM: Homo sapiens

<400> SEQUENCE: 210
agtcctctgg gcgtgctg                                        18

<210> SEQ ID NO 211
<211> LENGTH: 25
<212> TYPE: DNA
<213> ORGANISM: Homo sapiens

<400> SEQUENCE: 211
cacagctcag cacaacattc caagc                                25

<210> SEQ ID NO 212
<211> LENGTH: 23
<212> TYPE: DNA
<213> ORGANISM: Homo sapiens

<400> SEQUENCE: 212
ctgcatactt ggacactaaa gcc                                  23

<210> SEQ ID NO 213
<211> LENGTH: 24
<212> TYPE: DNA
<213> ORGANISM: Homo sapiens

<400> SEQUENCE: 213
atgttttcct cactcacact gaac                                 24

<210> SEQ ID NO 214
<211> LENGTH: 25
<212> TYPE: DNA
<213> ORGANISM: Homo sapiens

<400> SEQUENCE: 214
agcaacaaag cagccacagt ttcag                                25

<210> SEQ ID NO 215
<211> LENGTH: 23
<212> TYPE: DNA
<213> ORGANISM: Homo sapiens

<400> SEQUENCE: 215
acagaaagac tgagctcaag gtg                                  23

<210> SEQ ID NO 216
<211> LENGTH: 18
<212> TYPE: DNA
<213> ORGANISM: Homo sapiens

<400> SEQUENCE: 216
tgcaggcact gtgcttgg                                        18

```
<210> SEQ ID NO 217
<211> LENGTH: 25
<212> TYPE: DNA
<213> ORGANISM: Homo sapiens

<400> SEQUENCE: 217
aaccacgtct gctaacttgg agccc                                           25

<210> SEQ ID NO 218
<211> LENGTH: 25
<212> TYPE: DNA
<213> ORGANISM: Homo sapiens

<400> SEQUENCE: 218
tgtaaaaagc aaaatctctc tgtcc                                           25

<210> SEQ ID NO 219
<211> LENGTH: 24
<212> TYPE: DNA
<213> ORGANISM: Homo sapiens

<400> SEQUENCE: 219
agtccaatct ctccagtgag taac                                            24

<210> SEQ ID NO 220
<211> LENGTH: 25
<212> TYPE: DNA
<213> ORGANISM: Homo sapiens

<400> SEQUENCE: 220
aatggaagcg attctcccat gctca                                           25

<210> SEQ ID NO 221
<211> LENGTH: 22
<212> TYPE: DNA
<213> ORGANISM: Homo sapiens

<400> SEQUENCE: 221
gaccaggtgt ctctaaaaac cc                                              22

<210> SEQ ID NO 222
<211> LENGTH: 25
<212> TYPE: DNA
<213> ORGANISM: Homo sapiens

<400> SEQUENCE: 222
ttgcctgctg tatatgagta atgag                                           25

<210> SEQ ID NO 223
<211> LENGTH: 25
<212> TYPE: DNA
<213> ORGANISM: Homo sapiens

<400> SEQUENCE: 223
cctggagagt atgcgagaac ctacc                                           25

<210> SEQ ID NO 224
<211> LENGTH: 23
<212> TYPE: DNA
<213> ORGANISM: Homo sapiens

<400> SEQUENCE: 224
```

```
gaagacgtgg attttcctgg aag                                          23

<210> SEQ ID NO 225
<211> LENGTH: 25
<212> TYPE: DNA
<213> ORGANISM: Homo sapiens

<400> SEQUENCE: 225
tccaagtctt ccagtaaatc aagtc                                        25

<210> SEQ ID NO 226
<211> LENGTH: 25
<212> TYPE: DNA
<213> ORGANISM: Homo sapiens

<400> SEQUENCE: 226
tccagcaaat ccagtcttcc agcaa                                        25

<210> SEQ ID NO 227
<211> LENGTH: 25
<212> TYPE: DNA
<213> ORGANISM: Homo sapiens

<400> SEQUENCE: 227
aacaaatcat caacttccac tggtc                                        25

<210> SEQ ID NO 228
<211> LENGTH: 25
<212> TYPE: DNA
<213> ORGANISM: Homo sapiens

<400> SEQUENCE: 228
tggagggaat ctttggagat tagtg                                        25

<210> SEQ ID NO 229
<211> LENGTH: 25
<212> TYPE: DNA
<213> ORGANISM: Homo sapiens

<400> SEQUENCE: 229
tctaatcttg gggcctcaga caccc                                        25

<210> SEQ ID NO 230
<211> LENGTH: 23
<212> TYPE: DNA
<213> ORGANISM: Homo sapiens

<400> SEQUENCE: 230
gacattgagg acctcatcca aac                                          23

<210> SEQ ID NO 231
<211> LENGTH: 25
<212> TYPE: DNA
<213> ORGANISM: Homo sapiens

<400> SEQUENCE: 231
gacagaggca ttactttga agatc                                         25

<210> SEQ ID NO 232
<211> LENGTH: 25
<212> TYPE: DNA
<213> ORGANISM: Homo sapiens

<400> SEQUENCE: 232
```

```
ttgacttgtt cccccttcac actca                                              25
```

<210> SEQ ID NO 233
<211> LENGTH: 25
<212> TYPE: DNA
<213> ORGANISM: Homo sapiens

<400> SEQUENCE: 233

```
ctcagttctc ctcttttgga acaac                                              25
```

<210> SEQ ID NO 234
<211> LENGTH: 23
<212> TYPE: DNA
<213> ORGANISM: Homo sapiens

<400> SEQUENCE: 234

```
ttgaacccag attttccatt ggc                                                23
```

<210> SEQ ID NO 235
<211> LENGTH: 25
<212> TYPE: DNA
<213> ORGANISM: Homo sapiens

<400> SEQUENCE: 235

```
tctacgcctc tggggatatc tgctc                                              25
```

<210> SEQ ID NO 236
<211> LENGTH: 21
<212> TYPE: DNA
<213> ORGANISM: Homo sapiens

<400> SEQUENCE: 236

```
tggcactgtg gattctcaag g                                                  21
```

<210> SEQ ID NO 237
<211> LENGTH: 19
<212> TYPE: DNA
<213> ORGANISM: Homo sapiens

<400> SEQUENCE: 237

```
ctgggggtat gggcaggag                                                     19
```

<210> SEQ ID NO 238
<211> LENGTH: 25
<212> TYPE: DNA
<213> ORGANISM: Homo sapiens

<400> SEQUENCE: 238

```
caccagcgga ccagtttcag aggca                                              25
```

<210> SEQ ID NO 239
<211> LENGTH: 25
<212> TYPE: DNA
<213> ORGANISM: Homo sapiens

<400> SEQUENCE: 239

```
ctaatacagc tggtggagtt ctatc                                              25
```

<210> SEQ ID NO 240
<211> LENGTH: 25
<212> TYPE: DNA
<213> ORGANISM: Homo sapiens

```
<400> SEQUENCE: 240
agcaatccta gcacaataat gtttc                                   25

<210> SEQ ID NO 241
<211> LENGTH: 25
<212> TYPE: DNA
<213> ORGANISM: Homo sapiens

<400> SEQUENCE: 241
actcaataag ggcgttcttc cttgc                                   25

<210> SEQ ID NO 242
<211> LENGTH: 25
<212> TYPE: DNA
<213> ORGANISM: Homo sapiens

<400> SEQUENCE: 242
aggaattttt accaaaacca caagc                                   25

<210> SEQ ID NO 243
<211> LENGTH: 25
<212> TYPE: DNA
<213> ORGANISM: Homo sapiens

<400> SEQUENCE: 243
aacagaacct ttacaaaacc ctacc                                   25

<210> SEQ ID NO 244
<211> LENGTH: 24
<212> TYPE: DNA
<213> ORGANISM: Homo sapiens

<400> SEQUENCE: 244
aacagaccac cacgaccaac aaca                                    24

<210> SEQ ID NO 245
<211> LENGTH: 23
<212> TYPE: DNA
<213> ORGANISM: Homo sapiens

<400> SEQUENCE: 245
ttggtgtgac agtgttcttt gtg                                     23

<210> SEQ ID NO 246
<211> LENGTH: 25
<212> TYPE: DNA
<213> ORGANISM: Homo sapiens

<400> SEQUENCE: 246
aggaggagtt aggacttagg aatag                                   25

<210> SEQ ID NO 247
<211> LENGTH: 25
<212> TYPE: DNA
<213> ORGANISM: Homo sapiens

<400> SEQUENCE: 247
tgccttgctc agccacaatt cttgc                                   25

<210> SEQ ID NO 248
<211> LENGTH: 25
<212> TYPE: DNA
<213> ORGANISM: Homo sapiens
```

```
<400> SEQUENCE: 248
tgtggatttg aatgtgtgta caagc                                          25

<210> SEQ ID NO 249
<211> LENGTH: 24
<212> TYPE: DNA
<213> ORGANISM: Homo sapiens

<400> SEQUENCE: 249
ggcaccataa agccacttaa tagg                                           24

<210> SEQ ID NO 250
<211> LENGTH: 24
<212> TYPE: DNA
<213> ORGANISM: Homo sapiens

<400> SEQUENCE: 250
aagagccatg ccactcctac ccgg                                           24

<210> SEQ ID NO 251
<211> LENGTH: 22
<212> TYPE: DNA
<213> ORGANISM: Homo sapiens

<400> SEQUENCE: 251
ccctcactga gcctcagatt tc                                             22

<210> SEQ ID NO 252
<211> LENGTH: 19
<212> TYPE: DNA
<213> ORGANISM: Homo sapiens

<400> SEQUENCE: 252
gccgcctgga agcactaac                                                 19

<210> SEQ ID NO 253
<211> LENGTH: 25
<212> TYPE: DNA
<213> ORGANISM: Homo sapiens

<400> SEQUENCE: 253
tcccatttcc tgcctcagcc cattt                                          25

<210> SEQ ID NO 254
<211> LENGTH: 18
<212> TYPE: DNA
<213> ORGANISM: Homo sapiens

<400> SEQUENCE: 254
ggctggtctg cccctag                                                   18

<210> SEQ ID NO 255
<211> LENGTH: 22
<212> TYPE: DNA
<213> ORGANISM: Homo sapiens

<400> SEQUENCE: 255
accattgggt ctctgcaaat cc                                             22

<210> SEQ ID NO 256
<211> LENGTH: 25
<212> TYPE: DNA
```

<213> ORGANISM: Homo sapiens

<400> SEQUENCE: 256
actccgtcgc tccaattact tccga 25

<210> SEQ ID NO 257
<211> LENGTH: 25
<212> TYPE: DNA
<213> ORGANISM: Homo sapiens

<400> SEQUENCE: 257
aggacgagct atagaaaagc tattg 25

<210> SEQ ID NO 258
<211> LENGTH: 24
<212> TYPE: DNA
<213> ORGANISM: Homo sapiens

<400> SEQUENCE: 258
cattcaaaag cacagaagca catc 24

<210> SEQ ID NO 259
<211> LENGTH: 25
<212> TYPE: DNA
<213> ORGANISM: Homo sapiens

<400> SEQUENCE: 259
caccagcaag gtttccaact actgc 25

<210> SEQ ID NO 260
<211> LENGTH: 25
<212> TYPE: DNA
<213> ORGANISM: Homo sapiens

<400> SEQUENCE: 260
ttttccaggc taaagcaaat gaaag 25

<210> SEQ ID NO 261
<211> LENGTH: 24
<212> TYPE: DNA
<213> ORGANISM: Homo sapiens

<400> SEQUENCE: 261
ctatcctagc accattgttg catg 24

<210> SEQ ID NO 262
<211> LENGTH: 25
<212> TYPE: DNA
<213> ORGANISM: Homo sapiens

<400> SEQUENCE: 262
ttgctggtat caacacagcc tgcca 25

<210> SEQ ID NO 263
<211> LENGTH: 23
<212> TYPE: DNA
<213> ORGANISM: Homo sapiens

<400> SEQUENCE: 263
tgagtgagac tgagggatcg tag 23

<210> SEQ ID NO 264
<211> LENGTH: 19

```
<212> TYPE: DNA
<213> ORGANISM: Homo sapiens

<400> SEQUENCE: 264
gtggttggca ggagcaagc                                            19

<210> SEQ ID NO 265
<211> LENGTH: 25
<212> TYPE: DNA
<213> ORGANISM: Homo sapiens

<400> SEQUENCE: 265
cacactctca cactcgcacc cagaa                                     25

<210> SEQ ID NO 266
<211> LENGTH: 21
<212> TYPE: DNA
<213> ORGANISM: Homo sapiens

<400> SEQUENCE: 266
accagagggg agcaaaatcg a                                         21

<210> SEQ ID NO 267
<211> LENGTH: 20
<212> TYPE: DNA
<213> ORGANISM: Homo sapiens

<400> SEQUENCE: 267
tgcctctccc atcacttccc                                           20

<210> SEQ ID NO 268
<211> LENGTH: 27
<212> TYPE: DNA
<213> ORGANISM: Homo sapiens

<400> SEQUENCE: 268
cctctgtgtg gtccatcctt ggaagca                                   27

<210> SEQ ID NO 269
<211> LENGTH: 21
<212> TYPE: DNA
<213> ORGANISM: Homo sapiens

<400> SEQUENCE: 269
cagcacctga tggcctatca c                                         21

<210> SEQ ID NO 270
<211> LENGTH: 24
<212> TYPE: DNA
<213> ORGANISM: Homo sapiens

<400> SEQUENCE: 270
cagttcttca tgctccagac gtac                                      24

<210> SEQ ID NO 271
<211> LENGTH: 25
<212> TYPE: DNA
<213> ORGANISM: Homo sapiens

<400> SEQUENCE: 271
cgcatctcca gccacatccc tttga                                     25

<210> SEQ ID NO 272
```

```
<211> LENGTH: 25
<212> TYPE: DNA
<213> ORGANISM: Homo sapiens

<400> SEQUENCE: 272
cctcttgagg aaactggtgc aattg                                              25

<210> SEQ ID NO 273
<211> LENGTH: 22
<212> TYPE: DNA
<213> ORGANISM: Homo sapiens

<400> SEQUENCE: 273
tgattctgac atttggccca gc                                                 22

<210> SEQ ID NO 274
<211> LENGTH: 27
<212> TYPE: DNA
<213> ORGANISM: Homo sapiens

<400> SEQUENCE: 274
tctcaaatgc agggctgtaa cgctctc                                            27

<210> SEQ ID NO 275
<211> LENGTH: 22
<212> TYPE: DNA
<213> ORGANISM: Homo sapiens

<400> SEQUENCE: 275
gctagagcag gacttcgtct cc                                                 22

<210> SEQ ID NO 276
<211> LENGTH: 23
<212> TYPE: DNA
<213> ORGANISM: Homo sapiens

<400> SEQUENCE: 276
gagaagatct ggccttatgc cca                                                23

<210> SEQ ID NO 277
<211> LENGTH: 25
<212> TYPE: DNA
<213> ORGANISM: Homo sapiens

<400> SEQUENCE: 277
tctctggaac agctcatcgc cgcat                                              25

<210> SEQ ID NO 278
<211> LENGTH: 24
<212> TYPE: DNA
<213> ORGANISM: Homo sapiens

<400> SEQUENCE: 278
ggaaggctgc gacttgttaa tcaa                                               24

<210> SEQ ID NO 279
<211> LENGTH: 20
<212> TYPE: DNA
<213> ORGANISM: Homo sapiens

<400> SEQUENCE: 279
ctcctgacaa acacagcccc                                                    20
```

```
<210> SEQ ID NO 280
<211> LENGTH: 25
<212> TYPE: DNA
<213> ORGANISM: Homo sapiens

<400> SEQUENCE: 280
ccgtggtggt ctttatcctc ccgcc                                    25

<210> SEQ ID NO 281
<211> LENGTH: 25
<212> TYPE: DNA
<213> ORGANISM: Homo sapiens

<400> SEQUENCE: 281
gagagtggac ctggagaaga atcag                                    25

<210> SEQ ID NO 282
<211> LENGTH: 21
<212> TYPE: DNA
<213> ORGANISM: Homo sapiens

<400> SEQUENCE: 282
tagcatccaa gtcatccgcc t                                        21

<210> SEQ ID NO 283
<211> LENGTH: 23
<212> TYPE: DNA
<213> ORGANISM: Homo sapiens

<400> SEQUENCE: 283
agtccttcag ccaggagcca ggc                                      23

<210> SEQ ID NO 284
<211> LENGTH: 25
<212> TYPE: DNA
<213> ORGANISM: Homo sapiens

<400> SEQUENCE: 284
gttcgggatt cgatggattc tttgg                                    25

<210> SEQ ID NO 285
<211> LENGTH: 25
<212> TYPE: DNA
<213> ORGANISM: Homo sapiens

<400> SEQUENCE: 285
ccaaggccat cattgtattc tctgc                                    25

<210> SEQ ID NO 286
<211> LENGTH: 23
<212> TYPE: DNA
<213> ORGANISM: Homo sapiens

<400> SEQUENCE: 286
tctccatcca ccgaagcccc tgt                                      23

<210> SEQ ID NO 287
<211> LENGTH: 20
<212> TYPE: DNA
<213> ORGANISM: Homo sapiens

<400> SEQUENCE: 287
gcagcacctt caaccctcag                                          20
```

<210> SEQ ID NO 288
<211> LENGTH: 23
<212> TYPE: DNA
<213> ORGANISM: Homo sapiens

<400> SEQUENCE: 288
tctctgaaca acgagaaggt gct                                    23

<210> SEQ ID NO 289
<211> LENGTH: 24
<212> TYPE: DNA
<213> ORGANISM: Homo sapiens

<400> SEQUENCE: 289
cctacgagca cctgaccgca gagt                                   24

<210> SEQ ID NO 290
<211> LENGTH: 22
<212> TYPE: DNA
<213> ORGANISM: Homo sapiens

<400> SEQUENCE: 290
agccgctctg tttattggat gg                                     22

<210> SEQ ID NO 291
<211> LENGTH: 24
<212> TYPE: DNA
<213> ORGANISM: Homo sapiens

<400> SEQUENCE: 291
tctgacaaca acaaaacacc caga                                   24

<210> SEQ ID NO 292
<211> LENGTH: 27
<212> TYPE: DNA
<213> ORGANISM: Homo sapiens

<400> SEQUENCE: 292
acaccaccaa ttatgcacag tgaggct                                27

<210> SEQ ID NO 293
<211> LENGTH: 25
<212> TYPE: DNA
<213> ORGANISM: Homo sapiens

<400> SEQUENCE: 293
tggctccaag aagaagtttg acaag                                  25

<210> SEQ ID NO 294
<211> LENGTH: 25
<212> TYPE: DNA
<213> ORGANISM: Homo sapiens

<400> SEQUENCE: 294
tccttcagga aattcaggta cggat                                  25

<210> SEQ ID NO 295
<211> LENGTH: 26
<212> TYPE: DNA
<213> ORGANISM: Homo sapiens

<400> SEQUENCE: 295
cctgactgct tgctgcaacc agaacc                                 26

<210> SEQ ID NO 296
<211> LENGTH: 23
<212> TYPE: DNA
<213> ORGANISM: Homo sapiens

<400> SEQUENCE: 296
agtggagggg tttgtacaag aca                                              23

<210> SEQ ID NO 297
<211> LENGTH: 24
<212> TYPE: DNA
<213> ORGANISM: Homo sapiens

<400> SEQUENCE: 297
caaatgggac ttagactgga ggct                                             24

<210> SEQ ID NO 298
<211> LENGTH: 25
<212> TYPE: DNA
<213> ORGANISM: Homo sapiens

<400> SEQUENCE: 298
cgcctcatct tccagaacca caggg                                            25

<210> SEQ ID NO 299
<211> LENGTH: 24
<212> TYPE: DNA
<213> ORGANISM: Homo sapiens

<400> SEQUENCE: 299
ccacaagcaa accagctttc tttg                                             24

<210> SEQ ID NO 300
<211> LENGTH: 25
<212> TYPE: DNA
<213> ORGANISM: Homo sapiens

<400> SEQUENCE: 300
tgatcaggat tatggtttcc cgttc                                            25

<210> SEQ ID NO 301
<211> LENGTH: 26
<212> TYPE: DNA
<213> ORGANISM: Homo sapiens

<400> SEQUENCE: 301
tggcgagttc caacaccttt catggc                                           26

<210> SEQ ID NO 302
<211> LENGTH: 23
<212> TYPE: DNA
<213> ORGANISM: Homo sapiens

<400> SEQUENCE: 302
ggaagaggac atgacggaac aga                                              23

<210> SEQ ID NO 303
<211> LENGTH: 25
<212> TYPE: DNA
<213> ORGANISM: Homo sapiens

<400> SEQUENCE: 303

```
gtgttccagt gcctcttaat tgagg                                            25

<210> SEQ ID NO 304
<211> LENGTH: 27
<212> TYPE: DNA
<213> ORGANISM: Homo sapiens

<400> SEQUENCE: 304
caaagcacta aaccctgtcc gctggaa                                          27

<210> SEQ ID NO 305
<211> LENGTH: 18
<212> TYPE: DNA
<213> ORGANISM: Homo sapiens

<400> SEQUENCE: 305
ctgcagcagc agcaccag                                                    18

<210> SEQ ID NO 306
<211> LENGTH: 25
<212> TYPE: DNA
<213> ORGANISM: Homo sapiens

<400> SEQUENCE: 306
catcaggcac atgagtaaca aaggc                                            25

<210> SEQ ID NO 307
<211> LENGTH: 24
<212> TYPE: DNA
<213> ORGANISM: Homo sapiens

<400> SEQUENCE: 307
cccagctcct cctcatcctc tccc                                             24

<210> SEQ ID NO 308
<211> LENGTH: 23
<212> TYPE: DNA
<213> ORGANISM: Homo sapiens

<400> SEQUENCE: 308
gcagagatgg gaagtgaaag agc                                              23

<210> SEQ ID NO 309
<211> LENGTH: 25
<212> TYPE: DNA
<213> ORGANISM: Homo sapiens

<400> SEQUENCE: 309
tcaatgcctc agaaattcat tggtg                                            25

<210> SEQ ID NO 310
<211> LENGTH: 27
<212> TYPE: DNA
<213> ORGANISM: Homo sapiens

<400> SEQUENCE: 310
tgccacattg cttgctaatc tgtccag                                          27

<210> SEQ ID NO 311
<211> LENGTH: 23
<212> TYPE: DNA
<213> ORGANISM: Homo sapiens

<400> SEQUENCE: 311
```

```
gacagcttct tgcagcgata cag                                              23

<210> SEQ ID NO 312
<211> LENGTH: 19
<212> TYPE: DNA
<213> ORGANISM: Homo sapiens

<400> SEQUENCE: 312
ccttcctccc agtgcctga                                                   19

<210> SEQ ID NO 313
<211> LENGTH: 27
<212> TYPE: DNA
<213> ORGANISM: Homo sapiens

<400> SEQUENCE: 313
tcgtctatgc tgtcctcagt caaggcg                                          27

<210> SEQ ID NO 314
<211> LENGTH: 24
<212> TYPE: DNA
<213> ORGANISM: Homo sapiens

<400> SEQUENCE: 314
agagcacttc ctcatagacc ttgg                                             24

<210> SEQ ID NO 315
<211> LENGTH: 21
<212> TYPE: DNA
<213> ORGANISM: Homo sapiens

<400> SEQUENCE: 315
ttcaagccag gaagaagcag c                                                21

<210> SEQ ID NO 316
<211> LENGTH: 27
<212> TYPE: DNA
<213> ORGANISM: Homo sapiens

<400> SEQUENCE: 316
tgcattcagt ctagttcctg gttgccg                                          27

<210> SEQ ID NO 317
<211> LENGTH: 20
<212> TYPE: DNA
<213> ORGANISM: Homo sapiens

<400> SEQUENCE: 317
gcaagatggg ctacctggac                                                  20

<210> SEQ ID NO 318
<211> LENGTH: 20
<212> TYPE: DNA
<213> ORGANISM: Homo sapiens

<400> SEQUENCE: 318
ttaagcagac ctccccagga                                                  20

<210> SEQ ID NO 319
<211> LENGTH: 25
<212> TYPE: DNA
<213> ORGANISM: Homo sapiens
```

```
<400> SEQUENCE: 319
acccgcacaa tctgctcatt cctcg                                          25

<210> SEQ ID NO 320
<211> LENGTH: 24
<212> TYPE: DNA
<213> ORGANISM: Homo sapiens

<400> SEQUENCE: 320
tctccttagg gaagcggatt tgtc                                           24

<210> SEQ ID NO 321
<211> LENGTH: 22
<212> TYPE: DNA
<213> ORGANISM: Homo sapiens

<400> SEQUENCE: 321
ttcttcacca ccatcctcca ga                                             22

<210> SEQ ID NO 322
<211> LENGTH: 24
<212> TYPE: DNA
<213> ORGANISM: Homo sapiens

<400> SEQUENCE: 322
catcgcccgt gcggaattgt tcct                                           24

<210> SEQ ID NO 323
<211> LENGTH: 20
<212> TYPE: DNA
<213> ORGANISM: Homo sapiens

<400> SEQUENCE: 323
ctggccatct gcaagctgag                                                20

<210> SEQ ID NO 324
<211> LENGTH: 22
<212> TYPE: DNA
<213> ORGANISM: Homo sapiens

<400> SEQUENCE: 324
cagttcagcc ttcagttggt gg                                             22

<210> SEQ ID NO 325
<211> LENGTH: 27
<212> TYPE: DNA
<213> ORGANISM: Homo sapiens

<400> SEQUENCE: 325
agcaaggaag ccaatccaag tcaccaa                                        27

<210> SEQ ID NO 326
<211> LENGTH: 24
<212> TYPE: DNA
<213> ORGANISM: Homo sapiens

<400> SEQUENCE: 326
acccatatac caccactgga ttcc                                           24

<210> SEQ ID NO 327
<211> LENGTH: 23
<212> TYPE: DNA
<213> ORGANISM: Homo sapiens
```

```
<400> SEQUENCE: 327
cagtttggga atgcatggac acc                                          23

<210> SEQ ID NO 328
<211> LENGTH: 27
<212> TYPE: DNA
<213> ORGANISM: Homo sapiens

<400> SEQUENCE: 328
acctcctcct ctctcagacc gagttgg                                      27

<210> SEQ ID NO 329
<211> LENGTH: 25
<212> TYPE: RNA
<213> ORGANISM: Homo sapiens

<400> SEQUENCE: 329
cagcggcugu auauucuccu cccuu                                        25

<210> SEQ ID NO 330
<211> LENGTH: 21
<212> TYPE: RNA
<213> ORGANISM: Homo sapiens

<400> SEQUENCE: 330
ggucauauua caucggauau u                                            21

<210> SEQ ID NO 331
<211> LENGTH: 21
<212> TYPE: RNA
<213> ORGANISM: Homo sapiens

<400> SEQUENCE: 331
ggaaauauca ugcguguuau u                                            21

<210> SEQ ID NO 332
<211> LENGTH: 21
<212> TYPE: RNA
<213> ORGANISM: Homo sapiens

<400> SEQUENCE: 332
uggugcagcu agagaauuau u                                            21

<210> SEQ ID NO 333
<211> LENGTH: 21
<212> TYPE: RNA
<213> ORGANISM: Homo sapiens

<400> SEQUENCE: 333
ccucugagaa cccacugaau u                                            21

<210> SEQ ID NO 334
<211> LENGTH: 21
<212> TYPE: RNA
<213> ORGANISM: Homo sapiens

<400> SEQUENCE: 334
ggacaauccc acucccuucu u                                            21

<210> SEQ ID NO 335
<211> LENGTH: 21
<212> TYPE: RNA
```

```
<213> ORGANISM: Homo sapiens

<400> SEQUENCE: 335
agagaaaugu ugcaggaaau u                                              21

<210> SEQ ID NO 336
<211> LENGTH: 25
<212> TYPE: RNA
<213> ORGANISM: Homo sapiens

<400> SEQUENCE: 336
cagcuucuaa gaugcuguca aaguu                                          25

<210> SEQ ID NO 337
<211> LENGTH: 21
<212> TYPE: RNA
<213> ORGANISM: Homo sapiens

<400> SEQUENCE: 337
ccuaucggaa gaaggcaagu u                                              21

<210> SEQ ID NO 338
<211> LENGTH: 21
<212> TYPE: RNA
<213> ORGANISM: Homo sapiens

<400> SEQUENCE: 338
cauacagcuu cauaaauaau u                                              21

<210> SEQ ID NO 339
<211> LENGTH: 21
<212> TYPE: RNA
<213> ORGANISM: Homo sapiens

<400> SEQUENCE: 339
ggacacaauu acaacuaaau u                                              21

<210> SEQ ID NO 340
<211> LENGTH: 21
<212> TYPE: RNA
<213> ORGANISM: Homo sapiens

<400> SEQUENCE: 340
ggaggaauau cguagguaau u                                              21

<210> SEQ ID NO 341
<211> LENGTH: 21
<212> TYPE: RNA
<213> ORGANISM: Homo sapiens

<400> SEQUENCE: 341
gcagauucau gaagagaaau u                                              21

<210> SEQ ID NO 342
<211> LENGTH: 21
<212> TYPE: RNA
<213> ORGANISM: Homo sapiens

<400> SEQUENCE: 342
gguuaaagca cauuguagau u                                              21

<210> SEQ ID NO 343
<211> LENGTH: 25
```

```
<212> TYPE: DNA
<213> ORGANISM: Homo sapiens

<400> SEQUENCE: 343
ggccatcaag aatttactga aagca                                          25

<210> SEQ ID NO 344
<211> LENGTH: 22
<212> TYPE: DNA
<213> ORGANISM: Homo sapiens

<400> SEQUENCE: 344
tctgtgtggt ccatccttgg aa                                             22

<210> SEQ ID NO 345
<211> LENGTH: 21
<212> TYPE: DNA
<213> ORGANISM: Homo sapiens

<400> SEQUENCE: 345
tgcccacatc aaggagtatt t                                              21

<210> SEQ ID NO 346
<211> LENGTH: 19
<212> TYPE: DNA
<213> ORGANISM: Homo sapiens

<400> SEQUENCE: 346
ctttcgggtg acaaagacg                                                 19

<210> SEQ ID NO 347
<211> LENGTH: 21
<212> TYPE: DNA
<213> ORGANISM: Homo sapiens

<400> SEQUENCE: 347
catctgcaaa tcgtgactaa g                                              21

<210> SEQ ID NO 348
<211> LENGTH: 24
<212> TYPE: DNA
<213> ORGANISM: Homo sapiens

<400> SEQUENCE: 348
cagtcgacac attaaccttc cttc                                           24

<210> SEQ ID NO 349
<211> LENGTH: 25
<212> TYPE: DNA
<213> ORGANISM: Homo sapiens

<400> SEQUENCE: 349
ggcatccaag atacaaactc aaaga                                          25

<210> SEQ ID NO 350
<211> LENGTH: 23
<212> TYPE: DNA
<213> ORGANISM: Homo sapiens

<400> SEQUENCE: 350
agttccaatg ctggattacg tct                                            23

<210> SEQ ID NO 351
```

```
<211> LENGTH: 24
<212> TYPE: DNA
<213> ORGANISM: Homo sapiens

<400> SEQUENCE: 351
ccagaaagct cttgagttta ttcc                                          24

<210> SEQ ID NO 352
<211> LENGTH: 22
<212> TYPE: DNA
<213> ORGANISM: Homo sapiens

<400> SEQUENCE: 352
catctagttc ccgaaccatc tc                                            22

<210> SEQ ID NO 353
<211> LENGTH: 20
<212> TYPE: DNA
<213> ORGANISM: Homo sapiens

<400> SEQUENCE: 353
ctcaacccgc tcatctacac                                               20

<210> SEQ ID NO 354
<211> LENGTH: 22
<212> TYPE: DNA
<213> ORGANISM: Homo sapiens

<400> SEQUENCE: 354
tccttgggtt ctggcttaat ac                                            22

<210> SEQ ID NO 355
<211> LENGTH: 25
<212> TYPE: DNA
<213> ORGANISM: Homo sapiens

<400> SEQUENCE: 355
tcgctgcccc cttcactttc ttatt                                         25

<210> SEQ ID NO 356
<211> LENGTH: 20
<212> TYPE: DNA
<213> ORGANISM: Homo sapiens

<400> SEQUENCE: 356
tgcttcatgt tagtccccag                                               20

<210> SEQ ID NO 357
<211> LENGTH: 22
<212> TYPE: DNA
<213> ORGANISM: Homo sapiens

<400> SEQUENCE: 357
gggtctcact atattgctct gg                                            22

<210> SEQ ID NO 358
<211> LENGTH: 24
<212> TYPE: DNA
<213> ORGANISM: Homo sapiens

<400> SEQUENCE: 358
cctcagcctt ccaaaaccag gtgt                                          24
```